US005741896A

United States Patent [19]
Vuligonda et al.

[11] Patent Number: 5,741,896
[45] Date of Patent: Apr. 21, 1998

[54] O- OR S- SUBSTITUTED TETRAHYDRONAPHTHALENE DERIVATIVES HAVING RETINOID AND/OR RETINOID ANTAGONIST-LIKE BIOLOGICAL ACTIVITY

[75] Inventors: Vidyasagar Vuligonda, Irvine; Min Teng, Aliso Viejo; Richard L. Beard, Newport Beach; Alan T. Johnson, Rancho Santa Margarita; Yuan Lin, Walnut; Roshantha A. Chandraratna, Mission Viejo, all of Calif.

[73] Assignee: ALLERGAN, Irvine, Calif.

[21] Appl. No.: 667,664

[22] Filed: Jun. 21, 1996

[51] Int. Cl.$^6$ ............... C07C 245/10; A61K 31/655
[52] U.S. Cl. ............... 534/860; 514/150; 514/510; 514/561; 560/100; 560/110; 562/440
[58] Field of Search ............... 534/860, 861; 560/100, 110; 562/440; 514/510, 561

[56] References Cited

U.S. PATENT DOCUMENTS

| | | | |
|---|---|---|---|
| 4,096,341 | 6/1978 | Frazer | 560/85 |
| 4,326,055 | 4/1982 | Loeliger | 542/429 |
| 4,391,731 | 7/1983 | Boller et al. | 252/299.26 |
| 4,695,649 | 9/1987 | Magami et al. | 560/86 |
| 4,723,028 | 2/1988 | Shudo | 560/8 |
| 4,739,098 | 4/1988 | Chandraratna | 560/8 |
| 4,740,519 | 4/1988 | Shroot et al. | 514/443 |
| 4,810,804 | 3/1989 | Chandraratna | 514/311 |
| 4,826,969 | 5/1989 | Maignan et al. | 536/55.2 |
| 4,826,984 | 5/1989 | Berlin et al. | 546/134 |
| 4,855,320 | 8/1989 | Chatterjee et al. | 514/473 |
| 4,895,868 | 1/1990 | Chandraratna | 514/432 |
| 4,927,947 | 5/1990 | Chandraratna | 549/484 |
| 4,980,369 | 12/1990 | Chandraratna | 514/432 |
| 4,992,468 | 2/1991 | Chandraratna | 514/532 |
| 5,006,550 | 4/1991 | Chandraratna | 514/456 |
| 5,013,744 | 5/1991 | Chandraratna | 514/345 |
| 5,015,658 | 5/1991 | Chandraratna | 514/432 |
| 5,023,341 | 6/1991 | Chandraratna | 549/23 |
| 5,037,825 | 8/1991 | Klaus et al. | 514/233.8 |
| 5,045,551 | 9/1991 | Chandraratna | 514/337 |
| 5,053,523 | 10/1991 | Chandraratna | 549/398 |
| 5,068,252 | 11/1991 | Chandraratna | 514/543 |
| 5,089,509 | 2/1992 | Chandraratna | 514/337 |
| 5,130,335 | 7/1992 | Chandraratna | 514/510 |
| 5,134,159 | 7/1992 | Chandraratna | 514/456 |
| 5,162,546 | 11/1992 | Chandraratna | 549/23 |
| 5,175,185 | 12/1992 | Chandraratna | 514/445 |
| 5,183,827 | 2/1993 | Chandraratna | 514/444 |
| 5,202,471 | 4/1993 | Chandraratna | 562/473 |
| 5,231,113 | 7/1993 | Chandraratna | 514/510 |
| 5,234,926 | 8/1993 | Chandraratna | 514/253 |
| 5,248,777 | 9/1993 | Chandraratna | 546/165 |
| 5,264,456 | 11/1993 | Chandraratna | 514/461 |
| 5,264,578 | 11/1993 | Chandraratna | 546/269 |
| 5,272,156 | 12/1993 | Chandraratna | 514/314 |
| 5,278,318 | 1/1994 | Chandraratna | 549/23 |
| 5,324,744 | 6/1994 | Chandraratna | 514/456 |
| 5,324,840 | 6/1994 | Chandraratna | 546/318 |

(List continued on next page.)

FOREIGN PATENT DOCUMENTS

| | | | |
|---|---|---|---|
| 0130795 | 1/1985 | European Pat. Off. | C07D 311/58 |
| 0272921 | 6/1988 | European Pat. Off. | C07D 213/80 |
| 0284288 | 9/1988 | European Pat. Off. | C07D 401/04 |
| 176034A | 4/1989 | European Pat. Off. | C07C 63/66 |
| 0350846 | 7/1989 | European Pat. Off. | C07D 311/85 |
| 0617020 | 9/1994 | European Pat. Off. | C07D 213/82 |
| 0224030 | 6/1985 | Germany . | |
| 3708060 | 9/1987 | Germany | C07D 311/04 |
| 2190378 | 11/1987 | United Kingdom | C07C 39/21 |
| 85/00806 | 2/1985 | WIPO | A61K 31/00 |
| 85/04652 | 10/1985 | WIPO | A61K 31/19 |
| 91/16051 | 10/1991 | WIPO | A61K 31/44 |

OTHER PUBLICATIONS

Kessar et al.: Azasteroids S. Synthesis of 3, 6–dihydro–8–methoxy benzo[C]Phenathridin–1(2K)–one J. Chem. Soc., Perkin Trans. vol. 1 pp. 1158–1160, 1973.

Kagechika et al. in *J. Med. Chem.*, (1988) 31:2182–2192.

V. Retinoid Structure–Biological Activity Relationships, Chemistry and Biology of Synthetic Retinoids, (1990) pp. 324–356.

"Effects of 13–Cis–Retinoic Acid, All Trans–Retinoic Acid, and Acitretin on the Proliferation, Lipid Synthesis and Keratin Expression of Cultured Human Sebocytes in Vitro" C.C. Zouboulis, *The Journal of Investigative Dermatology*, (1991) 96/5:792–797.

"Organ Maintenance of Human Sebaceous Glands: in Vitro Effects of 13–Cis Retinoic Acid and Testosterone", John Ridden, et al., *Journal of Cell Science* (1990) 95:125–136.

"Characterization of Human Sebaceous Cells in Vitro", Thomas I. Doran, et al. *The Journal of Investigative Dermatology*, (1991) 96/3:.

"Retinobenzoic acids. 3. Structure–Activity Relationships of Retinoidal Azobenzene–4–Carboxylic Acids and Stilbene–4– Carboxylic Acids" by H. Kagechika et al., *Journal of Medicinal Chemistry*, (1989), 32:1098–1108.

Eyrolles, L. et al. "Retinoid Antagonists: Molecuular Design Based on the Ligand Superfamily Concept" *Med. Chem. Res.*, (1992) 2:361–367.

Liu, S. S. et al. "Systemic Pharmacokinetics of Acetylenic Retinoids in Rats", *Drug Metabolism and Disposition*, (1990) 18/6: 1071–1077.

*Primary Examiner*—C. Warren Ivy
*Assistant Examiner*—Charanjit S. Aulakh
*Attorney, Agent, or Firm*—Gabor L. Szekeres; Robert J. Baran; Martin A. Voet

[57] ABSTRACT

Compounds of the formula

[structure: tetrahydronaphthalene core with substituents $R_4$, $X_2$, $R_5$, $(R_2)_m$, $(R_3)_o$, $X_1$, and $-Z-Y(R_2)-A-B$]

where the symbols have the meaning described in the application, have retinoid-like or retinoid antagonist-like biological activity.

31 Claims, No Drawings

U.S. PATENT DOCUMENTS

| | | | |
|---|---|---|---|
| 5,326,898 | 7/1994 | Chandraratna | 560/17 |
| 5,344,959 | 9/1994 | Chandraratna | 560/100 |
| 5,346,895 | 9/1994 | Chandraratna | 514/247 |
| 5,346,915 | 9/1994 | Chandraratna | 514/432 |
| 5,348,972 | 9/1994 | Chandraratna | 514/432 |
| 5,348,975 | 9/1994 | Chandraratna | 514/456 |
| 5,349,105 | 9/1994 | Chandraratna | 564/163 |
| 5,354,752 | 10/1994 | Chandraratna | 514/252 |
| 5,380,877 | 1/1995 | Chandraratna | 549/60 |
| 5,391,753 | 2/1995 | Chandraratna | 546/63 |
| 5,399,561 | 3/1995 | Chandraratna | 514/252 |
| 5,399,586 | 3/1995 | Davies et al. | 514/448 |
| 5,407,937 | 4/1995 | Chandraratna | 514/256 |
| 5,414,007 | 5/1995 | Chandraratna | 514/365 |
| 5,426,118 | 6/1995 | Chandraratna | 514/337 |
| 5,434,173 | 7/1995 | Chandraratna | 514/354 |
| 5,451,605 | 9/1995 | Chandraratna et al. | 514/475 |
| 5,455,265 | 10/1995 | Chandraratna | 514/448 |
| 5,468,879 | 11/1995 | Chandraratna | 549/23 |
| 5,470,999 | 11/1995 | Chandraratna | 560/100 |
| 5,475,022 | 12/1995 | Chandraratna | 514/448 |
| 5,475,113 | 12/1995 | Chandraratna | 548/203 |
| 5,489,584 | 2/1996 | Vuligonda et al. | 514/188 |
| 5,498,755 | 3/1996 | Chandraratna et al. | 564/272 |
| 5,498,795 | 3/1996 | Song et al. | 562/474 |
| 5,514,825 | 5/1996 | Vuligonda et al. | 558/462 |
| 5,516,904 | 5/1996 | Chandraratna | 514/269 |
| 5,534,516 | 7/1996 | Chandraratna | 549/416 |
| 5,534,641 | 7/1996 | Song et al. | 549/416 |
| 5,543,534 | 8/1996 | Vuligonda et al. | 549/421 | ejection and facilitation of wound healing, including modulation of chelosis.

5,741,896

O- OR S- SUBSTITUTED TETRAHYDRONAPHTHALENE DERIVATIVES HAVING RETINOID AND/OR RETINOID ANTAGONIST-LIKE BIOLOGICAL ACTIVITY

1. FIELD OF THE INVENTION

The present invention relates to novel compounds having retinoid and/or retinoid antagonist-like biological activity. More specifically, the present invention relates to O- or S-substituted tetrahydronaphthalene derivatives which bind to retinoid receptors and have retinoid-like or retinoid antagonist-like biological activity.

2. BACKGROUND ART

Compounds which have retinoid-like activity are well known in the art, and are described in numerous United States and other patents and in scientific publications. It is generally known and accepted in the art that retinoid-like activity is useful for treating animals of the mammalian species, including humans, for curing or alleviating the symptoms and conditions of numerous diseases and conditions. In other words, it is generally accepted in the art that pharmaceutical compositions having a retinoid-like compound or compounds as the active ingredient are useful as regulators of cell proliferation and differentiation, and particularly as agents for treating skin-related diseases, including, actinic keratoses, arsenic keratoses, inflammatory and non-inflammatory acne, psoriasis, ichthyoses and other keratinization and hyperproliferative disorders of the skin, eczema, atopic dermatitis, Darriers disease, lichen planus, prevention and reversal of glucocorticoid damage (steroid atrophy), as a topical anti-microbial, as skin anti-pigmentation agents and to treat and reverse the effects of age and photo damage to the skin. Retinoid compounds are also useful for the prevention and treatment of cancerous and precancerous conditions, including, premalignant and malignant hyperproliferative diseases such as cancers of the breast, skin, prostate, cervix, uterus, colon, bladder, esophagus, stomach, lung, larynx, oral cavity, blood and lymphatic system, metaplasias, dysplasias, neoplasias, leukoplakias and papillomas of the mucous membranes and in the treatment of Kaposi's sarcoma. In addition, retinoid compounds can be used as agents to treat diseases of the eye, including, without limitation, proliferative vitreoretinopathy (PVR), retinal detachment, dry eye and other corneopathies, as well as in the treatment and prevention of various cardiovascular diseases, including, without limitation, diseases associated with lipid metabolism such as dyslipidemias, prevention of post-angioplasty restenosis and as an agent to increase the level of circulating tissue plasminogen activator (TPA). Other uses for retinoid compounds include the prevention and treatment of conditions and diseases associated with human papilloma virus (HPV), including warts and genital warts, various inflammatory diseases such as pulmonary fibrosis, ileitis, colitis and Krohn's disease, neurodegenerative diseases such as Alzheimer's disease, Parkinson's disease and stroke, improper pituitary function, including insufficient production of growth hormone, modulation of apoptosis, including both the induction of apoptosis and inhibition of T-Cell activated apoptosis, restoration of hair growth, including combination therapies with the present compounds and other agents such as Minoxidil$^R$, diseases associated with the immune system, including use of the present compounds as immunosuppressants and immunostimulants, modulation of organ transplant rejection and facilitation of wound healing, including modulation of chelosis.

U.S. Pat. Nos. 4,740,519 (Shroot et al.), 4,826,969 (Maignan et al.), 4,326,055 (Loeliger et al.), 5,130,335 (Chandraratna et al.), 5,037,825 (Klaus et al.), 5,231,113 (Chandraratna et al.), 5,324,840 (Chandraratna), 5,344,959 (Chandraratna.), 5,130,335 Chandraratna et al.), Published European Patent Application Nos. 0 176 034 A (Wuest et al.), 0 350 846 A (Klaus et al.), 0 176 032 A (Frickel et al.), 0 176 033 A (Frickel et al.), 0 253 302 A (Klaus et al.), 0 303 915 A (Bryce et al.), UK Patent Application GB 2190378 A (Klaus et al.), German Patent Application Nos. DE 3715955 A1 (Klaus et al.), DE 3602473 A1 (Wuest et al., and the articles J. Amer. Acad. Derm. 15: 756–764 (1986) (Sporn et al.), Chem. Pharm. Bull. 33: 404–407 (1985) (Shudo et al.), J. Med Chem. 1988 31, 2182–2192 (Kagechika et al.), Chemistry and Biology of Synthetic Retinoids CRC Press Inc. 1990 p 334–335, 354 (Dawson et al.), describe or relate to compounds which include a tetrahydronaphthyl moiety and have retinoid-like or related biological activity. U.S. Pat. No. 4,391,731 (Boller et al.) describes tetrahydronaphthalene derivatives which are useful in liquid crystal compositions.

Published European Patent application Nos. 0 661 259 A1 and 0 661 261 A1 (Bristol-Myers Squibb) describe further dihydronaphthalene and naphthalene derivatives which are said in the disclosures to have retinoid-like biological activity.

U.S. Pat. Nos. 4,980,369, 5,006,550, 5,015,658, 5,045, 551, 5,089,509, 5,134,159, 5,162,546, 5,234,926, 5,248,777, 5,264,578, 5,272,156, 5,278,318, 5,324,744, 5,346,895, 5,346,915, 5,348,972, 5,348,975, 5,380,877, 5,399,561, 5,407,937, (assigned to the same assignee as the present application) and patents and publications cited therein, describe or relate to chroman, thiochroman and 1,2,3,4-tetrahydroquinoline derivatives which have retinoid-like biological activity. Still further, several co-pending applications and recently issued patents which are assigned to the assignee of the present application, are directed to further compounds having retinoid-like activity.

Although pharmaceutical compositions containing retinoids have well established utility (as is demonstrated by the foregoing citation of patents and publications from the voluminous literature devoted to this subject) retinoids also cause a number of undesired side effects at therapeutic dose levels, including headache, teratogenesis, mucocutaneous toxicity, musculoskeletal toxicity, dyslipidemias, skin irritation, headache and hepatotoxicity. These side effects limit the acceptability and utility of retinoids for treating disease.

It is now general knowledge in the art that two main types of retinoid receptors exist in mammals (and other organisms). The two main types or families of receptors respectively designated the RARs and RXRs. Within each type there are subtypes; in the RAR family the subtypes are designated RAR$_\alpha$, RAR$_\beta$ and RAR$_\gamma$, in RXR the subtypes are: RXR$_\alpha$, RXB$_\beta$ and RXR$_\gamma$. It has also been established in the art that the distribution of the two main retinoid receptor types, and of the several sub-types is not uniform in the various tissues and organs of mammalian organisms. Moreover, it is generally accepted in the art that many unwanted side effects of retinoids are mediated by one or more of the RAR receptor subtypes. Accordingly, among compounds having agonist-like activity at retinoid receptors, specificity or selectivity for one of the main types or families, and even specificity or selectivity for one or more subtypes within a family of receptors, is considered a desirable pharmacological property. Some compounds bind to one or more RAR receptor subtypes, but do not trigger the response which is triggered by agonists of the same receptors. A compound that binds to a biological receptor but does not trigger an agonist-like response is usually termed an antagonist. Accordingly, the "effect" of compounds on retinoid receptors may fall in the range of having no effect at all, (inactive compound, neither agonist nor antagonist), the compound may elicit an agonist-like response on all receptor subtypes (pan-agonist), or a compound may be a partial agonist and/or partial antagonist of certain receptor subtypes if the compound binds to but does not activate certain receptor subtype or subtypes but elicits an agonist-like response in other receptor subtype or subtypes. A pan antagonist is a compound that binds to all known retinoid receptors but does not elicit an agonist-like response in any of the receptors.

It has been recently discovered and described in a pending application assigned to the same assignee as the present application that retinoid antagonist-like activity of a compound is also a useful property, in that such antagonist compounds can be utilized to block certain undesired side effects of retinoids, to serve as antidotes to retinoid overdose or poisoning, and may lend themselves to other pharmaceutical applications as well. More particularly, regarding the published scientific and patent literature in this field, published PCT application WO 94/14777 describes certain heterocyclic carboxylic acid derivatives which bind to RAR retinoid receptors and are said in the application to be useful for treatment of certain diseases or conditions, such as acne, psoriasis, rheumatoid arthritis and viral infections. A similar disclosure is made in the article by Yoshimura et al. J Med. Chem. 1995, 38, 3163–3173. Kaneko et al. Meal. Chem Res. (1991) 1:220–225; Apfel et al. Proc. Natl. Acad. Sci. USA Vol 89 pp 7129–7133 August 1992 Cell Biology; Eckhardt et al. Toxicology Letters. 70 (1994) 299–308; Keidel et al. Molecular and Cellular Biology, Vol 14, No. 1, January 1994, p 287–298; and Eyrolles et al. J. Med. Chem. 1994, 37, 1508–1517 describe compounds which have antagonist like activity at one or more of the RAR retinoid subtypes.

SUMMARY OF THE INVENTION

Among the compounds of Formulas 1 through 6, the present invention covers the compounds of Formula 1. Compounds of the remaining formulas are disclosed here inasmuch as the methods of their synthesis pertains to the best modes of the presently contemplated synthetic routes leading to the compounds of Formula 1. Thus the present invention pertains to compounds of Formula 1

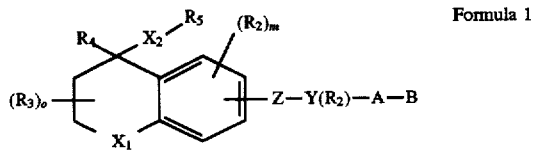

Formula 1 wherein $X_1$ is $[C(R_1)_2]_n$ where $R_1$ is independently H or alkyl of 1 to 6 carbons, and n is an integer between 0 and 2;

$X_2$ is S or O;

Z is $-N=N-$, $-N(O)=N-$, $-N=N(O)-$, $-N=CR_1-$, $-CR_1=N$, $-(CR_1=CR_1)_{n'}-$ where n' is an integer having the value 0–5, $-CO-NR_1-$, $-CS-NR_1-$, $-NR_1-CO$, $-NR_1-CS$, $-COO-$, $-OCO-$; $-CSO-$; $-OCS-$; $-CO-CR_1=CR_1$;

$R_2$ is hydrogen, lower alkyl of 1 to 6 carbons, F, Cl, Br, I, $CF_3$, fluoro substituted alkyl of 1 to 6 carbons, OH, SH, alkoxy of 1 to 6 carbons, or alkylthio of 1 to 6 carbons;

$R_3$ is hydrogen, lower alkyl of 1 to 6 carbons or F;

m is an integer having the value of 0–3;

o is an integer having the value of 0–4;

$R_4$ is hydrogen, alkyl of 1 to 10 carbons, alkenyl of 2 to 10 carbons and having 1 to 3 double bonds, alkynyl having 2 to 10 carbons and 1 to 3 triple bonds, carbocyclic aryl selected from the group consisting of phenyl, $C_1-C_{10}$-alkylphenyl, naphthyl, $C_1-C_{10}$-alkylnaphthyl, phenyl-$C_1-C_{10}$alkyl, napthyl-$C_1-C_{10}$alkyl; CN, or $(CH_2)_pCO_2R_8$ where p is an integer between 0 to 10;

$R_5$ is hydrogen, alkyl of 1 to 10 carbons, fluoro-substituted alkyl of 1 to 10 carbons, alkenyl of 2 to 10 carbons and having 1 to 3 double bonds, alkynyl having 2 to 10 carbons and 1 to 3 triple bonds, carbocyclic aryl selected from the group consisting of phenyl, $C_1-C_{10}$-alkylphenyl, naphthyl, $C_1-C_{10}$-alkylnaphthyl, phenyl-$C_1-C_{10}$alkyl, napthyl-$C_1-C_{10}$alkyl; $Si(C_{1-6}alkyl)_3$, $COR_{14}$, camphanoyl, $C(R_{15})(R_{16})X_2R_{17}$;

Y is a phenyl or naphthyl group, or heteroaryl selected from a group consisting of pyridyl, thienyl, furyl, pyridazinyl, pyrimidinyl, pyrazinyl, thiazolyl, oxazolyl, imidazolyl and pyrrazolyl, said phenyl and heteroaryl groups being optionally substituted with one or two $R_2$ groups, or when Z is $-(CR_1=CR_1)_{n'}-$ and n' is 3, 4 or 5 then Y represents a direct valence bond between said $(CR_2=CR_2)_{n'}$, group and B;

A is $(CH_2)_q$ where q is 0–5, lower branched chain alkyl having 3–6 carbons, cycloalkyl having 3–6 carbons, alkenyl having 2–6 carbons and 1 or 2 double bonds, alkynyl having 2–6 carbons and 1 or 2 triple bonds;

B is hydrogen, COOH or a pharmaceutically acceptable salt thereof, $COOR_8$, $CONR_9R_{10}$, $-CH_2OH$, $CH_2OR_{11}$, $CH_2OCOR_{11}$, CHO, $CH(OR_{12})_2$, $CHOR_{13}O$, $-COR_7$, $CR_7(OR_{12})_2$, $CR_7OR_{13}O$, or $Si(C_{1-6}alkyl)_3$, where $R_7$ is an alkyl, cycloalkyl or alkenyl group containing 1 to 5 carbons, $R_8$ is an alkyl group of 1 to 10 carbons or (trimethylsilyl)alkyl where the alkyl group has 1 to 10 carbons, or a cycloalkyl group of 5 to 10 carbons, or $R_8$ is phenyl or lower alkylphenyl, $R_9$ and $R_{10}$ independently are hydrogen, an alkyl group of 1 to 10 carbons, or a cycloalkyl group of 5–10 carbons, or phenyl or lower alkylphenyl, $R_{11}$ is lower alkyl, phenyl or lower alkylphenyl, $R_{12}$ is lower alkyl, and $R_{13}$ is divalent alkyl radical of 2–5 carbons;

$R_4$ is hydrogen, alkyl of 1 to 10 carbons, alkenyl of 2 to 10 carbons and having 1 to 3 double bonds, alkynyl having 2 to 10 carbons and 1 to 3 triple bonds, carbocyclic aryl selected from the group consisting of phenyl, $C_1-C_{10}$-alkylphenyl, naphthyl, $C_1-C_{10}$-alkylnaphthyl, phenyl-$C_1-C_{10}$alkyl, napthyl-$C_1-C_{10}$alkyl, and $R_{15}$ and $R_{16}$ are hydrogen or lower alkyl of 1 to 6 carbons, $R_{17}$ is lower alkyl of 1 to 6 carbons, or $R_{16}$ and $R_{17}$ jointly form a ring having a total of 4 to 5 carbons and the $X_2$ heteroatom;

compounds of Formula 2

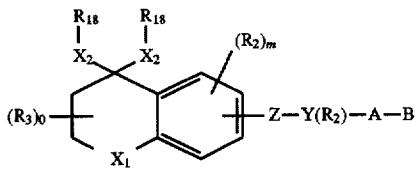

Formula 2 wherein $X_1$ is $[C(R_1)_2]_n$ where $R_1$ is independently H or alkyl of 1 to 6 carbons, and n is an integer between 0 and 2;

$X_2$ is S or O;

Z is $-N=N-$, $-N(O)=N-$, $-N=N(O)-$, $-N=CR_1-$, $-CR_1=N$, $-(CR_1=CR_1)_{n'}-$ where n' is an integer having the value 0–5, $-CO-NR_1-$, $-CS-NR_1-$, $-NR_1-CO$, $-NR_1-CS$, $-COO-$, $-OCO-$; $-CSO-$; $-OCS-$; $-CO-CR_1=CR_1-$;

$R_2$ is hydrogen, lower alkyl of 1 to 6 carbons, F, Cl, Br, I, $CF_3$, fluoro substituted alkyl of 1 to 6 carbons, OH, SH, alkoxy of 1 to 6 carbons, or alkylthio of 1 to 6 carbons;

$R_3$ is hydrogen, lower alkyl of 1 to 6 carbons or F;

m is an integer having the value of 0–3;

o is an integer having the value of 0–4;

Y is a phenyl or naphthyl group, or heteroaryl selected from a group consisting of pyridyl, thienyl, furyl, pyridazinyl, pyrimidinyl, pyrazinyl, thiazolyl, oxazolyl, imidazolyl and pyrrazolyl, said phenyl and heteroaryl groups being optionally substituted with one or two $R_2$ groups, or when Z is $-(CR_1=CR_1)_{n'}-$ and n' is 3, 4 or 5 then Y represents a direct valence bond between said $(CR_2=CR_2)_{n'}$ group and B;

A is $(CH_2)_q$ where q is 0–5, lower branched chain alkyl having 3–6 carbons, cycloalkyl having 3–6 carbons, alkenyl having 2–6 carbons and 1 or 2 double bonds, alkynyl having 2–6 carbons and 1 or 2 triple bonds;

B is hydrogen, COOH or a pharmaceutically acceptable salt thereof, $COOR_8$, $CONR_9R_{10}$, $-CH_2OH$, $CH_2OR_{11}$, $CH_2OCOR_{11}$, CHO, $CH(OR_{12})_2$, $CHOR_{13}O$, $-COR_7$, $CR_7(OR_{12})_2$, $CR_7OR_{13}O$, or $Si(C_{1-6}alkyl)_3$, where $R_7$ is an alkyl, cycloalkyl or alkenyl group containing 1 to 5 carbons, $R_8$ is an alkyl group of 1 to 10 carbons or (trimethylsilyl)alkyl where the alkyl group has 1 to 10 carbons, or a cycloalkyl group of 5 to 10 carbons, or $R_8$ is phenyl or lower alkylphenyl, $R_9$ and $R_{10}$ is independently are hydrogen, an alkyl group of 1 to 10 carbons, or a cycloalkyl group of 5–10 carbons, or phenyl or lower alkylphenyl, $R_{11}$ is lower alkyl, phenyl or lower alkylphenyl, $R_{12}$ is lower alkyl, and $R_{13}$ is divalent alkyl radical of 2–5 carbons, and $R_{18}$ is alkyl of 1 to 10 carbons, fluoro-substituted alkyl of 1 to 10 carbons, or the two $R_{18}$ groups jointly form a ring having a total of 3 to 6 carbons, or the two $X_2R_{18}$ groups jointly symbolize an oxo (=O) or a thio (=S) function, or each of the two $X_2R_{18}$ groups is H;

a compounds of Formula 3

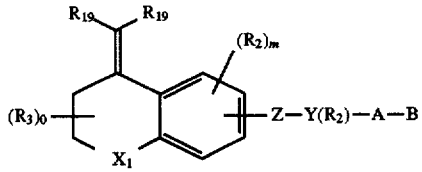

Formula 3 wherein $X_1$ is $[C(R_1)_2]_n$ where $R_1$ is independently H or alkyl of 1 to 6 carbons, and n is an integer between 0 and 2;

Z is $-N=N-$, $-N(O)=N-$, $-N=N(O)-$, $-N=CR_1-$, $-CR_1=N$, $-(CR_1=CR_1)_{n'}$, $-$ where n' is an integer having the value 0–5, $-CO-NR_1-$, $-CS-NR_1-$, $-NR_1-CO$, $-NR_1-CS$, $-COO-$, $-OCO-$; $-CSO-$; $-OCS-$; $-CO-CR_1=CR_1$;

$R_2$ is hydrogen, lower alkyl of 1 to 6 carbons, F, Cl, Br, I, $CF_3$, fluoro substituted alkyl of 1 to 6 carbons, OH, SH, alkoxy of 1 to 6 carbons, or alkylthio of 1 to 6 carbons;

$R_3$ is hydrogen, lower alkyl of 1 to 6 carbons or F;

m is an integer having the value of 0–3;

o is an integer having the value of 0–4;

Y is a phenyl or naphthyl group, or heteroaryl selected from a group consisting of pyridyl, thienyl, furyl, pyridazinyl, pyrimidinyl, pyrazinyl, thiazolyl, oxazolyl, imidazolyl and pyrrazolyl, said phenyl and heteroaryl groups being optionally substituted with one or two $R_2$ groups, or when Z is $-(CR_1=CR_1)_{n'}-$ and n' is 3, 4 or 5 then Y represents a direct valence bond between said $(CR_2=CR_2)_{n'}$ group and B;

A is $(CH_2)_q$ where q is 0–5, lower branched chain alkyl having 3–6 carbons, cycloalkyl having 3–6 carbons, alkenyl having 2–6 carbons and 1 or 2 double bonds, alkynyl having 2–6 carbons and 1 or 2 triple bonds;

B is hydrogen, COOH or a pharmaceutically acceptable salt thereof, $COOR_8$, $CONR_9R_{10}$, $-CH_2OH$, $CH_2OR_{11}$, $CH_2OCOR_{11}$, CHO, $CH(OR_{12})_2$, $CHOR_{13}O$, $-COR_7$, $CR_7(OR_{12})_2$, $CR_7OR_{13}O$, or $Si(C_{1-6}alkyl)_3$, where $R_7$ is an alkyl, cycloalkyl or alkenyl group containing 1 to 5 carbons, $R_8$ is an alkyl group of 1 to 10 carbons or (trimethylsilyl)alkyl where the alkyl group has 1 to 10 carbons, or a cycloalkyl group of 5 to 10 carbons, or $R_8$ is phenyl or lower alkylphenyl, $R_9$ and $R_{10}$ independently are hydrogen, an alkyl group of 1 to 10 carbons, or a cycloalkyl group of 5–10 carbons, or phenyl or lower alkylphenyl, $R_{11}$ is lower alkyl, phenyl or lower alkylphenyl, $R_{12}$ is lower alkyl, and $R_{13}$ is divalent alkyl radical of 2–5 carbons, and $R_{19}$ is independently hydrogen, alkyl of 1 to 10 carbons, fluoro-substituted alkyl of 1 to 10 carbons, alkenyl of 2 to 10 carbons and having 1 to 3 double bonds, alkynyl having 2 to 10 carbons and 1 to 3 triple bonds, carbocyclic aryl selected from the group consisting of phenyl, $C_1-C_{10}$-alkylphenyl, naphthyl, $C_1-C_{10}$alkylnaphthyl, phenyl-$C_1-C_{10}$alkyl, naphthyl-$C_1-C_{10}$alkyl; heteroaryl selected from the group consisting of pyridyl, thienyl, furyl, pyridazinyl, pyrimidinyl, pyrazinyl, thiazolyl, oxazolyl, imidazolyl and pyrrazolyl, said phenyl and heteroaryl groups being optionally substituted with one or two $R_2$ groups, further $R_{19}$ is independently CN, CHO, $CH(OR_{12})_2$, $CHOR_{13}O$, $(CH_2)_pCO_2R_8$, $(CH_2)_pCH_2OH$, $(CH_2)$ $_pCH_2OR_{11}$, $(CH_2)_pCH_2OCOR_{11}$, where p is an integer between 0 to 10, or the two $R_{19}$ groups jointly represent 3 to 8 methylene groups which together with the alkylidene carbon complete a ring, the ring optionally containing 1 to 2 double bonds and the ring being optionally substituted with 1 or 2 $R_2$ groups;

compounds of Formula 4

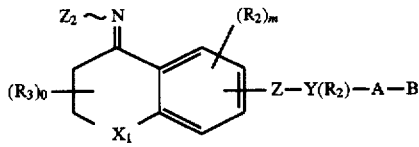

Formula 4 wherein $X_1$ is $[C(R_1)_2]_n$ where $R_1$ is independently H or alkyl of 1 to 6 carbons, and n is an integer between 0 and 2;

Z is $-N=N-$, $-N(O)=N-$, $-N=N(O)-$, $-N=CR_1-$, $-CR_1=N$, $-(CR_1=CR_1)_n$, — where n' is an integer having the value 0–5, $-CO-NR_1-$, $-CS-NR_1-$, $-NR_1-CO$, $-NR_1-CS$, $-COO-$, $-OCO-$; $-CSO-$; $-OCS-$; $-CO-CR_1=CR_1$;

$R_2$ is hydrogen, lower alkyl of 1 to 6 carbons, F, Cl, Br, I, $CF_3$, fluoro substituted alkyl of 1 to 6 carbons, OH, SH, alkoxy of 1 to 6 carbons, or alkylthio of 1 to 6 carbons;

$R_3$ is hydrogen, lower alkyl of 1 to 6 carbons or F;

m is an integer having the value of 0–3;

o is an integer having the value of 0–4;

Y is a phenyl or naphthyl group, or heteroaryl selected from a group consisting of pyridyl, thienyl, furyl, pyridazinyl, pyrimidinyl, pyrazinyl, thiazolyl, oxazolyl, imidazolyl and pyrrazolyl, said phenyl and heteroaryl groups being optionally substituted with one or two $R_2$ groups, or when Z is $-(CR_1=CR_1)_n-$ and n' is 3, 4 or 5 then Y represents a direct valence bond between said $(CR_2=CR_2)_n$ group and B;

A is $(CH_2)_q$ where q is 0–5, lower branched chain alkyl having 3–6 carbons, cycloalkyl having 3–6 carbons, alkenyl having 2–6 carbons and 1 or 2 double bonds, alkynyl having 2–6 carbons and 1 or 2 triple bonds;

B is hydrogen, COOH or a pharmaceutically acceptable salt thereof, $COOR_8$, $CONR_9R_{10}$, $-CH_2OH$, $CH_2OR_{11}$, $CH_2OCOR_{11}$, CHO, $CH(OR_{12})_2$, $CHOR_{13}O$, $-COR_7$, $CR_7(OR_{12})_2$, $CR_7OR_{13}O$, or $Si(C_{1-6}alkyl)_3$, where $R_7$ is an alkyl, cycloalkyl or alkenyl group containing 1 to 5 carbons, $R_8$ is an alkyl group of 1 to 10 carbons or (trimethylsilyl)alkyl where the alkyl group has 1 to 10 carbons, or a cycloalkyl group of 5 to 10 carbons, or $R_8$ is phenyl or lower alkylphenyl, $R_9$ and $R_{10}$ independently are hydrogen, an alkyl group of 1 to 10 carbons, or a cycloalkyl group of 5–10 carbons, or phenyl or lower alkylphenyl, $R_{11}$ is lower alkyl, phenyl or lower alkylphenyl, $R_{12}$ is lower alkyl, and $R_{13}$ is divalent alkyl radical of 2–5 carbons, and $Z_2$ is $OR_1$ or $OR_{18}$ where $R_{18}$ is phenyl, benzyl, lower alkyl or lower alkoxy substituted phenyl, or $Z_2$ is $OSi(R_2)_3$, $OCOR_{14}$, $OC(R_{15})(R_{16})X_2R_{17}$, $N(R_{14})_2$, $NHCON(R_{14})_2$, $NHCSN(R_{14})_2$, where $X_2$ is O or S; $R_{14}$ is hydrogen, alkyl of 1 to 10 carbons, alkenyl of 2 to 10 carbons and having 1 to 3 double bonds, alkynyl having 2 to 10 carbons and 1 to 3 triple bonds, carbocyclic aryl selected from the group consisting of phenyl, $C_1-C_{10}$-alkylphenyl, naphthyl, $C_1-C_{10}$-alkylnaphthyl, phenyl-$C_1-C_{10}$alkyl, naphthyl-$C_1-C_{10}$- alkyl; $R_{15}$ and $R_{16}$ are hydrogen or lower alkyl of 1 to 6 carbons, $R_{17}$ is lower alkyl of 1 to 6 carbons, or $R_{16}$ and $R_{17}$ jointly form a ring having a total of 4 to 5 carbons and the $X_2$ heteroatom;

compounds of Formula 5

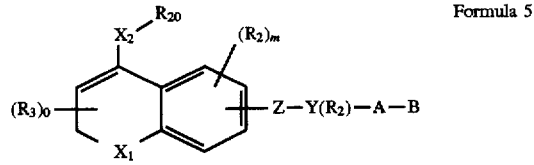

Formula 5 wherein $X_1$ is $[C(R_1)_2]_n$ where $R_1$ is independently H or alkyl of 1 to 6 carbons, and n is an integer between 0 and 2;

Z is $-N=N-$, $-N(O)=N-$, $-N=N(O)-$, $-N=CR_1-$, $-CR_1=N$, $-(CR_1=CR_1)_n$,— where n' is an integer having the value 0–5, $-CO-NR_1-$, $-CS-NR_1-$, $-NR_1-CO$, $-NR_1-CS$, $-COO-$, $-OCO-$; $-CSO-$; $-OCS-$; $-CO-CR_1=CR_1$;

$R_2$ is hydrogen, lower alkyl of 1 to 6 carbons, F, Cl, Br, I, $CF_3$, fluoro substituted alkyl of 1 to 6 carbons, OH, SH, alkoxy of 1 to 6 carbons, or alkylthio of 1 to 6 carbons;

$R_3$ is hydrogen, lower alkyl of 1 to 6 carbons or F;

m is an integer having the value of 0–3;

o is an integer having the value of 0–3;

Y is a phenyl or naphthyl group, or heteroaryl selected from a group consisting of pyridyl, thienyl, furyl, pyridazinyl, pyrimidinyl, pyrazinyl, thiazolyl, oxazolyl, imidazolyl and pyrrazolyl, said phenyl and heteroaryl groups being optionally substituted with one or two $R_2$ groups, or when Z is $-(CR_1=CR_1)_n-$ and n' is 3, 4 or 5 then Y represents a direct valence bond between said $(CR_2=CR_2)_n$ group and B;

A is $(CH_2)_q$ where q is 0–5, lower branched chain alkyl having 3–6 carbons, cycloalkyl having 3–6 carbons, alkenyl having 2–6 carbons and 1 or 2 double bonds, alkynyl having 2–6 carbons and 1 or 2 triple bonds;

B is hydrogen, COOH or a pharmaceutically acceptable salt thereof, $COOR_8$, $CONR_9R_{10}$, $-CH_2OH$, $CH_2OR_{11}$, $CH_2OCOR_{11}$, CHO, $CH(OR_{12})_2$, $CHOR_{13}O$, $-COR_7$, $CR_7(OR_{12})_2$, $CR_7OR_{13}O$, or $Si(C_{1-6}alkyl)_3$, where $R_7$ is an alkyl, cycloalkyl or alkenyl group containing 1 to 5 carbons, $R_8$ is an alkyl group of 1 to 10 carbons or (trimethylsilyl)alkyl where the alkyl group has 1 to 10 carbons, or a cycloalkyl group of 5 to 10 carbons, or $R_8$ is phenyl or lower alkylphenyl, $R_9$ and $R_{10}$ independently are hydrogen, an alkyl group of 1 to 10 carbons, or a cycloalkyl group of 5–10 carbons, or phenyl or lower alkylphenyl, $R_{11}$ is lower alkyl, phenyl or lower alkylphenyl, $R_{12}$ is lower alkyl, and $R_{13}$ is divalent alkyl radical of 2–5 carbons;

$X_2$ is O, S, SO or $SO_2$, and $R_{20}$ is $Si(C_{1-6}alkyl)3$, $R_{14}$, $COR_{14}$, $SO_2R_{21}$, where $R_{14}$ is hydrogen, alkyl of 1 to 10 carbons, alkenyl of 2 to 10 carbons and having 1 to 3 double bond, alkynyl having 2 to 10 carbons and 1 to 3 triple bonds, carbocyclic aryl selected from the group consisting of phenyl, $C_1-C_{10}$-alkylphenyl, naphthyl, $C_1-C_{10}$-alkylnaphthyl, phenyl-$C_1-C_{10}$-alkyl, napthyl-$C_1-C_{10}$-alkyl, or $R_{20}$ is hydroxyalkyl, aminoalkyl or thioalkyl having 1 to 10 carbons; and $R_{21}$ is alkyl of 1 to 10 carbons, fluoroalkyl of 1 to 10 carbons, or carbocyclic aryl selected from the group consisting of phenyl, $C_1$-$C_{10}$-alkylphenyl and phenyl-$C_1$-$C_{10}$-alkyl, and compounds of Formula 6

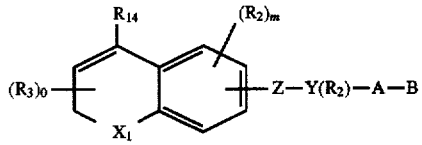

Formula 6 wherein $X_1$ is $[C(R_1)_2]_n$ where $R_1$ is independently H or alkyl of 1 to 6 carbons, and n is an integer between 0 and 2;

Z is —N=N—, —N(O)=N—, —N=N(O)—, —N=CR_1—, —CR_1=N, —(CR_1=CR_1)_{n'}— where n' is an integer having the value 0–5, —CO—NR_1—, —CS—NR_1—, —NR_1—CO, —NR_1—CS, —COO—, —OCO—; —CSO—; —OCS—; —CO—CR_1=CR_1;

$R_2$ is hydrogen, lower alkyl of 1 to 6 carbons, F, Cl, Br, I, $CF_3$, fluoro substituted alkyl of 1 to 6 carbons, OH, SH, alkoxy of 1 to 6 carbons, or alkylthio of 1 to 6 carbons;

$R_3$ is hydrogen, lower alkyl of 1 to 6 carbons or F;

m is an integer having the value of 0–3;

o is an integer having the value of 0–3;

Y is a phenyl or naphthyl group, or heteroaryl selected from a group consisting of pyridyl, thienyl, furyl, pyridazinyl, pyrimidinyl, pyrazinyl, thiazolyl, oxazolyl, imidazolyl and pyrrazolyl, said phenyl and heteroaryl groups being optionally substituted with one or two $R_2$ groups, or when Z is —(CR_1=CR_1)_{n'}— and n' is 3, 4 or 5 then Y represents a direct valence bond between said $(CR_2=CR_2)_{n'}$ group and B;

A is $(CH_2)_q$ where q is 0–5, lower branched chain alkyl having 3–6 carbons, cycloalkyl having 3–6 carbons, alkenyl having 2–6 carbons and 1 or 2 double bonds, alkynyl having 2–6 carbons and 1 or 2 triple bonds;

B is hydrogen, COOH or a pharmaceutically acceptable salt thereof, $COOR_8$, $CONR_9R_{10}$, —$CH_2OH$, $CH_2OR_{11}$, $CH_2OCOR_{11}$, CHO, $CH(OR_{12})_2$, $CHOR_{13}O$, —$COR_7$, $CR_7(OR_{12})_2$, $CR_7OR_{13}O$, or $Si(C_{1-6}alkyl)_3$, where $R_7$ is an alkyl, cycloalkyl or alkenyl group containing 1 to 5 carbons, $R_8$ is an alkyl group of 1 to 10 carbons or (trimethylsilyl)alkyl where the alkyl group has 1 to 10 carbons, or a cycloalkyl group of 5 to 10 carbons, or $R_8$ is phenyl or lower alkylphenyl, $R_9$ and $R_{10}$ independently are hydrogen, an alkyl group of 1 to 10 carbons, or a cycloalkyl group of 5–10 carbons, or phenyl or lower alkylphenyl, $R_{11}$ is lower alkyl, phenyl or lower alkylphenyl, $R_{12}$ is lower alkyl, and $R_{13}$ is divalent alkyl radical of 2–5 carbons, and $R_{14}$ is $(R_{15})_r$-substituted alkyl of 1–6 carbons, $(R_{15})_r$-substituted alkenyl of 1–6 carbons and 1 or 2 double bonds, $(R_{15})_r$-substituted alkynyl of 1–6 carbons and 1 or 2 triple bonds, $(R_{15})_r$-phenyl, $(R_{15})_r$-naphthyl, or $(R_{15})_r$-heteroaryl where the heteroaryl group has 1 to 3 heteroatoms selected from the group consisting of O, S and N. r is an integer having the values of 0–5, and $R_{15}$ is independently H, F, Cl, Br, I, $NO_2$, $N(R_8)_2$, $N(R_8)COR_8$, $NR_8CON(R_8)_2$, OH, $OCOR_8$, $OR_8$, CN, COOH, $COOR_8$ an alkyl group having 1 to 10 carbons, fluoro substituted alkyl group having 1 to 10 carbons, an alkenyl group having 1 to 10 carbons and 1 to 3 double bonds, alkynyl group having 1 to 10 carbons and 1 to 3 triple bonds, or a (trialkyl)silyl or (trialkyl) silyloxy group where the alkyl groups independently have 1 to 6 carbons.

In a second aspect, this invention relates to the use of the compounds of Formula 1 through Formula 6 for the treatment of skin-related diseases, including, without limitation, actinic keratoses, arsenic keratoses, inflammatory and non-inflammatory acne, psoriasis, ichthyoses and other keratinization and hyperproliferative disorders of the skin, eczema, atopic dermatitis, Darriers disease, lichen planus, prevention and reversal of glucocorticoid damage (steroid atrophy), as a topical anti-microbial, as skin anti-pigmentation agents and to treat and reverse the effects of age and photo damage to the skin. The compounds are also useful for the prevention and treatment of cancerous and precancerous conditions, including, premalignant and malignant hyperproliferative diseases such as cancers of the breast, skin, prostate, cervix, uterus, colon, bladder, esophagus, stomach, lung, larynx, oral cavity, blood and lymphatic system, metaplasias, dysplasias, neoplasias, leukoplakias and papillomas of the mucous membranes and in the treatment of Kaposi's sarcoma. In addition, the present compounds can be used as agents to treat diseases of the eye, including, without limitation, proliferative vitreoretinopathy (PVR), retinal detachment, dry eye and other corneopathies, as well as in the treatment and prevention of various cardiovascular diseases, including, without limitation, diseases associated with lipid metabolism such as dyslipidemias, prevention of post-angioplasty restenosis and as an agent to increase the level of circulating tissue plasminogen activator (TPA). Other uses for the compounds of the present invention include the prevention and treatment of conditions and diseases associated with Human papilloma virus (HPV), including warts and genital warts, various inflammatory diseases such as pulmonary fibrosis, ileitis, colitis and Krohn's disease, neurodegenerative diseases such as Alzheimer's a disease, Parkinson's disease and stroke, improper pituitary function, including insufficient production of growth hormone, modulation of apoptosis, including both the induction of apoptosis and inhibition of T-Cell activated apoptosis, restoration of hair growth, including combination therapies with the present compounds and other agents such as Minoxidil$^R$, diseases associated with the immune system, including use of the present compounds as immunosuppressants and immunostimulants, modulation of organ transplant rejection and facilitation of wound healing, including modulation of chelosis.

Alternatively, those compounds of the invention which act as a antagonists of one or more retinoid receptor subtypes are useful to prevent certain undesired side effects of retinoids which are administered for the treatment or prevention of certain diseases or conditions. For this purpose the retinoid antagonist compounds of the invention may be co-administered with retinoids. The compounds of the present invention are also useful in the treatment of acute or chronic toxicity resulting from overdose or poisoning by retinoid drugs or Vitamin A.

This invention also relates to a pharmaceutical formulation comprising a compound of Formula 1 through Formula 6 in admixture with a pharmaceutically acceptable excipient, said formulation being adapted for administration to a mammal, including a human being, to treat or alleviate the conditions which were described above as treatable by retinoids, to be co-administered with retinoids to eliminate or reduce side effects of retinoids, or to treat retinoid or Vitamin A overdose or poisoning.

BIOLOGICAL ACTIVITY, MODES OF ADMINISTRATION

ASSAY OF RETINOID-LIKE OR RETINOID ANTAGONIST-LIKE BIOLOGICAL ACTIVITY

A classic measure of retinoic acid activity involves measuring the effects of retinoic acid on ornithine decarboxylase. The original work on the correlation between retinoic acid and decrease in cell proliferation was done by Verma & Boutwell, Cancer Research, 1977, 37.2196–2201. That reference discloses that ornithine decarboxylase (ODC) activity increased precedent to polyamine biosynthesis. It has been established elsewhere that increases in polyamine synthesis can be correlated or associated with cellular proliferation. Thus, if ODC activity could be inhibited, cell hyperproliferation could be modulated. Although all cases for ODC activity increases are unknown, it is known that 12-O-tetradecanoylphorbol-13-acetate (TPA) induces ODC activity. Retinoic acid inhibits this induction of ODC activity by TPA. An assay essentially following the procedure set out in Cancer Research: 1662–1670,1975 may be used to demonstrate inhibition of TPA induction of ODC by compounds of this invention. Activity of exemplary compounds of the present invention in the above-described ODC assay is disclosed in Table 1 which provides the $IC_{60}$ concentration for the respective exemplary compound. ("$IC_{60}$" is that concentration of the test compound which causes 60% inhibition in the ODC assay. By analogy, $IC_{80}$, for example, is that concentration of the test compound which causes 80% inhibition in the ODC assay.)

TABLE 1

ODC Assay

| Compound No. | $IC_{60}$ (nmols) |
|---|---|
| A5 | 10.3 |
| D3 | 8.4 |
| C22b | 10 |
| E24 | 8.3 |
| A16 | 4.3 ($IC_{80}$) |
| C14 | 4 |
| E79 | 5.3 |
| D34 | 4.3 ($IC_{80}$) |
| C15 | 14.5 |
| E15 | 24.7 |
| A27 | 0.7 |
| E16 | 88.4 |
| A23 | 43.7 |
| A2 | 27 |
| E72b | 18 |
| E56a | 3.1 |
| D6 | 1.9 |

Other assays described below, measure the ability of the compounds of the present invention to bind to, and/or activate various retinoid receptor subtypes. When in these assays a compound binds to a given receptor subtype and activates the transcription of a reporter gene through that subtype, then the compound is considered an agonist of that receptor subtype. Conversely, a compound is considered an antagonist of a given receptor subtype if in the below described co-tranfection assays the compound does not cause significant transcriptional activation of the receptor regulated reporter gene, but nevertheless binds to the receptor with a $K_a$ value of less than approximately 1 micromolar. In the below described assays the ability of the compounds to bind to $RAR_\alpha$, $RAR_\beta$, $RAR_\gamma$, $RXR_\alpha$, $RXR_\beta$ and RXRreceptors, and the ability or inability of the compounds to activate transcription of a reporter gene through these receptor subtypes can be tested.

Specifically, a chimeric receptor transactivation assay which tests for agonist-like activity in the $RAR_\alpha$, $RAR_\beta$, $RAR_\gamma$, $RXR_\alpha$ receptor subtypes, and which is based on work published by Feigner P. L. and Holm M. (1989) Focus, 11 2 is described in detail in U.S. Pat. No. 5,455,265 the specification of which is hereby expressly incorporated by reference.

A holoreceptor transactivation assay and a ligand binding assay which measure the antagonist/agonist like activity of the compounds of the invention, or their ability to bind to the several retinoid receptor subtypes, respectively, are described in published PCT Application No. WO W093/11755 (particularly on pages 30–33 and 37–41) published on Jun. 24, 1993, the specification of which is also incorporated herein by reference. A description of the holoreceptor transactivation assay is also provided below.

HOLORECEPTOR TRANSACTIVATION ASSAY

CV1 cells (5,000 cells/well) were transfected with an RAR reporter plasmid MTV-TREp-LUC (50 ng) along with one of the RAR expression vectors (10 ng) in an automated 96-well format by the calcium phosphate procedure of Heyman et al. Cell 68, 397–406, (1992). For $RXR_\alpha$ and $RXR_\gamma$ transactivation assays, an RXR-responsive reporter plasmid CRBPII-tk-LUC (50 ng) along with the appropriate RXR expression vectors (10 ng) was used substantially as described by Heyman et al. above, and Allegretto et al. J. Biol. Chem. 268, 26625–26633. For $RXR_\beta$ transactivation assays, an RXR-responsive reporter plasmid CPRE-tk-LUC (50 mg) along with $RXR_\beta$ expression vector (10 mg) was used as described in above. These reporters contain DRI elements from human CRBPII and certain DRI elements from promoter, respectively. (see Mangelsdorf et al. The Retinoids: Biology, Chemistry and Medicine, pp 319–349, Raven Press Ltd., New York and Heyman et al., cited above) (1, 8). A β-galactosidase (50 ng) expression vector was used as an internal control in the transfections to normalize for variations in transfection efficiency. The cells were transfected in triplicate for 6 hours, followed by incubation with retinoids for 36 hours, and the extracts were assayed for luciferase and β-galactosidase activities. The detailed experimental procedure for holoreceptor transactivations has been described in Heyman et al. above, and Allegretto et al. cited above. The results obtained in this assay are expressed in $EC_{50}$ numbers, as they are also in the chimeric receptor transactivation assay. The Heyman et al. Cell 68, 397–406, Allegretto et al. J. Biol. Chem. 268, 26625–26633, and Mangelsdorf et al. The Retinoids: Biology, Chemistry and Medicine, pp 319–349, Raven Press Ltd., New York, are expressly incorporated herein by reference. The results of ligand binding assay are expressed in $K_d$ numbers. (See Cheng et al. Biochemical Pharmacology Vol. 22 pp 3099–3108, expressly incorporated herein by reference.)

Table 2 shows the results of the ligand binding assay for certain exemplary compounds of the invention for the receptor subtypes in the RAR group.

TABLE 2

| Compound No. | Ligand Binding Assay $K_d$ (nanomolar, nM) | | |
|---|---|---|---|
| | $RAR\alpha$ | $RAR\beta$ | $RAR\gamma$ |
| A6 | 125 | 36 | 127 |
| D4 | 1000 | 132 | 363 |
| C25 | 19 | 12 | 42 |
| E27 | 551 | 535 | >1000 |
| A18 | 538 | 193 | 162 |
| E80 | 394 | 531 | 901 |
| D34 | 235 | 200 | 530 |

TABLE 2-continued

Ligand Binding Assay

| Compound No. | $K_d$ (nanomolar, nM) | | |
|---|---|---|---|
| | RARα | RARβ | RARγ |
| E14 | 36 | 35 | 455 |
| A28 | 4 | 3 | 42 |
| E17 | 192 | 378 | >1000 |
| A24 | 283 | 92 | 259 |
| A2a | 150 | 219 | 421 |
| E67 | 77 | 302 | 375 |
| D7 | >1000 | 226 | >1000 |

Modes of Administration

The compounds of this invention may be administered systemically or topically, depending on such considerations as the condition to be treated, need for site-specific treatment, quantity of drug to be administered, and numerous other considerations.

In the treatment of dermatoses, it will generally be preferred to administer the drug topically, though in certain cases such as treatment of severe cystic acne or psoriasis, oral administration may also be used. Any common topical formulation such as a solution, suspension, gel, ointment, or salve and the like may be used. Preparation of such topical formulations are well described in the art of pharmaceutical formulations as exemplified, for example, by Remington's Pharmaceutical Science, Edition 17, Mack Publishing Company, Easton, Penn. For topical application, these compounds could also be administered as a powder or spray, particularly in aerosol form. If the drug is to be administered systemically, it may be confected as a powder, pill, tablet or the like or as a syrup or elixir suitable for oral administration. For intravenous or intraperitoneal administration, the compound will be prepared as a solution or suspension capable of being administered by injection. In certain cases, it may be useful to formulate these compounds by injection. In certain cases, it may be useful to formulate these compounds in suppository form or as extended release formulation for deposit under the skin or intramuscular injection.

Other medicaments can be added to such topical formulation for such secondary purposes as treating skin dryness; providing protection against light; other medications for treating dermatoses; medicaments for preventing infection, reducing irritation, inflammation and the like.

Treatment of dermatoses or any other indications known or discovered to be susceptible to treatment by retinoic acid-like compounds will be effected by administration of the therapeutically effective dose of one or more compounds of the instant invention. A therapeutic concentration will be that concentration which effects reduction of the particular condition, or retards it expansion. In certain instances, the compound potentially may be used in prophylactic manner to prevent onset of a particular condition.

A useful therapeutic or prophylactic concentration will vary from condition to condition and in certain instances may vary with the severity of the condition being treated and the patient's susceptibility to treatment. Accordingly, no single concentration will be uniformly useful, but will require modification depending on the particularities of the disease being treated. Such concentrations can be arrived at through routine experimentation. However, it is anticipated that in the treatment of, for example, acne, or similar dermatoses, that a formulation containing between 0.01 and 1.0 milligrams per milliliter of formulation will constitute a therapeutically effective concentration for total application. If administered systemically, an amount between 0.01 and 5 mg per kg per day of body weight would be expected to effect a therapeutic result in the treatment of many diseases for which these compounds are useful.

Those partial or pan retinoid antagonist compounds of the invention, when used to take advantage of their antagonist property, can be co-administered to mammals, including humans, with retinoid agonists and, by means of pharmacological selectivity or site-specific delivery, preferentially prevent the undesired effects of certain retinoid agonists. The antagonist compounds of the invention can also be used to treat Vitamin A overdose, acute or chronic, resulting either from the excessive intake of vitamin A supplements or from the ingestion of liver of certain fish and animals that contain high levels of Vitamin A. Still further, the antagonist compounds of the invention can also be used to treat acute or chronic toxicity caused by retinoid drugs. It has been known in the art that the toxicities observed with hypervitaminosis A syndrome (headache, skin peeling, bone toxicity, dyslipidemias) are similar or identical with toxicities observed with other retinoids, suggesting a common biological cause, that is RAR activation. Because the antagonist compounds of the present invention block RAR activation, they are suitable for treating the foregoing toxicities.

Generally speaking, for therapeutic applications in mammals, the antagonist compounds of the invention can be administered enterally or topically as an antidote to vitamin A, or antidote to retinoid toxicity resulting from overdose or prolonged exposure, after intake of the causative factor (vitamin A, vitamin A precursor, or other retinoid) has been discontinued. Alternatively, the antagonist compounds of the invention are co-administered with retinoid drugs, in situations where the retinoid provides a therapeutic benefit, and where the co-administered antagonist compound alleviates or eliminates one or more undesired side effects of the retinoid. For this type of application the antagonist compound may be administered in a site-specific manner, for example as a topically applied cream or lotion while the co-administered retinoid may be given enterally. For therapeutic applications the antagonist compounds of the invention, like the retinoid agonists compounds, are incorporated into pharmaceutical compositions, such as tablets, pills, capsules, solutions, suspensions, creams, ointments, gels, salves, lotions and the like, using such pharmaceutically acceptable excipients and vehicles which per se are well known in the art. For topical application, the antagonist compounds of the invention could also be administered as a powder or spray, particularly in aerosol form. If the drug is to be administered systemically, it may be confected as a powder, pill, tablet or the like or as a syrup or elixir suitable for oral administration. For intravenous or intraperitoneal administration, the compound will be prepared as a solution or suspension capable of being administered by injection. In certain cases, it may be useful to formulate these compounds by injection. In certain cases, it may be useful to formulate these compounds in suppository form or as extended release formulation for deposit under the skin or intramuscular injection.

The antagonist compounds also, like the retinoid agonists of the invention, will be administered in a therapeutically effective dose. A therapeutic concentration will be that concentration which effects reduction of the particular condition, or retards its expansion. When co-administering the compounds of the invention to block retinoid-induced toxicity or side effects, the antagonist compounds of the invention are used in a prophylactic manner to prevent onset of a particular condition, such as skin irritation.

A useful therapeutic or prophylactic concentration will vary from condition to condition and in certain instances may vary with the severity of the condition being treated and the patient's susceptibility to treatment. Accordingly, no single concentration will be uniformly useful, but will require modification depending on the particularities of the chronic or acute retinoid toxicity or related condition being treated. Such concentrations can be arrived at through routine experimentation. However, it is anticipated that a formulation containing between 0.01 and 1.0 milligrams per milliliter of formulation will constitute a therapeutically effective concentration for total application. If administered systemically, an amount between 0.01 and 5 mg per kg per day of body weight would be expected to effect a therapeutic result.

GENERAL EMBODIMENTS AND SYNTHETIC METHODOLOGY

Definitions

The term alkyl refers to and covers any and all groups which are known as normal alkyl, branched-chain alkyl and cycloalkyl. The term alkenyl refers to and covers normal alkenyl, branch chain alkenyl and cycloalkenyl groups having one or more sites of unsaturation. Similarly, the term alkynyl refers to and covers normal alkynyl, and branch chain alkynyl groups having one or more triple bonds.

Lower alkyl means the above-defined broad definition of alkyl groups having 1 to 6 carbons in case of normal lower alkyl, and as applicable 3 to 6 carbons for lower branch chained and cycloalkyl groups. Lower alkenyl is defined similarly having 2 to 6 carbons for normal lower alkenyl groups, and 3 to 6 carbons for branch chained and cyclo- lower alkenyl groups. Lower alkynyl is also defined similarly, having 2 to 6 carbons for normal lower alkynyl groups, and 4 to 6 carbons for branch chained lower alkynyl groups.

The term "ester" as used here refers to and covers any compound falling within the definition of that term as classically used in organic chemistry. It includes organic and inorganic esters. Where B (of Formula 1 through 6) is —COOH, this term covers the products derived from treatment of this function with alcohols or thiols preferably with aliphatic alcohols having 1–6 carbons. Where the ester is derived from compounds where B is —CH$_2$OH, this term covers compounds derived from organic acids capable of forming esters including phosphorous based and sulfur based acids, or compounds of the formula —CH$_2$OCOR$_{11}$ where R$_{11}$ is any substituted or unsubstituted aliphatic, aromatic, heteroaromatic or aliphatic aromatic group, preferably with 1–6 carbons in the aliphatic portions.

Unless stated otherwise in this application, preferred esters are derived from the saturated aliphatic alcohols or acids of ten or fewer a carbon atoms or the cyclic or saturated aliphatic cyclic alcohols and acids of 5 to 10 carbon atoms. Particularly preferred aliphatic esters are those derived from lower alkyl acids and alcohols. Also preferred are the phenyl or lower alkyl phenyl esters.

Amides has the meaning classically accorded that term in organic chemistry. In this instance it includes the unsubstituted amides and all aliphatic and aromatic mono- and di-substituted amides. Unless stated otherwise in this application, preferred amides are the mono- and di-substituted amides derived from the saturated aliphatic radicals of ten or fewer carbon atoms or the cyclic or saturated aliphatic-cyclic radicals of 5 to 10 carbon atoms. Particularly preferred amides are those derived from substituted and unsubstituted lower alkyl amines. Also is preferred are mono- and disubstituted amides derived from the substituted and unsubstituted phenyl or lower alkylphenyl amines. Unsubstituted amides are also preferred.

Acetals and ketals include the radicals of the formula -CK where K is (—OR)$_2$. Here, R is lower alkyl. Also, K may be —OR$_7$O— where R$_7$ is lower alkyl of 2–5 carbon atoms, straight chain or branched.

A pharmaceutically acceptable salt may be prepared for any compounds in this invention having a functionality capable of forming a salt, for example an acid functionality. A pharmaceutically acceptable salt is any salt which retains the activity of the parent compound and does not impart any deleterious or untoward effect on the subject to which it is administered and in the context in which it is administered.

Pharmaceutically acceptable salts may be derived from organic or inorganic bases. The salt may be a mono or polyvalent ion. Of particular interest are the inorganic ions, sodium, potassium, calcium, and magnesium. Organic salts may be made with amines, particularly ammonium salts such as mono-, di- and trialkyl amines or ethanol amines. Salts may also be formed with caffeine, tromethamine and similar molecules. Where there is a nitrogen sufficiently basic as to be capable of forming acid addition salts, such may be formed with any inorganic or organic acids or alkylating agent such as methyl iodide. Preferred salts are those formed with inorganic acids such as hydrochloric acid, sulfuric acid or phosphoric acid. Any of a number of simple organic acids such as mono-, di- or tri-acid may also be used.

Some of the compounds of the present invention may have trans and cis (E and Z) isomers. In addition, the compounds of the present invention may contain one or more chiral centers and therefore may exist in enantiomeric and diastereomeric forms. Still further oxime and related compounds of the present invention may exist in syn and anti isomeric forms. The scope of the present invention is intended to cover all such isomers per se, as well as mixtures of cis and trans isomers, mixtures of syn and anti isomers, mixtures of diastereomers and racemic mixtures of enantiomers (optical isomers) as well. In the present application when no specific mention is made of the configuration (cis, trans, syn or anti or R or S) of a compound (or of an asymmetric carbon) then a mixture of such isomers, or either one of the isomers is intended. In a similar vein, when in the chemical structural formulas of this application a straight line representing a valence bond is drawn to an asymmetric carbon, then isomers of both R and S configuration, as well as their mixtures are intended. Defined stereochemistry about an asymmetric carbon is indicated in the formulas (where applicable) by a solid triangle showing β configuration, or by a hashed line showing α configuration.

Referring now to the nomenclature used in naming the compounds of the invention and intermediate compounds leading thereto, the system for numbering the tetrahydronaphthalene ring is demonstrated as shown by the structural formulas of Compounds F, G and A2. Compound A2 is an exemplary compound of the invention within the scope of Formula 2 and Compounds F and G are two exemplary intermediates utilized in the synthesis of the compounds of the invention. The numbering systems illustrated here corresponds substantially to IUPAC rules, and will be readily apparent to those skilled in the art as it is applied in the ensuing description.

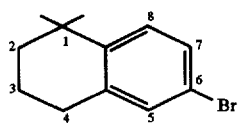

Compound F

-continued

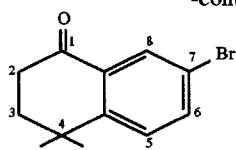

Compound G

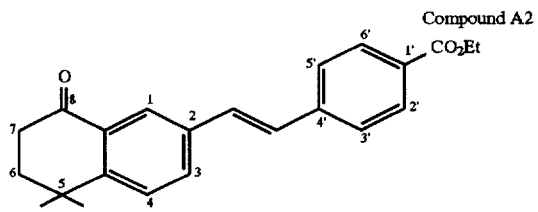

Compound A2

Generally speaking, the compounds of the invention are made in synthetic steps which involve the formation of the tetrahydronaphthalene, dihydronaphthalene, indane or suberane moiety, substituted with the desired $R_1$, $R_2$ and $R_3$ groups and with a reactive group, such as bromo group, that allows coupling with a reagent that introduces the —Z—Y($R_2$)—A—B group. Such a reagent can be generally described as $X_3$—Z—Y($R_2$)—A—B where $X_3$ is a reactive group, in many instances a leaving group, such as halogen. The —Z—Y($R_2$)—A—B group may also be formed in a series of reactions performed starting with the tetrahydronaphthalene, dihydronaphthalene, indane or suberane molecule that has the appropriate reactive group or reactive position in the aromatic nucleus.

The substituent or substituents in the 5 or 8 positions of the tetrahydronaphthalene or dihydronaphthalene (and by analogy in the corresponding positions of indane and suberan) which are designated as $R_4$ and $X_2R_5$ in Formula 1, as $(X_2R_{18})_2$ in Formula 2, $=C(R_{19})_2$ in Formula 3, $N=Z_2$ in Formula 4, $X_2R_{20}$ in Formula 5 and $R_{14}$ in Formula 6 may be introduced into the tetrahydronaphthalene or dihydronaphthalene ring moiety before coupling with the reagent $X_3$—Z—Y($R_2$)—A—B, or before formation of the —Z—Y($R_2$)—A—B group. In other examples coupling with the reagent $X_3$—Z—Y($R_2$)—A—B or formation of the —Z—Y($R_2$)—A—B group attached to the tetrahydronaphthalene or dihydronaphthalene nucleus is performed first to yield an intermediate that includes the tetrahydronaphthalene, dihydronaphthalene (and by analogy indane or suberane) moiety covalently linked to the —Z—Y($R_2$)—A—B B group, but which has a reactive group, preferably such as an oxo or trifluoromethanesulfonyloxy function, in the 5 or 8 position. In these cases the substituents of these two positions, as defined in Formulas 1–6, are introduced into the intermediate by appropriate reactions which are described in detail below.

The synthetic methodology employed for the synthesis of the compounds of the present invention may also include transformations of the group designated as —A—B in Formulas 1–6. Generally speaking these transformations involve reactions well within the skill of the practicing organic chemist. In this regard the following well known and published general principles and synthetic methodology are briefly described.

Carboxylic acids are typically esterified by refluxing the acid in a solution of the appropriate alcohol in the presence of an acid catalyst such as hydrogen chloride or thionyl chloride. Alternatively, the carboxylic acid can be condensed with the appropriate alcohol in the presence of dicyclohexylcarbodiimide and dimethylaminopyridine. The ester is recovered and purified by conventional means. Acetals and ketals are readily made by the method described in March, "Advanced Organic Chemistry," 2nd Edition, McGraw-Hill Book Company, p 810). Alcohols, aldehydes and ketones all may be protected by forming respectively, ethers and esters, acetals or ketals by known methods such as those described in McOmie, Plenum Publishing Press, 1973 and Protecting Groups, Ed. Greene, John Wiley & Sons, 1981.

To increase the value of n in the compounds of $X_3$—Z—Y($R_2$)—A—B or precursors thereof, before affecting the coupling or linkage with the tetrahydronaphthalene, dihydronaphthalene nucleus (where such compounds are not available from a commercial source) aromatic or heteroaromatic carboxylic acids are subjected to homologation by successive treatment under Arndt-Eistert conditions or other homologation procedures. Alternatively, derivatives which are not carboxylic acids may also be homologated by appropriate procedures. The homologated acids can then be esterified by the general procedure a outlined in the preceding paragraph.

Compounds of formula $X_3$—Z—Y($R_2$)—A—B (or of the invention s as set forth in Formulas 1 through 6, as applicable) where A is an alkenyl group having one or more double bonds can be made for example, by synthetic schemes well known to the practicing organic chemist; for example by Wittig and like reactions, or by introduction of a double bond by elimination of halogen from an alpha-halo-arylalkyl-carboxylic acid, ester or like carboxaldehyde. Compounds of formula $X_3$—Z—Y($R_2$)—A—B (or of the invention as set forth in Formulas 1 through 6, as applicable) where the A group has a triple (acetylenic) bond can be made by reaction of a corresponding aromatic methyl ketone with strong base, such as lithium diisopropyl amide, reaction with diethyl chlorophosphate and subsequent addition of lithium diisopropylamide.

The acids and salts derived from compounds of the invention are readily obtainable from the corresponding esters. Basic saponification with an alkali metal base will provide the acid. For example, an ester of the invention may be dissolved in a polar solvent such as an alkanol, preferably under an inert atmosphere at room temperature, with about a three molar excess of base, for example, lithium hydroxide or potassium hydroxide. The solution is stirred for an extended period of time, between 15 and 20 hours, cooled, acidified and the hydrolysate recovered by conventional means.

The amide may be formed by any appropriate amidation means known in the art from the corresponding esters or carboxylic acids. One way to prepare such compounds is to convert an acid to an acid chloride and then treat that compound with ammonium hydroxide or an appropriate amine. For example, the ester is treated with an alcoholic base solution such as ethanolic KOH (in approximately a 10% molar excess) at room temperature for about 30 minutes. The solvent is removed and the residue taken up in an organic solvent such as diethyl ether, treated with a dialkyl formamide and then a 10-fold excess of oxalyl chloride. This is all effected at a moderately reduced temperature between about −10 degrees and +10 degrees C. The last mentioned solution is then stirred at the reduced temperature for 1–4 hours, preferably 2 hours. Solvent removal provides a residue which is taken up in an inert organic solvent such as benzene, cooled to about 0 degrees C. and treated with concentrated ammonium hydroxide. The resulting mixture is stirred at a reduced temperature for 1–4 hours. The product is recovered by conventional means.

Alcohols are made by converting the corresponding acids to the acid chloride with thionyl chloride or other means (J. March, "Advanced Organic Chemistry", 2nd Edition, McGraw-Hill Book Company), then reducing the acid chloride with sodium borohydride (March, Ibid, pg. 1124), which gives the corresponding alcohols. Alternatively, esters may be reduced with lithium aluminum hydride at reduced temperatures. Alkylating these alcohols with appropriate alkyl halides under Williamson reaction conditions (March, Ibid, pg. 357) gives the corresponding ethers. These alcohols can be converted to esters by reacting them with appropriate acids in the presence of acid catalysts or dicyclohexylcarbodiimide and dimethylaminopyridine.

Aldehydes can be prepared from the corresponding primary alcohols using mild oxidizing agents such as pyridinium dichromate in methylene chloride (Corey, E. J., Schmidt, G., Tet. Lett., 399, 1979), or dimethyl sulfoxide/oxalyl chloride in methylene chloride (Omura, K., Swern, D., Tetrahedron, 1978, 34, 1651).

Ketones can be prepared from an appropriate aldehyde by treating the aldehyde with an alkyl Grignard reagent or similar reagent followed by oxidation.

Acetals or ketals can be prepared from the corresponding aldehyde or ketone by the method described in March, Ibid, p 810.

Reagents of formula $X_3$—Z—Y($R_2$)—A—B (or compounds of the invention as set forth in Formulas 1 through 6, as applicable) where B is H can be prepared from the corresponding halogenated aromatic or heteroaromatic compounds, preferably where the halogen is I.

SPECIFIC EMBODIMENTS

With reference to the symbol Y in Formulas 1 through 6, the preferred compounds of the invention are those where Y is phenyl, naphthyl, pyridyl, thienyl or furyl. Even more preferred are compounds where Y is phenyl, naphthyl or pyridyl. As far as substitutions on the Y (phenyl), Y (pyridyl) and (Y) naphthyl groups are concerned, compounds are preferred where the phenyl group is 1,4 (para) substituted, the naphthyl group is 2,6 substituted and where the pyridine ring is 2,5 substituted. (Substitution in the 2,5 positions in the "pyridine" nomenclature corresponds to substitution in the 6-position in the "nicotinic acid" nomenclature.) In the preferred compounds of the invention there is no optional $R_2$ substituent on the Y group.

The A—B group of the preferred compounds is $(CH_2)_n$, —COOH or $(CH_2)_n$—$COOR_8$, where $R_8$ is defined as above. Even more preferably n is zero and $R_8$ is lower alkyl.

Referring still to the preferred compounds of Formulas 1 through 6, the $X_1$ group is preferably $C(R_1)_2$, that is the preferred compounds are tetrahydronaphthalene or dihydronaphthalene derivatives. The aromatic portion of the tetrahydronaphthalene or dihydronaphthalene moiety is preferably substituted only by the —Z—Y($R_2$)—A—B group. In other words, in the preferred compounds there is no $R_2$ substituent (other than hydrogen). Similarly, in the preferred compounds of the invention there is no $R_3$ substituent (other than hydrogen). The $R_1$ substituent of the compounds of the invention is preferably lower alkyl, and even more preferably methyl.

Preferred Z groups are:

—$(CR_1\!=\!CR_1)_{n'}$— where n' is 0, 1, or 3 (when n' is 3 then Y represents a direct valence bond between the —$(CR_1\!=\!CR_1)_{n'}$— group and the —A—B group),

—N=N—,

—CO—$CR_1\!=\!CR_1$—,

—COO—, and

—CONH—.

Referring now specifically to compounds in accordance with Formula 1, compounds in these series are preferred where $X_2$ is O, the $R_4$ group is H, lower alkyl, or $CH_2COOR_8$, and $R_5$ is H, $Si(C_{1-6}alkyl)_3$, $COR_{14}$, $C(R_{15})(R_{16})X_2R_{17}$. $COCH_3$ for $COR_{14}$, and $CH_2OCH_3$ and 2-(1-tetrahydropyranyl) for the $C(R_{15})(R_{16})X_2R_{17}$ group are particularly preferred.

The most preferred compounds in accordance with Formula 1 are listed below in the Table for Formula 1A and with reference to that formula.

TABLE For Formula 1A

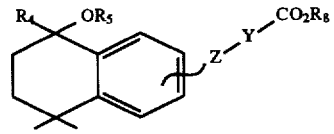

Formula 1A

| Compound No. | $R_4$ | $R_5$ | Z | Y | $R_8$ | Configuration, When Applicable and or position of substituent Z |
|---|---|---|---|---|---|---|
| A-32 | $CH_2COOEt$ | H | CH=CH | $1,4\text{-}C_6H_4$—[1] | Et | 2 |
| B-3 | H | t-butyl dimethyl silyl | — | $2,6\text{-}C_{10}H_6$[2] | Et | 2 |
| B-4 | H | H | — | $2,6\text{-}C_{10}H_6$[2] | Et | 2 |
| B-5 | H | H | — | $2,6\text{-}C_{10}\text{-}H_6$[2] | H | 2 |
| B-8 | H | $CH_2OCH_3$ | — | $2,6\text{-}C_{10}H_6$[2] | Et | 2 |
| B-9 | H | $CH_2OCH_3$ | — | $2,6\text{-}C_{10}H_6$[2] | H | 2 |
| B-10 | H | $COCH_3$ | — | $2,6\text{-}C_{10}H_6$ | Et | 2 |
| C-13 | H | H | polyene[4] | — | Et | 2 |
| C-19 | H | H | polyene[4] | — | H | 2 |
| C-26 | H | $CH_2OCH_3$ | polyene[4] | — | Et | 2 |
| C-27 | H | $CH_2OCH_3$ | polyene[4] | — | H | 2 |
| C-29 | H | THP[3] | polyene[4] | — | Et | 2 |
| C-31 | H | THP[3] | polyene[4] | — | H | 2 |
| D-1 | $CH_2COOEt$ | H | —N=N— | $1,4\text{-}C_6H_4$[1] | Et | 2 |
| D-5 | H | H | —N=N— | $1,4\text{-}C_6H_4$[1] | Et | 2 |

TABLE For Formula 1A

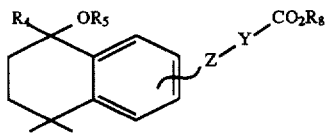

Formula 1A

| Compound No. | $R_4$ | $R_5$ | Z | Y | $R_8$ | Configuration, When Applicable and or position of substituent Z |
|---|---|---|---|---|---|---|
| D-6 | H | $CH_2OCH_3$ | $-N=N-$ | $1,4-C_6H_4{}^1$ | Et | 2 |
| D-7 | H | $CH_2OCH_3$ | $-N=N-$ | $1,4-C_6H_4{}^1$ | H | 2 |
| D-27 | H | $CH_2OCH_3$ | $CO-CH=CH-$ | $1,4-C_6H_4{}^1$ | H | 3 |
| E-32 | H | H | $CO-NH$ | $1,4-C_6H_4{}^1$ | Et | 2 |
| E-33 | H | H | $-CO-NH-$ | $1,4-C_6H_4{}^1$ | H | 2 |
| E-34 | H | $CH_2OCH_3$ | $-CO-NH-$ | $1,4-C_6H_4{}^1$ | Et | 2 |
| E-35 | H | $CH_2OCH_3$ | $-CO-NH$ | $1,4-C_6H_4{}^1$ | H | 2 |
| E-37 | H | H | $-CO-O-$ | $1,4-C_6H_4{}^1$ | $(CH_2)_2Si(CH_3)_3$ | 2 |
| E-38 | H | $CH_2OCH_3$ | $-CO-O-$ | $1,4-C_6H_4{}^1$ | $(CH_2)_2Si(CH_3)_3$ | 2 |
| E-39 | H | $CH_2OCH_3$ | $-CO-O-$ | $1,4-C_6H_4{}^1$ | H | 2 |
| E-40 | H | H | $-CO-O-$ | $1,4-C_6H_4{}^1$ | Et | 2 |
| E-41 | H | $CH_2OCH_3$ | $-CO-O-$ | $1,4-C_6H_4{}^1$ | Et | 2 |
| E-49 | $CH_2COOEt$ | $COCH_3$ | $-CO-NH-$ | $1,4-C_6H_4{}^1$ | Et | 2 |
| E-54 | $CH_2COOEt$ | H | $-CO-O-$ | $1,4-C_6H_4{}^1$ | Et | 2 |
| B-56 | H | $THP^3$ | $-CO-O-$ | $1,4-C_6H_4{}^1$ | Et | 2 |
| E-60 | H | $THP^3$ | $-CO-O-$ | $1,4-C_6H_4{}^1$ | Benzyl | 2 |
| E-64 | H | $THP^3$ | $-CO-O-$ | $1,4-C_6H_4{}^1$ | H | 2 |
| E-65 | H | $THP^3$ | $-CO-O-$ | $1,4-C_6H_4{}^1$ | H | 2 |
| E-66 | H | $THP^3$ | $-CO-O-$ | $1,4-C_6H_4{}^1$ | H | 2 |
| E-67 | H | $THP^3$ | $-CO-O-$ | $1,4-C_6H_4{}^1$ | H | 2 |
| E-70 | H | $THP^3$ | $-CO-NH-$ | $1,4-C_6H_4{}^1$ | Et | 2 |
| E-72 | H | $THP^3$ | $-CO-NH$ | $1,4-C_6H_4{}^1$ | Et | 2 |
| E-74 | H | $THP^3$ | $-CO-NH$ | $1,4-C_6H_4{}^1$ | H | 2 |
| E-75 | H | $THP^3$ | $-CO-NH$ | $1,4-C_6H_4{}^1$ | H | 2 |
| E-76 | H | $THP^3$ | $-CO-NH$ | $1,4-C_6H_4{}^1$ | H | 2 |
| E-77 | H | $THP^3$ | $-CO-NH$ | $1,4-C_6H_4{}^1$ | H | 2 |
| E-82 | H | H | $-CO-O-$ | $1,4-C_6H_4{}^1$ | Benzyl | 2 |

[1] $1,4-C_6H_4$ stands for 1,4-substituted phenyl
[2] $2,6-C_{10}H_6$ stands for 2,6-substituted naphthalene
[3] THP stands for 2-(1-tetrahydropyranyl).
[4] polyene stands for $-C(CH_3)=CH-CH=CH-(CH_3)=CH-$ Referring now to compounds in accordance with Formula 2, compounds in these series are preferred where the two $X_2R_{18}$ jointly symbolize an oxo (=O) group, or where the two $X_2R_{18}$ groups each symbolize an S-alkyl group, or where the two $X_2R_{18}$ groups jointly symbolize two sulphur atoms connected with a alkyledene bridge as in a cyclic thioketal function.

The most preferred compounds in accordance with Formula 2 are listed below in the Table for Formula 2A and with reference to that formula.

TABLE FOR FORMULA 2A

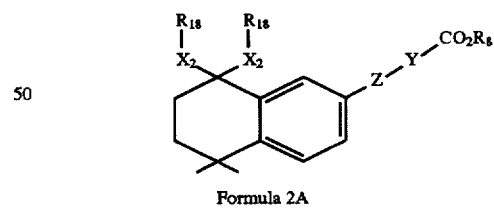

Formula 2A

| Compound No. | $X_2$ | $R_{18}$ | Z | Y | $R_8$ |
|---|---|---|---|---|---|
| A-2 | $O^1$ | — | $-CH=CH-$ | $1,4-C_6H_4{}^2$ | Et |
| A-2a | $O^1$ | — | $-CH=CH-$ | $1,4-C_6H_4{}^2$ | H |
| A-23 | S | $(CH_2)_3{}^3-$ | $-CH=CH-$ | $1,4-C_6H_4{}^2$ | Et |
| A-24 | S | $(CH_2)_3{}^3-$ | $-CH=CH-$ | $1,4-C_6H_4{}^2$ | H |
| B-1 | — | $H^4$ | — | $2,6-C_{10}H_6{}^5$ | Et |
| B-2 | — | $H^4$ | — | $2,6-C_{10}H_6{}^5$ | H |
| B-6 | $O^1$ | — | — | $2,6-C_{10}H_6{}^5$ | Et |
| B-7 | $O^1$ | — | — | $2,6-C_{10}H_6{}^5$ | H |
| C-5 | $O^1$ | — | polyene[6] | — | Et |
| D-10 | $O^1$ | — | $-N=N-$ | $1,4-C_6H_4{}^2$ | Et |
| E-28 | $O^1$ | — | $-CO-NH-$ | $1,4-C_6H_4{}^2$ | Et |

TABLE FOR FORMULA 2A

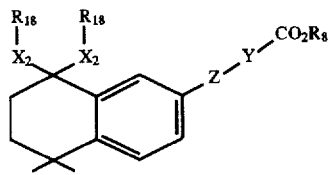

Formula 2A

| Compound No. | $X_2$ | $R_{18}$ | Z | Y | $R_8$ |
|---|---|---|---|---|---|
| E-29 | $O^1$ | — | —CO—NH— | $1,4\text{-}C_6H_4{}^2$ | H |
| E-36 | $O^1$ | — | —COO— | $1,4\text{-}C_6H_2{}^2$ | $(CH_2)_2Si(CH_3)_3$ |
| E-44 | $O^1$ | — | —COO— | $1,4\text{-}C_6H_4{}^2$ | Et |
| E-81 | $O^1$ | — | —COO— | $1,4\text{-}C_6H_4{}^2$ | benzyl |

[1] The two $X_2 - R_{18}$ jointly symbolize an oxo ($=O$) group;
[2] $1,4\text{-}C_6H_4$ stands for 1,4-substituted phenyl;
[3] The three methylene groups form a propylene bridge;
[4] Each of the two $X_2R_{18}$ groups is H;
[5] $2,6\text{-}C_{10}H_6$ stands for 2,6-substituted naphthalene.
[6] polyene stands for $-C(CH_3)=CH-CH=CH-(CH_3)=CH-$ Compounds in accordance with Formula 3 are preferred where the $R_{19}$ groups are alkyl, especially lower alkyl, most preferably methyl or ethyl, where the two $R_{19}$ groups together with the methyledene carbon form a 5 or 6 membered ring, and where the $R_{19}$ groups are phenyl. Compounds are also preferred in accordance with this formula where one of the $R_{19}$ groups is $COOR_8$, or COOH, and the other is H.

The most preferred compounds in accordance with Formula 3 are listed below in the Table for Formula 3A and with reference to that formula.

TABLE FOR FORMULA 3A

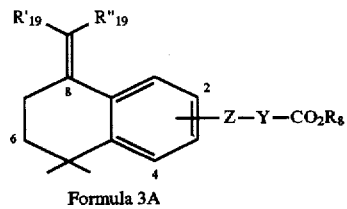

Formula 3A

| Compound No | $R_{19}'$ | $R_{19}''$ | Z | Y | $R_8$ | Configuration when applicable and/or position of substituent |
|---|---|---|---|---|---|---|
| A-25 | $CH_3$ | $CH_3$ | —CH=CH— | $1,4\text{-}C_6H_4{}^1$ | Et | 2 |
| A-26 | $CH_3$ | $CH_3$ | —CH=CH— | $1,4\text{-}C_6H_4{}^1$ | H | 2 |
| A-27 | $CH_2CH_3$ | $CH_2CH_3$ | —CH=CH— | $1,4\text{-}C_6H_4{}^1$ | Et | 2 |
| A-28 | $CH_2CH_3$ | $CH_2CH_3$ | —CH=CH— | $1,4\text{-}C_6H_4{}^1$ | H | 2 |
| A-29 | $(CH_2)_5{}^2$ | — | —CH=CH— | $1,4\text{-}C_6H_4{}^1$ | Et | 2 |
| A-31 | $(CH_2)_5{}^2$ | — | —CH=CH— | $1,4\text{-}C_6H_4{}^1$ | H | 2 |
| C-17a | COOEt | H | polyene[3] | — | Et | 2, anti |
| C-17b | COOEt | H | polyene[3] | — | Et | 2, syn |
| C-36 | $CH_3$ | $CH_3$ | polyene[3] | — | Et | 2 |
| C-41 | phenyl | phenyl | polyene3 | — | Et | 2 |
| D-2a | COOEt | H | —N=N— | $1,4\text{-}C_6H_4{}^1$ | Et | 2 |
| D-23 | $CH_3$ | $CH_3$ | —CO—CH=CH— | $1,4\text{-}C_6H_4{}^1$ | H | 3 |
| E-13 | $CH_3$ | $CH_3$ | —COO— | $1,4\text{-}C_6H_4{}^1$ | $CH_2CH_2SiME_3$ | 2 |
| E-14 | $CH_3$ | $CH_3$ | —COO— | $1,4\text{-}C_6H_4{}^1$ | H | 2 |
| E-15 | $CH_3$ | $CH_3$ | —COO— | $1,4\text{-}C_6H_4{}^1$ | Et | 2 |
| E-16 | $CH_3$ | $CH_3$ | —CONH— | $1,4\text{-}C_6H_4{}^1$ | Et | 2 |
| E-17 | $CH_3$ | $CH_3$ | —CONH— | $1,4\text{-}C_6H_4{}^1$ | H | 2 |
| E-50a | COOEt | H | —CONH— | $1,4\text{-}C_6H_4{}^1$ | Et | 2 |
| E-52 | COOH | H | —CONH— | $1,4\text{-}C_6H_4{}^1$ | H | 2, cis |
| E-53 | COOH | H | —CONH— | $1,4\text{-}C_6H_4{}^1$ | H | 2, trans |

[1] $1,4\text{-}C_6H_4$ stands for 1,4-substituted phenyl
[2] The 5-methylene groups together with the methyledene group form a 6-membered ring.
[3] polyene stands for $C(CH_3)=CH-CH=CH-C(CH_3)=CH-$ Referring now to compounds in accordance with Formula 4, compounds in these series are preferred where the $Z_2$ group is O-lower alkyl, especially $OCH_3$ or $OCH_2CH_3$. The most preferred compounds in accordance with Formula 4 are listed below in the Table for Formula 4A and with reference to that formula.

TABLE FOR FORMULA 4A

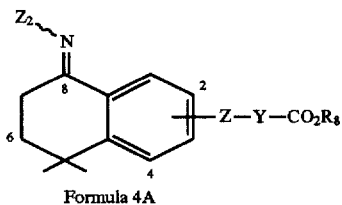

Formula 4A

| Compound No. | $Z_2$ | Z | Y | $R_8$ | Position of Z Substituent and/or configuration as Applicable |
|---|---|---|---|---|---|
| A-3  | $OCH_3$     | $-CH=CH-$     | $1,4\text{-}C_6H_4^1$    | Et           | 2, anti |
| A-4  | $OCH_3$     | $-CH=CH-$     | $1,4\text{-}C_6H_4^1$    | H            | 2, anti |
| A-5  | $OCH_2CH_3$ | $-CH=CH-$     | $1,4\text{-}C_6H_4^1$    | Et           | 2, anti |
| A-6  | $OCH_2CH_3$ | $-CH=CH-$     | $1,4\text{-}C_6H_4^1$    | H            | 2, anti |
| A-7  | OH          | $-CH=CH-$     | $1,4\text{-}C_6H_4^1$    | Et           | 2, anti |
| A-8  | OH          | $-CH=CH-$     | $1,4\text{-}C_6H_4^1$    | H            | 2, anti |
| B-11 | $OCH_3$     | —             | $2,6\text{-}C_{10}H_6^2$ | Et           | 2, anti |
| B-12 | $OCH_3$     | —             | $2,6\text{-}C_{10}H_6^2$ | H            | 2, anti |
| C-6  | $OCH_3$     | polyene$^3$   | —                        | Et           | 2, anti |
| C-22a| $OCH_3CH_3$ | polyene$^3$   | —                        | Et           | 2, syn  |
| C-22b| $OCH_2CH_3$ | polyene$^3$   | —                        | Et           | 2, anti |
| C-24 | $OCH_2CH_3$ | polyene$^3$   | —                        | H            | 2, syn  |
| C-25 | $OCH_2CH_3$ | polyene$^3$   | —                        | H            | 2, anti |
| D-3  | $OCH_3$     | $-N=N-$       | $1,4\text{-}C_6H_4^1$    | Et           | 2, anti |
| D-4  | $OCH_3$     | $-N=N-$       | $1,4\text{-}C_6H_4^1$    | H            | 2, anti |
| D-29 | $OCH_3$     | $-CO-CH=CH-$  | $1,4\text{-}C_6H_4^1$    | H            | 3       |
| E-30 | $OCH_3$     | $-CONH-$      | $1,4\text{-}C_6H_4^1$    | Et           | 2, anti |
| E-31 | $OCH_3$     | $-CONH-$      | $1,4\text{-}C_6H_4^1$    | H            | 2, anti |
| E-42 | $OCH_3$     | $-COO-$       | $1,4\text{-}C_6H_4^1$    | $(CH_3)SiMe_3$ | 2, anti |
| E-43 | $OCH_3$     | $-COO-$       | $1,4\text{-}C_6H_4^1$    | H            | 2, anti |
| E-46 | $OCH_3$     | $-COO-$       | $1,4\text{-}C_6H_4^1$    | Et           | 2, anti |

$^1$stands for 1,4-substituted phenyl
$^2$stands for 2,6-substituted naphthyl
$^3$polyene stands for $C(CH_3)=CH-CH=CH-C(CH_3)=CH-$ Compounds in accordance with Formula 5 are preferred where the $R_{20}$ group is lower alkyl, phenyl or $SO_2CF_3$.

The most preferred compounds in accordance with Formula 5 are listed below in the Table for Formula 5A and with reference to that formula.

TABLE FOR FORMULA 5A

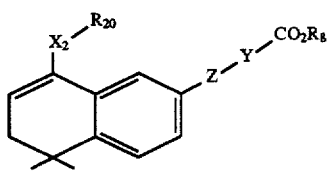

Formula 5A

| Compound No. | $X_2$ | $R_{20}$ | Z | Y | $R_8$ |
|---|---|---|---|---|---|
| A-9  | O      | $SO_2CF_3$ | $-CH=CH-$ | $1,4\text{-}C_6H_4^1$ | Et |
| A-16 | S      | phenyl     | $-CH=CH-$ | $1,4\text{-}C_6H_4^1$ | Et |
| A-18 | S      | phenyl     | $-CH=CH-$ | $1,4\text{-}C_6H_4^1$ | H  |
| A-17 | $SO_2$ | phenyl     | $-CH=CH-$ | $1,4\text{-}C_6H_4^1$ | Et |
| A-19 | $SO_2$ | phenyl     | $-CH=CH-$ | $1,4\text{-}C_6H_4^1$ | H  |
| A-20 | S      | $CH_2CH_3$ | $-CH=CH-$ | $1,4\text{-}C_6H_4^1$ | Et |

TABLE FOR FORMULA 5A

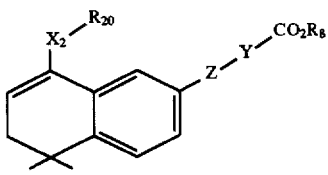

Formula 5A

| Compound No. | $X_2$ | $R_{20}$ | Z | Y | $R_8$ |
|---|---|---|---|---|---|
| A-21 | S | $CH_2CH_3$ | $-CH=CH-$ | $1,4-C_6H_4^1$ | H |
| A-22 | $SO_2$ | $CH_2CH_3$ | $-CH=CH-$ | $1,4-C_6H_4^1$ | H |
| C-10 | S | phenyl | polyene$_2$ | — | Et |
| C-11 | $SO_2$ | phenyl | polyene$_2$ | — | Et |
| C-12 | SO | phenyl | polyene$_2$ | — | Et |
| C-14 | O | $SO_2CF_3$ | polyene$_2$ | — | Et |
| C-28 | O | trimethylsilyl | polyene$_2$ | — | Et |
| D-11 | O | $SO_2CF_3$ | $-N=N-$ | $1,4-C_6H_4^1$ | Et |
| E-20 | S | phenyl | $-CONH-$ | $1,4-C_6H_4^1$ | Et |
| E-21 | S | phenyl | $-CONH-$ | $1,4-C_6H_4^1$ | H |
| E-22 | $SO_2$ | phenyl | $-CONH-$ | $1,4-C_6H_4^1$ | H |
| E-23 | S | phenyl | $-COO-$ | $1,4-C_6H_4^1$ | Et |
| E-24 | $SO_2$ | phenyl | $-COO-$ | $1,4-C_6H_4^1$ | Et |
| E-25 | S | phenyl | $-COO-$ | $1,4-C_6H_4^1$ | $(CH_2)_2Si(CH_3)_3$ |

TABLE FOR FORMULA 5A

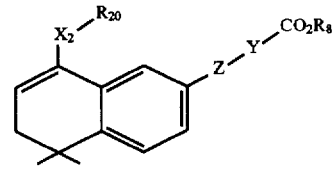

Formula 5A

| Compound No. | $X_2$ | $R_{20}$ | Z | Y | $R_8$ |
|---|---|---|---|---|---|
| E-26 | S | phenyl | $-COO-$ | $1,4-C_6H_4^1$ | H |
| E-27 | $SO_2$ | phenyl | $-COO-$ | $1,4-C_6H_4^1$ | H |

[1] stands for 1,4-substituted phenyl
[2] polyene stands for $C(CH_3)=CH-CH=CH-(CH_3)=CH$ Referring now to compounds in accordance with Formula 6, compounds in these series are preferred where the $R_{14}$ group is thiazolyl, more preferably 2-thiazolyl, thienyl, more preferably 2-thienyl, branched chain lower alkyl, more preferably t-butyl, or where $R_{14}$ is $CH_2COOR_8$ or $CH_2COOH$.

The most preferred compounds in accordance with Formula 6 are listed below in the Table for Formula 6A and with reference to that formula.

TABLE FOR FORMULA 6A

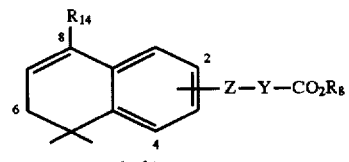

Formula 6A

| Compound No. | $R_{14}$ | Z | Y | $R_8$ | Position of Z Substituent |
|---|---|---|---|---|---|
| A-10 | 2-thiazolyl | $-CH=CH-$ | $1,4-C_6H_4^1$ | Et | 2 |
| A-12 | 2-thiazolyl | $-CH=CH-$ | $1,4-C_6H_4^1$ | H | 2 |
| A-13 | 2-thienyl | $-CH=CH-$ | $1,4-C_6H_4^1$ | Et | 2 |
| A-15 | 2-thienyl | $-CH=CH-$ | $1,4-C_6H_4^1$ | H | 2 |
| C-15 | 2-thienyl | polyene$_2$ | — | Et | 2 |
| C-20 | 2-thienyl | polyene$_2$ | — | H | 2 |
| C-46 | t-butyl | polyene$_2$ | — | Et | 2 |
| D-2b | $CH_2COOEt$ | $-N=N-$ | $1,4-C_6H_4^1$ | Et | 2 |
| D-12 | 2-thienyl | $-N=N-$ | $1,4-C_6H_4^1$ | Et | 2 |
| D-13 | 2-thienyl | $-N=N-$ | $1,4-C_6H_4^1$ | H | 2 |
| D-18 | $CH_2COOEt$ | $CO-CH=CH-$ | $1,4-C_6H_4^1$ | H | 3 |
| D-20 | t-butyl | $-CO-CH=CH-$ | $1,4-C_6H_4^1$ | H | 3 |
| D-34 | 2-thienyl | $CO-CH=CH-$ | $1,4-C_6H_4^1$ | H | 3 |
| E-7 | 2-thienyl | $-CO-NH-$ | $1,4-C_6H_4^1$ | Et | 2 |
| E-8 | 2-thienyl | $-CO-NH-$ | $1,4-C_6H_4^1$ | H | 2 |
| E-9 | 2-thienyl | $-COO-$ | $1,4-C_6H_4^1$ | Et | 2 |
| E-10 | 2-thienyl | $-COO-$ | $1,4-C_6H_4^1$ | $(CH_2)_2SiMe_3$ | 2 |
| E-11 | 2-thienyl | $-COO-$ | $1,4-C_6H_4^1$ | H | 2 |
| E-50b | $CH_2-COOEt$ | $-CO-NH-$ | $1,4-C_6H_4^1$ | Et | 2 |
| E-55 | $CH_2COOEt$ | $-COO-$ | $1,4-C_6H_4^1$ | Et | 2 |
| E-79 | t-butyl | $-CO-NH-$ | $1,4-C_6H_4^1$ | Et | 2 |
| E-80 | t-butyl | $-CO-NH-$ | $1,4-C_6H_4^1$ | H | 2 |

[1] stands for 1,4-substituted phenyl
[2] polyene stands for $C(CH_3)=CH-CH=CH-C(CH_3)=CH-$ The compounds of this invention can be made by the general procedures outlined above under the title "GENERAL EMBODIMENTS AND SYNTHETIC METHODOLOGY". The following chemical pathways represent the presently contemplated best synthetic routes to certain exemplary compounds of the invention illustrated here. However, the synthetic chemist will readily appreciate that the conditions set out here for these specific embodiments can be generalized to any and all of the compounds represented by Formulas 1 through 6.

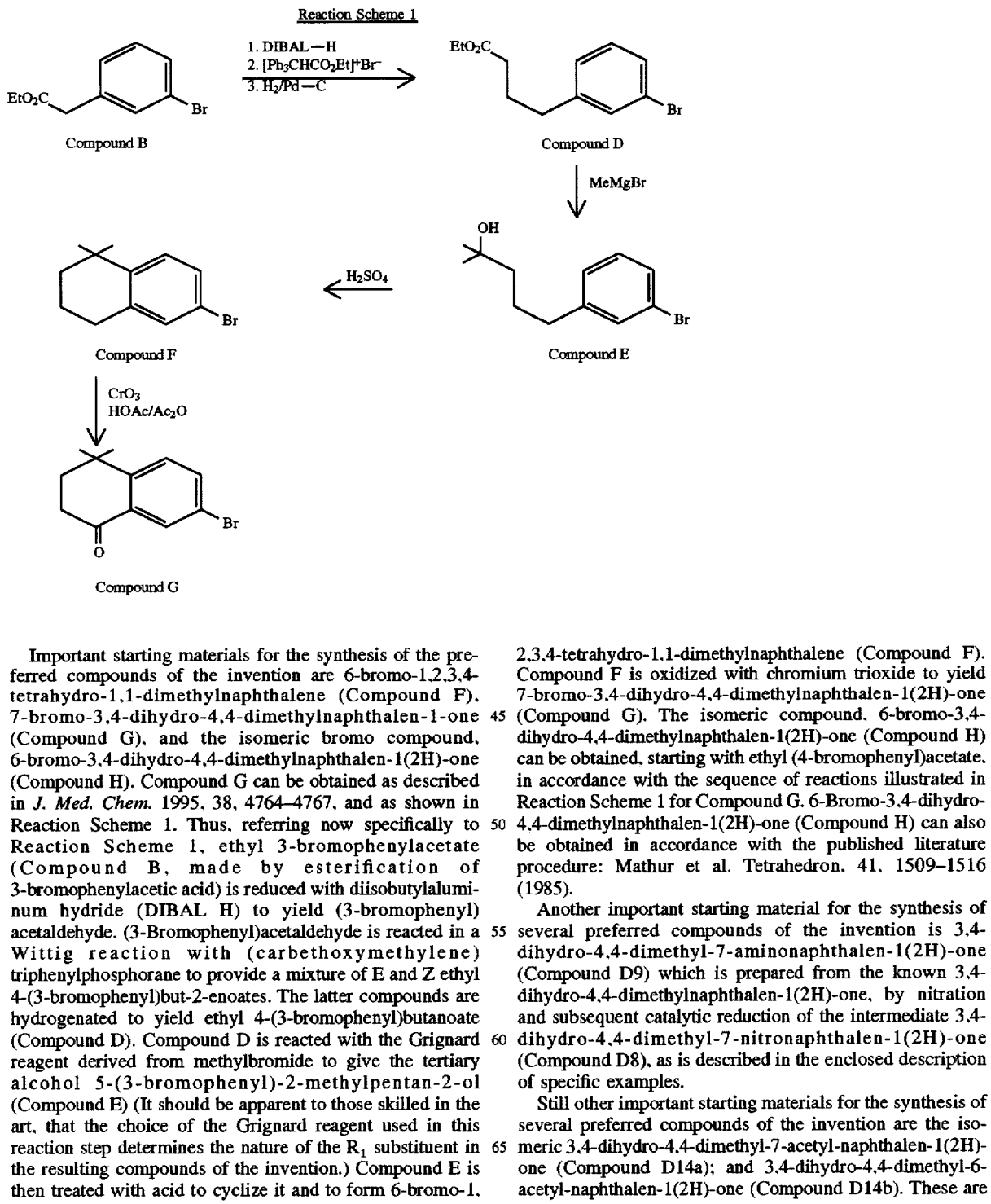

Important starting materials for the synthesis of the preferred compounds of the invention are 6-bromo-1,2,3,4-tetrahydro-1,1-dimethylnaphthalene (Compound F), 7-bromo-3,4-dihydro-4,4-dimethylnaphthalen-1-one (Compound G), and the isomeric bromo compound, 6-bromo-3,4-dihydro-4,4-dimethylnaphthalen-1(2H)-one (Compound H). Compound G can be obtained as described in *J. Med. Chem.* 1995, 38, 4764–4767, and as shown in Reaction Scheme 1. Thus, referring now specifically to Reaction Scheme 1, ethyl 3-bromophenylacetate (Compound B, made by esterification of 3-bromophenylacetic acid) is reduced with diisobutylaluminum hydride (DIBAL H) to yield (3-bromophenyl)acetaldehyde. (3-Bromophenyl)acetaldehyde is reacted in a Wittig reaction with (carbethoxymethylene)triphenylphosphorane to provide a mixture of E and Z ethyl 4-(3-bromophenyl)but-2-enoates. The latter compounds are hydrogenated to yield ethyl 4-(3-bromophenyl)butanoate (Compound D). Compound D is reacted with the Grignard reagent derived from methylbromide to give the tertiary alcohol 5-(3-bromophenyl)-2-methylpentan-2-ol (Compound E) (It should be apparent to those skilled in the art, that the choice of the Grignard reagent used in this reaction step determines the nature of the $R_1$ substituent in the resulting compounds of the invention.) Compound E is then treated with acid to cyclize it and to form 6-bromo-1, 2,3,4-tetrahydro-1,1-dimethylnaphthalene (Compound F). Compound F is oxidized with chromium trioxide to yield 7-bromo-3,4-dihydro-4,4-dimethylnaphthalen-1(2H)-one (Compound G). The isomeric compound, 6-bromo-3,4-dihydro-4,4-dimethylnaphthalen-1(2H)-one (Compound H) can be obtained, starting with ethyl (4-bromophenyl)acetate, in accordance with the sequence of reactions illustrated in Reaction Scheme 1 for Compound G. 6-Bromo-3,4-dihydro-4,4-dimethylnaphthalen-1(2H)-one (Compound H) can also be obtained in accordance with the published literature procedure: Mathur et al. Tetrahedron, 41, 1509–1516 (1985).

Another important starting material for the synthesis of several preferred compounds of the invention is 3,4-dihydro-4,4-dimethyl-7-aminonaphthalen-1(2H)-one (Compound D9) which is prepared from the known 3,4-dihydro-4,4-dimethylnaphthalen-1(2H)-one, by nitration and subsequent catalytic reduction of the intermediate 3,4-dihydro-4,4-dimethyl-7-nitronaphthalen-1(2H)-one (Compound D8), as is described in the enclosed description of specific examples.

Still other important starting materials for the synthesis of several preferred compounds of the invention are the isomeric 3,4-dihydro-4,4-dimethyl-7-acetyl-naphthalen-1(2H)-one (Compound D14a); and 3,4-dihydro-4,4-dimethyl-6-acetyl-naphthalen-1(2H)-one (Compound D14b). These are prepared by reacting 1,2,3,4-tetrahydro-1,1-dimethylnaphthalene with acetyl chloride in a Friedel-Crafts type reaction, followed by oxidation with chromium trioxide of the isomeric acetyl derivatives. These compounds can also be obtained by an alternative procedure from Compounds G and H respectively. The experimental conditions of these preparations are disclosed in the description of the specific examples.

Yet another important starting material for the synthesis of several preferred compounds of the invention is methyl 5,5-dimethyl-5,6-dihydro-naphthalen-8(7H)-one-2-carboxylate (Compound E2) which can be made by reaction of 7-bromo-3,4-dihydro-4,4-dimethylnaphthalen-1-one (Compound G) with $CO_2$ in the presence of t-butyl lithium, but is more advantageously prepared in the presence of palladium(II)-bis(triphenylphosphine)chloride and 1,3-bis(diphenylphosphino)propane catalysts by reaction with carbonmonoxide and methanol, as is described in the specific examples.

Referring now to Reaction Scheme 2 the synthesis of preferred examples of compounds of the invention are described, where the Z group, with reference to Formulas 1–6 is —CH═CH—. Compounds of this type of the invention are advantageously obtained in a direct coupling reaction between an ethenyl compound such as ethyl 4-vinylbenzoate, and a 6- or 7-bromonaphthalene-1(2H)-one derivative, such as Compound G or Compound H in a reaction commonly known as the Heck reaction. Reaction Scheme 2 exemplifies this reaction with 7-bromo-3,4-dihydro-4,4-dimethylnaphthalen-1(2H)-one (Compound G) as the starting material. A general formula for the ethenyl compounds which are suitable as reagents in the Heck reaction to provide these type of compounds of the invention is $CH_2$═$CH_2$—Y($R_2$)—A—B where the symbols have the same meaning as defined in connection with Formulas 1–6. These compounds are readily available in accordance with the chemical literature, or otherwise in accordance with state-of-the-art. The Heck reaction is well known in the art, and is usually conducted in a basic solvent, such as triethylamine, in the presence of a phosphine catalyst (such as tris(2-methylphenyl)phosphine or tri-O-tolylphosphine) in the presence of palladium(II)acetate catalyst.

Those skilled in the art will readily understand that the compounds of the invention which have an ethylene (—CH═CH—) or substituted ethylene (—$CR_1$═$CR_1$—) linking group can also be made by a Wittig or like (Horner Emmons) reactions, which are per se well known in the art. Those skilled in the art will also readily understand that the reaction sequence shown in Reaction Scheme 2 can be readily adapted for compounds where the tetrahydronaphthalene (or other rings within the scopes of Formulas 1–6) have $R_1$, $R_2$ and $R_3$ substituents other than specifically shown in this reaction scheme.

Reaction Scheme 2

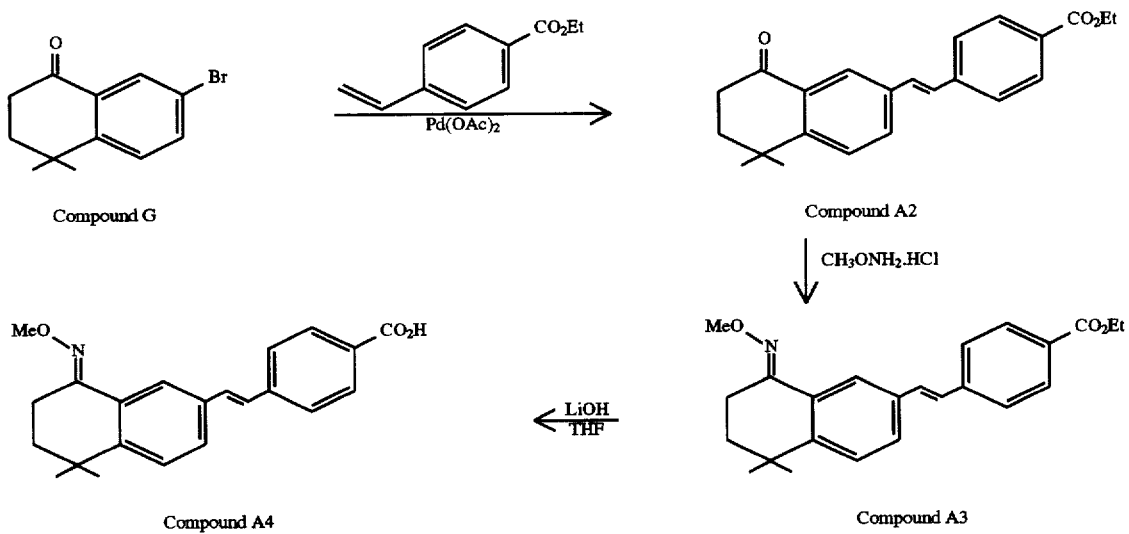

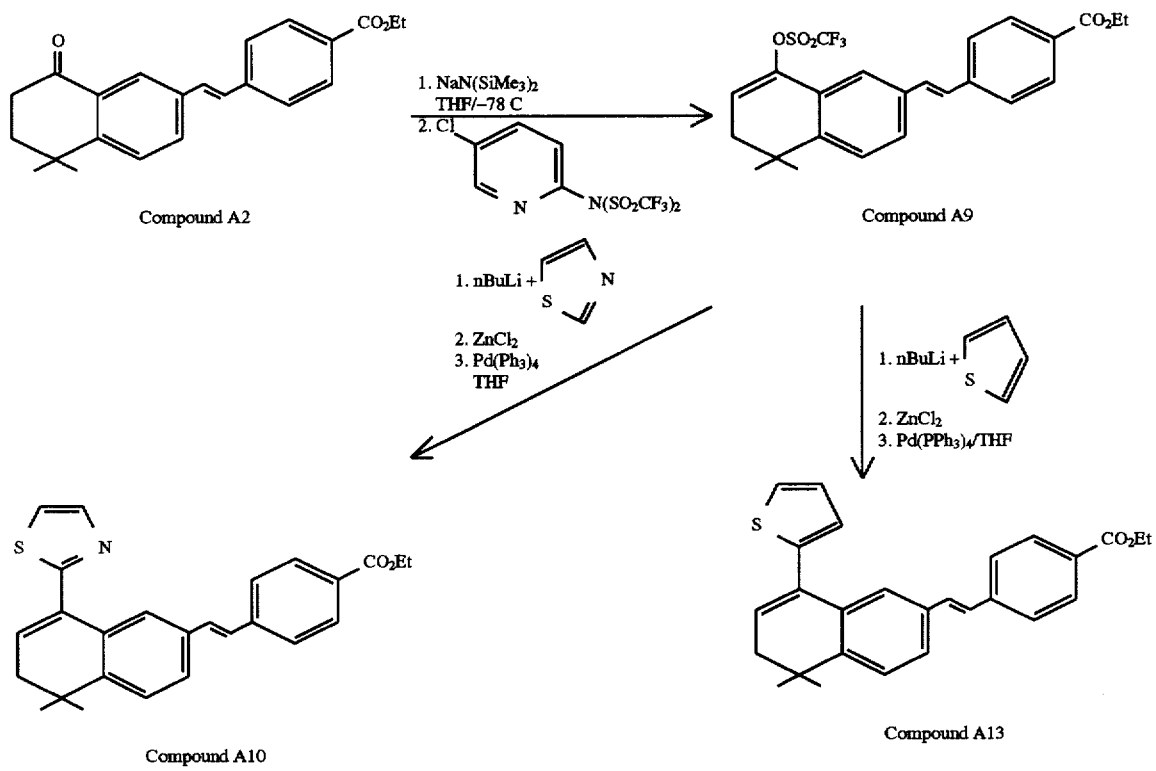

Thus in the example shown in Reaction Scheme 2 7-bromo-3,4-dihydro-4,4-dimethylnaphthalen-1(2H)-one (Compound G) is reacted with ethyl 4-vinylbenzoate to yield ethyl (E)-4-[2-(5,6-dihydro-5,5-dimethylnaphthalen-8(7H)-one-2-yl)ethenyl]-benzoate (Compound A2). Ethyl 4-vinylbenzoate is available in accordance with the chemical literature, Can. J. Chem (1973) 51, 897–914, which is expressly incorporated herein by reference. Compound A2 is an example for the compounds of the present invention within the scope of Formula 2. Compound A2 is reacted with methoxylamine hydrochloride in an alcoholic solvent (such as ethanol) in the presence of sodium acetate to yield the methyl oxime, ethyl (E)-4-[2-(5,5-dimethyl-5,6,-dihydro-8(7H)-anti-(O-methyl oxime)-naphthalen-2-yl)ethenyl]-benzoate (Compound A3). Compound A3 can be saponified by treatment with base, such as LiOH, to provide the free carboxylic acid, (E)-4-[2-(5,5-dimethyl-5,6,-dihydro-8(7H)-anti-(O-methyl oxime)-naphthalen-2-yl)ethenyl]-benzoic acid (Compound A4). Compounds A3 and A4 are compounds of the invention within the scope of Formula 4. The conditions for the saponification of Compound A3 to provide Compounds A4 serve as example for several saponification reactions which yield several compounds of the invention where the B group of Formulas 1–6 is a free carboxylic acid (COOH), or salt thereof.

Instead of methoxylamine hydrochloride, hydroxylamine hydrochloride, or ethoxylamine hydrochloride or other analogous reagents can be used to obtain the oximes or other O-alkyl, O-aryl analogs of Compounds A3 and A4, within the scope of Formula 4. Generally speaking and with reference to Formula 4, the oxo compounds, such as Compound A2 are reacted with a reagent of the formula $NH_2-Z_2$, where $Z_2$ is defined as in connection with Formula 4. Thus, the oxo compounds analogous to Compound A2 are reacted with a reagent of the formula $H_2N-Z_2$ to yield compounds of Formula 4. As is known, when the reagent $H_2N-Z_2$ is $NH_2OH$ or its salt, then the reaction is the formation of an oxime. Generally speaking the oximes are readily formed by reacting the oxo compounds with hydroxylamine hydrochloride in a polar solvent, such as a lower alkanol, in the presence of a buffering agent, such as sodium acetate. The reaction can be conducted under similar conditions with a reagent of the formula $NH_2OR_1$ or its salt (such as methoxylamine hydrochloride or ethoxylamine hydrochloride as demonstrated in Reaction Scheme 2) to yield compounds of Formula 4 where $Z_1$ is $OR_1$ ($R_1$ is defined as in connection with Formula 4). When the reagent $H_2N-Z_2$ is a primary amine then the reaction is the formation of an imine. The latter reaction is usually conducted in a polar (alcoholic) solvent. Further reagents, in accordance with the general formula $H_2NZ_2$ are those where $Z_2$ is $NHCON(R_{14})_2$ (formation of semicarbazone), $NHCSN(R_{14})_2$ (formation of thiosemicarbazone) and $N(R_{14})_2$ (formation of a hydrazone). (The symbol $R_{14}$ is defined as in connection with Formula 4.) The semicarbazones, thiosemicarbazones and hydrazones corresponding to Formula 4 can be prepared under conditions which are well known in the art for the formation of such derivatives of ketone compounds. Usually these conditions are similar to the conditions leading to the oximes described above. Typically, the hydrochloride salt of the reagent (semicarbazide, thiosemicarbazide or hydrazide) is reacted with the oxo compound such as Compound A2 in an alcoholic solvent, in the presence of sodium acetate.

Referring now again specifically to Reaction Scheme 2, ethyl (E)-4-[2-(5,6-dihydro-5,5-dimethylnaphthalen-8(7H)-one-2-yl)ethenyl]-benzoate (Compound A2) is reacted with sodium bis(trimethylsilyl)amide and 2-[N,N-bis (trifluoromethanesulfonyl)amino]-5-chloropyridine in an inert ether type solvent, such as tetrahydrofuran, at low temperatures (−78° C. and 0° C.). This provides first a sodium salt intermediate which is not isolated and not shown in the reaction scheme. The reactions ultimately result in the trifluoromethylsulfonyloxy derivative ethyl (E)-4-[2-(5,6-dihydro-5,5-dimethyl-8-(trifluoromethylsulfonyl)oxy-naphthalen-2-yl) ethenyl]-benzoate (Compound A9). Compound A9 is within the scope of Formula 5 of the present invention and is also an important intermediate for the synthesis of several compounds of the invention within the scope of Formula 6. Compound A9 is a trifluoromethylsulfonate derivative, which sometimes also called a "triflate" in the trade, and the $CF_3SO_2$ group is sometimes abbreviated as "Tf" in the reaction schemes.

As is shown further in Reaction Scheme 2 for the specific examples of thiazole and thiophene, respectively yielding Compounds A10 and A13, the triflate derivative Compound A9 is reacted with an organometal derivative derived from an ether type solvent in accordance with known practice in the art. The temperature range for the reaction between the reagent $R_{14}Li$ and the triflate derivatives is, generally speaking in the range of approximately −78° C. to 50° C. Compounds A10 and A13 and their analogs can be saponified, or subjected to further transformations, such as homologation and other state-of-the-art reactions which yield homologs and derivatives in accordance with the reactions discussed above.

Reaction Scheme 2 serves as an example of synthetic methodology used for preparing compounds of the present invention where the —Y($R_2$)—A—B group of Formulas 1–6 is linked to the tetrahydronaphthalene nucleus with the desired Z group, before the final substitution pattern is obtained by transformations of the tetrahydronaphthalene (or dihydronaphthalene) moiety.

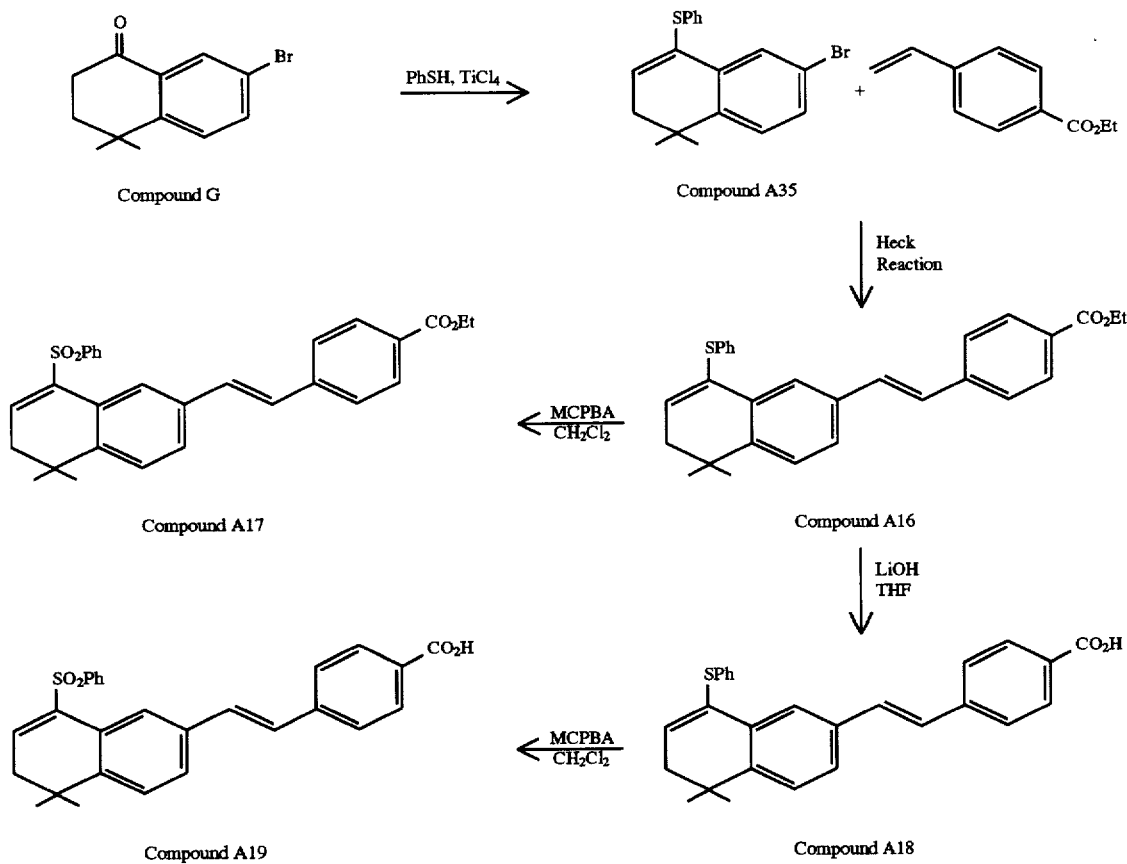

the compound $R_{14}H$, such that the formula of the organometal derivative is $R_{14}Met$ (Met stands for monovalent metal), preferably $R_{14}Li$. ($R_{14}$ is defined as in connection with Formula 6.) The reaction with the organometal derivative, preferably lithium derivative of the formula $R_{14}Li$ is usually conducted in an inert ether type solvent (such as tetrahydrofuran) in the presence of zinc chloride ($ZnCl_2$) and tetrakis(triphenylphosphine)palladium(O) (Pd (PPh_3)_4). The organolithium reagent $R_{14}Li$, if not commercially available, can be prepared from the compound $R_{14}H$ (or its halogen derivative $R_{14}—X_1$ where $X_1$ is halogen) in Reaction Scheme 3 provides further examples for the synthesis of compounds within the scope of Formula 5 where the linking group between the dihydronaphthalene moiety and the Y group is —CH=CH—. In the sequence of reactions described here the oxo function of a starting tetrahydronaphthalene-one moiety is modified before a Heck coupling reaction is performed. Specifically, in the example shown in the reaction scheme, 7-bromo-3,4-dihydro-4,4-dimethylnaphthalen-1(2H)-one (Compound G) is reacted with thiophenol in the presence of titanium tetrachloride and triethylamine in tetrahydrofuran (THF), to provide the intermediate 4,4-dimethyl-7-bromo-1-phenylthio-3,4-dihydronaphthalene (Compound A35). A similar reaction can be performed with ethanethiol as a reagent instead of thiophenol, to yield 2-bromo-5,6-dihydro-5,5-dimethyl-8-ethylthio-naphthalene (Compound A36) and other analogous compounds which are not shown in the reaction scheme. Compound A35 is reacted in the Heck reaction to yield ethyl (E)-4-[2-(5,6-dihydro-5,5-dimethyl-8-phenylthio-naphthalenyl)ethenyl]benzoate (Compound A16). Compound A16 is saponified to yield the carboxylic acid, (E)-4-[2-(5,6-dihydro-5,5-dimethyl-8-(phenylthio)-naphthalen-2-yl)ethenyl]benzoic acid (Compound A18), and is oxidized with m-chloroperoxybenzoic acid (MCPBA) to provide the corresponding phenylsulfonyl compound, ethyl (E)-4-[-2-(5,6-dihydro-5,5-dimethyl-8-(phenylsulfonyl)-naphthalenyl)ethenyl]benzoate (Compound A17). Compound A18 can also be oxidized under similar conditions to provide the free carboxylic acid (or salt thereof) of the phenylsulfonyl compound, (E)-4-[-2-(5,6-dihydro-5,5-dimethyl-8-phenylsulfonylnaphthalenyl)ethenyl]benzoic acid (Compound A19).

Reaction Scheme 4 discloses further examples for the preparation of compounds of the invention within the scope of Formula 2 where the group linking the tetrahydronaphthalene and Y(R$_2$)—A—B moieties is —CH=CH—. As is shown in the scheme, ethyl (E)-4-[2-(5,6-dihydro-5,5-dimethylnaphthalen-8(7H)-one-2-yl)ethenyl]-benzoate (Compound A2) is reacted with 1,3-propanedithiol in the presence of borontrifluoride diethyl etherate to yield the corresponding cyclic thioketal compound, ethyl (E)-4-[-2-(5,6,7,8-tetrahydro-5,5-dimethyl-8-(1,3-dithian-2-yl)naphthalen-2-yl)ethenyl]benzoate (Compound A23). Other ketal and thioketal analogs of this compound, within the scope of Formula 2 can be obtained by analogous reactions suitable for ketal and thioketal formation, which are per se well known in the art. Saponification of Compound A23 provides the corresponding free acid (or salt thereof), (E)-4-[2-(5,6,7,8-tetrahydro-5,5-dimethyl-8-(2-(1,3-dithian-2-yl)naphthalenyl)ethenyl]-benzoic acid (Compound A24).

Reaction Scheme 4

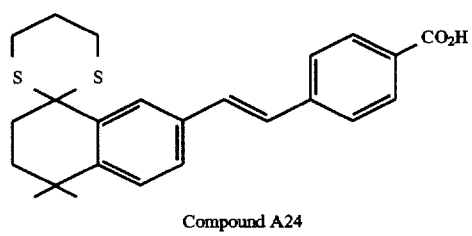

Compound A24

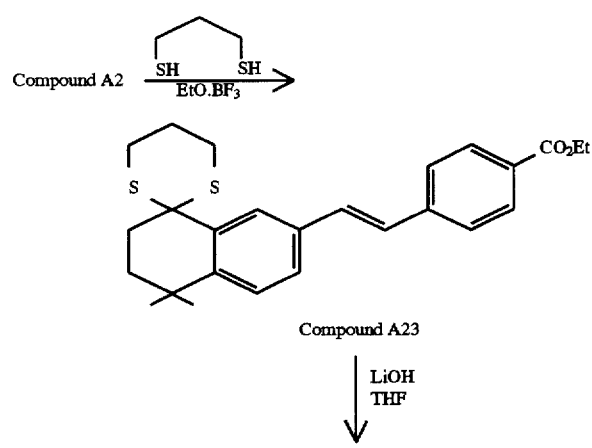

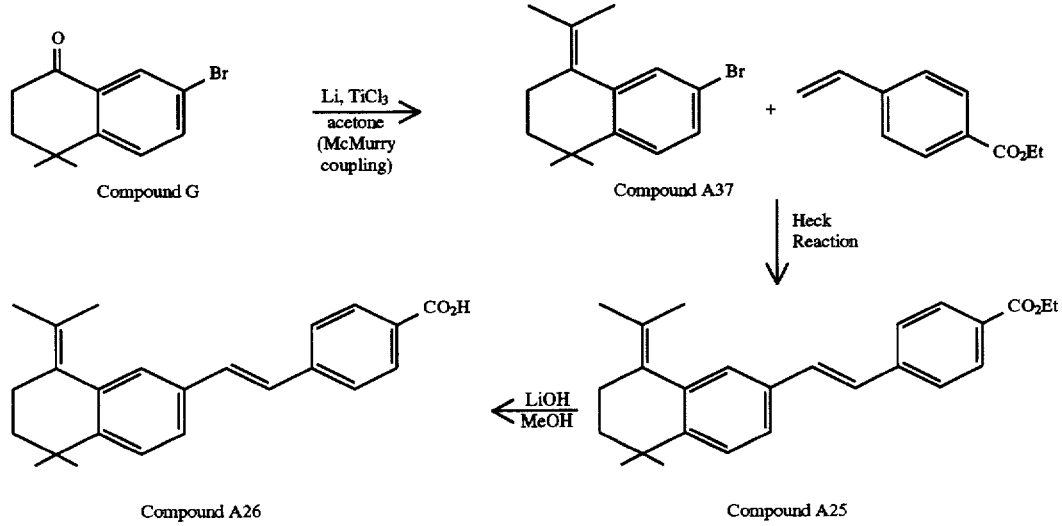

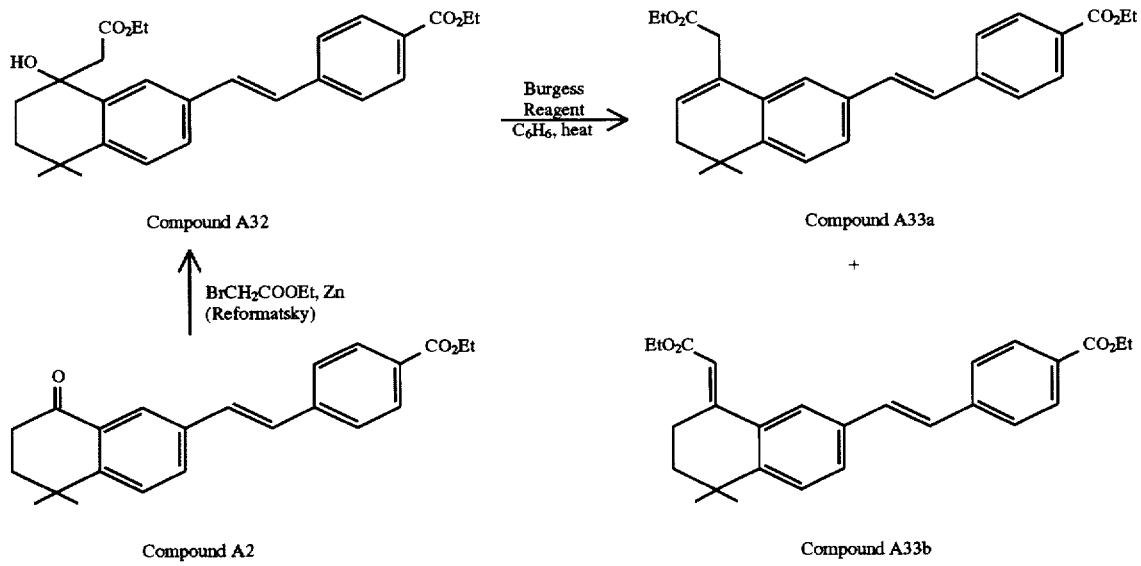

Reaction Scheme 5 provides examples for the synthesis of compounds of the invention within the scope of Formula 3. The synthesis of these compounds proceeds in accordance with methodology where the desired substituent is introduced into the tetrahydronaphthalene moiety before this moiety is coupled or linked to the desired Z—Y($R_2$)—A—B group, and in these examples also the Z group is —CH=CH—. Thus in accordance with this scheme, 7-bromo-3,4-dihydro-4,4-dimethylnaphthalen-1(2H)-one (Compound G) is reacted in a McMurry coupling reaction with acetone to provide 7-bromo-1(2H)-(propyliden-2-yl)-3,4-dihydro-4,4-dimethylnaphthalene (Compound A37). The reaction (McMurry coupling) is conducted at elevated temperature in the presence of lithium metal and titanium trichloride, in an inert ether type solvent, for example in refluxing 1,2-dimethoxyethane (DME). In other examples which are described in the Specific Examples, 3-pentanone, and cyclohexanone are used as ketone reagents, instead of the acetone shown in the reaction scheme. Compound A37 is then subjected to a Heck coupling reaction with an ethenyl reagent such as ethyl 4-vinylbenzoate shown in the scheme, to provide ethyl (E)-4-[2-(5,6-dihydro-5,5-dimethyl-8(7H)-(propyliden-2-yl)-naphthalen-2-yl)ethenyl]benzoate (Compound A25). Compound A25 is saponified under conditions described above to provide (E)-4-[2-(5,6-dihydro-5,5-dimethyl-8(7H)-(propyliden-2-yl)-naphthalen-2-yl)ethenyl]-benzoic acid (Compound A26).

Reaction Scheme 5 discloses another example for the preparation of compounds within the scope of Formula 3. In this example the substituent is introduced to replace the oxo function of tetrahydronaphthalene-2-one after the Z—Y($R_2$)—A—B group has already been coupled to the tetrahydronaphthalene nucleus. Thus, ethyl (E)-4-[2-(5,6-dihydro-5,5-dimethyl-naphthalen-8(7H)-one-2-yl)ethenyl]-benzoate (Compound A2) is reacted with ethyl bromoacetate in the presence of zinc metal in a Reformatsky reaction to provide (+/−) ethyl (E)-4-[2-(5,6,7,8-tetrahydro-5,5-dimethyl-8-hydroxy-8-(carbethoxymethyl)naphthalen-2-yl)ethenyl] benzoate (Compound A32). Compound A32 is itself within the scope of the present invention, within the scope of Formula 1. Compound A32 is dehydrated, as shown in the example by treatment with (methoxycarbonyl sulfamoyl) triethylammonium hydroxide (Burgess reagent) to yield a mixture of ethyl (E)-4-[2-(5,6-dihydro-5,5-dimethyl-8-(carbethoxymethyl)naphthalen-2-yl)ethenyl]benzoate (Compound A33a), and ethyl (E)-4-[2-(5,6-dihydro-5,5-dimethyl-8(7H)-anti(carbethoxymethylidenyl)-naphthalen-2-yl)ethenyl]benzoate (Compound A33b). Compound A33a is within the scope of Formula 6, and Compound A33b is within the scope of Formula 3.

Reaction Scheme 6

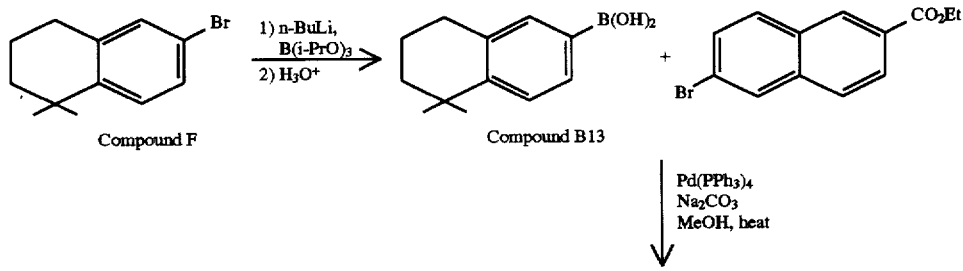

-continued
Reaction Scheme 6

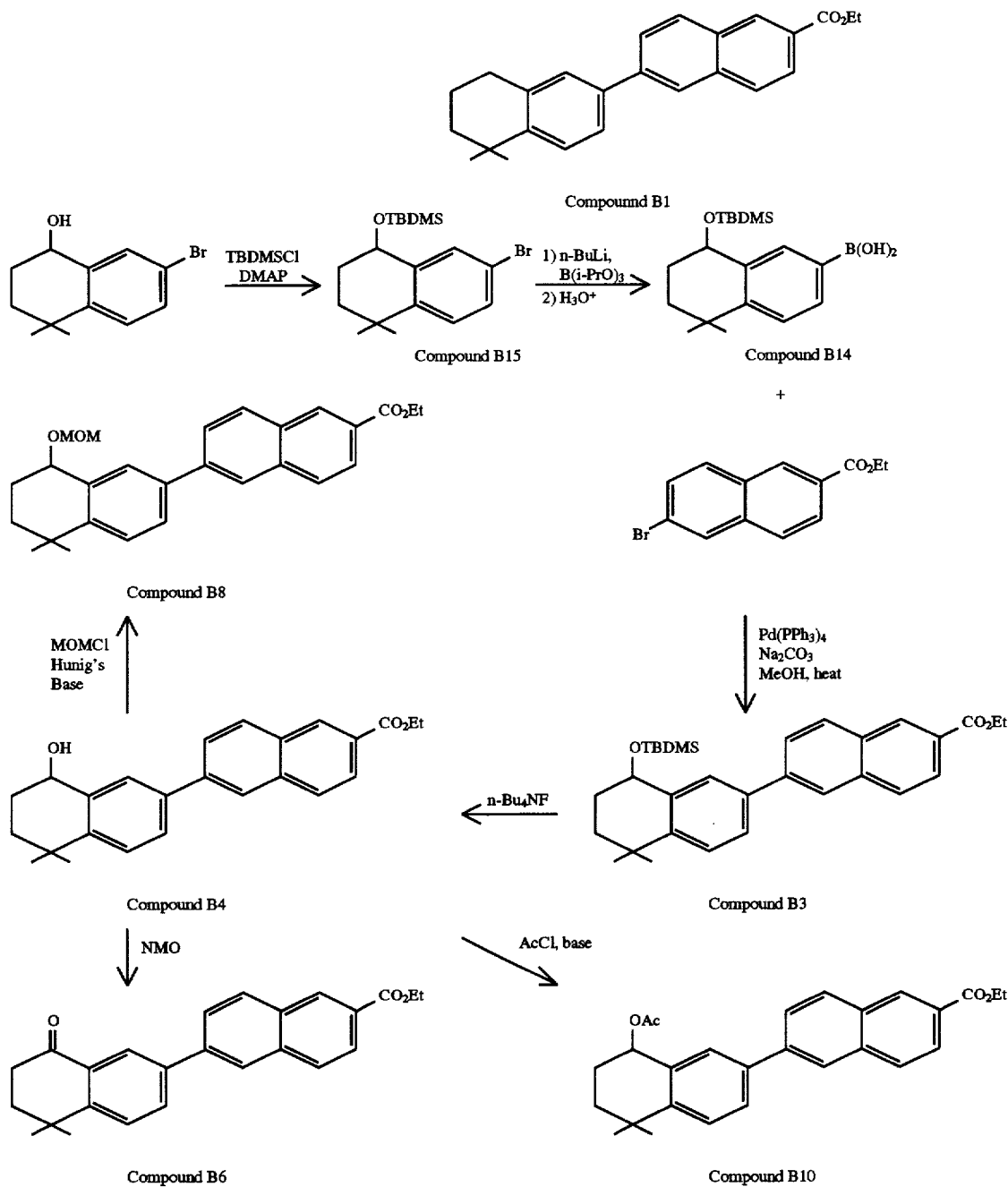

Reaction Scheme 6 provides examples for the synthesis of compounds of the invention where in accordance with Formulas 1–6 the Z group is —(CR$_1$═CR$_1$)$_{n'}$— and n' is 0; in other words where there is no linking group between the tetrahydronaphthalene or dihydronaphthalene nucleus and the Y(R$_2$)—A—B group. For the synthesis of these examples the starting material is 6-bromo-1,2,3,4-tetrahydro-1,1-dimethylnaphthalene (Compound F) which is reacted with n-butyl lithium and triisopropylborate in an aprotic solvent such as toluene to give after hydrolysis (5,6,7,8-tetrahydro-5,5-dimethylnaphth-2-yl)boronic acid (Compound B13). Compound B13 and related boronic acid derivatives (such as Compound B14 in this scheme) are suitable for coupling with a reagent having the formula X$_3$—Y(R$_2$)—A—B where X$_3$ is halogen, and the remaining symbols are defined as for Formulas 1–6. Reaction Scheme 6 illustrates this coupling reaction with ethyl 6-bromo-naphthalene-2-carboxylate in the presence of tetrakis-triphenyl-phosphine palladium(O) to yield ethyl-6-[5,6,7,8-tetrahydro-5,5-dimethyl-naphth-2-yl]naphthoate (Compound B1). Compound B1 of the invention is within the scope of Formula 2. Other reagents corresponding to formula X$_3$—Y(R$_2$)—A—B are readily available in accordance with the chemical literature and/or can be obtained in accordance with state-of-the-art synthetic methodology.

Examples for such other reagents are ethyl 4-bromobenzoate and ethyl 2-bromopyridine-5-carboxylate.

Continuing on with the description of Reaction Scheme 6, 6-bromo-1,2,3,4-tetrahydro-1,1-dimethyl-4-hydroxynaphthalene is reacted in the presence of base with t-butyldimethylsilyl chloride to provide 6-bromo-1,2,3,4-tetrahydro-1,1-dimethyl-4-(t-butyldimethylsilyloxy) naphthalene (Compound B15). The starting 6-bromo-1,2,3, 4-tetrahydro-1,1-dimethyl-4-hydroxynaphthalene can be obtained by reduction of 7-bromo-3,4-dihydro-4,4-dimethylnaphthalen-1(2H)-one (Compound G). Under conditions similar to the ones described above Compound B15 is converted to the boronic acid derivative (5,5-dimethyl-8-(t-butyldimethylsilyloxy)-5,6,7,8-tetrahydro-naphth-2-yl) boronic acid (Compound B14). Compound B14 is then coupled with ethyl 6-bromo-8 naphthalene-2-carboxylate to yield ethyl 6-[5,6,7,8-tetrahydro-5,5-dimethyl-8-(t-butyldimethylsilyloxy)-naphth-2-yl]naphth-2-oate (Compound B3). Compound B3 is then reacted with tetrabutylammonium fluoride to remove the t-butyldimethylsilyl blocking group and to give ethyl 6-[5, 6,7,8-tetrahydro-5,5-dimethyl-8-hydroxy-naphth-2-yl] naphth-2-oate (Compound B4). Compound B4 can be acylated to give ethyl 6-[5,6,7,8-tetrahydro-5,5-dimethyl-8-(O-acetyl)-naphth-2-yl]naphth-2-oate (Compound B10), or methoxymethylated with methoxymethyl chloride in the presence of base (preferably ethyl N,N-diisopropylamine, Hunig's base) to give ethyl 6-[5,6,7,8-tetrahydro-5,5-dimethyl-8-(methoxymethyloxy)-naphth-2-yl]naphth-2-oate (Compound B8), and oxidized with N-methyl morpholine N-oxide to provide ethyl 6-[5,5-dimethyl-5,6-dihydro-napthlen-8(7H)-one-2-yl]-naphthalen-2-oate (Compound B6). Compounds B8 and B10 of the invention are within the scope of Formula 1, whereas Compound B6 is within the scope of Formula 2. Compound B6 can be converted into the O-methyloxime (ethyl 6-[5,5-dimethyl-5,6-dihydro-napthlen-8(7H)-anti-(O-methyl-oxime)-2-yl]-naphthalen-2-oate (Compound B11) not shown in the scheme) and into other derivatives such as oximes, imines, hydrazones and the like, as is described above in connection with Reaction Scheme 2. Further derivatives of Compound B6 (and of analogous compounds) wherein the 8-oxo function of the molecule is modified can be obtained in accordance with the general synthetic methodology described in this specification. For example the trifluoromethylsulfonyl (triflate) derivative can be obtained in analogy to the reaction leading to Compound A9 as described in Reaction Scheme 2, and the trifluoromethylsulfonyl (triflate) derivative is reacted with the reagents $R_{14}Me$ to provide compounds of Formula 6.

Reaction Scheme 7

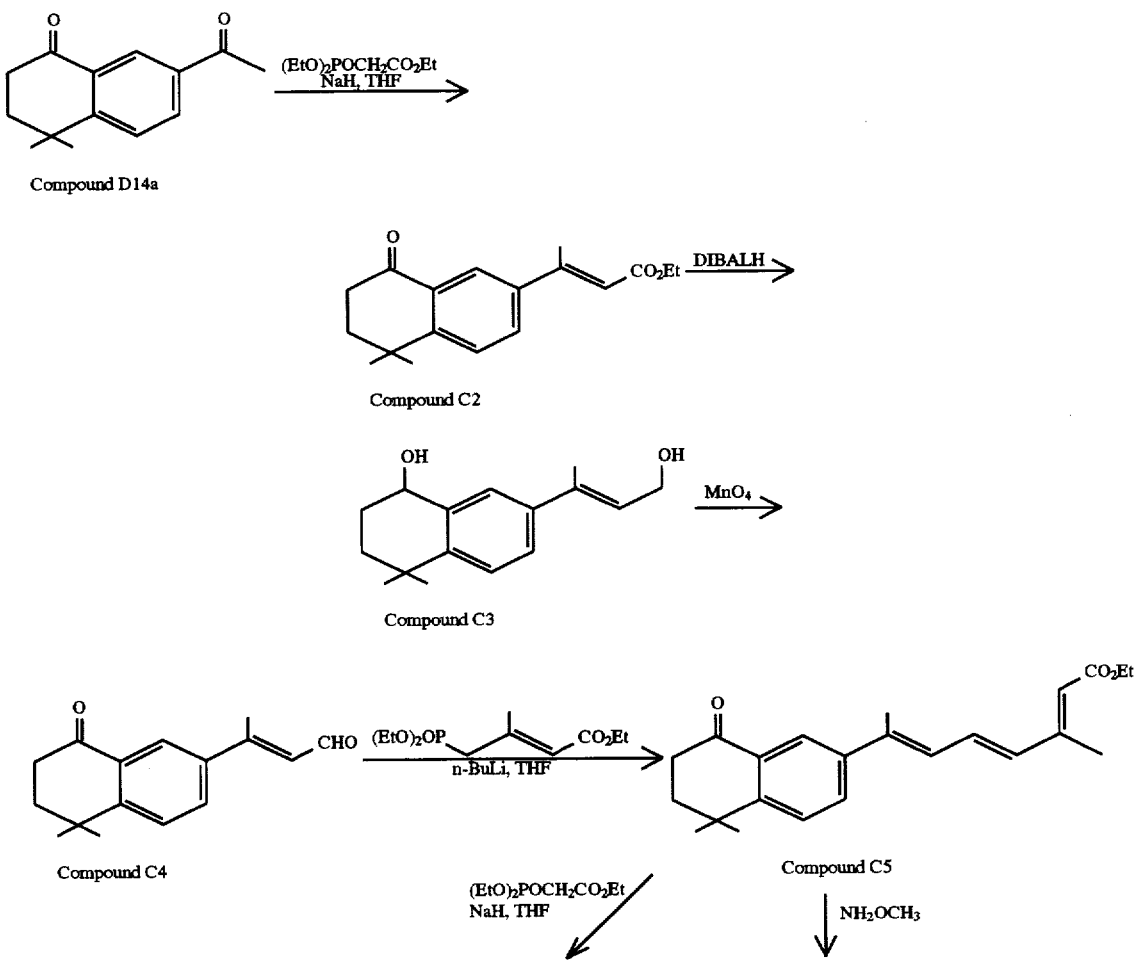

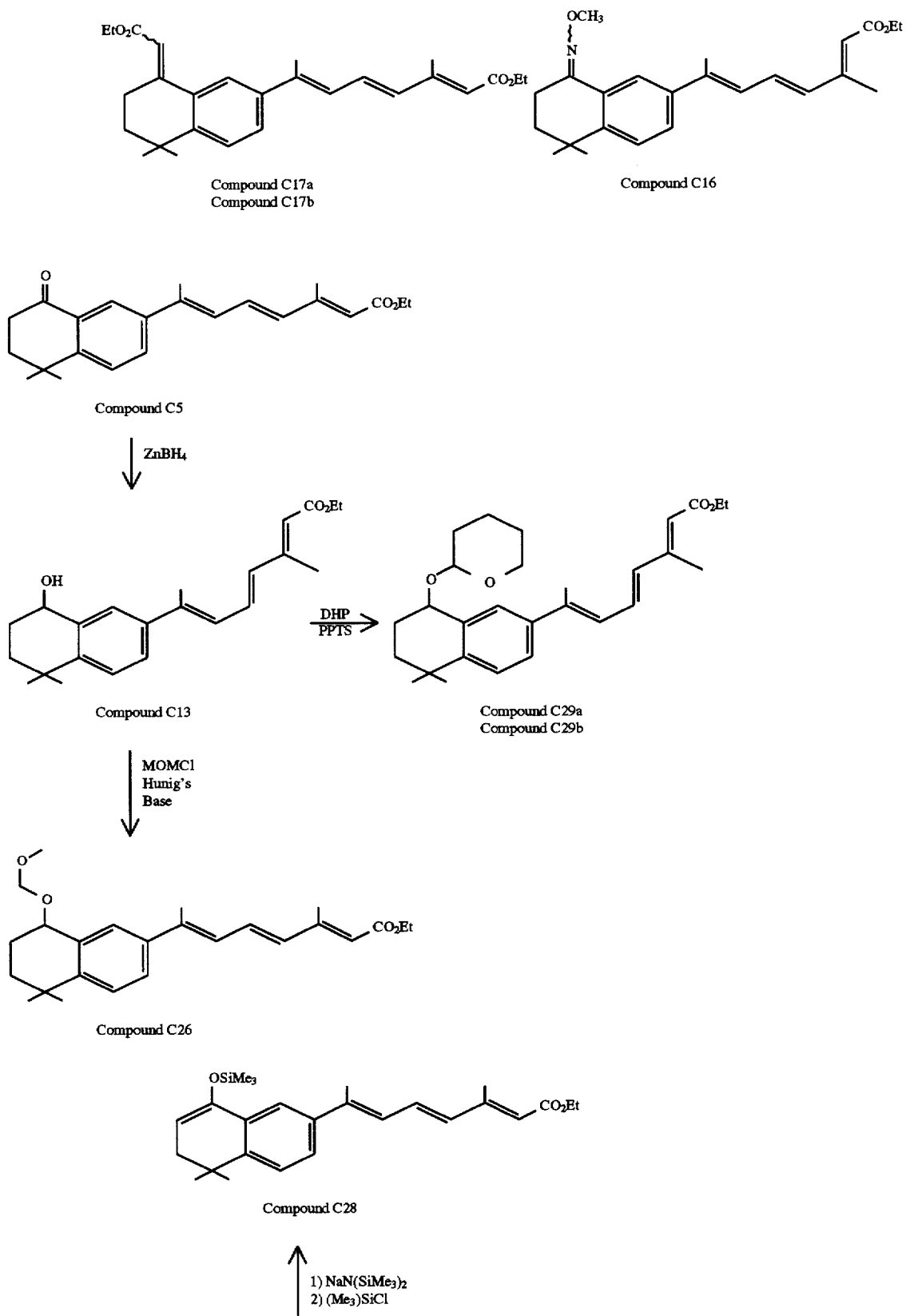

-continued
Reaction Scheme 7

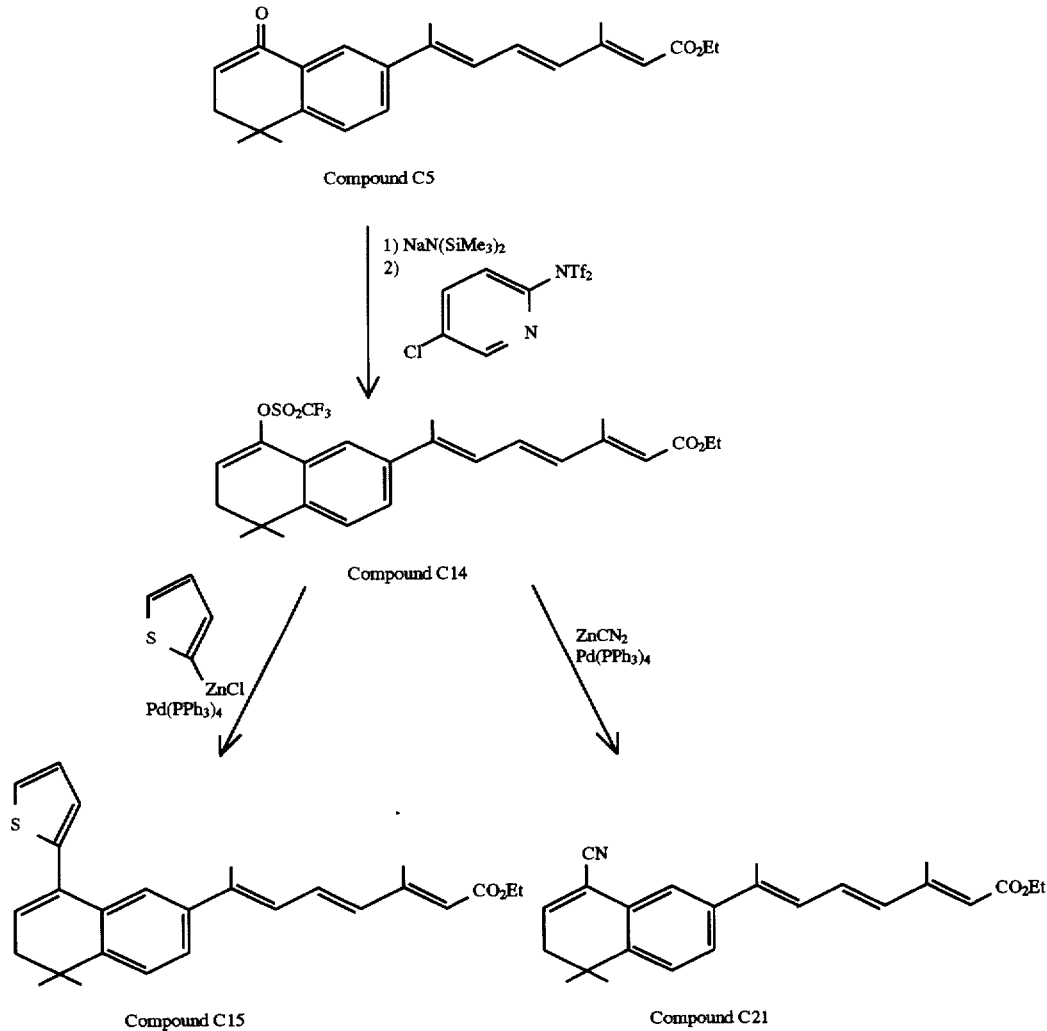

Reaction Scheme 7 discloses a preferred example of a synthetic route leading to compounds of the invention where with reference to Formulas 1–6 the symbol Z represents —$(CR_1=CR_1)_{n'}$—, where n' is 3, and there is no $Y(R_2)$ group. Thus, 4,4-dimethyl-7-acetyl-1,2,3,4-tetrahydronaphthalen-1(2H)-one (Compound D14a) is reacted in a Horner Emmons type reaction with triethylphosphonoacetate in the presence of sodium hydride in an ether type solvent such as tetrahydrofuran. Conditions of the Horner Emmons reaction are well known in the art, and it is also well known that usually a related Wittig type reaction can also be employed using a trialkylphosphonium reagent instead of the phosphonate reagent, to yield the same products as is obtained in the Horner Emmons reaction. The product of the Horner Emmons reaction in this example is ethyl 3-[4,4-dimethyl-1,2,3,4,-tetrahydronaphthalen-1(2H) one-7-yl]but-2(E)-enoate (Compound C2) which is reduced with diisobutyl aluminum hydride to provide 3-[1-hydroxy-4,4-dimethyl-1,2,3,4,-tetrahydronaphthalen-7-yl]but-2(E)-en-1-ol (Compound C3). Compound C3 is oxidized back to the aldehyde and ketone "stage" with manganese dioxide to give 3-[4,4-dimethyl-1,2,3,4,-tetrahydronaphthalen-1(2H) one-7-yl]but-2(E)-en-al (Compound C4). Compound C4 is subjected to yet another Horner Emmons type reaction with diethyl-(E)-3-ethoxycarbonyl-2-methylallylphosphonate (available from the chemical literature; see: Vuligunda et al. Biorganic Medical Chemistry Letters, (1996) 6 p213–218) in tetrahydrofuran in the presence of n-butyl lithium, to yield ethyl 7-[4,4-dimethyl-3,4,-dihydronaphthalen-1(2H)one-7-yl]-3,7-dimethyl-hept-2(E), 4(E), 6(E)trienoate (Compound C5).

Compound C5 of the invention is within the scope of Formula 2, and is also readily converted to further compounds of the invention in accordance with the generic principles disclosed in this specification. Several examples of reactions which provide further compounds of the invention using Compound C5 as the starting material are shown in Reaction Scheme 7. These reactions are described in less detail to the extent that they are of the types which have been described above. Thus, the "oxo" compound ethyl 7-[4,4-dimethyl-3,4,-dihydronaphthalen-1(2H)one-7-yl]-3,7-dimethyl-hept-2(E), 4(E), 6(E)trienoate (Compound C5) is saponified to yield the free acid (not shown in the scheme), is converted to the O-methyl-oxime derivative (Compound C16); to ethyl 7-[4,4-dimethyl-3,4-dihydro-1-(trimethylsiloxy)-naphth-7-yl]3,7-dimethyl-hepta-2(E),4(E),6(E)-trienoate (1-trimethylsilyloxy derivative Compound C28); and to ethyl 7-[4,4-dimethyl-3,4,-dihydronaphthalen-1-trifluoromethylsulfonyloxy-7-yl]-3,7-dimethyl-hept-2(E), 4(E), 6(E)trienoate ("triflate", Compound C14). Compounds C14 and C28 are within the scope of Formula 5, whereas Compound C16 is within the scope of Formula 4. Another Horner Emmons type reaction of Compound C5 which leads to compounds within the scope of Formula 3 (Compounds 17a and 17B) is shown in the scheme.

In the examples shown in Reaction Scheme 7 the "oxo" compound ethyl 7-[4,4-dimethyl-3,4,-dihydronaphthalen-1 (2H)one-7-yl]-3,7-dimethyl-hept-2(E), 4(E), 6(E)trienoate (Compound C5) is also reduced with ZnBH$_4$ to yield the corresponding secondary alcohol, ethyl 7-[4,4-dimethyl-1, 2,3,4,-tetrahydro naphthalen-1-hydroxy-7-yl]-3,7-dimethyl-hept-2(E), 4(E), 6(E)trienoate (Compound C13). Compound C13 is reacted with chloromethylmethyl ether to give (–/+)ethyl 7-[4,4-dimethyl-1,2,3,4-tetrahydro-1-(O-methoxymethyl)-naphth-7-yl]3,7-dimethyl-hepta-2(E),4(E), 6(E)-trienoate (Compound C26); alternatively it is reacted with 3,4-dihydro-2H-pyran in methylene chloride in the presence of p-toluene sulfonic acid (p-TsOH) to give the diastereomeric dihydropyranoxy derivatives, (+/–)ethyl 7-[4,4-dimethyl-1,2,3,4-tetrahydro-1(RS)-(2'(RS)-tetrahydropyranoxy)-naphth-2-yl]-3,7-dimethyl-hepta-2 (E),4(E),6(E)-trienoate (Compound C29a) and (+/–)ethyl 7-[4,4-dimethyl-1,2,3,4-tetrahydro-1(RS)-(2'(SR)-tetrahydropyranoxy)-naphth-2-yl]-3,7-dimethyl-hepta-2(E), 4(E),6(E)-trienoate (Compound C29b). Compounds C13, C26, C29a and C29b of the invention are within the scope of Formula 1.

The trifluoromethylsulfonate (triflate) derivative Compound C14 is itself an important starting material for the syntheses of several compounds of the invention within the scope of Formula 6; among these the preparations of ethyl 7-[4,4-dimethyl-3,4,-dihydronaphthalen-1-(2-thienyl)-7-yl] -3,7-dimethyl-hept-2(E), 4(E), 6(E)trienoate (Compound C15) and of ethyl 7-[4,4-dimethyl-3,4,-dihydronaphthalen-1-cyano-7-yl]-3,7-dimethyl-hept-2(E), 4(E), 6(E)trienoate (Compound 21) are illustrated in the reaction scheme.

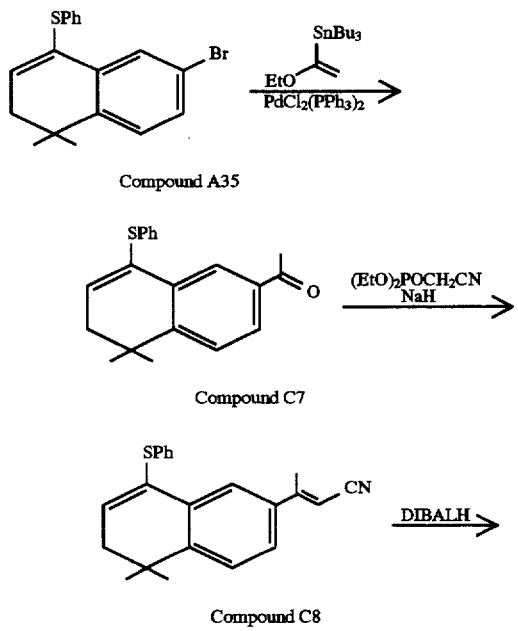

-continued
Reaction Scheme 8

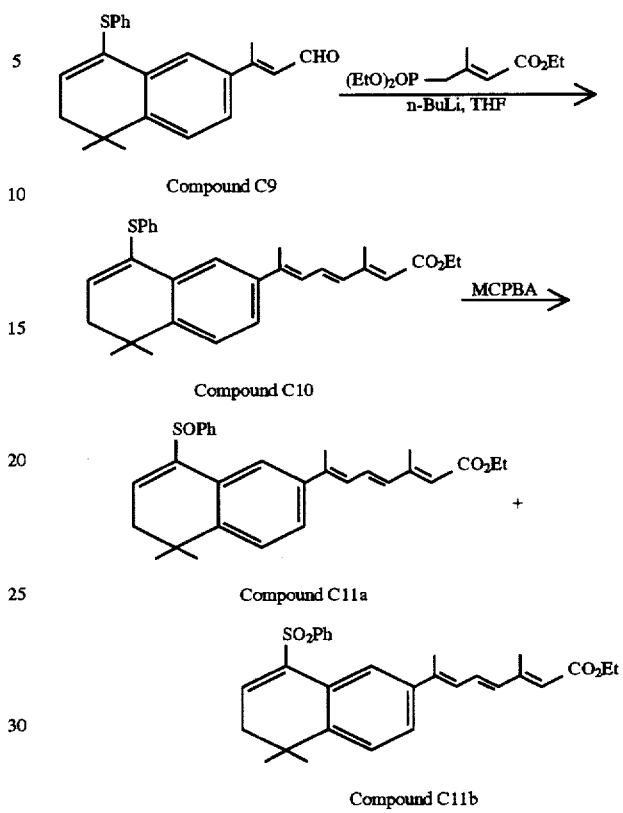

Reaction Scheme 8 discloses other examples for synthesizing preferred compounds of the invention where with reference to Formula 5 the symbol Z represents —(CR$_1$=CR$_1$)$_{n'}$—, where n' is 3, and there is no Y(R$_2$) group. The starting compound for the series of reactions shown in this scheme is 4,4-dimethyl-7-bromo-1-phenylthio-3,4-dihydronaphthalene (Compound A35) which can be obtained as shown in Reaction Scheme 3. Thus, referring now to Reaction Scheme 8, Compound A35 is reacted with 1-ethoxyvinyltributyltin (EVTB, available from Aldrich Chemical Co.) in the presence of bis (triphenylphosphine)palladium(II)chloride in tetrahydrofuran to provide, after acid work-up, 4,4-dimethyl-7-acetyl-1-phenylthio-3,4-dihydronaphthalene (Compound C7). Compound C7 is subjected to a Horner Emmons reaction (as described above) with diethylcyanomethylphosphonate (available from Aldrich Chemical Co.) to provide 3-[4,4-dimethyl-1-phenylthio-3,4-dihydronaphthalen-7-yl]but-2-en(E)-nitrile (Compound C8). Compound C8 is reduced with diisobutyl aluminium hydride to provide the corresponding aldehyde, 3-[4,4-dimethyl-1-phenylthio-3,4-dihydronaphthalen-7-yl]but-2-en(E)-aldehyde (Compound C9). Compound C9 is subjected to still another Horner Emmons reaction with the reagent diethyl-(E)-3-ethoxycarbonyl-2-methylallylphosphonate to yield ethyl 7-[4,4-dimethyl-1-phenylthio-3,4,-dihydronaphthalen-7-yl] -3,7-dimethyl-hept-2(E), 4(E), 6(E)trienoate (Compound C10). Compound C10 of the invention is within the scope of Formula 5.

In other preferred examples not shown in the schemes but described in the Specific Examples, a sequence of reaction which is analogous to the above-described reactions of Reaction Scheme 8 is conducted, starting with 7-bromo-1 (2H)-(propyliden-2-yl)-3,4-dihydro-4,4-dimethylnaphthalene (Compound A37), or with 7-bromo-1

(2H)-(phenylbenzylidenyl)-3,4-dihydro-4,4-dimethylnaphthalene (Compound C37) to provide further examples for compounds of the invention, such as ethyl-7-[1(2H)-(propyliden-2-yl)-3,4-dihydro-4,4-dimethyl-naphthalen-7-yl]-3,7-dimethyl-hept-2(E),4(E),6(E)-trienoate (Compound C36) and ethyl 7-[4,4-dimethyl-3,4-dihydro-1(2H)-phenylbenzylidenyl)-naphth-7-yl]-3,7-dimethyl-hepta-2(E),4(E),6(E)-trienoate (Compound C41). Compounds C36 and C41 of the invention are within the scope of Formula 3.

Compound C10 is converted by oxidation with meta-chloroperoxybenzoic acid to the corresponding sulfone and sulfoxide, ethyl 7-[4,4-dimethyl-1-phenylsulfonyl-3,4,-dihydronaphthalen-7-yl]-3,7-dimethyl-hept-2(E), 4(E), 6(E) trienoate (Compound C11a) and ethyl 7-[4,4-dimethyl-1-phenylsulfoxide-3,4,-dihydronaphthalen-7-yl]-3,7-dimethyl-hept-2(E), 4(E), 6(E)trienoate (Compound C11b), which are also within the scope of Formula 5.

Reaction Scheme 9

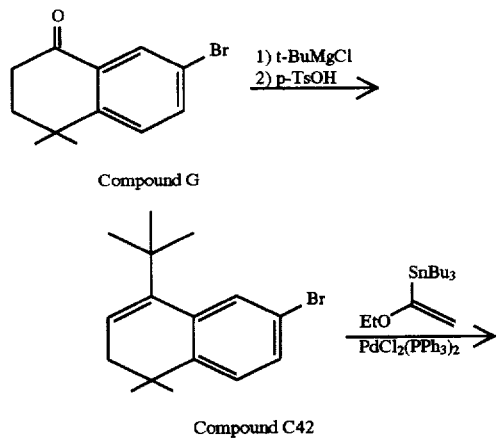

-continued
Reaction Scheme 9

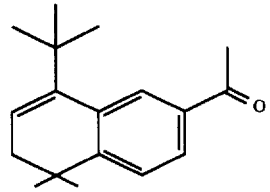

Compound C43

Reaction Scheme 9 discloses the preferred method of synthesis of a starting material from which certain examples for compounds of the invention within the scope of Formula 6 are preferably made. In accordance with this scheme 7-bromo-3,4-dihydro-4,4-dimethylnaphthalen-1(2H)-one (Compound G) is reacted with t-butylmagnesium chloride in tetrahydrofuran in the presence of 1,3-dimethyl-3,4,5,6-tetrahydro-2(H)-pyrimidinone (DMPU). Thereafter, the resulting intermediate tertiary alcohol is heated in the presence of acid (p-toluenesulfonic acid) to give 7-bromo-1-(1, 1-dimethylethyl)-3,4-dihydro-4,4-dimethylnaphthalene (Compound C42). Compound C42 is reacted with 1-ethoxyvinyltributyltin (EVTB) in the presence of Pal(0) catalyst to yield after acidic work-up 7-acetyl-1-(1,1-dimethylethyl)-3,4-dihydro-4,4-dimethylnaphthalene (Compound C43). Compound C43 is subjected to a sequence of reactions of the type described above in connection with Reaction Scheme 8, starting with a Horner Emmons reaction with diethyl cyanomethylphosphonate, to eventually provide ethyl 7-[4,4-dimethyl-3,4-dihydro-1-(1, 1-dimethylethyl)-naphth-7-yl]-3,7-dimethyl-hepta-2(E),4 (E),6(E)-trienoate (Compound C46). Compound C46 of the invention is within the scope of Formula 6.

Reaction Scheme 10

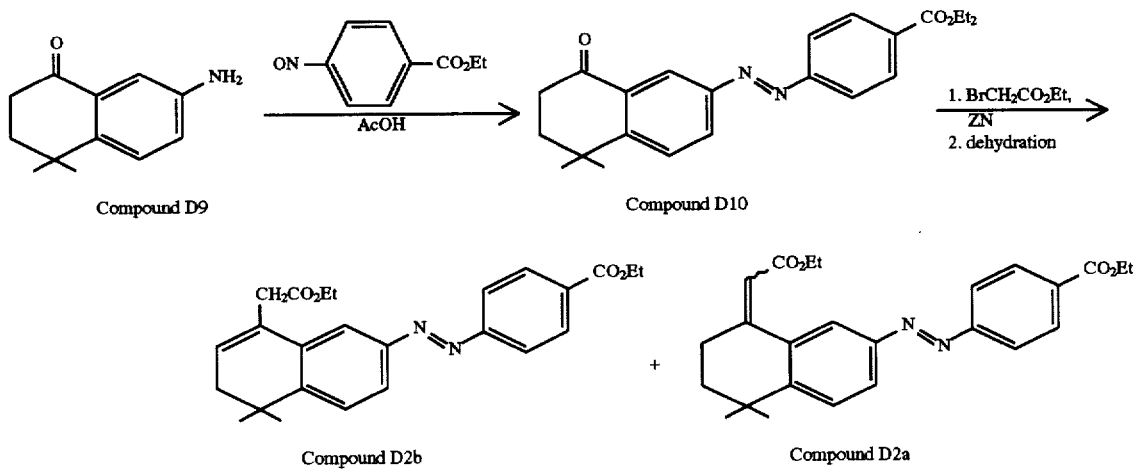

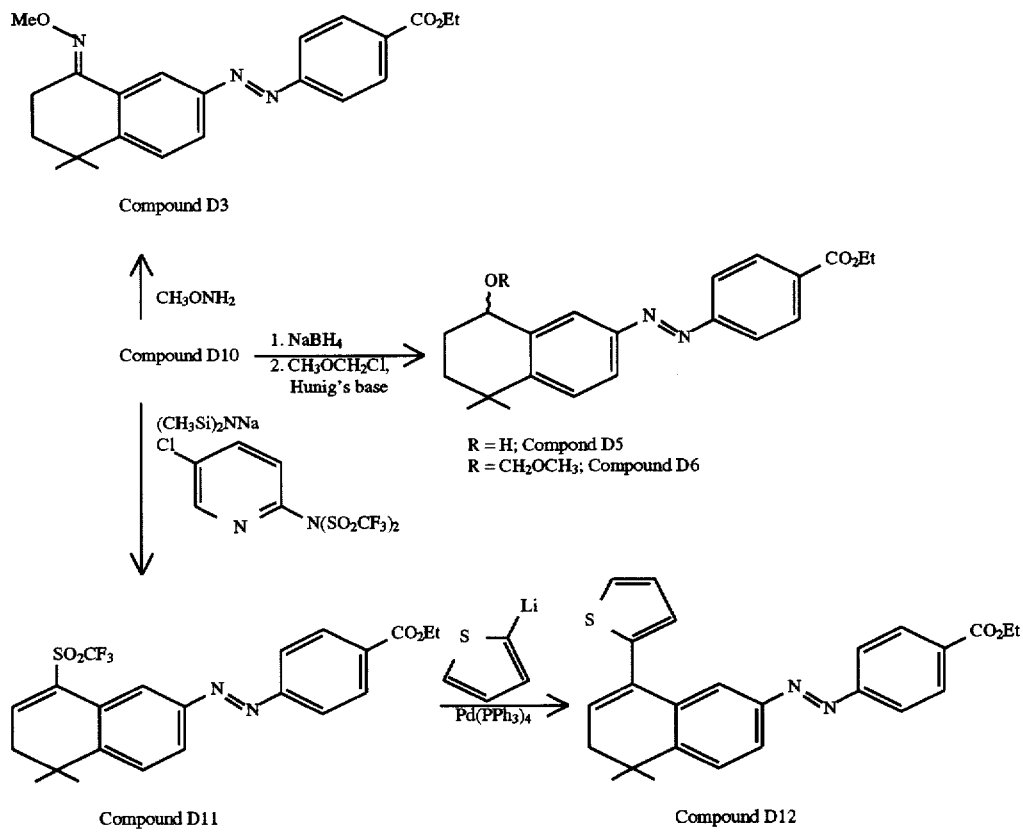

Reaction Scheme 10 discloses a preferred synthetic route to certain examplary compounds of the invention where, with reference to Formulas 1–6 the Z group is —N=N— (azo) moiety. For the examples shown in this scheme the starting compound is 3,4-dihydro-4,4-dimethyl-7-amino-naphthalen-1(2H)-one (Compound D9). Compound D9 is coupled with a nitroso compound of the formula ON-Y($R_2$) —A—B, which in the herein shown example is ethyl 4-nitrosobenzoate (available in accordance with the chemical literature; see Kagechika et al. J. Med. Chem. (1989) 32, 1098–1108). The coupling reaction is conducted in glacial acetic acid and yields ethyl 4-[(5,6-dihydro-5,5-dimethyl-8(7H)-one-naphthalen-2-yl)azo]-benzoate (Compound D10). Compound D10 of the invention is within the scope of Formula 2. Compound D10 is reacted in a Reformatsky reaction with ethyl bromoacetate to provide (+/–) ethyl 4-[(5,5-dimethyl-8-hydroxy-8-carbethoxymethyl-5,6,7,8-tetrahydronaphth-2-yl)azo]benzoate (Compound D1). Compound D1 of the invention is within the scope of Formula 1. Dehydration of Compound D1 with dicyclohexylcarbodiimide and cuprous chloride in benzene provides the isomeric compounds ethyl 4-[(5,5-dimethyl-8(7H)-(carbethoxymethylidenyl)-5,6-dihydronaphthalen-2-yl)azo]benzoate (Compound D2a) and ethyl 4-[(5,5-dimethyl-8-(carbethoxymethyl)-5,6-dihydronaphthalen-2-yl)azo]benzoate (Compound D2b). Compound D2a of the invention is within the scope of Formula 3, and Compound D2b is within the scope of Formula 6.

The "oxo" compound ethyl 4-[(5,6-dihydro-5,5-dimethyl-8(7H)-one-naphthalen-2-oyl)azo]-benzoate (Compound D10) serves as starting material for reactions which lead to further compounds of the invention in accordance with synthetic methodology that has been described above. More particularly, in the examples shown in Reaction Scheme 10 Compound D10 is converted into the O-methyl oxime derivative ethyl 4-[(8(7H)-anti-(O-methyl oxime)-5,5-dimethyl-5,6-dihydronaphthalen-2-yl)azo]benzoate (Compound D3), into the "triflate" ethyl 4-[(5,6-4 dihydro-5,5-dimethyl-8-(trifluoromethylsulfonyl)oxy-naphthalen-2-yl)azo]-benzoate (Compound D11) and is reduced to the secondary alcohol (+/–) ethyl 4-[(5,5-dimethyl-8-hydroxy-5,6,7,8-tetrahydronaphthalen-2-yl)azo]benzoate (Compound D3). The O-methyl oxime derivative (Compound D3) of the invention is within the scope of Formula 4, the "triflate" Compound D11 is in the scope of Formula 5, whereas the secondary alcohol Compound D5 is within the scope of Formula 1.

The secondary alcohol, Compound D5 is further converted into the methoxymethyl derivative (+/–) ethyl 4-[(5,5-dimethyl-8-(methoxymethyloxy)-5,6,7,8-tetrahydronaphthalen-2-yl) azo]benzoate (Compound D6) within the scope of Formula 1, and the "triflate" is reacted with thienyl lithium in the presence of $ZnCl_2$ and Pd(0) catalyst to provide ethyl 4-[(5,5-dimethyl-8-(2-thienyl)-5,6-dihydronaphthalen-2-yl)azo]benzoate (Compound D12).

Reaction Scheme 11

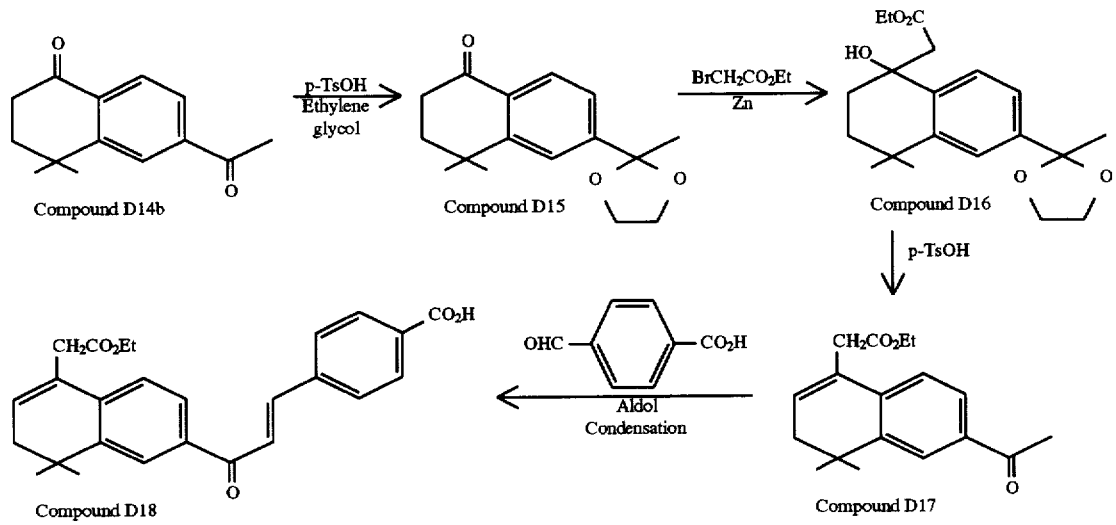

Referring now to Reaction Scheme 11 a preferred example for the synthesis of those compounds of the invention is described where, with reference to Formulas 1–6 the Z group is —CO—CR$_1$=CR$_1$—. As it will become apparent from the reaction scheme, these compounds are obtained as a result of an aldol condensation between an appropriately substituted tetrahydro or dihydronaphthalene ketone derivative and an aldehyde of the formula OCH—Y(R$_2$)A—B. In the example shown in Reaction Scheme 11 the exocyclic ketone function of 3,4-dihydro-4,4-dimethyl-6-acetyl-naphthalen-1(2H)-one (Compound D14b) is reacted with ethylene glycol and acid to provide 6-(2-methyl-1,3-dioxolan-2-yl)-3,4-dihydro-4,4-dimethylnaphthalen-1(2H)-one (Compound D15) where one ketone function is protected. Compound D15 is then reacted with ethyl bromoacetate in a Reformatsky reaction to give (+/−) 6-(2-methyl-1,3-dioxolan-2-yl)]-1,2,3,4-tetrahydro-4,4-dimethyl-1-hydroxyl-(carboethoxymethyl)-naphthlene (Compound D16). Treatment with acid of Compound D16 removes the 1,3-dioxolanyl protecting group and also introduces a double bond into the tetrahydronaphthalene nucleus, thus providing 3,4-dihydro-4,4-dimethyl-1-(carbethoxymethyl)-6-acetyl-naphthalene (Compound D17).

An alternate method for obtaining dihydronaphthalene compounds having the 6-acetyl substituent and a substituent in the 1-position (attached to the vinylic carbon) is to react Compound D15 with sodium bis(trimethylsilyl)amide and 2-[N,N-bis(trifluoromethylsulfonyl)amino]-5-chloropyridine in an inert ether type solvent, such as tetrahydrofuran, at low temperatures (−78° C. and 0° C.). As noted above in connection with an analogous "triflate" forming reaction, this reaction proceeds through a sodium salt intermediate which is usually not isolated. The overall reaction results in a trifluoromethylsulfonyloxy derivative, which is therafter reacted with an organometal derivative, again in analogy to the preceding description of synthesizing compounds a of Formula 6 from the "triflate" derivatives.

Returning now to the description of Reaction Scheme 11, Compound D17 is reacted with 4-carboxybenzaldehyde in an aldol condensation reaction to give ethyl (E)-4-[3-(3,4-dihydro-4,4-dimethyl-1-(carbethoxymethyl)-naphthalen-6-yl)-prop-1-en-3-one]benzoate (Compound D18). The just described aldol condensation reaction is conducted in the presence of base in an alcoholic solvent. Preferably, the reaction is conducted in methanol or ethanol in the presence of sodium hydroxide. Those skilled in the art will recognize the aldol condensation reaction of this example as a Claisen-Schmidt reaction. (See March: Advanced Organic Chemistry: Reactions, Mechanisms, and Structure, pp 694 695 McGraw Hill (1968). Examples of other reagents analogous to 4-carboxybenzaldehyde and suitable for the condensation reaction to introduce heterocyclic Y(R$_2$) groups into the compounds of the present invention 1) are: 5-carboxypyridine-2-carboxaldehyde, 4-carboxypyridine-2-carboxaldehyde, 4-carboxythiophene-2-carboxaldehyde, 5-carboxythiophene-2-carboxaldehyde, 4-carboxyfuran-2-carboxaldehyde, 5-carboxyfuran-2-carboxaldehyde, 4-carboxyacetophenone, 2-acetylpyridine-5-carboxylic acid, 2-acetylpyridine-4-carboxylic acid, 2-acetyl-thiophene-4-carboxylic acid, 2-acetylthiophene-5-carboxylic acid, 2-acetylfuran-4-carboxylic acid, and 2-acetylfuran-5-carboxylic acid. The latter compounds are available in accordance with the chemical literature; see for example Decroix et al., J. Chem. Res.(S), 1978, 4, 134; Dawson et al., J. Med. Chem., 1983, 29, 1282; and Queguiner et al., Bull Soc. Chimique de France, 1969, No. 10, pp 3678–3683. Compound D18 of the invention is within the scope of Formula 6.

To obtain further preferred examples of the compounds of the invention where the Z group is —CO—CR$_1$=CR$_1$ — the aldol condensation reaction shown in Reaction Scheme 11 is performed on the following compounds:

3,4-dihydro-4,4-dimethyl-6-acetyl-1-(1,1-dimethylethyl) naphthalene (Compound D19);

6-Acetyl-1(2H)-(propyliden-2-yl)-3,4-dihydro-4,4-dimethylnaphthalene (Compound D22);

(+/−) 1-(methoxymethyloxy)-6-acetyl-1,2,3,4-tetrahydro-4,4-dimethylnaphthalene (Compound D26); and 6-Acetyl-1(2H)-(O-methyl oxime)-3,4-dihydro-4,4-dimethylnaphthalene (Compound D28)

to provide respectively the following examples of compounds of the invention:

(E)-4-[3-(3,4-dihydro-4,4-dimethyl-1-(1,1-dimethyl-ethyl)naphth-6-yl)-prop-1-en-3-one]benzoic acid (Compound D20, Formula 6);

(E)-4[3-{1(2H)-(propyliden-2-yl)-3,4-dihydro-4,4-dimethylnaphthalen-6-yl}-prop-1-en-3-one]benzoic acid (Compound D23, Formula 3);

(E)-4-[3-(1,2,3,4-tetrahydro-4,4-dimethyl-1-(methoxymethyloxy)-naphthalen-6-yl)-prop-1-en-3-one]benzoic acid (Compound D27, Formula 1), and (E)-4[3-{1(2H)-(O-methyloxime)-3,4-dihydro-4,4-dimethylnaphthalen-6-yl}-prop-1-en-3-one]benzoic acid (Compound D29, Formula 4).
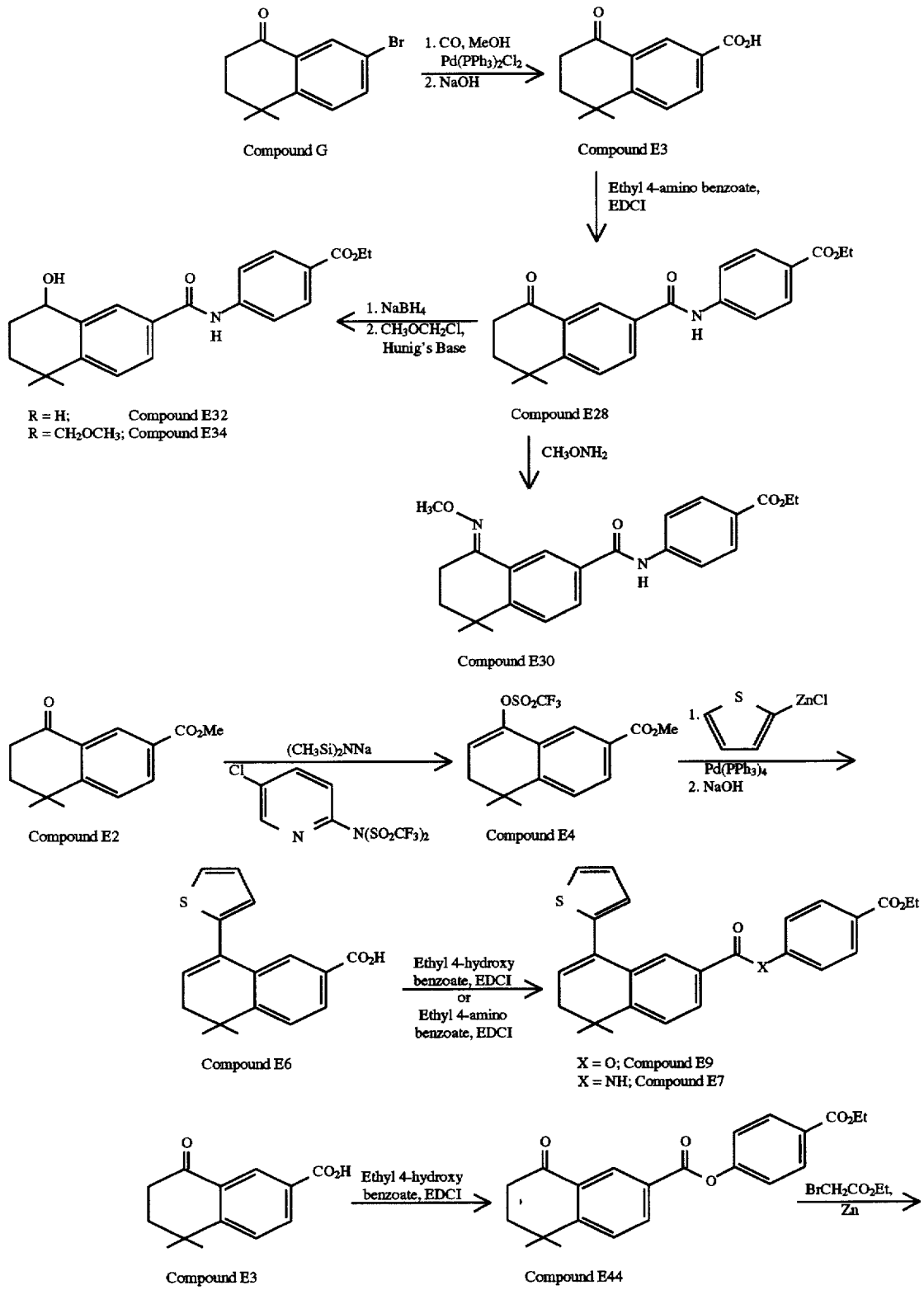
Reaction Scheme 12

-continued
Reaction Scheme 12

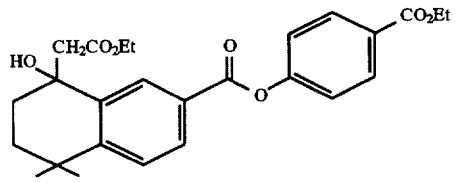

Compound E54

Reaction Scheme 12 discloses the presently preferred methods for synthesizing preferred examples of compounds of the invention where with reference to Formulas 1–6 the Z group is —COO— or —CONH—. As is shown in the scheme, 7-bromo-3,4-dihydro-4,4-dimethylnaphthalen-1 (2H)-one (Compound G) is reacted with carbon monoxide in the presence of palladium(II)-bis(triphenylphosphine) chloride, 1,3-bis(diphenylphosphino)-propane, DMSO, methanol and triethylamine to obtain the corresponding carboxylic acid methyl ester, methyl 5,5-dimethyl-5,6-dihydronaphthalen-8(7H)-one-2-carboxylate (Compound E2), which is thereafter saponified to provide 5,5-dimethyl-5,6-dihydro-naphthalen-8(7H)-one-2-carboxylic acid (Compound E3). Compound E3 is a free carboxylic acid which is reacted either with compounds of the formula H$_2$N—Y(R$_2$)—A—B to provide compounds of the invention where Z is —CONH—, or with compounds of the formula HO-Y(R$_2$)—A—B to provide compounds of the invention where Z is —COO—. Those skilled in the art will recognize that these compounds of the invention are amide and ester compounds, respectively. Generally speaking several known methods for amide and ester formation may be employed for their synthesis from Compound E3 or analogous carboxylic acid compounds. For example, Compound E3 or analogous carboxylic acid compounds can be converted into the acid chloride by known methods and thereafter reacted with the amines or esters of formula H$_2$N—Y(R$_2$)—A—B or formula HO—Y(R$_2$)—A—B respectively. The presently preferred method for synthesis, however utilizes the reagents 1-(3-dimethylaminopropyl)-3-ethylcarbodiimide hydrochloride (EDCI) and 4-N,N-dimethylaminopyridine in an aprotic solvent for the amide or ester formation. Those skilled in the art will also recognize that the compounds of formula H$_2$N—Y(R$_2$)—A—B and formula HO—Y(R$_2$)—A—B are aromatic or heteroaromatic amines or hydroxyl derivatives, which can be obtained in accordance with the state-of-the-art.

Referring now back to Reaction Scheme 12 that describes certain preferred specific examples, 5,5-dimethyl-5,6-dihydro-naphthalen-8(7H)-one-2-carboxylic acid (Compound E3) is reacted in the presence of 1-(3-dimethylaminopropyl)-3-ethylcarbodimide hydrochloride (EDCI) and 4-(dimethylamino)pyridine in methylene chloride to give ethyl 4-[(5,5-dimethyl-8-(7H)-one-5,6-dihydronaphthalen-2-yl)carboxamido]benzoate (Compound 28). Compound 28 of the invention is in the scope of Formula 2. Reaction Scheme 12 discloses its conversion by reactions of the type described above, to ethyl 4-[(5,5-dimethyl-8(7H)-anti-(O-methyloxime)-5,6-dihydronaphthalen-2-yl)carboxamido]benzoate (Compound E30, Formula 4) and (+/−) 4-[(5,5-dimethyl-8-hydroxy-5,6,7,8-tetrahydronaphthalen-2-yl)carboxamido]benzoic acid (Compound E32, Formula 1). Compound E32 is converted to the methoxymethyl derivative (+/−) ethyl 4-[(5,5-dimethyl-8-(O-methoxymethyl)-5,6,7,8-tetrahydronaphthalen-2-yl)carboxamido]benzoate (Compound E34) within the scope of Formula 1. Each of these amide compounds can have their respective COOEt group saponified to provide the free carboxylic acid or its salt.

Referring still to Reaction Scheme 12, methyl 5,5-dimethyl-5,6-dihydro-naphthalen-8(7H)-one-2-carboxylate (Compound E2) is converted, under conditions described above for analogous reactions, into the trifluoromethylsulfonyl ("triflate") derivative, methyl 5,5-dimethyl-5,6-dihydro-8-(trifluoromethylsulfonyl)oxy-naphthalene-2-carboxylate (Compound E4). Compound E4 serves as an important intermediate for the synthesis of compounds within the scope of Formula 6. In the preferred examples shown in the reaction scheme, Compound E4 is reacted with the lithium derivative of thiophene in the presence of ZnCl$_2$ and Pd(O) catalyst to provide the thienyl substituted carboxylic acid methyl ester, (Compound E5). The latter compound is saponified to give 5,5-dimethyl-5,6-dihydro-8-(2-thienyl)-naphthalene-2-carboxylic acid (Compound E6). Compound E6 is coupled with ethyl 4-aminobenzoate to give ethyl 4-[[(5,5-dimethyl-5,6-dihydro-8-(2-thienyl)-naphthalen-2-yl)carboxamido]-benzoate (Compound E7), and with ethyl 4-hydroxybenzoate to provide ethyl 4-[[(5,5-dimethyl-5,6-dihydro-8-(2-thienyl)-naphthalen-2-yl)carbonyl]oxy]-benzoate (Compound E9). Compounds E7 and E9 of the invention are within the scope of Formula 6.

As it will be readily recognized in the art, the free carboxylic acid derivatives of the invention could not be obtained (or could be obtained only with difficulty) from the carbonyloxy compounds of the present invention by a process of saponification of the ester compounds such as Compound E9. However, the above-mentioned free carboxylic acids, such as 4-[[(5,5-dimethyl-5,6-dihydro-8-(2-thienyl)-naphthalen-2-yl)carbonyl]oxy]-benzoic acid (Compound E11) can be obtained from the corresponding 2-(trimethylsilyl)ethyl esters (such as 2-(trimethylsilyl)ethyl 4-[[(5,5-dimethyl-5,6-dihydro-8-(2-thienyl)-naphthalen-2-yl)carbonyl]oxy]-benzoate, (Compound E10) by treatment with tetrabutylammonium fluoride. Compound E10 and like compounds can be obtained by coupling reactions of the type described above, utilizing, for example, 2-trimethylsilylethyl 4-hydroxybenzoate. The latter reactions are not shown in Reaction Scheme 12 but specific examples are described below.

5,5-Dimethyl-5,6-dihydro-naphthalen-8(7H)-one-2-carboxylic acid (Compound E3) is also coupled with ethyl 4-hydroxybenzoate to provide ethyl 4-[[(5,5-dimethyl-8 (7H)-one-5,6-dihydronaphthalen-2-yl)carbonyl]oxy] benzoate (Compound E44) within the scope of Formula 2. Compound E44 is subjected to a Reformatsky reaction with ethyl bromoacetate to yield (+/−) ethyl 4-[[(5,5-dimethyl-8-hydroxy-8-(carbethoxy)-5,6,7,8-tetrahydronaphthalen-2-yl) carbonyl]oxy]benzoate (Compound E54). Although the following reactions are not shown in the scheme, an additional preferred example of compounds of the invention is obtained when Compound E44 is reduced with sodium borohydride to give ethyl 4-[[(5,5-dimethyl-5,6,7,8-tetrahydro-8-hydroxynaphthalen-2-yl)carbonyl]oxy]-benzoate (Compound E40). The latter is converted into tetrahydropyranyl derivatives (within the scope of Formula 1) as is disclosed in detail in the Specific Examples.

To obtain still more specific examples for the compounds of the invention where the Z group is —COO— or —CONH— 7-bromo-3,4-dihydro-4,4-dimethylnaphthalen-1(2H)-one (Compound G) is subjected to a Reformatsky reaction with ethyl bromoacetate, and the resulting (+/−) ethyl 2-(1-hydroxy-1,2,3,4-tetrahydro-4,4-dimethyl-7-bromo-naphthalen-1-yl)acetate (Compound 47) is subjected to the series of reactions shown in Reaction Scheme 12. These compounds, although not specifically shown in the scheme, are disclosed in detail in the appended Specific Examples.

Reaction Scheme 13

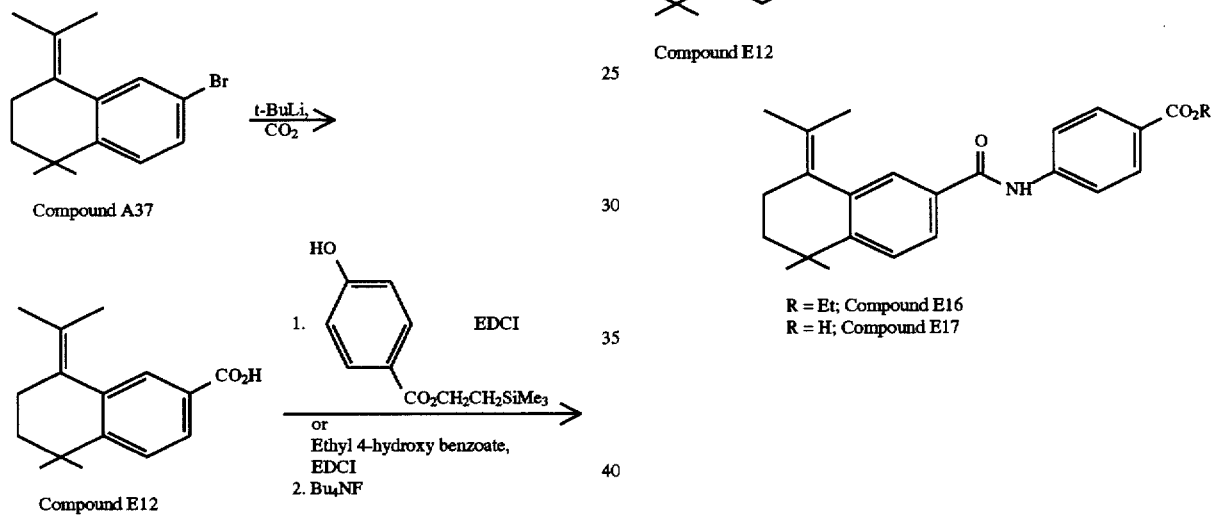

-continued
Reaction Scheme 13

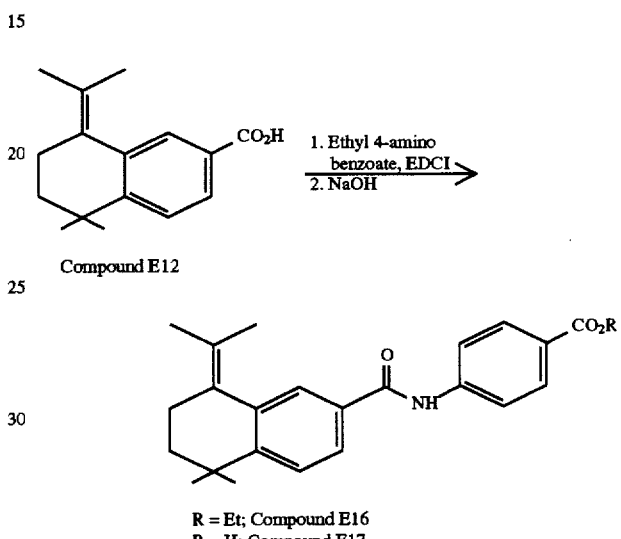

Reaction Scheme 14

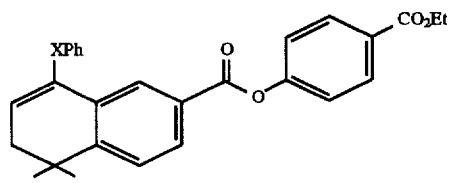

X = S;   Compound E23
X = SO2; Compound E24

-continued
Reaction Scheme 14

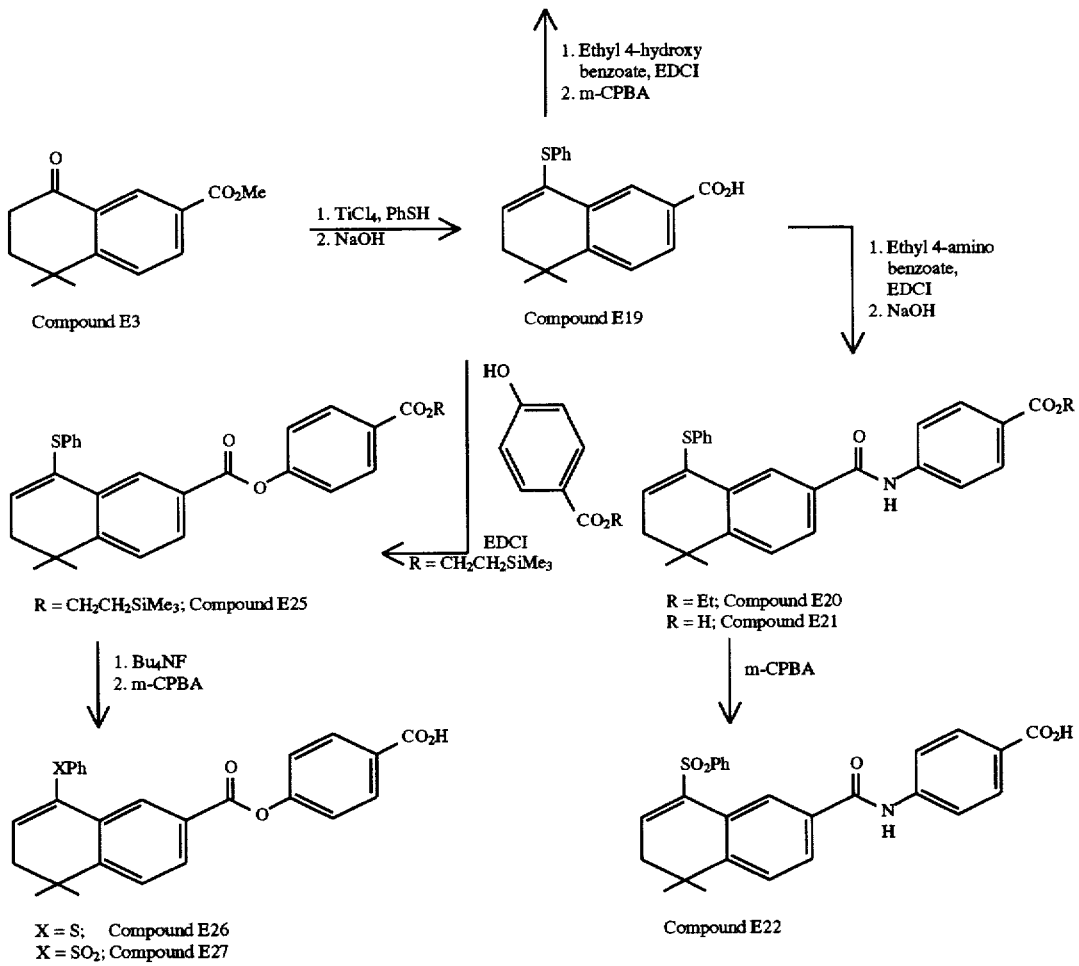

Reaction Scheme 13 discloses examples for the synthesis of several preferred compounds of the invention within the scope of Formula 3. The reactions shown in this scheme are analogous to the reactions disclosed in the foregoing description and reaction schemes and therefore will be readily understood by those skilled in the art and do not require further explanation here. A detailed experimental description for the preparation of compounds shown in this scheme is provided in the description of the Specific Examples. The same applies to Reaction Scheme 14, which discloses examples for the synthesis of several preferred compounds of the invention within the scope of Formula 5.

Compounds of the invention where with reference to the Formulas 1–6 the Z group is —N(O)═N— or —N═N (O)— can be prepared by oxidation of compounds where the Z group is —N═N—. A suitable oxidizing agent for this purpose is meta-chloroperoxybenzoic acid; typically both isomers of the azoxy compounds are formed in reactions using this agent.

Compounds of the present invention where with reference to Formula 1–6, Z is —OCO—, $NR_1CO$, as well as the corresponding thioester and thioamide analogs, can be prepared from the intermediates having a bromo function on the aromatic portion of the tetrahydronaphthalene or dihydronaphthalene nucleus, for example such as Compounds G, H, A35, A37, B15 and C42. In these compounds the bromo function is replaced with an amino or hydroxyl group, in analogy to the teachings of U.S. Pat. No. 5,324,744, the specification of which is expressly incorporated herein by reference.

Compounds of the present invention where with reference to Formula 1–6, Z is —N═$CR_1$— or —$CR_1$═N— will be readily recognized by those skilled in the art as Schiff bases. These compounds can be made by reaction between a primary amine and aldehyde or ketone. In order to obtain these compounds where the Z is —N═$CR_1$— an amine of the structure where the $NH_2$ group is attached to the aromatic portion of the tetrahydronaphthalene or dihydronaphthalene nucleus, is reacted with an aldehyde or ketone of the structure $OCR_1$—Y($R_2$)—A—B. An example for such an amine is Compound D9. Schiff bases of the structure where Z is —$CR_1$═N— can be obtained by reaction of an amine of the formula $NH_2$—Y($R_2$)—A—B with an aldehyde or ketone where the aldehyde or ketone function is attached to the aromatic portion of the tetrahydronaphthalene or dihydronaphthalene nucleus. Compounds D14a and D14b serve as examples.

Compounds of the present invention where with reference to Formula 1–6, the $X_1$ group is $[C(R_1)_2]_n$ and n is zero (0), can be made starting with 6-bromo-indan-1-one (or an appropriately substituted derivative). In these synthetic schemes 6-bromo-indan-1-one is used in analogy to 7-bromo-3,4-dihydro-4,4-dimethylnaphthalen-1(2H)-one (Compound G) as a starting material. 6-bromo-3,3- dimethyl-indan-1-one is available accordance with the chemical literature. (See Smith, J. G.,; Massicotte, M. P. *Org. Prep. Proced. Int.*, 1978, 10 123–131.)

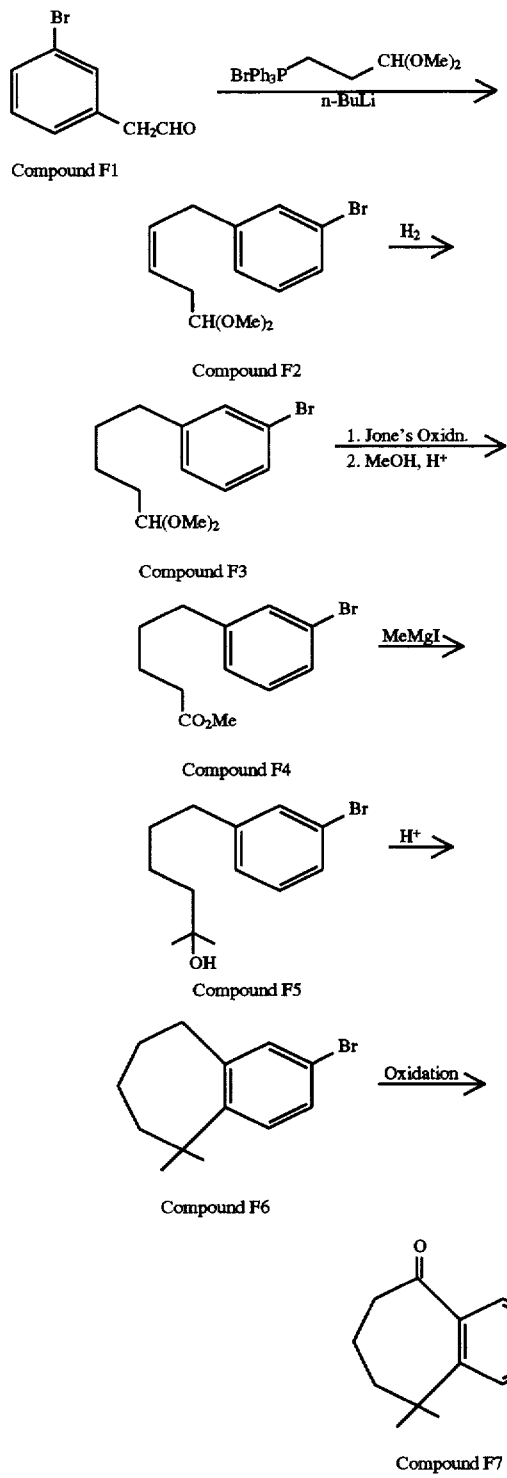

Reaction Scheme 15

Compound F1

Compound F2

Compound F3

Compound F4

Compound F5

Compound F6

Compound F7

Compounds of the invention where with reference to Formula 1–6, the $X_1$ group is $[C(R_1)_2]_n$ and n is 2 can be made from 8-bromo-2,3,4,5-tetrahydro-5,5-dimethyl-1-(2H)-suberan-one (Compound F7) which is used as a starting material in analogy to Compound G. Compound F7 can be made in accordance with the reaction sequence shown in Reaction Scheme 15. As is shown in the scheme, (3-bromophenyl)acetaldehyde (Compound F1) is subjected to a Wittig reaction to obtain a 5 carbon chain attached to the aromatic nucleus, and the resulting Compound F2 is hydrogenated and subjected to Jones oxidation followed by esterification, to provide methyl (3-bromophenyl)pentanoate (Compound F4). Compound F4 is reacted with a Grignard reagent to provide a tertiary alcohol (Compound F5), which is cyclized to provide 8-bromo-2,3,4,5-tetrahydro-5,5-dimethyl-suberan (Compound F6). Compound F6 is oxidized with $CrO_3$ to yield 8-bromo-2,3,4,5-tetrahydro-5,5-dimethyl-1-(2H)-suberan-one (Compound F7).

SPECIFIC EXAMPLES

Ethyl (4-bromophenyl)acetate (Compound A)

A solution of 43 g (200 mmol) of 4-bromophenylacetic acid and 0.2 g of conc. $H_2SO_4$ in 470 ml of ethanol was refluxed for 16 hours. The reaction mixture was cooled to ambient temperature, stirred with 6 g of solid $K_2CO_3$ for 30 minutes and then filtered. The filtrate was concentrated in vacuo, diluted with $Et_2O$ (200 ml), washed with 10% aqueous $NaHCO_3$ (10 ml) and brine (10 ml), dried over $MgSO_4$ and concentrated in vacuo to give the title compound as a colorless oil.

PMR ($CDCl_3$): δ 1.25 (3H, t, J=7.0 Hz), 3.56 (2H, s), 4.15 (2H, q, J=7.0 Hz), 7.16 (2H, d, J=8.4 Hz), 7.45 (2H, d, J=8.4 Hz).

Ethyl (3-bromophenyl)acetate (Compound B)

Employing the same general procedure as for the preparation of ethyl (4-bromophenyl)acetate (Compound A), 100 g (463 mmol) of 3-bromophenylacetic acid was converted into the title compound (yellow oil) using 2 g of conc. $H_2SO_4$ and 500 ml of ethanol.

PMR ($CDCl_3$): δ 1.26 (3H, t, J=7.0 Hz), 3.56 (2H, s), 4.16 (2H, q, J=7.0 Hz), 7.16–7.26 (2H, m), 7.38–7.46 (2H, m).

Ethyl 4-(4-bromophenyl)butanoate (Compound C)

To a cold solution (–78° C.) of 15 g (62 mmol) of ethyl (4-bromophenyl)acetate (Compound A) in 150 ml of $CH_2Cl_2$ was added dropwise (over a span of 1 hour) 65 ml (65 mmol) of diisobutylaluminum hydride (DIBAL-H, 1M solution in hexane). After the DIBAL-H addition was complete, the reaction was stirred at –78° C. for an additional hour. The reaction was quenched by the dropwise addition of methanol (10 ml), followed by water (10 ml) and 10% HCl (40 ml). The mixture was then warmed to 0° C., stirred for 10 minutes and then washed with water (15 ml), 10% aqueous $NaHCO_3$ (10 ml) and brine (10 ml). The organic phase was dried over $MgSO_4$ and the solvent distilled off at ambient temperature to give crude (4-bromophenyl)acetaldehyde. To a cold solution (0° C.) of this crude aldehyde in 150 ml of $CH_2Cl_2$ was added a solution of 26 g (74.6 mmol) of (carbethoxymethylene) triphenylphosphorane in 50 ml of $CH_2Cl_2$. The mixture was stirred for 16 hours, concentrated in vacuo and purified by flash chromatography (silica, 10% EtOAc-hexane) to give ethyl 4-(4-bromophenyl)but-2-enoate as a mixture of E:Z isomers. This isomeric mixture was dissolved in 150 ml of EtOAc and hydrogenated over 1 g of 10% Pd/C for 6 hours. The catalyst was filtered off and the filtrate concentrated in vacuo to give the title compound as a white solid.

PMR ($CDCl_3$): δ 1.26 (3H, t, J=7.1 Hz), 1.88–1.99 (2H, m), 2.31 (2H, t, J=7.5 Hz), 2.61 (2H, t, J=7.5 Hz), 4.28 (2H, q, J=7.1 Hz), 7.05 (2H, d, J=8.4 Hz), 7.40 (2H, d, J=8.4 Hz).

Ethyl 4-(3-bromophenyl)butanoate (Compound D)

Employing the same general multistep preparation as for ethyl 4-(4-bromophenyl)butanoate (Compound C), 60 g (246 mmol) of ethyl (3-bromophenyl)acetate (Compound B) was converted into the title compound (oil) using 255 ml (255 mmol) of diisobutylaluminum hydride (DIBAL-H, 1M in hexane), 85.8 g (250 mmol) of (carbethoxymethylene)triphenylphosphorane and 1.7 g of 10% Pd/C.

PMR (CDCl$_3$): δ 1.26 (3H, t, J=7.1 Hz), 1.89–2.00 (2H, m), 2.31 (2H, t, J=7.5 Hz), 2.63 (2H, t, J=7.2 Hz), 4.15 (2H, q, J=7.1 Hz), 7.10–7.35 (4H, m).

5-(3-bromophenyl)-2-methylpentan-2-ol (Compound E)

To a cold solution (0° C.) of 17 g (63 mmol) of ethyl 4-(3-bromophenyl)butanoate (Compound D) in 40 ml of THF was added 63 ml (189 mmol) of methylmagnesium bromide (3.0M solution in THF). The reaction was stirred at 0° C. for 2 hours, quenched by the slow addition of ice cold water (30 ml) followed by 10% HCl (30 ml) and then extracted with Et$_2$O (4×60 ml). The combined organic layer was washed with 10% aqueous NaHCO$_3$ (10 ml), water (10 ml) and brine (10 ml), dried over MgSO$_4$ and concentrated in vacuo. Purification by Kugelrohr distillation gave the title compound as a colorless oil.

PMR (CDCl$_3$): δ 1.20 (6H, s), 1.43–1.55 (2H, m), 1.62–1.78 (2H, m), 2.60 (2H, t, J=6.0 Hz), 7.10–7.41 (4H, m).

6-Bromo-1,2,3,4-tetrahydro-1,1-dimethylnaphthalene (Compound F)

15.0 g (58.3 mmol) of 5-(3-bromophenyl)-2-methylpentan-2-ol (Compound E) was cooled to 0° C. and then 2.8 ml of conc. H$_2$SO$_4$ was added. The mixture was stirred for 2.5 hours, diluted with water (20 ml) and extracted with Et$_2$O (3×40 ml). The combined organic layers were washed with water, sat. aqueous NaHCO$_3$ and brine, dried over MgSO$_4$ and concentrated in vacuo. Purification by Kugelrohr distillation gave the title compound as a colorless oil.

PMR (CDCl$_3$): δ 1.25 (6H, s), 1.61–1.66 (2H, m), 1.74–1.82 (2H, m), 2.73 (2H, t, J=6.0 Hz), 7.16–7.26 (3H, m).

7-Bromo-3,4-dihydro-4,4-dimethylnaphthalen-1(2H)-one (Compound G)

To a cold mixture (0° C.) of 209 g (200 mmol) of chromium trioxide, 100 ml (1.06 mol) of acetic anhydride and 200 ml (3.5 mol) of acetic acid was added a solution of 10 g (41.8 mmol) of 6-bromo-1,2,3,4-tetrahydro-1,1-dimethylnaphthalene (Compound F) in 125 ml of benzene. The reaction mixture was stirred for 1 hour, quenched with ice cold water and extracted with Et$_2$O (3×100 ml). The organic layer was dried over MgSO$_4$, concentrated in vacuo, and purified by column chromatography (silica, 10% EtOAc-hexane) to give the title compound as a white solid.

PMR (CDCl$_3$): δ 1.28 (6H, s), 2.01 (2H, t, J=6.0 Hz), 2.72 (2H, t, J=6.0 Hz), 7.31 (1H, d, J=9.0 Hz), 7.61 (1H, dd, J=3.0, 9.0 Hz), 8.11 (1H, d, J=3.0 Hz).

6-Bromo-3,4-dihydro-4,4-dimethylnaphthalen-1(2H)-one (Compound H)

Employing a published procedure (Mathur, N. C.; Snow, M. S.; Young, K. M.; and Pincock, J. A. Tetrahedron, 41, 1509–1516 (1985)), ethyl 4-(4-bromophenyl)butanoate (Compound C) was converted into the title compound. Alternatively, the title compound can be obtained using similar reactions that were used to convert ethyl 4-(3-bromophenyl)butanoate (Compound D) into 7-bromo-3,4-dihydro-4,4-dimethylnaphthalen-1(2H)-one (Compound G)

Ethyl (E)-4-[2-(5,6-dihydro-5,5-dimethyl-naphthalen-8(7H)-one-2-yl)ethenyl]-benzoate (Compound A2)

To a solution of 520.0 mg (2.00 mmol) of 3,4-dihydro-4,4-dimethyl-7-bromo-naphthalen-1(2H)-one (Compound G), and 510.0 mg (2.90 mmol) of ethyl 4-vinylbenzoate in 4.0 mL of triethylamine (degassed by sparging with argon for 25 minutes), was added 124.0 mg (0.40 mmol) of tris(2-methylphenyl) phosphine, followed by 44.0 mg (0.20 mmol) of palladium(II)acetate. The resulting solution was heated to 95° C. for 2.5 h, cooled to room temperature, and concentrated under reduced pressure. Purification by column chromatography (10% EtOAc/hexanes) afforded the title compound as a colorless solid.

$^1$H NMR (CDCl$_3$): δ 1.41 (t, J=7.1 Hz, 3H), 1.41 (s, 6H), 2.04 (t, J=6.5 Hz, 2H), 2.76 (t, J=6.5 Hz, 2H), 4.39 (q, J=7.1 Hz, 2H), 7.20 (s, 2H), 7.45 (d, J=8.2 Hz, 1H), 7.57 (d, J=8.4 Hz, 2H), 7.69 dd, J=2.0, 8.2 Hz, 1H), 8.03 (d, J=8.4 Hz, 2H), 8.19 (d, J=2.0 Hz, 1H).

(E)-4-[2-(5,6,7,8-tetrahydro-5,5-dimethyl-8-oxo-2-naphthalenyl)ethenyl]-benzoic acid (Compound A2a)

Employing the same general procedure as for the preparation of (E)-4-[2-(5,6,7,8-tetrahydro-5,5-dimethyl-8-anti-(O-methyl oxime)-2-naphthalenyl)ethenyl]-benzoic acid (Compound A4) 110 mg (0.32 mmol) of ethyl (E)-4-[2-(5,6,7,8-tetrahydro-5,5-dimethyl-8-oxo-2-naphthalenyl)ethenyl]-benzoate (Compound A2) was converted into the title compound using 1.0 mL (1.5 mmol) of LiOH (1.5M aqueous solution) and 0.5 mL of methanol. 1H NMR (DMSO) δ 1.36 (s, 6 H), 1.96 (t, J=6.7 Hz, 3 H), 2.69 (t, J=6.7 Hz, 2 H), 7.35 (d, J=16.4 Hz, 1 H), 7.49 (d, J=16.4 Hz, 1 H), 7.58 (d, J=8.4 Hz, 1 H), 7.74 (d, J=8.4 Hz, 2 H), 7.89 (overlapping d, 3 H), 8.05 (s, 1 H).

Ethyl (E)-4-[2-(5,5-dimethyl-5,6,-dihydro-8(7H)-anti-(O-methyl oxime)-naphthalen-2-yl)ethenyl]-benzoate (Compound A3)

A solution of 298 mg (0.85 mmol) of ethyl (E)-4-[2-(5,5-dimethyl-5,6,-dihydro-naphthalen-8(7H)-one-2-yl) ethenyl]-benzoate (Compound A2), 290 mg (3.4 mmol) of methoxylamine hydrochloride and 610 mg (4.5 mmol) of sodium acetate in 7.0 mL of EtOH and 5.0 mL of tetrahydrofuran was stirred at ambient temperature for 96 h and refluxed for 3 h. An additional 0.24 g (1.8 mmol) of methoxylamine hydrochloride was added and the mixture refluxed for another 1 h. The mixture was concentrated in vacuo, the residue was diluted with water and extracted with EtOAc (2×). The combined organic layer was dried over MgSO$_4$, and concentrated in vacuo. The crude material was purified by flash chromatography (silica, 5% ethyl acetate in hexanes) to afford the title compound as a yellow oil.

$^1$H NMR (CDCl$_3$): δ 1.30 (s, 6 H), 1.41 (t, J=7.1 Hz, 3 H), 1.73 (t, J=6.9 Hz, 2 H), 2.80 (t, J=6.9 Hz, 2 H), 4.04 (s, 3H), 4.39 (q, J=7.1 Hz, 2 H), 7.13 (d, J=16.4 Hz, 1 H), 7.22 (d, J=16.4 Hz, 1 H), 7.36 (d, J=8.2 Hz, 1 H), 7.50 (dd, J=2.0, 8.2 Hz, 1 H), 7.57 (d, J=8.4 Hz, 2 H), 8.03 (d, J=8.4 Hz, 2 H), 8.11 (d, S=2.0 Hz, 1 H).

(E)-4-[2-(5,5-Dimethyl-5,6,-dihydro-8(7H)-anti-(O-methyl oxime)-naphthalen-2-yl)ethenyl]-benzoic acid (Compound A4)

To a solution of 183 mg (0.48 mmol) of ethyl (E)-4-[2-(5,5-dimethyl-5,6,-dihydro-8(7H)-anti-(O-methyl oxime)-naphthalen-2-yl)ethenyl]-benzoate (Compound A3) in 4.0 mL of tetrahydrofuran and 1.0 mL of methanol was added 1.0 mL (2.4 mmol) of LiOH (2.4M aqueous solution). The mixture was stirred at ambient temperature for 19 h, and concentrated in vacuo. The residue was diluted with water and acidified to pH 1 with 10% HCl, and extracted with ethyl acetate (2×). The organic phase was washed with brine, dried with MgSO$_4$ and concentrated in vacuo. Recrystallization of the crude product using acetonitrile afforded the title compound as white crystals.

$^1$H NMR (DMSO-D$_6$): δ 1.24 (s, 6 H), 1.66 (t, J=6.6 Hz, 2 H), 2.72 (t, J=6.6 Hz, 2 H), 3.95 (s, 1 H), 7.26 (d, J=16.5 Hz, 1 H), 7.44 (d, J=8.2 Hz, 1 H), 7.44 (d, J=16.5 Hz, 1 H), 7.67 (d, J=8.2 Hz, 1 H), 7.74 (d, J=8.1 Hz, 2 H), 7.92 (d, J=8.1 Hz, 2 H), 8.01 (s, 1 H).

Ethyl (E)-4-[2-(5,5-dimethyl-5,6,-dihydro-8(7H)-anti-(O-ethyl oxime)-naphthalen-2-yl)ethenyl]-benzoate (Compound A5)

Employing the same general procedure as for the preparation of ethyl (E)-4-[2-(5,5-dimethyl-5,6,-dihydro-8(7H)-anti-(O-methyl oxime)-naphthalen-2-yl)ethenyl]-benzoate (Compound A3) 146 mg (0.42 mmol) of ethyl (E)-4-[2-(5,5-dimethyl-5,6, dihydronaphthalen-8(7H)-one-2-yl)ethenyl]-benzoate (Compound A2) was converted into the title compound (white solid) using 167 mg (1.7 mmol) of ethoxylamine hydrochloride, 337 mg (2.5 mmol) of sodium acetate, 5.0 mL of EtOH and 1.0 mL of tetrahydrofuran.

$^1$H NMR (CDCl$_3$): δ 1.28 (s, 6 H), 1.35 (t, J=7.1 Hz, 3 H), 1.39 (t, J=7.1 Hz, 3 H), 1.71 (t, J=6.9 Hz, 2 H), 2.80 (t, J=6.9 Hz, 2 H), 4.27 (q, J=7.1 Hz, 2 H), 4.37 (q, J=7.1 Hz, 2 H), 7.11 (d, J=16.4 Hz, 1 H), 7.21 (d, J=16.4 Hz, 1 H), 7.34 (d, J=8.2 Hz, 1 H), 7.48 (dd, J=1.9, 8.2 Hz, 1 H), 7.55 (d, J=8.4 Hz, 2 H), 8.01 (d, J=8.4 Hz, 2 H), 8.11 (d, J=1.9 Hz, 1 H).

(E)-4-[2-(5,5-Dimethyl-5,6,-dihydro-8(7H)-anti-(O-ethyl oxime)-naphthalen-2-yl)ethenyl]-benzoic acid (Compound A6)

Employing the same general procedure as for the preparation of (E)-4-[2-(5,5-dimethyl-5,6,-dihydro-8(7H)-anti-(O-methyl oxime)-naphthalen- 2-yl)ethenyl]-benzoic acid (Compound A4) 81 mg (0.21 mmol) of ethyl (E)-4-[2-(5,5-dimethyl-5,6-dihydro-8(7H)-anti-(O-ethyl oxime)-naphthalen-2-yl)ethenyl]-benzoate (Compound A5) was converted into the title compound (white solid) using 1.0 mL (1.8 mmol) of LiOH (1.8M aqueous solution).

$^1$H NMR (Acetone-D$_6$): δ 1.30 (s, 6 H), 1.31 (t, J=7.1 Hz, 3 H), 1.73 (t, J=6.9 Hz, 2 H), 2.78 (t, J=6.9 Hz, 2 H), 4.23 (q, J=7.1 Hz, 2 H), 7.30 (d, J=16.4 Hz, 1H), 7.41 (d, J=16.4 Hz, 1 H), 7.41 (d, J=8.2 Hz, 1 H), 7.66 (dd, J=1.9, 8.2 Hz, 1 H), 7.76 (d, J=8.4 Hz, 2 H), 8.03 (d, J=8.4 Hz, 2 H), 8.15 (d, J=1.9 Hz, 1 H).

Ethyl (E)-4-[2-(5,5-dimethyl-5,6,-dihydro-8(7H)-anti-(oxime )-naphthalen-2-yl)ethenyl]-benzoate (Compound A7)

Employing the same general procedure as for the preparation of ethyl (E)-4-[2-(5,5-dimethyl-5,6,-dihydro-8(7H)-anti-(O-methyl oxime)-naphthalen-2-yl)ethenyl]-benzoate (Compound A3) 190 mg (0.55 mmol) of ethyl (E)-4-[2-(5,5-dimethyl-5,6-dihydronaphthalen-8(7H)-one-2-yl)ethenyl]-benzoate (Compound A2) was converted into the title compound using 152 mg (1.7 mmol) of hydroxylamine hydrochloride, 430 mg (3.2 mmol) of sodium acetate, 6.0 mL of EtOH and 1.0 mL of tetrahydrofuran.

$^1$H NMR (CDCl$_3$): δ 1.32 (s, 6 H), 1.41 (t, J=7.1 Hz, 3 H), 1.77 (t, J=7.0 Hz, 2 H), 2.91 (t, J=7.0 Hz, 2 H), 4.39 (q, J=7.1 Hz, 2 H), 7.13 (d, J=16.4 Hz, 1 H), 7.20 (d, J=16.4 Hz, 1 H), 7.39 (d, J=8.2 Hz, 1 H), 7.49 (m, J=1.8 Hz, 1 H), 7.53 (d, J=8.4 Hz, 2 H), 8.02 (d, J=8.4 Hz, 2 H), 8.08 (d, J=1.8 Hz, 1 H), 8.48 (s, 1 H).

(E)-4-[2-(5,5-Dimethyl-5,6,-dihydronaphthalen-8(7H)-anti(oxime)-2-yl)ethenyl]-benzoic acid (Compound A8)

Employing the same general procedure as for the preparation of (E)-4-[2-(5,5-dimethyl-5,6,-dihydro-8(7H)-anti-(O-methyl oxime)-naphthalen-2-yl)ethenyl]-benzoic acid (Compound A4) 104 mg (0.29 mmol) of ethyl (E)-4-[2-(5,5-dimethyl-5,6,-dihydro-8(7H)-anti-(oxime)-naphthalen-2-yl)ethenyl]-benzoate (Compound A7) was converted into the title compound using 1.0 mL (1.5 mmol) of LiOH (1.5M aqueous solution).

$^1$H NMR (DMSO-D$_6$): δ 1.24 (s, 6 H), 1.66 (t, J=6.7 Hz, 2 H), 1.71 (t, J=6.7 Hz, 2 H), 7.23 (d, J=16.5 Hz, 1 H), 7.41 (d, J=8.3 Hz, 1 H), 7.42 (d, J=16.5 Hz, 1 H), 7.62 (dd, J=1.7, 8.3 Hz, 1 H), 7.73 (d, J=8.5 Hz, 2 H), 7.92 (d, J=8.5 Hz, 2 H), 8.03 (d, J=1.7 Hz, 1 H).

Ethyl (E)-4-[2-(5,6-dihydro-5,5-dimethyl-8-(trifluoromethylsulfonyl)oxy-naphthalen-2-yl)ethenyl]-benzoate (Compound A9)

To a cold (−78° C.) solution of 440.0 mg (2.40 mmol) of sodium bis(trimethylsilyl)amide in 10.0 mL of THF was added 700.0 mg (2.00 mmol) of ethyl (E)-4-[2-(5,6-dihydro-5,5-dimethyl-naphthalen-8(7H)-one-2-yl)ethenyl]-benzoate (Compound A2) as a solution in 25.0 mL of THF. After stirring at −78° C. for 1.5 h, 960.0 mg (2.40 mmol) of 2[N,N-bis trifloromethylsulfonyl)amino]-5-chloropyridine was added in one portion. After 30 min, the solution was warmed to 0° C. and stirred for 3 h. The reaction was quenched by the addition of saturated aqueous NH$_4$Cl, and extracted with EtOAc. The combined extracts were washed with 5% aqueous NaOH, dried (NaSO$_4$), and the solvents removed under reduced pressure. The title compound was isolated as a colorless solid after column chromatography (7% EtOAc/hexanes).

$^1$H NMR (CDCl$_3$): δ 1.32 (s, 6H), 1.41 (t, J=7.1 Hz, 3H), 2.43 (d, J=4.9 Hz, 2H), 4.39 (q, J=7.1 Hz, 2H), 6.00 (t, J=4.9 Hz, 1H), 7.10 (d, J=16.4 Hz, 1H), 7.20 (d, J=16.4 Hz, 1H), 7.33 (d, J=8.0 Hz, 1H), 7.49 (d, J=8.0 Hz, 1H), 7.52 (s, 1H), 7.57 (d, J=8.4 Hz, 2H), 8.04 (d, J=8.4 Hz, 1H).

Ethyl (E)-4-[2-(5,5-dimethyl-8-(thiazol-2-yl)-5,6-dihydronaphthalen-2-yl)ethenyl]-benzoate (Compound A10)

To a cold (−78° C.) solution of thiazole (0.38 g (0.10 mL, 1.4 mmol) in THF (2.0 mL) was added n-butyl lithium (1.6M solution in hexanes, 0.5 mL, 0.8 mmol) and stirred for 30 min. To this solution was added 0.176 g (1.3 mmol) of zinc chloride in 3.0 mL of tetrahydrofuran and stirred for 45 min. The resulting turbid solution was transferred, via cannula, to a flask containing a mixture of 0.17 g (0.35 mmol) of ethyl (E)-4-[2-(5,5-dimethyl-8-(trifluoromethylsulfonyl)oxy-5,6-dihydronaphthalen-2-yl)

ethenyl]benzoate (Compound A9) and 15 mg (0.01 mmol) of tetrakis(triphenylphosphine)palladium(0) in 3.0 mL of tetrahydrofuran. The reaction mixture was stirred for 1 h at ambient temperature and 1.5 h at 55° C. The reaction mixture was treated with aqueous NH$_4$Cl, and extracted with EtOAc (2×). The combined organic layer was washed with brine and dried (MgSO$_4$). The solvent was removed under reduced pressure and the crude product was purified by flash chromatography (silica, 20% ethyl acetate in hexane) to afford the title compound as a white solid.

$^1$H NMR (CDCl$_3$): δ 1.34 (s, 6 H), 1.40 (t, J=7.1 Hz, 3 H), 2.41 (d, J=4.9 Hz, 2 H), 4.37 (q, J=7.1 Hz, 2 H), 6.56 (t, J=4.9 Hz, 1 H), 7.03 (d, J=16.4 Hz, 1 H), 7.18 (d, J=16.4 Hz, 1 H), 7.34 (d, J=3.4 Hz, 1 H), 7.38 (d, J=8.1 Hz, 1 H), 7.48 (dd, J=1.8, 8.4 Hz, 1 H), 7.53 (d, J=8.4 Hz, 2 H), 7.86 (d, J=1.8 Hz, 1 H), 7.93 (d, J=3.4 Hz, 1 H), 8.00 (d, J=8.4 Hz, 2 H).

(E)-4-[2-(-5,5-Dimethyl-8-(thiazol-2-yl)-5,6-dihydronaphthalen-2-yl)ethenyl]-benzoic acid (Compound A12)

Employing the same general procedure as for the preparation of (E)-4-[2-(5,5-dimethyl-5,6,-dihydro-8(7H)-anti-(O-methyl oxime)-naphthalen- 2-yl)ethenyl]-benzoic acid (Compound A4), 20 mg (0.05 mmol) of ethyl (E)-4-[2-(5,6-dihydro-5,5-dimethyl-8-(thiazol-2-yl)-naphthalen-2-yl) ethenyl]-benzoate (Compound A10) was converted into the title compound (white solid).

$^1$H NMR (CDCl$_3$): δ 1.28 (s, 6 H), 2.39 (d, J=4.9 Hz, 2 H), 6.63 (t, J=4.9 Hz, 1 H), 7.15 (d, J=16.4 Hz, 1 H), 7.36 (d, J=16.4 Hz, 1 H), 7.43 (d, J=8.2 Hz, 1 H), 7.63 (d, J=8.2 Hz, 1 H), 7.70 (d, J=8.2 Hz, 2 H), 7.77 (d, J=3.3 Hz, 1 H), 7.90 (m, J=8.2 Hz, 3 H), 7.97 (d, J=3.3 Hz, 1 H).

Ethyl (E)-4-[2-(-5,5-dimethyl-8-(2-thienyl)-5,6-dihydronaphthalen-2-yl)ethenyl]-benzoate (Compound A13)

A solution of lithiothiophene was prepared by the addition of 0.10 g (0.095 mL, 1.2 mmol) of thiophene to a cold solution (−78° C.) of 0.61 g (0.90 mL, 1.4 mmol, 1.6M in hexanes) of n-butyl lithium in 2.0 mL of tetrahydrofuran. The solution was stirred at −78° C. for 35 min and then a solution of 0.158 g (1.2 mmol) of zinc chloride in 2.0 mL of tetrahydrofuran was added. The resulting solution was stirred at −78° C. to room temperature for 1 h and then the organozinc was added via cannula to a mixture of 0.212 g (0.44 mmol) of ethyl (E)-4-[2-(5,5-dimethyl-8-(trifluoromethylsulfonyl)oxy-5,6-dihydronaphthalen-2-yl) ethenyl]benzoate (Compound A9) and 18 mg (0.016 mmol) of tetrakis(triphenylphosphine)palladium(0) in 2.0 mL of tetrahydrofuran. The resulting mixture was stirred at room temperature for 10 min and then heated at 50° C. for 1 h. The reaction was quenched by the addition of sat. aqueous NH$_4$Cl. The mixture was extracted with EtOAc (2×), and washed with brine. The organic phase was dried over Na$_2$SO$_4$ and then concentrated in vacuo. The crude material product was purified by flash chromatography (silica, 15% ethyl acetate in hexanes) to afford the title compound as a solid.

$^1$H NMR (CDCl$_3$): δ 1.34 (s, 6 H), 1.40 (t, J=7.1 Hz, 3 H), 2.34 (d, J=4.8 Hz, 2 H), 4.37 (q, J=7.1 Hz, 2 H), 6.22 (t, J=4.8 Hz, 1 H), 7.02 (d, J=16.4 Hz, 1 H), 7.10–7.12 (m, 2 H), 7.15 (d, J=16.4 Hz, 1 H), 7.29–7.33 (m, 1 H), 7.37 (d, J=8.0 Hz, 1 H), 7.45 (dd, J=1.8, 8.0 Hz, 1 H), 7.52 (d, J=8.5 Hz, 2 H), 7.53 (d, J=1.8 Hz, 1 H), 8.00 (d, J=8.4 Hz, 2 H).

(E)-4-[2-(-5,5-Dimethyl-8-(2-thienyl)-5,6-dihydronaphthalen-2-yl)ethenyl]-benzoic acid (Compound A15)

Employing the same general procedure as for the preparation of (E)-4-[2-(5,5-dimethyl-5,6,-dihydro-8(7H)-anti-(O-methyl oxime)-naphthalen-2-yl)ethenyl]-benzoic acid (Compound A4) 98 mg (0.24 mmol) of ethyl (E)-4-[2-(-5,5-dimethyl-8-(2-thienyl)-5,6-dihydronaphthalen-2-yl) ethenyl]-benzoate (Compound A13) was converted into the title compound (white solid).

$^1$H NMR (DMSO-D$_6$): δ 1.27 (s, 6H), 2.32 (d, J=4.8 Hz, 2 H), 6.23 (t, J=4.8 Hz, 1 H), 7.14 (d, J=16.4 Hz, 1 H), 7.14–7.15 (overlapping d, 2 H), 7.36 (d, J=16.4 Hz, 1 H), 7.43 (d, J=8.1 Hz, 1 H), 7.48 (d, J=1.7 Hz, 1 H), 7.54 (t, J=3.1 Hz, 1 H), 7.62 (dd, J=1.7, 8.1 Hz, 1 H), 7.68 (d, J=8.4 Hz, 2 H), 7.88 (d, J=8.4 Hz, 2 H).

Ethyl (E)-4-[2-(5,6-dihydro-5,5-dimethyl-8-(phenylthio)-naphthalenyl)ethenyl]benzoate (Compound A16)

To a degassed solution of 0.35 g (1.0 mmol) of 2-bromo-5,6-dihydro-5,5-dimethyl-8-(phenylthio)-naphthalene (Compound A35) and 0.34 g (1.9 mmol) of ethyl 4-vinylbenzoate in 4.0 mL of triethylamine, was added 0.066 g (0.2 mmol) of tri-o-tolylphosphine and then 0.025 g (0.1 mmol) of palladium(II) acetate. The reaction was heated at 90° C. for 2.25 h. The reaction was concentrated in vacuo. The residue was purified by flash chromatography (silica, 5% ethyl acetate in hexane), followed by recrystallization using EtOH to afford the title compound as white crystals.

$^1$H NMR (CDCl$_3$): δ 1.35 (s, 6 H), 1.40 (t, J=7.1 Hz, 3 H), 2.41 (d, J=4.7 Hz, 2 H), 4.38 (q, J=7.1 Hz, 2 H), 6.55 (t, J=4.7 Hz, 1 H), 6.93 (d, J=16.3 Hz, 1 H), 7.08–7.16 (m, 2 H), 7.22–7.27 (m, 6 H), 7.32 (d, J=8.2 Hz, 1 H), 7.38 (dd, J=1.7, 8.0 Hz, 1 H), 7.49 (d, J=8.4 Hz, 2 H ), 7.81 (d, J=1.7 Hz, 1 H), 8.00 (d, J=8.4 Hz, 2 H).

Ethyl (E)-4-[2-(5,6-dihydro-5,5-dimethyl-8-(phenylsulfonyl)-naphthalenyl)ethenyl]benzoate (Compound A17)

To a solution of 0.090 g (0.2 mmol) of ethyl (E)-4-[2-(5,6-dihydro-5,5-dimethyl-8-(phenylthio)-naphthalenyl) ethenyl]benzoate (Compound A16) in 2.0 mL of methylene chloride was added dropwise a solution of 140 mg (0.45 mmol, 50–60%) of m-chloroperoxybenzoic acid in 2.0 mL of methylene chloride and the reaction stirred at room temperature for 3.5 h. The mixture was diluted with water and extracted with methylene chloride (2×). The organic phase was dried over MgSO$_4$ and concentrated in vacuo. The crude product was purified by flash chromatography (silica, 30% ethyl acetate in hexanes) followed by recrystallization in EtOH to afford the title compound as a solid.

$^1$H NMR (CDCl$_3$): δ 1.22 (s, 6 H), 1.42 (t, J=7.1 Hz, 3 H), 2.50 (d, J=4.9 Hz, 2 H), 4.39 (q, J=7.1 Hz, 2 H), 7.00 (d, J=16.4 Hz, 1 H), 7.13 (d, J=16.4 Hz, 1 H), 7.29 (d, J=8.4 Hz, 1 H), 7.40 (dd, J=1.7, 8.1 Hz, 1 H), 7.46–7.57 (m, 6 H), 7.97 (m, 2 H), 8.04 (d, J=8.4 Hz, 2 H), 8.11 (d, J=1.7 Hz, 1 H).

(E)-4-[2-(5,6-dihydro-5,5-dimethyl-8-(phenylthio)-naphthalen-2-2-yl)ethenyl]benzoic acid (Compound A18)

Employing the same general procedure as for the preparation of (E)-4-[2-(5,5-dimethyl-5,6,-dihydro-8(7H)-anti-(O-methyl oxime)-naphthalen-2-yl)ethenyl]-benzoic acid (Compound A4), 60 mg (0.14 mmol) of ethyl (E)-4-[2-(5,6-dihydro-5,5-dimethyl-8-(phenylthio)-naphthalen-2-yl) ethenyl]benzoate (Compound A16) was converted into the title compound (white solid).

$^1$H NMR (DMSO-D$_6$): δ 1.29 (s, 6 H), 2.40 (d, J=4.6 Hz, 3 H), 6.61 (t, J=4.6 Hz, 1 H), 7.05 (d, J=16.4 Hz, 1 H), 7.17–7.20 (m, 1 H), 7.28–7.35 (m, 4 H), 7.38 (d, J=8.1 Hz, 1 H), 7.52 (dd, J=1.6, 8.1 Hz, 1 H), 7.67 (d, J=8.4 Hz, 2 H), 7.73 (d, J=1.6 Hz, 1 H), 7.90 (d, J=8.4 Hz, 2 H).

(E)-4-[-2-(5,6-dihydro-5,5-dimethyl-8-(phenylsulfonyl)-naphthalenyl)ethenyl]benzoic acid (Compound A19)

To a cold solution (0° C.) of 61 mg (0.15 mmol) of (E)-4-[2-(5,6-dihydro-5,5-dimethyl-8-(phenylthio)-naphthalen-2-yl)ethenyl]benzoic acid (Compound A18) in 5.0 mL of methylene chloride and 2.0 mL of tetrahydrofuran was added dropwise a cold solution (0° C.) of 70 mg (0.22 mmol, 50–60%) of m-chloroperoxybenzoic acid in 4.0 mL of methylene chloride and the reaction stirred at 0° C. for 7 min. The mixture was diluted with water and extracted with methylene chloride (2×). The organic phase was dried over $Na_2SO_4$ and concentrated in vacuo. Recrystallization from acetonitrile gave the title compound as a solid.

$^1$H NMR (DMSO-D$_6$): δ 1.16 (s, 6 H), 2.54 (d, J=4.6 Hz, 2 H), 7.08 (d, J=16.4 Hz, 1 H), 7.35–7.41 (m, 2 H), 7.48 (t, J=4.6 Hz, 1 H), 7.56 (d, J=8.7 Hz, 1 H), 7.63–7.68 (m, 3 H), 7.75 (d, J=8.2 Hz, 2 H), 7.93–7.96 (m, 3 H), 8.03 (d, J=8.2 Hz, 2 H).

Ethyl (E)-4-[-2-(5,6-dihydro-5,5-dimethyl-8-(ethylthio)-naphthalen-2-yl)ethenyl]benzoate (Compound A20)

To a degassed solution of 0.50 g (1.7 mmol) of 2-bromo-5,6-dihydro-5,5-dimethyl-8-(ethylthio)-naphthalene (Compound A36) and 0.45 g (2.5 mmol) of ethyl 4-vinylbenzoate in 4.0 mL of triethylamine, was added 109 mg (0.36 mmol) of tri-o-tolylphosphine and then 35 mg (0.16 mmol) of palladium(II) acetate. The reaction was heated at 90° C. for 2.25 h. The reaction was concentrated in vacuo and purified by flash chromatography (silica, 2% ethyl acetate in hexane) to afford the title compound as a colorless oil.

$^1$H NMR (CDCl$_3$): δ 1.29 (s, 6 H), 1.30 (t, J=7.4 Hz, 3 H), 1.41 (t, J=7.1 Hz, 3 H), 2.31 (d, J=4.8 Hz, 2 H), 2.75 (q, J=7.4 Hz, 2 H), 4.38 (q, J=7.1 Hz, 2 H), 6.20 (t, J=4.8 Hz, 1 H), 7.12 (d, J=16.3 Hz, 1 H), 7.24 (d, J=16.3 Hz, 1 H), 7.32 (d, J=8.0 Hz, 1 H), 7.41 (dd, J=1.7, 8.0 Hz, 1 H), 7.57 (d, J=8.4 Hz, 2 H), 7.89 (d, J=1.7 Hz, 1 H), 8.02 (d, J=8.4 Hz, 2 H).

(E)-4-[-2-(5,6-dihydro-5,5-dimethyl-8-(ethylthio)-naphthalen-2-yl)ethenyl]benzoic acid (Compound A21)

Employing the same general procedure as for the preparation of (E)-4-[2-(5,5-dimethyl-5,6,-dihydro-8(7H)-anti-(O-methyl oxime)-naphthalen-2-yl)ethenyl]-benzoic acid (Compound A4), 206 mg (0.52 mmol) of ethyl (E)-4-[-2-(5,6-dihydro-5,5-dimethyl-8-(ethylthio)-naphthalen-2-yl)ethenyl]benzoate (Compound A20) was converted into the title compound (white solid).

$^1$H NMR (DMSO-D$_6$): δ 1.22 (t, J=7.1 Hz, 3 H), 1.23 (s, 6 H), 2.27 (d, J=4.9 Hz, 2 H), 2.75 (q, J=7.1 Hz, 2 H), 6.15 (t, J=4.9 Hz, 1 H), 7.24 (d, J=16.4 Hz, 1 H), 7.37 (d, J=8.1 Hz, 1 H), 7.45 (d, J=16.4 Hz, 1 H), 7.75 (m, 3 H), 7.92 (d, J=8.1 Hz, 2 H).

(E)-4-[-2-(5,6-dihydro-5,5-dimethyl-8-(ethylsulfonyl)-naphthalen-2-yl)ethenyl]benzoate (Compound A22)

To a cold solution (0° C.) of 44 mg (0.12 mmol) of ethyl (E)-4-[2-(5,6-dihydro-5,5-dimethyl-8-(ethylthio)-naphthalen-2-yl)ethenyl]benzoic acid (Compound A21) in 4.0 mL of methylene chloride and 0.5 mL of tetrahydrofuran was added dropwise a cold solution (0° C.) of 55 mg (0.18 mmol, 50–60%) of m-chloroperoxybenzoic acid in 3.0 mL of methylene chloride and the reaction stirred at 0° C. for 30 min. The mixture was diluted with water and extracted with methylene chloride (2×). The organic phase was diluted with EtOAc, dried over $Na_2SO_4$ and then concentrated in vacuo. Recrystallization from acetonitrile gave the title compound as a solid.

$^1$H NMR (DMSO-D$_6$): δ 1.16 (t, J=7.3 Hz, 1 H), 1.25 (s, 6 H), 2.50 (d, J=4.8 Hz, 2 H), 3.32 (q, J=7.3 Hz, 2 H), 7.18 (t, J=4.8 Hz, 1 H), 7.25 (d, J=16.4 Hz, 1 H), 7.46 (d, J=16.4 Hz, 1 H), 7.49 (d, J=8.1 Hz, 1 H), 7.71 (dd, J=1.5, 8.1 Hz), 1 H), 7.76 (d, J=8.4 Hz, 2 H), 7.94 (d, J=8.4 Hz, 2 H), 8.04 (d, J=1.5 Hz, 1 H).

Ethyl (E)-4-[-2-(5,6,7,8-tetrahydro-5,5-dimethyl-8-(1,3-dithian-2-yl)naphthalen-2-yl)ethenyl]benzoate (Compound A23)

To a cold solution (0° C.) of 140 mg (0.40 mmol) of ethyl (E)-4-[2-(5,5-dimethyl-5,6,-dihydro-naphthalen-8(7H)-one-2-yl)ethenyl]-benzoate (Compound A2), in 6.0 mL of methylene chloride was added dropwise 130 mg (0.12 mL, 1.2 mmol) of 1,3-propanedithiol and 0.17 g (0.15 mL, 102 mmol) of borontrifluoride diethyl etherate. The reaction stirred between 0° C. and room temperature for 4 h. The mixture was diluted with aqueous sat. potassium carbonate, and extracted with ether (2×). The organic phase was washed with brine, dried over MgSO$_4$ and then concentrated in vacuo. The crude product was purified by flash chromatography (silica, 10% ethyl acetate in hexane) to afford the title compound as a solid.

$^1$H NMR (CDCl$_3$): δ 1.29 (s, 6 H), 1.39 (t, J=7.1 Hz, 3 H), 1.83 (m, 2 H), 2.00 (m, 1 H), 2.09 (m, 1 H), 2.62 (m, 2 H), 2.74 (m, 2 H), 3.17 (m, 2 H), 4.36 (q, J=7.1 Hz, 2 H), 7.09 (d, J=16.4 Hz, 1 H), 7.20 (d, J=16.4 Hz, 1 H), 7.30 (d, J=8.2 Hz, 1 H), 7.41 (dd, J=1.9, 8.2 Hz, 1 H), 7.55 (d, J=8.4 Hz, 2 H), 8.00 (d, J=8.4 Hz, 1 H), 8.10 (d, J=1.9 Hz, 2 H).

(E)-4-[2-(5,6,7,8-Tetrahydro-5,5-dimethyl-8-(2-(1,3-dithian-2-yl)naphthalenyl)ethenyl]-benzoic acid (Compound A24)

Employing the same general procedure as for the preparation of (E)-4-[2-(5,5-dimethyl-5,6,-dihydro-8(7H)-anti-(O-methyl oxime)-naphthalen-2-yl)ethenyl]-benzoic acid (Compound A4), 81 mg (0.18 mmol) of ethyl (E)-4-[2-(5,6,7,8-tetrahydro-5,5-dimethyl-8-(1,3-dithian-2-yl)naphthalen-2-yl)ethenyl]benzoate (Compound A23) was converted into the title compound (white solid).

$^1$H NMR (C$_3$OD): δ 1.28 (s, 6 H), 1.83 (m, 2 H), 1.93 (m, 1 H), 2.19 (m, 1 H), 2.66 (m, 4 H), 3.22 (m, 2 H), 7.18 (d, J=16.4 Hz, 1 H), 7.28 (d, J=16.4 Hz, 1 H), 7.36 (d, J=8.2 Hz, 1 H), 7.48 (dd, J=1.9, 8.2 Hz, 1 H), 7.66 (d, J=8.4 Hz, 2 H), 8.00 (d, J=8.4 Hz, 1 H), 8.12 (d, J=1.9 Hz, 2 H).

Ethyl (E)-4-[2-(5,6-tetrahydro-5,5-dimethyl-8-(propyliden-2-yl)-naphthalen-2-yl)ethenyl]-benzoate (Compound A25)

To a degassed solution of 0.36 g (1.3 mmol) of 7-bromo-1(2H)-(propyliden-2-yl)-3,4-dihydro-4,4-dimethylnaphthalene (Compound A37) and 0.44 g (2.5 mmol) of ethyl 4-vinylbenzoate in 3.6 g (5.0 mL, 36 mmol) of triethylamine, was added 88 mg (0.29 mmol) of tri-o-tolylphosphine and then 33 mg (0.15 mmol) of palladium(II)

acetate. The reaction was heated at 95° C. for 4 h. The reaction was concentrated in vacuo and purified by flash chromatography (silica, 1% ethyl acetate in hexane) to afford the title compound as an oil.

$^1$H NMR (CDCl$_3$): δ 1.24 (s, 6 H), 1.39 (t, J=7.1 Hz, 3 H), 1.64 (t, J=6.8 Hz, 2 H), 1.89 (s, 3 H), 2.00 (s, 3 H), 2.51 (t, J=6.8 Hz, 2 H), 4.38 (q, J=7.1 Hz, 2 H), 7.02 (d, J=16.4 Hz, 1 H), 7.18–7.37 (overlapping d, 3 H), 7.41 (s, 1 H), 7.58 (d, J=8.4 Hz, 2 H), 8.02 (d, J=8.4 Hz, 2 H).

(E)-4-[2-(5,6-dihydro-5,5-dimethyl-8(7H)-(propyliden-2-yl)-naphthalen-2-yl)ethenyl]-benzoic acid (Compound A26)

Employing the same general procedure as for the preparation of (E)-4-[2-(5,5-dimethyl-5,6,-dihydro-8(7H)-anti-(O-methyl oxime)-naphthalen-2-yl)ethenyl]benzoic acid (Compound A4) 95 mg (0.25 mmol) of ethyl (E)-4-[2-(5,6,7,8-tetrahydro-5,5-dimethyl-8-(methylethyliden-2-yl) naphthalen-2-yl)ethenyl]benzoate (Compound A25) was converted into the title compound using 1.0 mL (2.3 mmol) of LiOH (2.3M aqueous solution).

$^1$H NMR (CDCl$_3$): δ 1.26 (s, 6 H), 1.64 (t, J=6.9 Hz, 2 H), 1.86 (s, 3 H), 2.02 (s, 3 H), 2.53 (t, J=6.9 Hz, 2 H), 7.07 (d, J=16.4 Hz, 1 H), 7.22–7.38 (overlapping d, 3 H), 7.42 (s, 1 H), 7.58 (d, J=8.4 Hz, 2 H), 8.08 (d, J=8.4 Hz, 2 H).

Ethyl (E)-4-[2-(7,8-dihydro-5,5-dimethyl-8(7H)-(pentyliden-3-yl)-naphthalen-2-yl)ethenyl]-benzoate (Compound A27)

To a degassed solution of 0.30 g (0.98 mmol) of 7-bromo-1(2H)-(pentyliden-3-yl)3,4-dihydro-4,4-dimethylnaphthalene (Compound A38) and 0.17 g (0.97 mmol) of ethyl 4-vinylbenzoate in 3.63 g (5.0 mL, 36 mmol) of triethylamine, was added 61 mg (0.2 mmol) of tri-o-tolylphosphine and then 23 mg (0.10 mmol) of palladium(II) acetate. The reaction was heated at 95° C. for 6.5 h. The reaction was then concentrated in vacuo and purified by flash chromatography (silica, 100% hexane) followed by recrystallization from ethanol gave the title compound as white crystals.

$^1$H NMR (CDCl$_3$): δ 1.05 (t, J=7.3 Hz, 3 H), 1.20 (t, J=7.4 Hz, 3 H), 1.24 (s, 6 H), 1.39 (t, J=7.2 Hz, 3 H), 1.65 (t, J=6.8 Hz, 2 H), 2.22 (q, J=7.4 Hz, 2 H), 2.31 (q, J=7.3 Hz, 2 H), 2.50 (t, J=6.8 Hz, 2 H), 4.36 (q, J=7.2 Hz, 2 H), 7.04 (d, J=16.4 Hz, 1 H), 7.17 (d, J=16.4 Hz, 1 H), 7.28 (d, J=8.1 Hz, 1 H), 7.34 (d, J=8.1 Hz, 1 H), 7.39 (s, 1 H), 7.53 (d, J=8.4 Hz, 2 H), 8.00 (d, J=8.4 Hz, 2 H).

(E)-4-[2-(5,6-Dihydro-5,5-dimethyl-8(7H)-(pentyliden-3-yl)-naphthalen-2-yl)ethenyl]benzoic acid (Compound A28)

Employing the same general procedure as for the preparation of (E)-4-[2-(5,5-dimethyl-5,6,-dihydro-8(7H)-anti-(O-methyl oxime)-naphthalen-2-yl)ethenyl]-benzoic acid (Compound A4), 150 mg (0.37 mmol) of ethyl (E)-4-[2-(5,6,-dihydro-5,5-dimethyl-8(7H)-(pentyliden-3-yl)-naphthalen-2-yl)ethenyl]-benzoate (Compound A27) was converted into the title compound (white solid).

$^1$H NMR (Acetone-D$_6$): δ 1.08 (t, J=7.4 Hz, 3 H), 1.22 (t, J=7.1 Hz, 3 H), 1.26 (s, 6 H), 1.67 (t, J=7.1 Hz, 3 H), 2.25 (q, J=7.4 Hz, 2 H), 2.33 (q, J=7.4 Hz, 2 H), 2.50 (t, J=7.1 Hz, 2 H), 7.13 (d, J=16.4 Hz, 1 H), 7.28 (d, J=16.4 Hz, 1 H), 7.31 (d, J=8.6 Hz, 1 H), 7.34 (m, 2 H), 7.62 (d, J=8.4 Hz, 2 H), 7.98 (d, J=8.4 Hz, 2 H).

Ethyl (E)-4-[2-(5,6-dihydro-5,5-dimethyl-8(7H)-(cyclohexylidenyl)naphthalen-2-yl)ethenyl]-benzoate (Compound A29)

To a degassed solution of 0.40 g (1.3 mmol) of 7-bromo-1(2H)-(cyclohexylidenyl)-3,4-dihydro-4,4-dimethylnaphthalene (Compound A39) and 0.62 g (3.5 mmol) of ethyl 4-vinylbenzoate in 2.2 g (3.0 mL, 22 mmol) of triethylamine, was added 76 mg (0.25 mmol) of tri-o-tolylphosphine and then 29 mg (0.13 mmol) of palladium(II) acetate. The reaction was heated at 95° C. for 2.5 h. The reaction was then concentrated in vacuo and purified by flash chromatography (silica, 1% ethyl acetate in hexane) to afford the title compound as a white solid.

$^1$H NMR (CDCl$_3$): δ 1.27 (s, 6 H), 1.39 (t, J=7.1 Hz, 3 H), 1.62 (m, 8 H), 2.34 (m, 2 H), 2.53 (m, 4 H), 4.37 (q, J=7.1 Hz, 2 H), 7.04 (d, J=16.4 Hz, 1 H), 7.18 (d, J=16.4 Hz, 1 H), 7.28–7.35 (m, 3H), 7.53 (d, J=8.4 Hz, 2 H), 8.01 (d, J=8.4 Hz, 2 H).

(E)-4-[2-(5,6-Dihydro-5,5-dimethyl-8(7H)-(cyclohexylidenyl)-naphthalen-2-yl)ethenyl]benzoic acid (Compound A31)

Employing the same general procedure as for the preparation of (E)-4-[2-(5,5-dimethyl-5,6,-dihydro-8(7H)-anti-(O-methyl oxime)-naphthalen-2-yl)ethenyl]-benzoic acid (Compound A4), 280 mg (0.68 mmol) of ethyl (E)-4-[2-(5,6-dihydro-5,5-dimethyl-8(7H)-(cyclohexylidenyl)-naphthalen-2-yl)ethenyl]benzoate (Compound A29) was converted into the title compound using 2.0 mL (3.3 mmol) of LiOH (1.7M aqueous solution).

$^1$H NMR (DMSO-D$_6$): δ 1.28 (s, 6 H), 1.59–1.67 (m, 8 H), 2.36 (m, 2 H), 2.48–2.57 (m, 4 H), 7.08 (d, J=16.3 Hz, 1 H), 7.20–7.38 (m, 5 H), 7.59 (d, J=8.4 Hz, 1 H), 8.09 (d, J=8.4 Hz, 2 H).

(+/−) Ethyl (E)-4-[2-(5,6,7,8-tetrahydro-5,5-dimethyl-8-hydroxy-8-(methylcarbethoxy) naphthalen-2-yl)ethenyl]benzoate (Compound A32)

To a refluxing solution of 0.75 g (11.5 mmol) of granular zinc in 5.0 mL of benzene was added a solution of ethyl (E)-4-[2-(5,5-dimethyl-5,6,-dihydro-naphthalen-8(7H)-one-2-yl)ethenyl]-benzoate (Compound A2) in 5.0 mL of benzene followed by 0.27 g (0.18 mmol) of ethyl bromoacetate. The resulting mixture was refluxed for 24 h. The reaction was cooled, filtered through celite. The filtrate was washed with 10% HCl, sat. aqueous NaHCO$_3$ and brine. The organic phase was dried over Na$_2$SO$_4$ and concentrated in vacuo. The crude material was purified by flash chromatography (silica, 10% ethyl acetate in hexane) to afford the title compound as a white solid.

$^1$H NMR (CDCl$_3$): δ 1.30 (t, g=7.1 Hz, 3 H), 1.30 (3H, s), 1.34 (3H, s), 1.41 (t, J=7.1 Hz, 3 H), 1.77 (m, 2 H), 2.09 (m, 2 H), 2.82 (d, J=3.4 Hz, 2 H), 4.17 (s, 1 H), 4.22 (q, J=7.1 Hz, 2 H), 4.38 (q, J=7.1 Hz, 2 H), 7.10 (d, J=16.4 Hz, 1 H), 7.20 (d, J=16.4 Hz, 1 H), 7.31 (d, J=8.2 Hz, 1 H), 7.42 (dd, J=1.9, 8.2 Hz, 1 H), 7.55 (d, J=8.4 Hz, 2 H), 7.75 (d, J=1.9 Hz, 1 H), 8.03 (d, J=8.4 Hz, 2 H).

Ethyl (E)-4-[2-(5,6-dihydro-5,5-dimethyl-8-(methylcarbethoxy)naphthalen-2-yl)ethenyl] benzoate (Compound A33a)

Ethyl (E)-4-[2-(5,6-dihydro-5,5-dimethyl-8(7H)-anti (carbethoxymethylidenyl)-naphthalen-2-yl)ethenyl] benzoate (Compound A33b)

To a solution of 0.25 g (0.57 mmol) of (+/−)ethyl (E)-4-[2-(5,6,7,8-tetrahydro-5,5-dimethyl-8-hydroxy-8-(methylcarbethoxy)-naphthalen-2-yl)ethenyl]benzoate (Compound A32) in 11.0 mL of benzene was added 1.0 g (4.2 mmol) of Burgess reagent and the resulting solution was heated at 55° C. for 30 min. The reaction was cooled and concentrated in vacuo, the residue was diluted with water and extracted with EtOAc (2×), the organic layers were washed with brine, dried over $Na_2SO_4$, and concentrated in vacuo to afford a mixture of title compounds in a 3:1 ratio (endo:exo). The title compounds were seperated by flash chromatography (silica, 5% ethyl acetate in hexane) to afford the pure isomers as white solids.

Compound A33a:

$^1$H NMR (CDCl$_3$) δ 1.21 (t, J=7.1 Hz, 3 H), 1.30 (s, 6H), 1.41 (t, J=7.1 Hz, 3 H), 2.82 (d, J=4.3 Hz, 2 H), 3.51 (s, 2 H), 4.12 (q, J=7.1 Hz, 2 H), 4.38 (q, J=7.1 Hz, 2 H), 5.97 (t, J=4.3 Hz, 1 H), 7.05 (d, J=16.4 Hz, 1 H), 7.19 (d, J=16.4 Hz, 1 H), 7.30–7.40 (m, 3 H), 7.47 (d, J=8.4 Hz, 2 H), 8.03 (d, J=8.4 Hz, 2 H).

4,4-Dimethyl-7-bromo-1-phenylthio-3,4-dihydronaphthalene (Compound A35)

To a stirred solution of 4,4-dimethyl-7-bromo-3,4-dihydronaphthalen-1(2H)one (Compound G, 1.48 g, 5.9 mmol), titanium tetrachloride (1.09 g, 5.7 mmol) and THF (10 mL) was added a mixture of thiophenol (660 mg, 6 mmol), triethylamine (1.16 g, 11.5 mmol) and THF (20 mL) via an addition funnel at ambient temperature. The mixture was stirred for 5 h, and water (10 mL) was added, extracted with ether (3×50 mL). The combined organic layer was washed successively with water (10 mL), 10% NaHCO$_3$ (10 mL) and brine (10 mL). The organic layer was dried (MgSO$_4$) and the solvent distilled off at reduced pressure. After silica gel chromatography the title compound was obtained as a colorless oil.

$^1$H NMR (CDCl$_3$): δ 1.31 (s, 6H), 2.39 (d, J=4.9 Hz, 2H), 6.54 (t, J=4.9 Hz, 1H), 7.10–7.35 (m, 7H), 7.78 (d, J=2.0 Hz, 1H).

2-Bromo-5,6-dihydro-5,5-dimethyl-8-(ethylthio)-naphthalene (Compound A36)

To a solution of 1.03 g (4.1 mmol) of 7-bromo-3,4-dihydro-4,4-dimethylnaphthalen-1(2H)-one (Compound G) in 30.0 mL of tetrahydrofuran, was added dropwise 0.49 g (0.85 mL, 7.8 mmol) of titaniumtetrachloride and the resulting solution stirred for 10 min. A solution of 35 mg (0.50 mL, 6.7 mmol) of ethanethiol and 0.54 g (0.75 mL, 5.4 mmol) of triethylamine in 10.0 mL of tetrahydrofuran was added and the reaction stirred at room temperature for 13 h. The mixture was diluted with water and extracted with ether (2×). The organic phase was washed with brine, dried over Na$_2$SO$_4$ and then concentrated in vacuo. Purification by flash chromatography (silica, 100% hexane) gave the title compound as an oil.

$^1$H NMR (CDCl$_3$): δ 1.25 (s, 6 H), 1.27 (t, J=7.1 Hz, 3 H), 2.29 (d, J=4.8 Hz, 2 H), 2.70 (q, J=7.1 Hz, 2 H), 6.23 (t, J=4.8 Hz, 1 H), 7.17 (d, J=8.2 Hz, 1 H), 7.35 (dd, J=1.7, 8.2 Hz, 1 H), 7.85 (d, J=2.1 Hz, 2H).

7-Bromo-1(2H)-(propyliden-2-yl)-3,4-dihydro-4,4-dimethylnaphthalene (Compound A37)

To a slurry of titanium trichloride (5 g, 32 mmol) in DME (80 mL) was added lithium wire in small portions (0.7 g, 100 mmol) under argon atmosphere. The mixture was refluxed for 1 h, cooled to ambient temperature and a solution of acetone (928 mg, 16 mmol) and 7-bromo-3,4-dihydro-4,4-dimethylnaphthalen-1(2H)-one (Compound G, 1.0 g, 3.96 mmol) in 20 mL of DME was added. The resultant mixture was refluxed for 16 h under argon atmosphere. The reaction mixture was then cooled to ambient temperature and diluted with hexane (100 mL). And thereafter filtered through a pad of florisil. The filtrate was concentrated under reduced pressure and purified by flash chromatography (silica, 100% hexane) to afford the title compound as a colorless oil.

$^1$H NMR (CDCl$_3$): δ 1.19 (s, 6H), 1.56 (t, J=6.9 Hz, 2H), 1.81 (s, 3H), 1.94 (s, 3H), 2.44 (t, J=7.1 Hz, 2H), 7.11 (d, J=8.3 Hz, 1H), 7.23 (dd, J=2.1, 8.4 Hz, 1H), 7.35 (d, J=2.1 Hz, 1H).

7-Bromo-1(2H)-(pentyliden-2-yl)-3,4-dihydro-4,4-dimethylnaphthalene (Compound A38)

Employing the same general procedure as for the preparation of 7-bromo-1(2H)-(propyliden-2-yl)-3,4-dihydro-4,4-dimethylnaphthalene (Compound A37), 1.0 g (3.97 mmol) of 4,4-dimethyl-7-bromo-3,4-dihydronaphthalen-1(2H)one (Compound G) was converted into the title compound using 1.37 g (15.9 mmol) of 3-pentanone, 1.92 g (277 mmol) of lithium and 12.2 g (79.4 mmol) of titanium trichloride.

$^1$HNMR (CDCl$_3$): δ 1.04 (t, J=7.5 Hz, 3H), 1.14 (t, J=7.5 Hz, 3H), 1.23 (s, 6H), 1.63 (t, J=7.1 Hz, 2H), 2.21 (q, J=7.5 Hz, 2H), 2.29 (q, J=7.5 Hz, 2H), 2.49 (t, J=7.1 Hz, 2H), 7.15 (d, J=8.3 Hz, 1H), 7.29 (dd, J=2.2,8.3 Hz, 1H), 7.36 (d, J=2.2 Hz, 1H).

7-Bromo-1(2H)-(cyclohexylidenyl)-3,4-dihydro-4,4-dimethylnaphthalene (Compound A39)

Employing the same general procedure as for the preparation of 7-bromo-1(2H)-(propyliden-2-yl)-3,4-dihydro-4,4-dimethylnaphthalene (Compound A37), 1.0 g (3.97 mmol) of 4,4-dimethyl-7-bromo-3,4-dihydronaphthalen-1(2H)one (Compound G) was converted into the title compound using 1.56 g (15.9 mmol) of cyclohexanone, 1.92 g (277 mmol) of lithium and 12.2 g (79.4 mmol) of titanium trichloride.

$^1$HMR (CDCl$_3$): δ 1.23 (s, 6H), 1.50–1.65 (m, 8H), 2.33 (br s, 2H), 2.45 (t, J=5.5 Hz, 2H), 2.50 (t, J=7.1 Hz, 2H), 7.15 (d, J=8.1 Hz, 1H), 7.26 (d, J=1.6 Hz, 1H), 7.29 (br s, 1H).

Ethyl-6-[5,6,7,8-tetrahydro-5,5-dimethyl-naphth-7-yl]naphth-2-oate (Compound B1)

To a degassed solution of 0.39 g (1.4 mmol) of ethyl 6-bromonaphthalene-2-carboxylate and 3.0 mL of toluene, was added sequentially 49 mg (0.04 mmol) of tetrakis-triphenylphosphine palladium(O), 2.0 mL (2.0 mmol) of 1M sodium carbonate and then a solution of 0.32 g (1.6 mmol) of (5,6,7,8tetrahydro-5,5-dimethylnaphth-2-yl)boronic acid (Compound B13) in 3.0 mL of MeOH. The reaction was heated at 80° C. for 6 h, diluted with 2N Na$_2$CO$_3$, and extracted with CH$_2$Cl$_2$ (2×), the organic layer was washed with brine, dried over MgSO$_4$, and concentrated in vacuo to give an oil. Flash chromatography (silica, 5% ethyl acetate in hexane) of the crude material gave the title compound as a white solid.

$^1$H NMR (CDCl$_3$, 300 MHz): δ 1.35 (s, 6 H), 1.46 (t, J=7.1 Hz, 3 H), 1.70–1.74 (m, 2 H), 1.85–1.89 (m, 2 H), 2.88 (t, J=6.3 Hz, 2 H), 4.46 (q, J=7.1 Hz, 2H), 7.42 (d, J=1.7 Hz, 1 H), 7.46 (d, J=8.2 Hz, 1 H), 7.52 (dd, J=2.0, 8.2 Hz, 1 H), 7.80 (dd, J=1.7, 8.5 Hz, 1 H), 7.91 (d, J=8.6 Hz, 1 H), 8.00 (d, J=8.5 Hz, 1 H), 8.05 (s, 1 H), 8.08 (dd, J=1.7, 8.6 Hz, 1 H), 8.61 (s, 1 H).

6-[5,6,7,8-Tetrahydro-5,5-dimethyl-naphth-7-yl]-2-naphthoic acid (Compound B2)

Employing the same general procedure as for the preparation of (E)-4-[2-(5,6,7,8-tetrahydro-5,5-dimethyl-8-anti- (O-methyl oxime)-naphthalen-2-yl)ethenyl]-benzoic acid (Compound A4) 50 mg (0.14 mmol) of ethyl-6-[5,6,7,8-tetrahydro-5,5-dimethyl-naphth-7-yl]naphth-2-oate (Compound B1) was converted into the title compound (white solid).

$^1$H NMR (DMSO-D$_6$, 300 MHz): δ__1.28 (s, 6 H), 1.64–1.68 (m, 2 H), 1.77–1.80 (m, 2 H), 2.82 (t, J=5.7 Hz, 2 H), 7.48 (d, d=8.4 Hz, 1 H), 7.49 (s, 1 H), 7.58 (d, J=8.4 Hz, 1 H), 7.89 (dd, J=1.8, 8.7 Hz, 1 H), 7.98 (dd, J=1.8, 8.7 Hz, 1 H), 8.05 (d, J=8.7 Hz, 1 H), 8.17 (d, J=8.7 Hz, 1 H), 8.24 (s, 1 H), 8.60 (s, 1 H).

Ethyl-6-[5,6,7,8-tetrahydro-5,5-dimethyl-8-(t-butyldimethylsilyloxy)-naphth-7-yl]naphth-2-oate (Compound B3)

To a degassed solution of 722 mg (2.6 mmol) of ethyl 6-bromonaphthalenecarboxylate in 6.0 mL of toluene, was added sequentially 90 mg (0.08 mmol) of tetrakis-triphenylphosphine palladium (O), 5.0 mL (10.0 mmol) of 2M sodium carbonate, and a solution of 1.018 g (3.1 mmol) of (5,6,7,8-tetrahydro-5,5-dimethyl-8-(t-butyldimethylsilyloxy)naphth-2-yl)boronic acid (Compound B14) in 3.0 mL of MeOH. The reaction was heated at 90° C. for 15 h. The reaction was diluted with 2N Na$_2$CO$_3$, and extracted with CH$_2$Cl$_2$ (2×), the organic layer was washed with brine, dried over MgSO$_4$, and concentrated in vacuo to give an oil. The crude product was purified flash chromatography (silica, 5% ethyl acetate in hexane) to afford the title compound as a white solid.

$^1$H NMR (CDCl$_3$, 300 MHz): δ__0.20 (s, 3 H), 0.23 (s, 3 H), 1.00 (s, 9 H), 1.35 (s, 6 H), 1.46 (t, 3 H, J=7.1 Hz), 1.70–2.10 (m, 4 H), 4.46 (q, J=7.1 Hz, 2H), 4.83 (dd, J=4.7, 8.2 Hz, 1 H), 7.42 (d, J=8.2 Hz, 1 H), 7.60 (dd, J=2.1, 8.2 Hz, 1 H), 7.79–7.82 (overlapping s, dd, 2 H), 7.90 (d, J=8.7 Hz, 1 H), 7.92 (d, J=8.5 Hz, 1 H), 8.06–8.1 (overlapping s, dd, 2 H), 8.62 (s, 1 H).

Ethyl-6-[5,6,7,8-tetrahydro-5,5-dimethyl-8-hydroxy-naphth-7-yl]naphth-2-oate (Compound B4)

To a cold (0° C.) solution of 1.15 g (2.4 mmol) of ethyl-6-[5,6,7,8-tetrahydro-5,5-dimethyl-8-(t-butyldimethylsilyloxy)-naphth-7-yl]naphth-2-oate (Compound B3) in 12.0 mL of tetrahydrofuran, was added 3.1 g (12.0 mL, 12.0 mmol, 1.0M in tetrahydrofuran) of tetrabutylammoniumfluoride and the mixture was stirred between 0° C. to room temperature for 3 h. The reaction was then concentrated in vacuo, diluted with water, and extracted with ether (2×), the organic layer was washed with brine, dried over MgSO$_4$, and concentrated in vacuo to give a solid. Recrystallization from ethanol gave the title compound as a white solid.

$^1$H NMR (CDCl$_3$, 300 MHz): δ__1.32 (s, 3 H), 1.39 (s, 3 H), 1.46 (t, J=7.1 Hz, 3 H), 1.66–1.72 (m, 1 H), 1.90–1.99 (m, 3 H), 2.11–2.20 (m, 1 H), 4.47 (q, J=7.1 Hz, 2H), 4.85 (t, J=5.0 Hz, 1H), 7.46 (d, J=8.2 Hz, 1 H), 7.63 (dd, J=2.1, 8.2 Hz, 1 H), 7.81 (dd, J=1.8, 8.7 Hz, 1 H), 7.83 (s, 1 H), 7.90 (d, J=8.5 Hz, 1 H), 8.00 (d, J=8.7 Hz, 1 H), 8.08 (overlapping, 2 H), 8.61 (s, 1 H).

6-[5,6,7,8-Tetrahydro-5,5-dimethyl-8-hydroxy-naphth-7-yl]-2-naphthoic acid (Compound B5)

Employing the same general procedure as for the preparation of (E)-4-[2-(5,6,7,8-tetrahydro-5,5-dimethyl-8-anti-(O-methyl oxime)-naphthalen-2-yl)ethenyl]-benzoic acid (Compound A4) 124 mg (0.33 mmol) of ethyl-6-[5,6,7,8-tetrahydro-5,5-dimethyl-8-hydroxy-naphth-7-yl]naphth-2-oate (Compound B4) was converted into the title compound.

$^1$H NMR (DMSO, 300 MHz): δ__1.25 (s, 3 H), 1.29 (s, 3 H), 1.58–1.99 (m, 4 H), 3.33 (s, 1 H), 4.62 (s, 1 H), 7.47 (d, J=8.2 Hz, 1 H), 7.66 (dd, J=2.0, 8.2 Hz, 1 H), 7.85 (d, J=2.0 Hz, 1 H), 7.89 (dd J=1.7, 8.6 Hz, 1 H), 8.00 (dd, J=1.7, 8.6 Hz, 1 H), 8.07 (d, J=8.6 Hz, 1 H), 8.19 (d, J=8.6 Hz, 1 H), 8.24 (s, 1 H), 8.61 (s, 1 H).

Ethyl-6-[5,5-dimethyl-5,6-dihydro-naphthlen-8(7H)-one-2-yl]-naphthalen-2-oate (Compound B6)

To a solution of 101 mg (0.27 mmol) of ethyl-6-[5,6,7,8-tetrahydro-5,5-dimethyl-8-hydroxy-naphth-7-yl]naphth-2-oate (Compound B4) in 1.5 mL of methylene chloride was added 50 mg (0.43 mmol) of N-methylmorpholine N-oxide and 6.0 mg (0.017 mmol) of tetrapropylammonium perruthenate(VII). The reaction was stirred at room temperature for 3 h, diluted with water, and extracted with CH$_2$Cl$_2$ (2×). The combined organic layer was washed with brine, dried over MgSO$_4$, and concentrated in vacuo to give a foam. The title compound was obtained as a white solid after flash chromatography (silica, 10% ethyl acetate in hexane).

$^1$H NMR (CDCl$_3$, 300 MHz): δ 1.46 (overlapping s, 6 H), 1.46 (overlapping t, J=7.1 Hz, 3 H), 2.09 (t, J=6.4 Hz, 2 H), 2.80 (t, J=6.4 Hz, 2 H), 4.46 (q, J=7.1 Hz, 2H), 7.57 (d, J=8.2 Hz, 1 H), 7.83 (dd, J=1.8, 8.6 Hz, 1 H), 7.90–7.95 (several d, 2 H), 8.04 (d, J=8.4 Hz, 1 H), 8.09–8.12 (overlapping s, dd, 2 H), 8.41 (d, J=2.1 Hz, 1 H), 8.63 (s, 1 H).

6-[5,5-Dimethyl-5,6-dihydro-naphthlen-8(7H)-one-2-yl]-2-naphthoic acid (Compound B7)

Employing the same general procedure as for the preparation of (E)-4-[2-(5,6,7,8-tetrahydro-5,5-dimethyl-8-anti-(O-methyl oxime)-2-naphthalenyl)ethenyl]-benzoic acid (Compound A4) 58 mg (0.16 mmol) of ethyl -6-[5,5-dimethyl-5,6-dihydro-naphthlen-8(7H)-one-2-yl]-naphthalen-2-oate (Compound B6) was converted into the title compound (white solid).

$^1$H NMR (DMSO-D$_6$, 300 MHz): δ__1.41 (s, 6 H), __2.01 (t, J=6.7 Hz, 2 H), 2.74 (t, J=6.7 Hz, 2 H), 7.71 (d, J=8.3 Hz, 1 H), 7.93 (dd, J=1.8, 8.7 Hz, 1 H), 7.93 (dd, J=1.7, 8.5 Hz, 1 H), 8.07–8.13 (several d, 3 H), 8.22 (d, J=8.5 Hz, 1 H), 8.26 (s, 2 H), 8.32 (s, 1 H), 8.63 (s, 1 H).

Ethyl-6-[5,6,7,8-tetrahydro-5,5-dimethyl-8-(methoxymethyloxy)-naphth-7-yl]naphth-2-oate (Compound B5)

To a cold (0° C.) solution of 130 mg (0.35 mmol) of ethyl-6-[5,6,7,8-tetrahydro-5,5-dimethyl-8-(hydroxy)-naphth-7-yl]naphth-2-oate (Compound B4) in 2.0 mL of methylene chloride was added 50 mg (0.15 mL, 0.86 mmol) of Hunig's base, followed by 0.21 g (0.20 mL, 2.6 mmol) of chloromethyl methyl ether was added and stirred at room temperature for 14 h. About 500 mgs of t-butylammonium iodide was then added and the reaction was warmed to 35° C. for one additional hour. The reaction was diluted with water, and extracted with CH$_2$Cl$_2$ (2×). The combined organic layer was washed with brine, dried over MgSO$_4$, and concentrated in vacuo to give an oil. The title compound was obtained as an oil after flash chromatography (silica, 10% ethyl acetate).

$^1$H NMR (CDCl$_3$, 300 MHz): δ__1.31 (s, 3 H), 1.40 (s, 3 H), 1.46 (t, 3 H, J=7.1 Hz), 1.60 (m, 1 H), 1.98–2.08 (m, 3 H), 3.51 (s, 3 H), 4.46 (q, J=7.1 Hz, 2H), 4.75 (t, J=4.5 Hz,

1 H), 4.83 (d, J=7.0 Hz, 1 H), 4.93 (d, J=7.0 Hz, 1 H), 7.48 (d, J=8.2 Hz, 1 H), 7.63 (dd, J=2.0, 8.2 Hz, 1 H), 7.70 (d, J=2.0 Hz, 1 H), 7.80 (dd J=1.7, 8.5 Hz, 1 H), 7.92 (d, J=8.5 Hz, 1 H), 8.01 (d, J=8.7 Hz, 1 H), 8.05 (s, 1 H), 8.09 (dd, J=1.7, 8.7 Hz, 1 H), 8.62 (S, 1 H).

6-[5,6,7,8-Tetrahydro-5,5-dimethyl-8-(methoxymethyloxy)-naphth-7-yl]-2-naphthoic acid (Compound B9)

Employing the same general procedure as for the preparation of (E)-4-[2-(5,6,7,8-tetrahydro-5,5-dimethyl-8-anti-(O-methyloxime)- 2-naphthalenyl)ethenyl]-benzoic acid (Compound A4) 90 mg (0.21 mmol) of ethyl-6-[5,6,7,8-tetrahydro-5,5-dimethyl-8-(methoxymethyloxy)-naphth-7-yl]naphth-2-oate (Compound B8) was converted into the title compound (white solid).

$^1$H NMR (DMSO-D$_6$, 300 MHz): δ__1.26 (s, 3 H), 1.34 (s, 3 H), 1.59 (m, 1 H), 1.98 (m, 3 H), 3.34 (s, 3 H), 4.68 (t, J=4.5 Hz, 1 H), 4.78 (d, J=6.8 Hz, 1 H), 4.84 (d, J=6.8 Hz, 1 H), 7.54 (d, J=8.3 Hz, 1 H), 7.70 (s, 1 H), 7.73 (d, J=8.3 Hz, 1 H), 7.90 (d J=8.7 Hz, 1 H), 8.00 (d, J=8.7 Hz, 1 H), 8.09 (d, J=8.7 Hz, 1 H), 8.21 (d, J=8.7 Hz, 1 H), 8.24(s, 1 H), 8.63 (s, 1 H).

Ethyl-6-[5,6,7,8-tetrahydro-5,5-dimethyl-8-(O-acetyl)-naphth-7-yl]naphth-2-oate (Compound B10)

To a cold (0° C.) solution of 61 mg (0.16 mmol) of ethyl-6-[5,6,7,8-tetrahydro-5,5-dimethyl-8-hydroxy)-naphth-7-yl]naphth-2-oate (Compound B4) in 2.0 mL of methylene chloride stirring under argon at 0° C. was added successively, 76 mg (0.10 mL, 0.72 mmol) of triethylamine, 0.22 g (0.20 mL, 2.8 mmol) of acetylchloride and 7 mg (0.06 mmol) of 4-dimethylaminopyridine. The reaction was stirred at room temperature for 90 h, diluted with water, and extracted with CH$_2$Cl$_2$ (2x). The combined organic layer was washed with brine, dried over MgSO$_4$, and concentrated in vacuo. The title a compound was obtained as an oil after flash chromatography using silica, 10% ethyl acetate in hexane.

$^1$H NMR (CDCl$_3$, 300 MHz): δ__1.31 (s, 3 H), 1.43 (s, 3 H), 1.46 (t, 3 H, J=7.1 Hz), 1.67–1.72 (m, 1 H), 1.94–2.12 (m, 3 H), 2.12 (s, 3 H), 4.46 (q, J=7.1 Hz, 2H), 6.06 (t, J=4.4 Hz, 1 H), 7.51 (d, J=8.2 Hz, 1 H), 7.61 (d, J=2.0 Hz, 1 H), 7.67 (dd, J=2.0, 8.2 Hz, 1 H), 7.78 (dd J=1.7, 8.6 Hz, 1 H), 7.93 (d, J=8.6 Hz, 1 H), 8.01 (d, J=8.7 Hz, 1 H), 8.04 (s, 1 H), 8.09 (dd, J=1.7, 8.7 Hz, 1 H), 8.62 (s, 1 H).

Ethyl-6-[5,5-dimethyl-5,6-dihydro-naphthlen-8(7H)-anti-(O-methyl-oxime)-2yl]-naphthalen-2-oate (Compound B11)

A solution of 29 mg (0.08 mmol) of ethyl-6-[5,5-dimethyl-5,6-dihydro-naphthalen-8(7H)-one-2-yl]-naphthalen-2-oate (Compound B6), 27 mg (0.32 mmol) of methoxylamine hydrochloride and 68 mg (0.5 mmol) of sodium acetate in 2.0 mL of EtOH and 0.5 mL of tetrahydrofuran was heated at 50° C. for 18 h. An additional 27 mg of methoxylamine hydrochloride was added and the mixture refluxed for another 2 h. The mixture was concentrated in vacuo. The residue was diluted with water and extracted with EtOAc (2x). The combined organic layer was dried over MgSO$_4$, and concentrated in vacuo. Flash chromatography (silica, 5% ethyl acetate in hexanes) of the crude material afforded the title compound as a solid.

$^1$H NMR (CDCl$_3$, 300 MHz): δ__1.35 (s, 6 H), —1.46 (t, J=7.1 Hz, 3 H), 1.77 (t, J=6.9 Hz, 2 H), 2.84 (t, J=6.9 Hz, 2 H), 4.04 (s, 3H), 4.45 (q, J=7.1 Hz, 2H), 7.47 (d, J=8.2 Hz, 1H), 7.67 (dd, J=2.1, 8.2 Hz, 1 H), 7.83 (dd, J=1.8, 8.5 Hz, 1 H), 7.94 (d, J=8.6 Hz, 1 H), 8.02 (d, J=8.6 Hz, 1 H), 8.07–8.10 (m, 2 H), 8.34 (d, J=2.1 Hz, 1 H), 8.63 (s, 1 H).

6-[5,5-Dimethyl-5,6-dihydro-naphthlen-8(7H)-anti-(O-methyl-oxime)-2-yl]-2-naphthoic acid (Compound B12)

Employing the same general procedure as for the preparation of (E)-4-[2-(5,6,7,8-tetrahydro-5,5-dimethyl-8-anti-(O-methyloxime)-2-naphthalenyl)ethenyl]-benzoic acid (Compound A4) 22 mg (0.06 mmol) of ethyl -6-[5,5-dimethyl-5,6-dihydro-naphthlen-8(7H)-anti-(O-methyl-oxime)-2-yl]-naphthalen-2-oate (Compound B11) was converted into the title compound (white solid).

$^1$H NMR (DMSO-D$_6$, 300 MHz): δ__1.30 (s, 6 H), –1.72 (t, J=6.9 Hz, 3 H), 2.78 (t, J=6.9 Hz, 2 H), 3.97 (s, 3 H), 7.59 (d, J=8.2 Hz, 1 H), 7.81 (dd, J=2.1, 8.2 Hz, 1 H), 7.89 (dd, J=1.8, 8.7 Hz, 1 H), 8.00 (dd, J=1.7, 8.6 Hz, 1 H), 8.12 (d, J=8.7 Hz, 1 H), 8.21–8.26 (m, 3 H), 8.64 (s, 1 H).

(5,6,7,8-Tetrahydro-5,5-dimethylnaphth-2-yl)boronic acid (Compound B13)

To a cold (−78° C.) solution of 2.02 g (8.4 mmol) of 6-bromo-1,2,3,4-tetrahydro-1,1-dimethylnaphthalene in 11.0 mL of toluene, was added 4.6 g (6.8 mL, 10.9 mmol, 1.6M in hexane) of n-BuLi. The resulting solution was stirred at −78° C. for 45 min. and then 2.40 g (3.0 mL, 12.7 mmol) of triisopropylborate was dropwise added and the reaction stirred at room temperature for 12 h. The reaction was then diluted with 10% HCl, and extracted with ether (2x). The combined organic layer was washed with brine, dried over MgSO$_4$, and concentrated in vacuo to give an oil. Recrystallization from hexane afforded the title compound as a white solid. $^1$H NMR (CDCl$_3$, 300 MHz): δ__1.34 (s, 6 H), 1.71 (m, 2 H), 87 (m, 2H), 1.89(t, J=6.3 Hz, 2H), 7.47 (d, J=7.8 Hz, 1H),7.89 (s, 1 H), 7.99 (d, J=7.8 Hz, 1 H).

(5,5-Dimethyl-8-(t-butyldimethylsilyloxy)-5,6,7,8-tetrahydro-naphth-2-yl)boronic acid (Compound B14)

Employing the same general procedure as for the preparation of 1,2,3,4-tetrahydro-1,1-dimethylnaphthyl-6-boronic acid (Compound B13) 12.40 g (34 mmol) of 6-bromo-1,2,3,4-tetrahydro-1,1-dimethyl-4-(t-butyldimethylsilyloxy) naphthalene (Compound B15) was converted into the title compound using 18.4 g (27.0 mL, 43 mmol, 1.6M in hexane) of n-BuLi and 9.37 g (11.50 mL, 50 mmol) of triisopropylborate.

$^1$H NMR (CDCl$_3$, 300 MHz): δ__0.22 (s, 3 H), 0.28 (s, 3 H), 0.98 (s, 9 H), 1.33 (s, 3 H), 1.38 (s, 3 H), 1.62–2.09 (m, 4 H), 4.87 (m, 1 H), 7.39 (d, J=7.8 Hz, 1 H), 8.07 (d, J=7.8 Hz, 1 H), 8.29 (s, 1 H).

2-(5,6,7,8-tetrahydro-5,5-dimethy-8-(t-butyldimethylsilyloxy)naphthyl)bromide (Compound B15)

To a solution of 10.61 g (42 mmol) of 6-bromo-1,2,3,4-tetrahydro-1,1-dimethyl-4-hydroxynaphthalene in 100 mL of methylene chloride stirring at 0° C. under argon, was added 5.23 g (7.20 mL, 52 mmol) of triethylamine, 0.55 g (4.5 mmol) of 4-dimethylaminopyridine, and 7.71 g (51 mmol) of t-butyldimethylsilyl chloride consecutively. The resulting solution was stirred at 0° C. to room temperature for 90 hours. The reaction was then diluted with water, and extracted with methylene chloride (2×), the organic layers dried over $Na_2SO_4$, and concentrated in vacuo to give an oil. Purification was done using flash chromatography (silica, 4% ethyl acetate in hexane) to give the title compound as an oil.

$^1$H NMR (CDCl$_3$, 300 MHz): δ 0.15 (s, 3H), 0.18 (s, 3H), 0.95 (s, 9H), 1.25 (s, 3H), 1.26 (s, 3H), 1.61–2.03 (m, 4H), 4.67 (m, 1H), 7.13 (d, J=8.5 Hz, 1H), 7.30 (dd, J=2.1, 8.5 Hz, 1H), 7.51 (d, J=2.1 Hz, 1H).

4,4-Dimethyl-7-acetyl-3,4-dihydronaphthalen-1(2H)-one (Compound C1)

A solution of 4,4-dimethyl-7-bromo-3,4-dihydronaphthalen-1(2H)one (Compound G) (1.78 g, 7 mmol), 1-ethoxyvinyltributyltin (EVTB) (3.3 g, 9.12 mmol), bis(triphenylphosphine)palladium(II)chloride (260 mg, 0.23 mmol) in THF (25 mL) was refluxed for 24 h under argon atmosphere. To the reaction, additional EVTB (1.5 g, 4.1mmol) and bis(triphenylphosphine)palladium(II)chloride (200 mg, 0.2 mmol) were added and the mixture was and refluxed for an additional 24 h. The reaction mixture was cooled to room temperature and 10% hydrochloric acid (10 ml) was added. After 10 min, the mixture was extracted with ether (3×50 mL), the combined organic layer was washed with water (10 mL), 10% sodiumbicarbonate (10 mL), brine (10 mL), dried with magnesium sulfate. Solvent was removed under reduced pressure, and after purification by flash chromatography the title compound was obtained as a white solid.

$^1$H NMR (CDCl$_3$): δ 1.38 (s, 6H), 2.02 (t, J=6.54 Hz, 2H), 2.73 (t, J=6.54 Hz, 2H), 7.31 (d, J=8.43 Hz, 1H), 7.63 (dd, J=2.20, 8.43 Hz, 1H), 8.13 (d, J=2.20 Hz, 1H).

Ethyl 3-[4,4-dimethyl-3,4-dihydronaphthalen-1(2H) one-7-yl]but-2(E)-enoate (Compound C2)

To a cold (−78° C.) slurry of sodiumhydride (336 mg, 14 mmol) in THF (10 mL) was added triethylphosphonoacetate (3.58 g, 16 mmol). Cooling was discontinued and the mixture was stirred at ambient temperature. After 30 min, a solution of 4,4-dimethyl-7-acetyl-1,2,3,4-tetrahydronaphthalen-1(2H)-one (Compound C1, 800 mg, 3.7 mmol) in THF (4 mL) was added and stirred for 36 h. The reaction mixture was diluted with ether (120 mL), and washed with water (10 mL), brine (10 mL), dried with magnesium sulfate. Solvent was removed under reduced pressure, chromatographic purification gave the title compound as a colorless oil.

$^1$H NMR (CDCl$_3$): δ 1.33 (t, J=7.1 Hz, 3H), 1.41 (s, 6H), 2.04 (t, J=7.0 Hz, 2H), 2.59 (s, 3H), 2.76 (t, J=7.0 Hz, 2H), 4.23 (q, J=7.1 Hz, 2H), 6.19 (s, 1H), 7.44 (d,J=8.3 Hz, 1H), 7.65 (dd, J=2.0, 8.3 Hz, 1H), 8.15 (d, J=2.0 Hz, 1H).

3-[1-Hydroxy-4,4-dimethyl-1,2,3,4,-tetrahydronaphthalen-7-yl]but-2(E)-en-1-ol (Compound C3)

To a cold (−78° C.) solution of ethyl 3-[4,4-dimethyl-1,2,3,4,-tetrahydronaphthalen-1(2H)one-7-yl]but-2(E)-enoate (Compound C2, 2.7 g, 9.4 mmol) in methylenechloride (20 mL) was added diisobutylaluminum hydride (DibAl-H, 1M solution in methylenechloride) (45 mL). The reaction was gradually warmed to −10° C. The reaction was quenched by adding methanol (3 mL), water (10 mL), 10% hydrochloric acid (40 mL) and stirred for 10 min. The mixture was extracted with methylenechloride (3×50 mL). The combined organic layer was washed with water (10 mL), 10% sodiumbicarbonate (10 mL), brine (10 mL), dried with magnesium sulfate. Solvent was removed under reduced pressure to obtain the title compound as a white solid.

1HNMR (CDCl$_3$): d 1.24 (s, 3H), 1.31 (s, 3H), 1.57–1.70 (m, 2H), 1.82–1.96 (m, 2H), 2.03 (s, 3H), 4.29 (d, J=6.6 Hz, 2H), 4.68 (brs, 1H), 5.95 (t, J=6.6 Hz, 1H), 7.28 (brs, 2H), 7.48 (s, 1H).

3-[4,4-Dimethyl-3,4,-dihydronaphthalen-1(2H)one-7-yl]but-2(E)-en-al (Compound C4)

To a solution of 3-[1-hydroxy-4,4-dimethyl-1,2,3,4,-tetrahydronaphthalen-7-yl]but-2(E)-en-1-ol (Compound C3, 1.5 g, 6.1 mmol) in dichloromethane (35 mL) was added manganese dioxide (9 g, 106 mmol) in two portions and stirred at room temperature for 48 h. After filtering out the manganese dioxide and removing the solvent under reduced pressure the product was isolated as a white solid.

$^1$H NMR (CDCl$_3$): δ 1.41 (s, 6H), 2.03 (t, J=6.4 Hz, 2H), 2.58 (s, 3H), 2.75 (t, J=6.4 Hz, 2H), 6.41 (d, J=7.7 Hz, 1H), 7.48 (d, J=8.31, 1H), 7.71 (dd, J=2.2, 8.31 Hz, 1H), 8.20 (d, J=2.2 Hz), 10.18 (d, J=7.7 Hz, 1H).

Ethyl 7-[4,4-dimethyl-3,4,-dihydronaphthalen-1(2H) one-7-yl]-3,7-dimethyl-hept-2(E), 4(E), 6(E) trienoate (Compound C5)

To a cold (−78° C.) solution of diethyl-(E)-3-ethoxycarbonyl-2-methylallylphosphonate in THF was added n-BuLi (1.6 mmol solution in hexanes, 2.2 mL, 3.5 mmol) followed by 3-[4,4-dimethyl-1,2,3,4,-tetrahydronaphthalen-1(2H)one-7-yl]but-2(E)-en-al (Compound C4, 300 mg, 1.24 mmol) in THF (2 mL). The mixture was stirred for 16 h at −78° C. The mixture was treated with water and extracted with ether (3×40 mL). The combined organic layer was washed with water (10 mL), brine (10 mL) and dried with MgSO$_4$. Solvent was removed under reduced pressure, the crude product was purified by column chromatography, followed by HPLC to give the title compound as a solid.

$^1$H NMR (CDCl$_3$): δ 1.30 (t, J=7.1 Hz, 3H), 1.40 (s, 6H), 2.03 (t, J=6.8 Hz, 2H), 2.26 (s, 3H), 2.38 (s, 3H), 2.75 (t, J=6.8 Hz, 2H), 4.20 (q, J=7.1 Hz, 2H), 5.82 (s, 1H), 6.41 (s, J=15.0 Hz, 1H), 6.64 (d, J=11.0 Hz, 1H), 7.01 (dd, J=11.0, 15.0 Hz, 1H), 7.41 (d, J=8.2 Hz, 1H), 7.66 (dd, J=2.0, 8.2 Hz, 1H), 8.14 (d, J=2.0 Hz).

4,4-Dimethyl-7-acetyl-1-phenylthio-3,4-dihydronaphthalene (Compound C7)

Employing the procedure used for the preparation of 4,4-dimethyl-7-acetyl-3,4-dihydronaphthalen-1(2H)-one (Compound C1) 1.2 g, (3.5 mmol) of 4,4-dimethyl-7-Bromo-1-phenylthio-3,4-dihydronaphthalene (Compound A35) was converted to the title compound.

$^1$H NMR (CDCl$_3$): δ 1.35 (s, 6H), 2.42 (d, J=4.8 Hz, 2H), 2.43 (s, 3H), 6.59 (t, J=4.8 Hz, 1H), 7.10–7.27 (m, 4H), 7.32 (d, J=8.5 Hz, 1H), 7.40 (d, J=8.1 Hz, 1H), 7.82 (dd, J=1.9, 8.1 Hz, 1H), 8.18 (d, J=1.9 Hz, 1H).

3-[4,4-Dimethyl-1-phenylthio-3,4-dihydronaphthalen-7-yl]but-2-en(E)-nitrile (Compound C8)

Employing the procedure used for the preparation of ethyl 3-[4,4-dimethyl-3,4-dihydronaphthalen-1(2H) one-7-yl]but-2(E)-enoate (Compound C2) instead using diethylcyanomethylphosphonate (1.77 g, 10 mmol), sodium hydride (220 mg, 9 mmol) and 4,4-dimethyl-7-acetyl-1-phenylthio-3,4- dihydronaphthalene (Compound C7, 924 mg, 3 mmol) was converted to the title compound.

¹H NMR (CDCl₃): δ 1.34 (s, 6H), 2.30 (s, 3H), 2.42 (d, J=4.6 Hz, 2H), 5.38 (s, 1H), 6.61 (t, J=4.6 Hz, 1H), 7.10–7.37 (m, 7H), 7.69 (d, J=1.9 Hz, 1H). 3-[4,4-Dimethyl-1-phenylthio-3,4-dihydronaphthalen-7-yl]but-2-en(E)-aldehyde (Compound C9)

To a cold (−78° C.) solution of 3-[4,4-dimethyl-1-phenylthio-3,4-dihydronaphthalen-7-yl]but-2-en(E)-nitrile (Compound C8, 400 mg, 1.2 mmol), in dichloromethane (10 mL) was added diisobutylaluminum hydride (DiBA-H) (1M solution in dichloromethane, 2.5 mL, 2.5 mmol). The reaction was warmed to −40° C. gradually over a period of 1 h. Then the reaction was quenched by adding methanol (1.5 mL), diluted with ether: ethylacetate (1:1, 100 mL), washed with 10% HCl (10 mL), water (10 mL), and brine (10 mL). The organic layer was dried (MgSO₄) and the solvent was removed under reduced pressure. The title compound was obtained as a colorless oil after silicagel chromatography.

¹H NMR (CDCl₃): δ 1.36 (s, 6H), 2.40 (d, J=1.3 Hz, 3H), 2.42 (d, J=4.7 Hz, 2H), 6.25 (dd, J=1.3, 7.9 Hz, 1H), 6.60 (t, J=4.7 Hz, 1H), 7.10–7.43 (m, 7H), 7.81 (d, J=1.9 Hz, 1H), 10.11 (d, J=7.9 Hz, 1H).

Ethyl 7-[4,4-dimethyl-1-(phenylthio)-3,4,-dihydronaphthalen-7-yl]-3,7-dimethyl-hept-2(E), 4 (E), 6(E)trienoate (Compound C10)

Employing the procedure used for the preparation of ethyl 7-[4,4-dimethyl-3,4,-dihydronaphthalen-1(2H)one-7-yl]-3,7-dimethyl-hept-2(E), 4(E), 6(E)trienoate (Compound C5) instead using diethyl-(E)-3-ethoxycarbonyl-2-methylallylphosphonate (786 mg, 3 mmol), n-BuLi (2.8 mmol), 3-[4,4-dimethyl-1-phenylthio-3,4-dihydronaphthalen-7-yl]but-2-en(E)-aldehyde (Compound C9, 280 mg, 0.84 mmol) was converted to the title compound.

¹H NMR (CDCl₃): δ 1.32 (t, J=7.1 Hz, 3H), 1.36 (s, 6H), 2.12 (s, 3H), 2.38 (s, 3H), 2.41 (d, J=4.7 Hz, 2H), 4.20 (q, J=7.1 Hz, 2H), 5.82 (s, 1H), 6.29 (d, J=14.8 Hz, 1H), 6.33 (d, J=9.9 Hz, 1H), 6.58 (t, J=4.7 Hz, 1H), 6.96 (dd, J=9.9, 14.8 Hz, 1H), 7.12–7.38 (m, 7H), 7.74 (d, J=1.7 Hz, 1H).

Ethyl 7-[4,4-dimethyl-1-phenylsulfonyl-3,4,-dihydronaphthalen-7-yl]-3,7-dimethyl-hept-2(E), 4 (E), 6(E)trienoate (Compound C11a) Ethyl 7-[4,4-dimethyl-1-phenylsulfoxide-3,4,-dihydronaphthalen-7-yl]-3,7-dimethyl-hept-2(E), 4(E), 6(E)trienoate (Compound C11b)

To a cold (0° C.) solution of ethyl 7-[4,4-dimethyl-1-phenylthio-3,4,-dihydronaphthalen-7-yl]-3,7-dimethyl-hept-2(E), 4(E), 6(E)trienoate (Compound C10, 44 mg, 0.1 mmol) in dichloromethane (3 mL) was added m-chloroperoxybenzoic acid (approximately 60% concentration, 30 mg, 0.1 mmol). The mixture was stirred for 2 h at 0° C., diluted with dichloromethane (40 mL) and washed successively with 10% sodiumbicarbonate (5 mL), water (5 mL) and brine (5 mL). The organic layer was dried (MgSO₄) and the solvent was removed under reduced pressure. The title compounds were obtained after separation of the mixture by silicagel chromatography.

Ethyl 7-[4,4-dimethyl-1-phenylsulfonyl-3,4,-dihydronaphthalen-7-yl]-3,7-dimethyl-hept-2(E), 4 (E), 6(E)trienoate (Compound 11a)

¹H NMR (CDCl₃): δ 1.23 (s, 6H), 1.31 (t, J=7.1 Hz, 3H), 2.17 (s, 3H), 2.39 (s, 3H), 2.51 (d, J=4.9 Hz, 2H), 4.20 (q, J=7.1 Hz, 2H), 5.84 (s, 1H), 6.36 (d, J=15.1 Hz, 1H), 6.41 (d, J=13.0 Hz, 1H), 6.99 (dd, J=12.0, 15.1 Hz), 1H), 7.27 (d, J=1.7 Hz, 1H), 7.34 (dd, J=1.9, 8.2 Hz, 1H), 7.45–7.60 (m, 4H), 7.93–8.0 (m, 3H).

Ethyl 7-[4,4-dimethyl-1-phenylsulfoxide-3,4,-dihydronaphthalen-7-yl]-3,7-dimethyl-hept-2(E), 4 (E), 6(E)trienoate (Compound 11b)

¹H NMR (CDCl₃): δ 1.32 (s, 3H), 1.30 (s, 3H), 1.31 (t, J=7.1 Hz, 3H), 2.15 (s, 3H), 2.38 (s, 3H), 2.50 (d, J=4.6 Hz, 2H), 4.19 (q, J=7.1 Hz, 2H), 5.84 (s, 1H), 6.36 (d, J=15.0 Hz, 1H), 6.39 (d, J=11.6 Hz, 1H), 6.90–7.04 (m, 2H), 7.24–7.32 (m, 2H), 7.41–7.50 (m 3H), 7.53 (d, J=1.8 Hz, 1H), 7.74 (dd, a=2.5, 8.0 Hz, 2H).

Ethyl 7-[4,4-dimethyl-1,2,3,4,-tetrahydronaphthalen-1-hydroxy-7-yl]-3,7-dimethyl-hept-2(E), 4(E), 6(E) trienoate (Compound C13)

To cold (0° C.) solution of ethyl 7-[4,4-dimethyl-3,4,-dihydronaphthalen-1(2H)one-7-yl]-3,7-dimethyl-hept-2(E), 4(E), 6(E)trienoate (Compound C5, 6 mg, 0.02 mmol) in ether (3 mL) was added ZnBH₄ (0.5M solution in ether, 0.5 mL). The mixture was stirred for 30 min. and quenched the with water, diluted with ether (30 mL). The organic layer was washed with water (5 mL), 10% HCl (5 mL), water (5 mL), 10% NaHCO₃ (5 mL) and brine (5 mL). The organic layer was dried with MgSO₄, and the solvent was removed under reduced pressure to obtain the title compound as a white solid.

¹H NMR (CDCl₃): δ 1.26 (s, 3H), 1.30 (t, J=7.1 Hz, 3H), 1.34 (s, 3H), 1.58–1.70 (m, 1H), 1.82–1.95 (m, 2H), 2.05–2.15 (m, 1H), 2.25 (s, 3H), 2.38 (s, 3H), 4.18 (q, J=7.1 Hz), 4.75 (brs, 1H), 5.81 (s, 1H), 6.37 (d, J=15.1 Hz, 1H), 6.60 (d, J=11.2 Hz, 1H), 7.02 (dd, J=11.2, 15.1 Hz, 1H), 7.31 (d, J=8.3 Hz, 1H), 7.39 (dd, J=2.1, 8.3 Hz, 1H).

Ethyl 7-[4,4-dimethyl-3,4,-dihydronaphthalen-1-trifluoromethylsulfonyloxy-7-yl]-3,7-dimethyl-hept-2(E), 4(E), 6(E)trienoate (Compound C14)

To a cold (−78° C.) stirring solution of ethyl 7-[4,4-dimethyl-3,4,-dihydronaphthalen-1(2H)one-7-yl]-3,7-dimethyl-hept-2(E), 4(E), 6(E)trienoate (Compound C5, 190 mg, 0.55 mmol), in THF (10 mL) was added sodium bis(trimethylsilyl)amide (1M solution in THF, 0.5 mL, 0.5 mmol). After 20 min. 2-N,N-bis(trifluoromethylsulfonyl)amino-5-chloropyridine (216 mg, 0.6 mmol) in THF (2 mL) was added, after another 20 min. the temperature was increased to −10° C. and the mixture was stirred at this temperature for another 20 min. The reaction was quenched by adding aqueous NH₄Cl (10 mL), extracted with ether (3×30 mL). The combined organic layer was washed successively with water (10 mL) and brine (10 mL), dried with MgSO₄. The solvent was removed, and the resulting crude mixture was purified by silicagel chromatography and HPLC to afford the title compound as a white solid.

¹H NMR (CDCl₃): δ 1.31 (t, J=7.1 Hz, 3H), 1.32 (s, 6H), 2.25 (s, 3H), 2.39 (s, 3H), 2.43 (d, J=4.9, 2H), 4.19 (q, J=7.1 Hz, 2H), 5.83 (s, 1H), 5.99 (t, J=4.9 Hz, 1H), 6.40 (d, J=15.0 Hz, 1H), 6.57 (d, J=11.3 Hz, 1H), 7.01 (dd, J=11.3, 15.0 Hz, 1H), 7.30 (d, J=8.0 Hz, 1H), 7.46 (dd, J=1.9, 8.0 Hz, 1H), 7.47 (d, J=1.9 Hz, 1H).

Ethyl 7-[4,4-dimethyl-3,4,-dihydronaphthalen-1-(2-thienyl)-7-yl]-3,7-dimethyl-hept-2(E), 4(E), 6(E) trienoate (Compound C15)

To a cold (−78° C.) solution of thiophene (252 mg, 3 mmol) in THF (2 mL) was added t-BuLi (1.4M solution in cyclohexane, 2 mL, 2.8 mmol) and the mixture was warmed to −30° C. over a period of 30 min. The mixture was recooled to −78° C. and a solution of zinc chloride (408 mg, 3 mmol) in THF (1 mL) was added to it. The white turbid mixture was warmed to ambient temperature and stirred for 30 min. This mixture was transferred to a flask containing ethyl 7-[4,4-dimethyl-3,4,-dihydronaphthalen-1-trifluoromethylsulfonyloxy-7-yl]-3,7-dimethyl-hept-2(E), 4(E), 6(E)trienoate (Compound C14, 118 mg, 0.25 mmol), palladium tetrakis(triphenylphosphine) (250 mg, 0.22 mmol) and THF (1 mL). The reactants were heated to 50° C. for 3 h. and then the reaction was quenched by adding aqueous NH$_4$Cl (10 mL). The reaction mixture was extracted with ethylacetate (3×20 mL). The combined organic layer was washed with water (10 mL) and brine (10 mL), dried with MgSO$_4$. The solvent was removed under reduced pressure and the title compound was obtained as pale yellow solid after silicagel chromatography.

$^1$H NMR (CDCl$_3$): δ 1.29 (t, J=7.1 Hz), 1.33 (s, 6H), 2.18 (s, 3H), 2.33 (d, J=4.8 Hz, 2H), 2.36 (s, 3H), 4.17 (q, J=7.1 Hz, 2H), 5.79 (s, 1H), 6.21 (t, J=4.8 Hz, 1H) 6.33 (d, J=15.1 Hz, 1H), 6.48 (d, J=11.5 Hz, 1H), 6.98 (dd, J=11.5, 15.1 Hz, 1H), 7.08 (br d, J=3.4 Hz, 2H), 7.26–7.29 (m, 1H), 7.32–7.41 (m, 2H), 7.52 (d, J=1.6 Hz, 1H).

Ethyl 7-[4,4-dimethyl-3,4,-dihydronaphthalen-1(2H)-(anti)(O-methyl-oxime)-7-yl]-3,7-dimethyl-hept-2(E), 4(E), 6(E)trienoate (Compound C16)

To a solution of ethyl 7-[4,4-dimethyl-3,4,-dihydronaphthalen-1(2H)one-7-yl]-3,7-dimethyl-hept-2(E), 4(E), 6(E)trienoate (Compound C5, 25 mg, 0.07 mmol) in ethanol (2 mL) and THF (2 mL), was added sodium acetate trihydrate (103 mg, 0.75 mmol) followed by methoxylamine hydrochloride (42 mg, 0.5 mmol). The mixture was stirred at ambient temperature for 16 h and diluted with ether (60 mL). The ether layer was washed successively with 10% NaHCO$_3$ (5 mL), water (5 mL) and brine (10 mL). The organic layer was dried with MgSO$_4$ and the solvent was removed under reduced pressure. After purification by chromatography on silicagel the title compound was obtained as a white solid.

$^1$H NMR (CDCl$_3$): δ 1.29 (s, 6H), 1.30 (t, J=7.1 Hz, 3H), 1.72 (t, J=7.0 Hz, 2H), 2.27 (s, 3H), 2.39 (s, 3H), 2.80 (t, J=7.0 Hz, 2H), 4.03 (s, 3H), 4.18 (q, J=7.1 Hz, 2H), 5.82 (s, 1H), 6.40 (d, J=15.0 Hz, 1H), 6.60 (2, J=11.0 Hz, 1H), 7.03 (dd, J=11.0, 15.0 Hz, 1H), 7.33 (d, J=8.3 Hz, 1H), 7.44 (dd, J=2.1 Hz, 8.3 Hz, 1H), 8.07 (d, J=2.1 Hz, 1H).

Ethyl 7-[4,4-dimethyl-3,4,-dihydronaphthalen-1(2H)-(anti)(carbethoxymethylenyl)-7-yl]-3,7-dimethyl-hept-2(E), 4(E), 6(E)trienoate (Compound C17a)

Ethyl 7-[4,4-dimethyl-3,4,-dihydronaphthalen-1(2H)-(syn) (carbethoxymethylenyl)-7-yl]-3,7-dimethyl-hept-2(E), 4(E), 6(E)trienoate (Compound C17b)

To a cold (−78° C.) slurry of sodium hydride (24 mg, 1 mmol) in THF (3 mL) was added triethylphosphonoacetate (300 mg, 1.4 mmol). The mixture was stirred for 30 min. at 0° C. To this mixture a solution of ethyl 7-[4,4-dimethyl-3,4,-dihydronaphthalen-1(2H)one-7-yl]-3,7-dimethyl-hept-2(E), 4(E), 6(E)-trienoate (Compound C5, 50 mg, 0.15 mmol) in THF (2 mL) was added and stirred at ambient temperature for 48 h. The reaction was quenched by adding water (5 mL) and extracted with ethyl acetate (3×30 mL). The combined organic layer was washed with water (5 mL), brine (5 mL) and dried (MgSO$_4$). The solvent was removed under reduced pressure and the title compounds were obtained after silicagel chromatography and HPLC separation.

Ethyl 7-[4,4-dimethyl-3,4,-dihydronaphthalen-1(2H)-(anti) (carbethoxymethylenyl)-7-yl]-3,7-dimethyl-hept-2(E), 4(E), 6(E)trienoate (Compound 17a)

$^1$H NMR (CDCl$_3$): δ 1.30 (s, 6H), 1.30 (t, J=7.1 Hz, 3), 1.34 (t, J=7.1 Hz, 3H), 1.73 (t, J=6.6 Hz, 2H), 2.26 (s, 3H), 2.38 (s, 3H), 3.24 (t, J=6.6 Hz, 2H), 4.13–4.28 (m, 4H), 5.82 (s, 1H), 6.31 (s, 1H), 6.40 (d, J=15.0 Hz, 1H), 6.57 (d, J=11.5 Hz, 1H), 7.01 (dd, J=11.5, 15.0 Hz, 1H), 7.35 (d, J=8.3 Hz, 1H), 7.46 (dd, J=1.9, 8.3 Hz, 1H), 7.66 (d, J=1.9 Hz, 1H).

Ethyl 7-[4,4-dimethyl-3,4,-dihydronaphthalen-1(2H)-(syn) (carbethoxymethylenyl)-7-yl]-3,7-dimethyl-hept-2(E), 4(E), (E)trienoate (Compound C17b)

$^1$H NMR (CDCl$_3$): δ 1.25 (t, J=7.1 Hz, 3H), 1.28 (t, J=7.1 Hz, 3H), 1.32 (s, 6H), 1.83 (t, J=6.5 Hz, 2H), 2.23 (s, 3H), 2.38 (s, 3H), 2.54 (t, J=6.5 Hz, 2H), 4.12–4.25 (m, 4H), 5.81 (s, 2H), 6.38 (d, J=15.1 Hz, 1H), 6.57 (d, J=11.0 Hz, 1H), 7.01 (dd, J=11.0, 15.1 Hz, 1H), 7.30 (d, J=8.3 Hz, 1H), 7.46 (dd, J=1.9, 8.3 Hz, 1H), 7.72 (d, J=1.9 Hz, 1H).

7-[4,4-Dimethyl-1,2,3,4,-tetrahydronaphthalen-1-hydroxy-7-yl]-3,7-dimethyl-hept-2(E), 4(E), 6(E) trienoic acid (Compound C19)

To a solution of ethyl 7-[4,4-dimethyl-1,2,3,4,-tetrahydronaphthalen-1-hydroxy-7-yl]-3,7-dimethyl-hept-2(E), 4(E), 6(E)trienoate (Compound C13, 35 mg, 0.1 mmol) in THF (3 mL) and methanol (1 mL), was added lithiumhydroxide (1M solution in water, 0.3 mL, 0.3 mmol) and warmed to 60° C. for 6 h. The reaction mixture was diluted with ether: ethylacetate (1:1, 40 mL), acidified with 10% aqueous HCl to pH 6. The organic layer was washed with water (5 mL), brine (5 mL) and dried (MgSO4), and the solvent was removed under reduced pressure. After purification by preparative TLC the title compound was obtained as a pale yellow solid.

$^1$H NMR (CDCl$_3$): δ 1.26 (s, 3H), 1.34 (s, 3H), 1.55–1.65 (m, 1H), 1.70–2.10 (m, 3H), 2.27 (s, 3H), 2.40 (s, 3H), 4.77 (t, J=5.6 Hz, 1H), 5.84 (s, 1H), 6.41 (d, J=15.1 Hz, 1H), 6.62 (d, J=11.1 Hz, 1H), 7.08 (dd, J=11.1, 15.1 Hz, 1H), 7.32 (d, J=8.3 Hz, 1H), 7.40 (dd, J=1.9, 8.3 Hz, 1H), 7.57 (d, J=1.9 Hz, 1H).

7-[4,4-Dimethyl-3,4,-dihydronaphthalen-1-(2-thienyl)-7-yl]-3,7-dimethyl-hept-2(E), 4(E), 6(E) trienoic acid (Compound C20)

Employing the procedure used for the preparation of 7-[4,4-dimethyl-1,2,3,4,-tetrahydronaphthalen-1-hydroxy-7-yl]-3,7-dimethyl-hept-2(E), 4(E), 6(E)trienoic acid (Compound C19), 20 mg (0.05 mmol) of ethyl 7-[4,4-dimethyl-3,4,-dihydronaphthalen-1-(2-thienyl)-7-yl]-3,7-dimethyl-hept-2(E), 4(E), 6(E)trienoate (Compound C15) was converted to the title compound.

$^1$H NMR (C$_3$COC$_3$): δ 1.30 (s, 6H), 2.19 (s, 3H), 2.32 (d, J=4.8 Hz, 2H), 2.35 (s, 3H), 5.84 (s, 1H), 6.22 (t, J=4.8 Hz, 1H), 6.47 (d, J=15.1 Hz, 1H), 6.58 (d, J=11.0 Hz, 1H), 7.05–7.18 (m, 3H), 7.38–7.55 (m, 4H).

Ethyl 7-[4,4-dimethyl-3,4,-dihydronaphthalen-1-cyano-7-yl]-3,7-dimethyl-hept-2(E), 4(E), 6(E) trienoate (Compound C21)

To a solution of ethyl 7-[4,4-dimethyl-3,4,-dihydronaphthalen-1-trifluoromethylsulfonyloxy-7-yl]-3,7- dimethyl-hept-2(E), 4(E), 6(E)trienoate (Compound C14, 87 mg, 0.18 mmol) in THF (10 mL) were added tetrakis (triphenylphosphine)palladium (10 mg, 0.01 mmol) and zinc cyanide(42 mg, 0.36 mmol). The mixture was heated to 50° C. for 1 h. Additional quantities of tetrakis (triphenylphosphine)palladium (10 mg, 0.01 mmol) and zinc cyanide (42 mg, 0.36 mmol) were added and the mixture heated to 50° C. for another 1 h. The reaction was quenched with water (5 mL), extracted with ethyl acetate (2×20 mL), and the combined organic layer was washed with water, followed by brine. The organic layer was dried (MgSO$_4$) and solvent removed under reduced pressure. After silicagel chromatography the title compound was isolated as a solid.

$^1$H NMR (CDCl$_3$): δ 1.29 (s, 6H), 1.30 (t, J=7.1 Hz, 3H), 2.26 (s, 3H), 2.39 (s, 3H), 2.41 (d, J=4.8 Hz, 2H), 4.18 (% J=7.1 Hz, 2H), 5.83 (s, 1H), 6.41 (d, J=15.0 Hz, 1H), 6.61 (d, J=11.0 Hz, 1H), 6.87 (t, J=4.8 Hz, 1H), 7.01 (dd, J=11.0, 15.0 Hz, 1H), 7.32 (d, J=8.2 Hz, 1H), 7.44 (dd, J=2.0, 8.2 Hz, 1H), 7.57 (d, J=2.0 Hz, 1H).

Ethyl 7-[4,4-dimethyl-3,4-dihydro-1(2H)-syn-(O-ethyl oxime)-naphth-7-yl]3,7-dimethyl-hepta-2(E),4(E),6(E)-trienoate (Compound 22a)

Ethyl 7-[4,4-dimethyl-3,4-dihydro-1(2H)-anti-(O-ethyl oxime)-naphth-7-yl]3,7-dimethyl-hepta-2(E),4(E),6(E)-trienoate (Compound C22b)

To a solution of ethyl 7-[4,4-dimethyl-3,4-dihydronaphthalen-1(2H)one-7-yl]3,7-dimethyl-hepta-2(E),4(E),6(E)-trienoate (Compound C5, 128 mg, 0.4 mmol) in THF (10 mL) and ethanol (10 mL), was added 0-ethylhydroxylamine hydrochloride (280 mg, 2.8 mmol), sodium acetate trihydrate (600 mg, 4.4 mmol) and the mixture was stirred at ambient temperature for 80 h. The reaction mixture was diluted with ethyl acetate (50 mL) and washed with water (10 mL) and brine (50 mL). The organic phase was dried over MgSO$_4$ and then concentrated in vacuo to a yellow oil. Purification by column chromatography (silica, 10% EtOAc-hexane) followed by HPLC separation (partisil 10, 10% EtOAc-hexane) afforded the title compounds as white solid in the ratios of 1 (syn): 7 (anti).

Ethyl 7-[4,4-dimethyl-3,4-dihydro-1(2H)-syn-(O-ethyl oxime)-naphth-7-yl]3,7-dimethyl-hepta-2(E),4 (E),6(E)-trienoate (Compound C22a)

$^1$H NMR (CDCl$_3$): δ 1.27–1.39 (m, 12H), 1.88 (t, J=6.3 Hz, 2H), 2.25 (s, 3H), 2.39 (s, 3H), 2.56 (t, J=6 Hz, 2H), 4.19 (m, 4H), 5.81 (s, 1H), 6.34 (d, J=15.0 Hz, 1H), 6.57 (d, J=11.0 Hz, 1H), 7.03 (dd, J=11.4, 15.0 Hz, 1H), 7.36 (d, J=8.4 Hz, 1H), 7.46 (dd, J=2.0, 8.6 Hz, 1H), 8.65 (d, J=2.0 Hz, 1H).

Ethyl 7-[4,4-dimethyl-3,4-dihydro-1(2H)-anti-(O-ethyl oxime)-naphth-7-yl]3,7-dimethyl-hepta-2(E),4 (E),6(E)-trienoate (Compound C22b)

$^1$H NMR (CDCl$_3$): δ 1.28–1.31 (m, 9H), 1.36 (t, J=8.2 Hz, 3H), 1.73 (t, J=6.9 Hz, 2H) 2.27 (s, 3H), 2.40 (s, 3H), 2.82 (t, J=6.9 Hz, 2H), 4.20 (q, J=7.2 Hz, 2H), 4.3 (q, J=7.1 Hz, 2H), 5.83 (s, 1H), 6.38 (d, J=15.1 Hz, 1H), 6.59 (d, J=11.0 Hz, 1H), 7.03 (dd, J=11.2, 15.1 Hz, 1H), 7.32 (d, J=8.3 Hz, 1H), 7.42 (dd, J=2.1, 8.2 Hz, 1H), 8.09 (d, J=2.0 Hz, 1H).

7-[4,4-dimethyl-3,4-dihydro-1(2H)-syn-(O-ethyl oxime)-naphth-7-yl]3,7-dimethyl-hepta-2(E),4(E),6 (E)-trienoic acid (Compound C24)

To a solution of ethyl 7-[4,4-dimethyl-3,4-dihydro-1(2H) -syn-(O-ethyl oxime)-naphth-7-yl]3,7-dimethyl-hepta-2(E), 4(E),6(E)-trienoate (Compound C22a, 7.8 mg, 0.02 mmol) in THF (1 mL) and ethanol (1 mL), was added 1M lithium hydroxide (0.08 mL, 0.08 mmol) and the mixture was stirred at ambient temperature for 8 days. Thereafter the reaction mixture was diluted with Et$_2$O:EtOAc (1:1, 10 ml) and acidified with 10% HCl to pH 4. The organic layer was washed with water (5 mL), brine (10 ml), dried (MgSO$_4$) and the solvent was removed under reduced pressure. Recrystallization from EtOAc/hexane gave the title compound as a pale yellow solid.

$^1$H NMR (CDCl$_3$): δ 1.32 (s, 6H), 1.36 (t, J=7.1 Hz, 3H), 1.88(t, J=8.7 Hz, 2H), 2.25 (s, 3H), 2.39 (s, 3H), 2.55 (t, J=6.5 Hz, 2H), 4.20 (q, J=7.0 Hz, 2H), 5.84 (s, 1H), 6.36 (d, J=15.0 Hz, 1H), 6.58 (d, J=11.0 Hz, 1H), 7.03 (dd, J=11.2, 15.1 Hz, 1H), 7.36 (d, J=8.4 Hz, 1H), 7.47 (dd, J=2.0, 8.6 Hz, 1H), 8.65 (d, J=2.0 Hz, 1H).

7-[4,4-dimethyl-3,4-dihydro-1(2H)-anti-(O-ethyl oxime)-naphth-7-yl]3,7-dimethyl-hepta-2(E),4(E),6 (E)-trienoic acid (Compound C25)

To a solution of ethyl 7-[4,4-dimethyl-3,4-dihydro-1(2H) -anti-(O-ethyl oxime)-naphth-7-yl]3,7-dimethyl-hepta-2(E), 4(E),6(E)-trienoate (Compound C22b, 40 mg, 0.1 mmol) in THF (2 mL) and ethanol (2 mL), was added 1M lithium hydroxide (2 mL, 2 mmol) and the mixture was stirred at ambient temperature for 3 days and thereafter at 50° C. for 8 h. The reaction mixture was diluted with Et$_2$O: EtOAc (1:1, 10ml), and then acidified with 10% HCl to pH 4. The organic layer was washed with water (5 mL), brine (10 ml), dried (MgSO$_4$) and the solvent was removed under reduced pressure. Recrystallization from EtOAc/hexane gave the title compound as a pale yellow solid.

$^1$H NMR (CDCl$_3$): δ 1.30 (s, 6H), 1.36 (t, J=7.0 Hz, 3H), 1.73 (t, J=7.0 Hz, 2H) 2.28 (s, 3H), 2.41 (s, 3H), 2.81 (t, J=6.9 Hz, 2H), 4.25 (% J=7.1 Hz, 2H), 5.86 (s, 1H), 6.41 (d, J=15.0 Hz, 1H), 6.60 (d, J=11.4 Hz, 1H), 7.03 (dd, J=11.4, 15.1 Hz, 1H), 7.32 (d, J=8.4 Hz, 1H), 7.42 (dd, J=2.1, 8.4 Hz, 1H), 8.09 (d, J=2.0 Hz, 1H).

(–/+)Ethyl 7-[4,4-dimethyl-1,2,3,4-tetrahydro-1-(O-methoxymethyl)-naphth-7-yl]3,7-dimethyl-hepta-2 (E),4(E),6(E)-trienoate (Compound C26)

To a solution of (–/+)ethyl 7-[4,4-dimethyl-1,2,3,4-tetrahydro-1-hydroxy -naphth-7-yl]3,7-dimethyl-hepta-2(E) ,4(E),6(E)-trienoate (Compound C13, 67 mg, 0.19 mmol) in CH$_2$Cl$_2$ (1 mL) were added N,N-diisopropylethylamine (91 mg, 1.1 mmol), chloromethyl methyl ether (294 mg, 2.3 mmol) and the mixture was stirred at ambient temperature for 12 h. Then the reaction mixture was diluted with water (5 mL) and Et$_2$O (25 mL) and washed with water (10 mL) and brine (10 mL). The organic phase was dried over MgSO$_4$ and concentrated in vacuo to a yellow oil. Purification by flash column chromatography (silica, 10% EtOAc-hexane) followed by reverse phase HPLC separation (partisil 10 ODS-2, 5% H$_2$O-AcCN) afforded the title compound as a pale yellow oil.

$^1$H NMR (CDCl$_3$): δ 1.24 (s, 3H), 1.29 (t, J=7.1 Hz, 3H), 1.34 (s, 3H), 1.55–1.60(m, 1H), 1.91–2.05 (m, 3H), 2.24 (s, 3H), 2.38 (s, 3H), 3.48(s, 3H), 4.16 (q, J=7.1 Hz, 2H), 4.65 (t, J=4.7 Hz, 1H), 4.76(d, J=7.0 Hz, 1H), 4.87(d, J=7.0 Hz, 1H), 5.80 (s, 1H), 6.33 (d, J=15.2 Hz, 1H), 6.55 (d, J=11.5 Hz, 1H), 7.01 (dd, J=11.1, 15.0 Hz, 1H), 7.31 (d, J=8.3 Hz, 1H), 7.37 (dd, J=2.1, 8.4 Hz, 1H), 7.43 (d, J=2.1 Hz, 1H).

(+/–) 7-[4,4-dimethyl-1,2,3,4-tetrahydro-1-(O-methoxymethyl)-naphth-7-yl]3,7-dimethyl-hepta-2 (E),4(E),6(E)-trienoic acid (Compound C27)

Employing the same general procedure as for the preparation of 7-[4,4-dimethyl-3,4-dihydro-1(2H)-anti-(O-ethyl oxime)-naphth-7-yl]3,7-dimethyl-hepta-2(E),4(E),6(E)-trienoic acid (Compound C25). (–/+)ethyl 7-[4,4-dimethyl-1,2,3,4-tetrahydro-1-(O-methoxymethyl)-naphth-7-yl]3,7-dimethyl-hepta-2(E),4(E),6(E)-trienoate (Compound C26, 20 mg, 0.05 mmol) was converted into the title compound (white solid).

¹H NMR (acetone-d₆): δ 1.23 (s, 3H), 1.30 (s, 3H), 1.55–1.60 (m, 1H), 1.89–1.97 (m, 3H), 2.26 (s, 3H), 2.36 (s, 3H), 3.40 (s, 3H), 4.59 (t, J=3.9 Hz, 1H), 4.72 (d, J=6.9 Hz, 1H), 4.81 (d, J=7.0 Hz, 1H), 5.85 (s, 1H), 6.49 (d, J=15.1 Hz, 1H), 6.66 (d, J=11.3 Hz, 1H), 7.12 (dd, J=11.1 Hz, 1H), 7.36 (d, J=8.3 Hz, 1H), 7.43 (dd, J=2.1, 8.3 Hz, 1H), 7.49 (d, J=2.0 Hz, 1H).

Ethyl 7-[4,4-dimethyl-3,4-dihydro-1-(trimethylsiloxy)-naphth-2-yl]3,7-dimethyl-hepta-2(E),4(E),6(E)-trienoate (Compound C28)

To a solution of ethyl 7-[4,4-dimethyl-3,4-dihydronaphthalen-1(2H)one-7-yl]3,7-dimethyl-hepta-2(E),4(E),6(E)-trienoate (Compound C5, 114 mg, 0.33 mmol) in anhydrous THF (10 mL) was added sodium bis-(trimethylsilyl) amide (0.36 ml, 0.36 mmol) at –78° C. under argon. The reaction was stirred at –78° C. for 20 minutes. To this reaction solution was then added a solution of trimethylsilylchloride (70.8 mg, 0.65 mmol) in HMPA (0.1 mL) and anhydrous THF (5 ml) at –78° C. The reaction was allowed to stir at –78° C. for 2 h. Then the reaction mixture was diluted with Et₂O (25 mL) and washed with water (10 mL), brine (10 mL). The organic phase was dried over MgSO₄ and concentrated in vacuo to a yellow oil. The product was purified by flash column chromatography (silica, 10% EtOAc-hexane) to afford the title compound as a pale yellow oil.

¹H NMR (acetone-d₆): δ 0.26 (s, 9H), 1.23 (t, J=7.1 Hz, 3H), 1.26 (s, 6H), 2.25 (m, 5H), 2.37 (m, 3H), 4.08 (q, J=7.1 Hz, 2H), 5.15 (t, J=4.6 Hz, 1H), 5.83 (s, 1H), 6.48 (d, J=15.1 Hz, 1H), 6.65 (d, J=11.0 Hz, 1H), 7.13 (dd, J=11.1, 15.0 Hz, 1H), 7.26 (d, J=8.1 Hz, 1H), 7.40 (dd, J=2.1, 8.1 Hz, 1H), 7.60 (d, J=2.1 Hz, 1H).

(+/–)Ethyl 7-[4,4-dimethyl-1,2,3,4-tetrahydro-1(RS)-(2'(RS)-tetrahydropyranoxy)-3,7-dimethyl-naphth-2-yl]hepta-2(E),4(E),6(E)-trienoate (Compound C29a)

(+/–)Ethyl 7-[4,4-dimethyl-1,2,3,4-tetrahydro-1(RS)-(2'(SR)-tetrahydropyranoxy)-3,7-dimethyl-naphth-2-yl]hepta-2(E),4(E),6(E)-trienoate (Compound C29b)

To a solution of (–/+)ethyl 7-[4,4-dimethyl-1,2,3,4-tetrahydro-1-hydroxy-naphth-7-yl]3,7-dimethyl-hepta-2(E),4(E),6(E)-trienoate (Compound C13, 110 mg, 0.3 mmol) in anhydrous CH₂Cl₂ (2 mL) was added 3,4-dihydro-2H-pyran (62 mg, 0.7 mmol) followed by pyridinium p-toluenesulfonate (10 mg, 0.04 mmol). The reaction mixture was stirred at ambient temperature for 24 h. The reaction mixture was diluted with Et₂O (20 mL) and washed successively with saturated NaHCO₃ (10 mL), water (10 mL) and brine (10 mL). The organic phase was dried over MgSO₄ and concentrated in vacuo to a yellow oil. Purification by flash column chromatography (silica, 15% EtOAc-hexane)followed by reverse phase HPLC separation (partisil 10 ODS-2, 5% H₂O-AcCN) afforded the title compounds as pale yellow oils. (+/–)Ethyl 7-[4,4-dimethyl-1,2,3,4-tetrahydro-1(RS)-(2'(RS)-tetrahydropyranoxy)-3,7-dimethyl-naphth-2-yl]hepta-2(E),4(E),6(E)-trienoate (Compound C29a)

¹H NMR (CDCl₃): δ 1.25–1.31 (m, 9H), 1.52–2.03 (m, 10H), 2.24 (s, 3H), 2.38 (s, 3H), 3.50–3.60 (m, 1H), 4.01–4.07 (m, 1H), 4.12 (q, J=7.1 Hz, 2H), 4.77 (t, J=4.5 Hz, 1H), 4.94 (t, J=3.5 Hz, 1H), 5.80 (s, 1H), 6.32 (d, J=15.0 Hz, 1H), 6.56 (d, J=11.5 Hz, 1H), 7.02 (dd, J=11.1, 15.0 Hz, 7.28 (d, J=8.3 Hz, 1H), 7.36 (dd, J=2.1, 8.3 Hz, 1H), 7.62 (d, J=2.0 Hz, 1H). (+/–)Ethyl 7-[4,4-dimethyl-1,2,3,4-tetrahydro-1(RS)-(2'(SR)-tetrahydropyranoxy)-3,7-dimethyl-naphth-2-yl]hepta-2(E),4(E),6(E)-trienoate (Compound C29b)

¹H NMR (CDCl₃): δ 1.25–1.32 (m, 9H), 1.52–2.08 (m, 10H), 2.45 (s, 3H), 2.38 (s, 3H), 3.54–3.61 (m, 1H), 3.97–4.03 (m, 1H), 4.14 (q, J=7.1 Hz, 2H), 4.68 (t, J=5.0 Hz, 1H), 4.87 (t, J=4.4 Hz, 1H), 5.81 (s, 1H), 6.34 (d, J=15.2 Hz, 1H), 6.54 (d, J=11.0 Hz, 1H), 7.01 (dd, J=11.2, 15.1 Hz, 1H), 7.30–7.40 (m, 3H)

(+/–)7-[4,4-Dimethyl-1,2,3,4-tetrahydro-1(RS)-(2'(RS)-tetrahydropyranoxy)-3,7-dimethyl-naphth-2-yl]hepta-2(E),4(E),6(E)-trienoic acid (Compound C31)

Employing the same general procedure as for the preparation of 7-[4,4-dimethyl-3,4-dihydro-1(2H)-anti-(O-ethyl oxime)-naphth-7-yl]3,7-dimethyl-hepta-2(E),4(E),6(E)-trienoic acid (Compound C25), (+/–)ethyl 7-[4,4-dimethyl-1,2,3,4-tetrahydro-1(RS)-(2'(RS)-tetrahydropyranoxy)-3,7-dimethyl-naphth-2-yl]hepta-2(E),4(E),6(E)-trienoate (Compound C29a, 15 mg, 0.03 mmol) was converted into the title compound (white solid).

¹H NMR (acetone-d₆): δ 1.24 (s, 3H) 1.29 (s, 3H), 1.52–2.03 (m, 10H), 2.26 (s, 3H), 2.37 (s, 3H), 3.56–3.61 (m, 1H), 3.99–4.03 (m, 1H), 4.70 (t, J=4.5 Hz, 1H), 4.91 (t, J=3.7 Hz, 1H), 5.80 (s, 1H), 6.49 (d, J=15.0 Hz, 1H), 6.66 (d, J=11.3 Hz, 1H), 7.13 (dd, J=11.1, 15.0 Hz, 1H), 7.34 (d, J=8.3 Hz, 1H), 7.42 (dd, J=2.1, 8.3 Hz, 1H), 7.63 (d, J=2.0 Hz, 1H).

7-Acetyl-1(2H)-(propyliden-2-yl)-3,4-dihydro-4,4-dimethylnaphthalene (Compound C33)

To a solution of 7-bromo-1(2H)-(propyliden-2-yl)-3,4-dihydro-4,4-dimethylnaphthalene (Compound A37, 698 mg, 2.5 mmol) in anhydrous THF (15 mL) was added (1-ethoxyvinyl)tributyltin (1.8 g, 5 mmol) and bis (triphenylphosphine)palladium(II) chloride (20 mg). The resultant mixture was refluxed under argon atmosphere for 24 h. The reaction mixture was cooled to ambient temperature and quenched with 10% HCl(5 mL), stirred for 20 minutes and extracted with Et₂O (3×20 mL). The organic layer was washed with water (10 mL), saturated NaHCO₃ (10 mL), brine (10 mL) and dried over MgSO₄. The crude material was purified by flash column chromatography (silica, 5% EtOAc-hexane) to afford the title compound as a colorless oil.

¹H NMR (CDCl₃): δ 1.25 (s, 6H), 1.60 (t, J=6.9 Hz, 2H), 1.84 (s, 3H), 1.97 (s, 3H), 2.49 (t, J=6.9 Hz, 2H), 2.57 (s, 3H), 7.35 (d, J=8.3 Hz, 1H), 7.73 (dd, J=2.0, 8.2 Hz, 1H), 7.85 (d, J=1.9 Hz, 1H).

3-[1(2H)-(Propyliden-2-yl))-3,4-dihydro-4,4-dimethylnaphthalen-7-yl]but-2(E)-en-nitrile (Compound C34)

To a slurry NaH (117 mg, 4.8 mmol) in anhydrous THF (10 mL) was added a solution of ethyleyanomethylphosphonate (947 mg, 5.4 mmol) in THF (2 mL) at –78° C. under argon atmosphere. The reaction was allowed to warm to ambient temperature and a solution of 7-acetyl-1(2H)-(propyliden-2-yl)-3,4-dihydro-4,4-dimethylnaphthalene (Compound C33, 394 mg, 1.6 mmol) in 5 mL of THF was added dropwise. The resultant reaction was stirred for 16 h at ambient temperature and quenched with water (5 mL). After extraction with EtOAc (2×10 mL), the combined organic layer was dried over MgSO$_4$, and concentrated in vacuo. The crude product was purified by flash column chromatography (silica, 5% EtOAc-hexane) to afford the title compound as a colorless oil.

$^1$H NMR (CDCl$_3$): δ 1.24 (s, 6H), 1.60 (t, J=7.0 Hz, 2H), 1.85 (s, 3H), 1.96 (s, 3H), 2.45 (s, 3H), 2.49 (t, J=6.8 Hz, 2H), 5.59 (s, 1H), 7.24–7.35 (m, 3H). 3-[1(2H)-(Propyliden-2-yl)-3,4-dihydro-4,4-dimethylnaphthalen-7-yl]but-2(E)-en-aldehyde (Compound C35)

To a solution of 3-[1(2H)-(propyliden-2-yl)-3,4-dihydro-4,4-dimethylnaphthalen-7-yl]but-2(E)-en-onitrile (Compound C34, 311 mg, 1.2 mmol) in anhydrous CH$_2$Cl$_2$ (10 ml) was added a solution of diisobutylaluminum hydride (1M in CH$_2$Cl$_2$) (2.8 ml, 2.8 mmol) dropwise at –78° C., under argon atmosphere. The reaction was allowed to stir at –78° C. for 6 h. A mixture of H$_2$O (10 ml) and CH$_2$Cl$_2$ (10 ml) was added and the resultant gel was filtered. The filtrate was concentrated in vacuo to a yellow oil. Purification by flash column chromatography (silca, 10% EtOAc-hexane) afforded the title compound as a pale yellow oil.

$^1$H NMR (CDCl$_3$): is 1.26 (s, 6H), 1.62 (t, J=7.0 Hz, 2H), 1.86 (s, 3H), 1.98 (s, 3H), 2.50 (t, J=6.9 Hz, 2H), 2.57 (s, 3H), 6.40 (d, J=9.3 Hz, 1H), 7.35–7.39 (m, 2H), 7.45 (d, J=1.9 Hz, 1H), 10.17 (d, J=7.9 Hz, 1H).

Ethyl-7-[1(2H)-(propyliden-2-yl)-3,4-dihydro-4,4-dimethyl-naphthalen-7-yl]-3,7-dimethyl-hept-2(E),4(E),6(E)-trienoate (Compound C36)

Employing the same general procedure as for the preparation of ethyl 7-[4,4-dimethyl-3,4-dihydronaphthalen-1(2H)one-7-yl]3,7-dimethyl-hepta-2(E),4(E),6(E)-trienoate (Compound C5), 3-[1(2H)-(propyliden-2-yl)-3,4-dihydro-4,4-dimethylnaphthalen-7-yl]but-2(E)-en-aldehyde (Compound C35, 178 mg, 0.6 mmol) was converted into the title compound (pale yellow thick syrup).

$^1$H NMR (CDCl$_3$): δ 1.24 (s, 6H), 1.27 (t, J=7.0 Hz, 3H), 1.60 (t, J=6.9 Hz, 2H), 1.84 (s, 3H), 1.98 (s, 3H), 2.24 (s,3H), 2.37 (s, 3H), 2.48 (t, J=6.7 Hz, 2H), 4.14 (q, J=7.1 Hz, 2H), 5.79 (s, 1H), 6.33 (d, J=14.9 Hz, 1H), 6.54 (d, J=10.9 Hz, 1H), 6.98 (dd, J=11.0, 15.0 Hz, 1H), 7.25–7.28 (m, 2H), 7.36 (s, 1H).

7-Bromo-1(2H)-(phenylbenzyliden-yl)-3,4-dihydro-4,4-dimethylnaphthalene (Compound C37)

Employing the same general procedure as for the preparation of 7-bromo-1(2H)-(propyliden-2-yl)-3,4-dihydro-4,4-dimethylnaphthalene (Compound A37), 7-bromo-3,4-dihydro-4,4-dimethylnaphthalen-1(2H)-one (Compound G, 1.0 g, 3.96 mmol) was converted into the title compound (white solid) using titanium trichloride (5 g, 32 mmol), lithium wire (0.7 g, 100 mmol) and benzophenone (800 mg, 4.4 mmol).

$^1$H NMR (CDCl$_3$): δ 1.31 (s, 6H), 1.66 (t, J=6.6 Hz, 2H), 2.52 (t, J=6.8Hz, 2H), 6.92 (d, J=1.7 Hz, 1H), 6.98–7.00 (m, 2H), 7.15–7.21 (m, 6H), 7.25–7.36 (m, 4H). 7-Acetyl-1(2H)-(phenylbenzyliden-yl)-3,4-dihydro-4,4-dimethylnaphthalene (Compound C38)

Employing the same general procedure as for the preparation of 7-acetyl-1(2H)-(propyliden-2-yl)-3,4-dihydro-4,4-dimethylnaphthalene (Compound C33), 7-bromo-1(2H)-(phenylbenzyliden-yl)-3,4-dihydro-4,4-dimethylnaphthalene (Compound C37, 255 mg, 0.63 mmol) was converted into the title compound (colorless oil) using (1-ethoxyvinyl)tributyltin (353 mg, 0.97 mmol) and bis(triphenylphosphine)palladium(II) chloride (20 mg).

$^1$H NMR (CDCl$_3$): δ 1.34 (s, 6H), 1.70 (t, J=6.4 Hz, 2H), 1.99 (s, 3H), 2.57 (t, J=6.7 Hz, 2H), 7.01–7.04 (m, 2H), 7.12–7.45 (m, 10H), 7.65 (dd, J=1.9, 8.3 Hz, 1H).

3-(1 (2H)-(phenylbenzylidenyl)-3,4-dihydro-4,4-dimethylnaphth-7-yl)-but-2(E)-enonitrile (Compound C39)

Employing the same general procedure as for the preparation of 3-(1(2H)-(propyliden-2-yl)-3,4-dihydro-4,4-dimethylnaphthyl)but-2(E)-enonitrile (Compound C34), the 7-acetyl-1(2H)-(phenylbenzylidenyl)-3,4-dihydro-4,4-dimethylnaphthalene (Compound 38, 206 mg, 0.56 mmol) was converted into the title compound (colorless oil) using 327 mg (1.85 mmol) of ethylcyanomethylphosphonate and 40.3 mg (1.68 mmol) of sodium hydride.

$^1$H NMR (CDCl$_3$): δ 1.34 (s, 6H), 1.70 (t, J=6.3 Hz, 2H), 2.03 (s, 3H), 2.57 (t, J=6.8Hz, 2H), 4.88 (s, 1H), 7.01 (dd, J=2.0, 7.3 Hz, 2H), 7.14–7.37 (m, 11H).

3-(1(2H)-(phenylbenzylidenyl)-3,4-dihydro-4,4-dimethylnaphth-7-yl)-but-2(E)-enaldehyde (Compound C40)

Employing the same general procedure as for the preparation of 3-(1(2H)-(propyliden-2-yl)-3,4-dihydro-4,4-dimethylnaphthyl)-but-2(E)-enaldehyde (Compound C35), 3-(1(2H)-(phenylbenzylidenyl)-3,4-dihydro-4,4-dimethylnaphth-7-yl)-but-2-enonitrile (Compound C39, 156 mg, 0.40 mmol) was converted into the title compound (pale yellow solid) using 0.9 ml (0.88 mmol) of diisobutylaluminum hydride (1M in CH$_2$Cl$_2$).

$^1$H NMR (CDCl$_3$): δ 1.35 (s, 6H), 1.70 (t, J=6.5 Hz, 2H), 2.04 (s, 3H), 2.57 (t, J=6.7 Hz, 2H), 5.88 (d, J=7.7 Hz, 1H), 7.02 (dd, J=1.5, 7.4 Hz, 2H), 7.12–7.36 (m, 11H), 9.98 (d, J=7.8 Hz, 1H).

Ethyl 7-[4,4-dimethyl-3,4-dihydro-1(2H)-(phenylbenzylidenyl)-naphth-7-yl]-3,7-dimethyl-hepta-2(E),4(E),6(E)-trienoate (Compound C41)

Employing the same general procedure as for the preparation of ethyl 7-[4,4-dimethyl-3,4-dihydronaphthalen-1(2H)one-7-yl]3,7-dimethyl-hepta-2(E),4(E),6(E)-trienoate (Compound C5), 3-(1(2H)-(phenylbenzylidenyl)-3,4-dihydro-4,4-dimethylnaphth-7-yl)-but-2(E)-enaldehyde (Compound C40, 101 mg, 0.26 mmol) was converted into the title compound (pale yellow thick oil).

$^1$H NMR (CDCl$_3$): δ 1.28 (t, J=7.1 Hz, 3H), 1.34 (s, 6H), 1.69 (t, J=6.3 Hz, 2H), 1.85 (s, 3H), 2.32 (s, 3H), 2.54 (t, J=6.9 Hz, 2H), 4.14 (q, J=7.1 Hz, 2H), 5.74 (d, J=8.7 Hz, 1H), 5.77 (s, 1H), 6.15 (d, J=14.9 Hz, 1H), 6.80 (dd, J=11.2, 15.0 Hz, 1H), 7.04–7.36 (m, 13H).

7-Bromo-1-(1,1-dimethylethyl)-3,4-dihydro-4,4-dimethylnaphthalene (Compound C42)

In a flame dried round bottom flask 7-bromo-3,4-dihydro-4,4-dimethylnaphthalen-1(2H)-one (Compound G, 2.0 g, 7.93 mmol) was dissolved in anhydrous THF (50 ml) and 3,4,5,6,-tetrahydro-2(H)-pyrimidinone (DMPU) (11.5 ml, 95.16 mmol) was added, under argon atmosphere. The reaction was then cooled to –20° C. and a solution of t-butyl magnesium chloride (16 ml, 31.7 mmol) (2M in Et$_2$O) was added dropwise and stirred at –20° C. for 2 h and at ambient temperature for 1 h, under argon atmosphere. The reaction was quenched at 0° C. with saturated ammonium chloride solution (20 ml) and extracted with EtOAc (2×50 ml). The combined extract was washed with water (20 ml), brine (20 ml) and dried over MgSO₄. The solvent was evaporated under reduced pressure to afford a yellow oil. To this yellow oil were added MeOH (50 ml) and p-tolylsulfonic acid (100 mg). The resultant reaction solution was heated in an oil bath (60° C.) for 3 h. The reaction was cooled and quenched with water (20 ml), extracted with EtOAc (2×50 ml). The combined extract was washed with saturated NaHCO₃ (20 ml), water (20 ml), brine (20 ml), and dried over MgSO₄. The solvent was concentrated in s vacuo and the title compound was obtained as a colorless oil after purification by flash chromatography (silica, hexane).

$^1$H NMR (CDCl₃): δ 1.17 (s, 6H), 1.32 (s, 9H), 2.10 (d, J=5.0 Hz, 2H), 5.95 (t, J=4.9 Hz, 1H), 7.13 (d, J=8.3 Hz, 1H), 7.24 (dd, J=2.1, 8.3 Hz, 1H), 7.74 (d, J=2.0 Hz, 1H).

7-Acetyl-1-(1,1-dimethylethyl)-3,4,-dihydro-4,4-dimethylnaphthalene (Compound C43)

Employing the same general procedure as for the preparation of 7-acetyl-1(2H)-(propyliden-2-yl)-3,4-dihydro-4,4-dimethylnaphthalene (Compound C33), 7-bromo-1-(1,1-dimethylethyl)-3,4-dihydro-4,4-dimethylnaphthalene (Compound C42, 539 mg, 1.84 mmol) was converted into the title compound (white solid), using (1-ethoxyvinyl) tributyltin (2.6 g, 7.36 mmol) and bis(triphenylphosphine) palladium(II) chloride (80 mg).

$^1$H NMR (CDCl₃): δ 1.25 (s, 6H), 1.39 (s, 9H), 2.16 (d, J=4.9 Hz, 2H), 2.60 (s, 3H), 6.00 (t, J=4.9 Hz, 1H), 7.39 (d, J=8.1 Hz, 1H), 7.75 (dd, J=1.7, 8.0 Hz, 1H), 8.29 (d, J=1.8 Hz, 1H).

3-[1-(1,1-dimethylethyl)-3,4-dihydro-4,4-dimethylnaphthyl]-2-but-2(E)-enonitrile (Compound C44)

Employing the same general procedure as for the preparation of 3-(1-propylidene)-1,2,3,4-tetrahydro-4,4-dimethylnaphthyl)but-2(E)-enonitrile (Compound C34), 7-acetyl-1-(1,1-dimethylethyl)-3,4-dihydro-4,4-dimethylnaphthalene (Compound C43, 326 mg, 1.26 mmol) was converted into the title compound (white solid) using 742 mg (4.19 mmol) of ethylcyanomethylphosphonate and 91 mg (3.80 mmol) of sodium hydride.

$^1$H NMR (CDCl₃): δ 1.22 (s, 6H), 1.36 (s, 9H), 2.14 (d, J=4.9 Hz, 2H), 2.47 (s ,3H), 5.58 (s, 1H), 6.00 (t, J=4.9 Hz, 1H), 7.26 (dd, J=2.0, 8.2 Hz, 1H), 7.32 (d, J=8.1 Hz, 1H), 7.73 (d, J=1.9 Hz, 1H).

3-[1-(1,1-dimethylethyl)-3,4-dihydro-4,4-dimethylnaphth-7-yl]-but-2(E)-enaldehyde (Compound C45)

Employing the same general procedure as for the preparation of 3-(1-propylidene)-1,2,3,4-tetrahydro-4,4-dimethylnaphthyl)-but-2(E)-enaldehyde (Compound C35), (E)-3-(1-(1,1-dimethylethyl)-3,4-dihydro-4,4-dimethylnaphthyl)-but-2)E)-enonitrile (Compound C45, 256 mg, 0.95 mmol) was converted into the title compound (pale yellow solid) using 2.8 ml (2.84 mmol) of diisobutylaluminum hydride (1M in CH₂Cl₂).

$^1$H NMR (CDCl₃): δ 1.25 (s, 6H), 1.30 (s, 9H), 2.16 (d, J=5.0 Hz, 2H), 2.60 (s, 3H), 6.01 (t, J=4.9 Hz, 1H), 6.41 (d, J=7.8 Hz, 1H), 7.38 (m, 2H), 7.86 (s, 1H), 10.19 (d, J=8.0 Hz, 1H).

Ethyl 7-[4,4-dimethyl-3,4-dihydro-1-(1,1-dimethylethyl)-naphth-7-yl]-3,7-dimethyl-hepta-2(E) ,4(E),6(E)-trienoate (Compound C46)

Employing the same general procedure as for the preparation of ethyl 3,7-dimethyl-7-[5,5-dimethyl-5,6,7,8-tetrahydro-8-oxo-naphth-2-yl]hepta-2(E),4(E),6(E)-trienoate (Compound C5, (E)-3-[1-(1,1-dimethylethyl)-3,4-dihydro-4,4-dimethyl-naphthyl]-2-butene-1-aldehyde (Compound C45, 82.6 mg, 0.29 mmol) was converted into the title compound (pale yellow solid).

$^1$H NMR (CDCl₃): δ 1.24 (s, 6H), 1.28 (t, J=7.1 Hz, 3H), 1.39 (s, 9H), 2.15 (d, J=4.9 Hz, 2H), 2.28 (s, 3H), 2.40 (s, 3H), 4.15 (q, J=7.1 Hz, 2H), 5.83 (s, 1H), 5.97 (t, J=4.9 Hz, 1H), 6.36 (d, J=15.2 Hz, 1H), 6.54 (d, J=11.5 Hz, 1H), 7.00 (dd, J=11.1, 15.0 Hz, 1H), 7.31 (s, 2H), 7.78 (s, 1H).

(+/−) Ethyl 4-[(5,5-dimethyl-8-hydroxy-8-carbethoxymethyl-5,6,7,8-tetrahydronaphth-2-yl) azo]benzoate (Compound D1)

To a refluxing solution of zinc dust (0.15 g, 20 mesh, activated prior to use by washing with 2% of hydrochloric acid, water, 95% ethanol, acetone and anhydrous ether, then dried in vacuum for several hours) in 6 ml of dry benzene was slowly added a mixture of bromo ethyl acetate (0.082 ml ,0.74 mmol) and ethyl 4-[(5,5-dimethyl-5,6-dihydronaphthalen-8(7H)-one-2-yl)azo]benzoate (Compound D10, 0.13 g, 0.371 mmol) in 6 ml of dry benzene. The resulting mixture was refluxed for 2 h then cooled to room temperature. The precipitate was filtered through celite and the filtrate was washed with cold 15% sulfuric acid. The organic phase was washed with saturated sodium bicarbonate, brine, dried over Na₂SO₄, filtered and concentrated to give a red oil. Purification by flash chromatography (silica gel, 30% ethyl acetate in hexane) afforded the title compound as a red oil.

$^1$H NMR (CDCl₃): δ 1.28 (t, J=7.14 Hz, 3H), 1.34 (3H, s), 1.37 (s, 3H), 1.43 (t, J=7.14 Hz, 3H), 1.81 (m, 2H), 2.12 (m, 2H), 2.90 (q, J=7.14 Hz, 2H), 4.22 (q, J=7.14 Hz, 2H), 4.42 (q, J=7.14 Hz, 2H), 7.46 (d, J=8.43 Hz, 1H), 7.80 (dd, J=2.07, 6.35 Hz, 1H), 7.91 (d, J=8.55 Hz, 2H), 8.17 (d, J=8.55 Hz, 2H), 8.20 (d, J=2.20 Hz, 1H).

Ethyl 4-[(5,5-dimethyl-8(7H)-(carbethoxymethylideneyl)-5,6-dihydronaphthalen-2-yl)azo]benzoate (Compound D2a)

Ethyl 4-[(5,5-dimethyl-8-(carbethoxymethyl)-5,6-dihydronaphthalen-2-yl)azo]benzoate (Compound D2b)

A solution of (+/−) ethyl 4-[(5,5-dimethyl-8-hydroxy-8-carbethoxymethyl-5,6,7,8-tetrahydronaphth-2-yl) azo] benzoate (Compound D1, 108 mg, 0.25 mmol), DCC (55.9 mg, 0.271 mmol) and CuCl (36.6 mg, 0.37 mmol) in 8 ml of dry benzene was heated under reflux for 7 days. After cooling to room temperature, the solids were filtered out and the solution was extracted with ethyl acetate. The combined organic layer was washed with brine and dried over Na₂SO₄. The solvent was removed under reduced pressure, the crude material was purified by flash chromatography (silicagel, 10% ethyl acetate in hexane) to afford the pure title compounds as red oils. Ethyl 4-[(5,5-dimethyl-8(7H)-(carbethoxymethylidenyl)-5,6-dihydronaphthalen-2-yl)azo] benzoate (Compound D2a)

$^1$H NMR (CDCl₃): δ 1.35 (m, 9H), 1.44 (t, J=7.14 Hz, 3H), 1.79 (t, J=6.75 Hz, 2H), 3.29 (t, J=6.59 Hz, 2H), 4.27 (q, J=7.14 Hz, 2H), 4.44 (q, J=7.14 Hz, 2H), 6.47 (s, 1H), 7.55 (d, J=8.42 Hz, 1H), 7.97 (m, 3H), 8.22 (m, 3H). Ethyl 4-[(5,5-dimethyl-8-(carbethoxymethyl)-5,6-dihydronaphthalen-2-yl)azo]benzoate (Compound D2b)

$^1$H NMR (CDCl₃): δ 1.22 (t, J=7.10 Hz, 3H), 1.35 (s, 6H), 1.44 (t, J=7.14 Hz, 3H), 2.32 (d, J=4.39 Hz, 2H), 3.56 (s 2H), 4.17 (q, J=7.14 Hz, 2H), 4.44 (q, J=7.14 Hz, 2H), 6.20 (t, J=4.45 Hz, 1H), 7.48 (d, J=8.80 Hz, 1H), 7.81 (m, 2H), 7.92 (d, J=8.49 Hz, 2H), 8.20 (d, J=8.48 Hz, 2H).

Ethyl 4-[(8(7H)-anti-(O-methyl oxime)-5,5-dimethyl-5,6-dihydronaphthalen-2-yl)azo]benzoate (Compound D3)

A solution of ethyl 4-[(5,5-dimethyl-5,6-dihydronaphthalen-8(7H)-one-2-yl)azo]benzoate (Compound D10, 0.13 g, 0.371 mmol) (40 mg, 0.114 mmol), NaOAc (29.3 mg, 0.286 mmol) and methoxy amine hydrochloride (14.3 mg, 0.137 mmol) in 3 ml of EtOH and 2 ml of THF was stirred at room temperature for two weeks. The solvent was distilled off and the residue was diluted with ethyl acetate. The solution was washed with NaHCO$_3$ (sat.), water, brine and dried over Na$_2$SO$_4$. The solvent was removed under reduced pressure, the residue was purified by flash chromatography to afford the title compound as a red solid (34.8 mg).

$^1$H NMR (CDCl$_3$): δ 1.35 (s, 3H), 1.44 (t, J=7.14 Hz, 3H), 1.78 (t, J=6.96 Hz, 2H), 2.83 (t, J=6.90 Hz, 2H), 4.06 (s, 3H), 4.43 (q, J=7.14 Hz, 2H), 7.51 (d, J=8.48 Hz, 1H), 7.82 (dd, J=2.20, 6.35 Hz, 1H), 7.96 (d, J=8.55 Hz, 2H), 8.21 (d, J=8.48 Hz, 2H), 8.56 (d, J=2.14 Hz, 1H).

4-[(8(7H)-Anti-(O-methyl oxime)-5,5-dimethyl-5,6-dihydronaphthalen-2-yl)azo]benzoic acid (Compound D4)

A solution of ethyl 4-[(8(7H)-anti-(O-methyl oxime)-5,5-dimethyl-5,6-dihydronaphthalen-2-yl)azo]benzoate (Compound D3, 57.7 mg, 0.16 mmol) and 2 ml of aqueous NaOH (12%) in 4 ml of THF and 2 ml of EtOH was stirred overnight at room temperature. The reaction was acidified with 10% HCl (to pH 4 and extracted with EtOAc. The combined organic layer was washed with water and brine, and dried over Na$_2$SO$_4$. Solvent was removed under reduced pressure of afford the title compound as a red solid.

$^1$H NMR (acetone-d$_6$): δ 1.35 (s, 3H), 1.78 (t, J=6.96 Hz, 2H), 2.82 (t, J=6.90 Hz, 2H), 4.00 (s, 3H), 7.67 (d, J=8.54 Hz, 1H), 7.90 (dd, J=2.20, 6.59 Hz, 1H), 8.03 (d, J=8.66 Hz, 2H), 8.24 (d, J=8.48 Hz, 2H), 8.54 (d, J=2.14 Hz, 1H).

(+/−) Ethyl 4-[(5,5-dimethyl-8-hydroxy-5,6,7,8-tetrahydronaphthalen-2-yl)azo]benzoate (Compound D5)

To a solution of ethyl 4-[(5,5-dimethyl-5,6-dihydronaphthalen-8(7H)-one-2-yl)azo]benzoate (Compound D10, 60 mg, 0.171 mmol) in 2 ml of THF and 7 ml of EtOH at 0° C. was added NaBH$_4$ (6.5 mg, 0.171 mmol) and the mixture stirred for 3 h. The reaction was quenched by slow addition of cold water. Solvent was removed under reduced pressure and the residue was extracted with ethyl acetate. The organic layer was washed with brine, dried (MgSO$_4$) and solvent removed under reduced pressure. The crude product was purified by flash chromatography (silica, ethyl acetate/hexane, 1:3) to afford the title compound as a red oil.

$^1$H NMR (CDCl$_3$): δ 1.31 (s, 3H), 1.38 (s, 3H), 1.43 (t, J=7.14 Hz, 3H), 1.68 (m, 1H), 1.92 (m, 2H), 2.13 (m, 1H), 4.42 (q, J=7.14 Hz, 2H), 4.85 (m, 1H), 7.49 (d, J=8.48 Hz, 1H), 7.85 (dd, J=2.2, 6.29 Hz, 1H), 7.94 (d, J=8.61 Hz, 2H), 8.05 (d, J=2.13 Hz, 1H), 8.20 (d, J=8.55 Hz, 2H).

(+/−) Ethyl 4-[(5,5-dimethyl-8-(methoxymethyloxy)-5,6,7,8-tetrahydronaphthalen-2-yl)azo]benzoate (Compound D6)

To a solution of (+/−) ethyl 4-[(5,5-dimethyl-8-hydroxy-5,6,7,8-tetrahydronaphthalen-2-yl)azo]benzoate (Compound D5, 49.7 mg, 0.141 mmol) in 4 ml of dry CH$_2$Cl$_2$ at 0° C. was added isopropyl ethyl amine (0.152 ml, 0.847 mmol) followed by chloromethyl methyl ether (0.0323 ml, 0.423 mmol). The reaction mixture was stirred at room temperature for 12 h. Solvent was removed under reduced pressure, the residue was dissolved in ethyl acetate and the solution was washed with NaHCO$_3$ (sat.), and brine. The organic layer was dried (MgSO$_4$). The solvent s was removed under reduced pressure, the residue was purified by flash chromatography (silica, ethyl acetate: hexane, 1:3) to afford the title compound as a red oil.

$^1$H NMR (CDCl$_3$): δ 131 (s, 3H), 1.39 (s, 3H), 1.43 (t, J=7.08 Hz, 3H), 1.64 (m, 1H), 2.07 (m, 3H), 3.52 (s, 3H), 4.43 (q, J=7.08 Hz, 2H), 4.75 (t, J=5.06 Hz, 1H), 4.84 (d, J=6.90 Hz, 1H), 4.93 (d, J=6.90 Hz, 1H), 7.50 (d, J=8.43 Hz, 1H), 7.83 (dd, J=2.19, 6.29 Hz, 1H), 7.95 (m, 3H), 8.19 (d, J=8.55 Hz, 2H).

(+/−) 4-[(5,5-Dimethyl-8-(methoxymethyloxy)-5,6,7,8-tetrahydronaphthalen-2-yl)azo]benzoic acid (Compound D7)

Using the same procedure as for the preparation of 4-[(8(7H)-anti-(O-methyl oxime)-5,5-dimethyl-5,6-dihydronaphthalen-2-yl)azo]benzoic acid (Compound D4), (+/−) ethyl 4-[(5,5-dimethyl-8-(methoxymethyloxy)-5,6,7,8-tetrahydronaphthalen-2-yl)azo]benzoate (Compound D6, 34 mg, 0.093 mmol) was converted into the title compound (red solid).

$^1$H NMR (acetone-d$_6$): δ 132 (s, 3H), 1.37 (s, 3H), 1.63 (m, 1H), 1.99 (m, 3H), 3.45 (s, 3H), 4.75 (t, J=6.1 Hz, 1H), 4.80 (d, J=6.96 Hz, 1H), 4.89 (d, J=6.96 Hz, 1H), 7.62 (d, J=8.55 Hz, 1H), 7.84 (dd, J=2.19, 6.29 Hz, 1H), 8.00 (m, 3H), 8.22 (d, J=8.55 Hz, 2H).

3,4-dihydro-4,4-dimethyl-7-nitro-naphthalen-1(2H)-one (Compound D8)

To 1.7 mL (3.0g, 30.6 mmol, 18M) H$_2$SO$_4$ at −5° C. (ice-NaCl bath) was slowly added 783.0 mg (4.49 mmol) of 3,4-dihydro-4,4-dimethyl-naphthalen-1(2H)-one. A solution of HNO$_3$ (426.7 mg 6.88 mmol, 0.43 mL, 16M), and 1.31g (0.013 mol, 0.74 mL, 18M) of H$_2$SO$_4$ were slowly added. After 20 min, ice was added and the resulting mixture was extracted with EtOAc. The combined extracts were concentrated under reduced pressure to give a yellow oil from which the title compound, a pale yellow solid, was isolated by column chromatography (10% EtOAC/hexanes).

$^1$H NMR (CDCl$_3$): δ 8.83 (1H, d, J=2.6 Hz), 8.31 (1H, dd, J=2.8, 8.9 Hz), 7.62 (1H, d, J=8.7 Hz), 2.81 (2H, t, J=6.5 Hz), 2.08 (2H, t, J=6.5 Hz), 1.45 (6H, s).

3,4-dihydro-4,4-dimethyl-7-amino-naphthalen-1(2H)-one (Compound D9)

A solution of 230.0 mg (1.05 mmol) 3,4-dihydro-4,4-dimethyl-7-nitro-naphthalen-1(2H)-one (Compound D8) in 5.0 mL of EtOAc was stirred at room temperature with a catalytic amount of 10% Pd-C under 1 atm of H$_2$ for 24 h. The catalyst was removed by filtration through a pad of Celite, and the filtrate concentrated under reduced pressure to give the title compound as a dark green oil.

$^1$H NMR (CDCl$_3$): δ 7.30 (1H, d, J=2.7 Hz), 7.22 (1H, d, J=8.4 Hz), 6.88 (1H, dd, J=2.7, 8.5 Hz), 2.70 (2H, t, J=6.6 Hz), 1.97 (2H, t, J=6.6 HZ), 1.34 (6H, s).

Ethyl 4-[(5,6-dihydro-5,5-dimethyl-8(7H)-one-naphthalen-2-yl)azo]-benzoate (Compound D10)

To a solution of 198.7 mg (1.05 mmol) 3,4-dihydro-4,4-dimethyl-7-amino-naphthalen-1(2H)-one (Compound D9)

in 5.0 mL glacial acetic acid was added 180.0 mg (1.00 mmol) of ethyl 4-nitrosobenzoate. The resulting solution was stirred overnight at room temperature, and then concentrated under reduced pressure. The product was isolated from the residual oil as a red solid, by column chromatography (15% EtOAc-hexanes).

$^1$H NMR (CDCl$_3$): δ 8.57 (1H, d, J=2.0 Hz), 8.19 (2H, d, J=8.4 Hz), 8.07 (1H, d, J=8.0 Hz), 7.94 (2H, d, J=8.4 Hz), 7.58 (1H, d, J=8.6 Hz), 4.41 (2H, q, J=7.1 Hz), 2.79 (2H, t, J=6.6 Hz), 2.07 (2H, t, J=7.02 Hz), 1.44 (6H, s), 1.42 (3H, t, J=7.1 Hz).

Ethyl 4-[(5,6-dihydro-5,5-dimethyl-8-(trifluoromethylsulfonyl)oxy-naphthalen-2-yl)azo]-benzoate (Compound D11)

To a solution of 90.4 mg sodium bis(trimethylsilyl)amide (0.48 mmol, 0.48 mL of a 1.0M THF solution) in 2.0 mL THF at −78° C., was added 153.0 mg (0.437 mmol) of ethyl 4-[(5,6-dihydro-5,5-dimethyl-8(7H)-one-naphthalen-2-yl) azo]-benzoate (Compound D10) in 2.0 mL THF. The dark red solution was stirred at −78° C. for 30 min and then 204.0 mg (0.520 mmol) 2-[N,N-bis(trifluoromethylsulfonyl) amino]-5-chloropyridine was added as a solution in 2.0 mL THF. The reaction mixture was allowed to warm to room temperature and after 3 h was quenched by the addition of H$_2$O. The organic layer was concentrated to a red oil under reduced pressure. The product was isolated by column chromatography (25% EtOAc/hexanes) as a red oil.

$^1$H NMR (CDCl$_3$): d 8.21 (2H, d, J=8.6 Hz), 7.96 (2H, d, J=8.6 Hz), 7.94 (2H, m), 7.49 (1H, d, J=8.2 Hz), 6.08 (1H, t, J=2.5 Hz), 4.42 (2H, q, J=7.1 Hz), 2.49 (2H, d, J=4.8 Hz), 1.44 (3H, t, J=7.1 Hz), 1.38 (6H, s).

Ethyl 4-[(5,5-dimethyl-8-(2-thienyl)-5,6-dihydronaphthalen-2-yl)azo]benzoate (Compound D12)

To a cold solution (−78° C.) of thiophene (0.07 ml, 0.75 mmol) in 1.5 ml of THF was added t-BuLi (0.457 ml, 0.75 mmol, 1.7M in pentane) and stirred for 2 h. To this solution, ZnCl$_2$ (168 mg, 1.2 mmol) in 1.5 ml of THF was added. The resulting solution was warmed to room temperature, stirred for 1 h and was added (via cannula) to a solution of ethyl 4-[(5,6-dihydro-5,5-dimethyl-8-trifluoromethylsulfonyloxy-naphthalen-2-yl)azo]benzoate (Compound D11, 150 mg, 0.30 mmol) and tetrakis (triphenylphosphine)palladium(0) (10.6 mg) in 2.5 ml of THF. The resulting mixture was heated at 50° C. for 2.5 h. The reaction was diluted with sat. aqueous NH$_4$Cl and extracted with ethyl acetate. The combined organic layer was dried over Na$_2$SO$_4$ and concentrated to an oil. The crude product was purified by flash chromatography (silica, ethyl acetate:hexane 5:95) to afford the title compound as a red foam.

$^1$H NMR (CDCl$_3$): δ 1.40 (s, 6H), 1.44 (t, J=7.14 Hz, 3H), 2.41 (d, J=4.82 Hz, 2H), 4.42 (q, J=7.14 Hz, 2H), 6.29 (t, J=4.83 Hz, 1H), 7.14 (m, 2H), 7.32 (dd, J=1.52, 3.36, 1H), 7.53 (d, J=8.31 Hz, 1H), 7.84 (dd, J=2.08, 6.17 Hz, 1H), 7.92 (d, J=8.60 Hz, 2H), 8.03 (d, J=2.07 Hz, 1H), 8.18 (d, J=8.61 Hz, 2H).

4-[(5,5-Dimethyl-8-(2-thienyl)-5,6-dihydronaphthalen-2-yl)azo]benzoic acid (Compound D13)

Using the same procedure as for the preparation of 4-[(8(7H)-anti-(O-methyl oxime)-5,5-dimethyl-5,6-dihydronaphthalen-2-yl)azo]benzoic acid (Compound D4), ethyl 4-[(5,5-dimethyl-8-(2-thienyl)-5,6-dihydronaphthalen-2-yl)azo]benzoate (Compound 12, 100 mg, 0.258 mmol) was converted into the title compound (red solid).

$^1$H NMR (acetone-d$_6$): δ 1.40 (s, 6H), 2.43 (d, J=4.83 Hz, 2H), 2.82 (b, 1H), 6.32 (t, J=4.88 Hz, 1H), 7.19 (m, 2H), 7.50 (d, J=4.88 Hz, 1H), 7.65 (d, J=8.24 Hz, 1H), 7.95 (m, 4H), 8.21 (d, J=8.55 Hz, 2H).

3,4-dihydro-4,4-dimethyl-7-acetyl-naphthalen-1(2H)-one (Compound D14a); and 3,4-dihydro-4,4-dimethyl-6-acetyl-naphthalen-1(2H)-one (Compound D14b)

To a cold (0° C.) mixture of aluminum chloride (26.3 g, 199.0 mmol) in dichloromethane (55 mL) were added acetylchloride (15 g, 192 mmols) and 1,2,3,4-tetrahydro-1,1-dimethylnaphthalene (24.4 g, 152 mmols) in dichloromethane (20 mL) over 20 minutes. The reaction mixture was warmed to ambient temperature and stirred for 4 h. Ice (200 g) was added to the reaction flask and the mixture diluted with ether (400 mL). The layers were separated and the organic phase was washed with 10% HCl (50 mL), water (50 mL), 10% aqueous sodium bicarbonate, and saturated aqueous NaCl (50 mL) and thereafter dried over MgSO$_4$. The solvent was removed by distillation to afford a yellow oil which was dissolved in benzene (50 mL).

To a cold (0° C.) solution of acetic acid (240 mL) and acetic anhydride (120 mL) was added chromiumtrioxide (50 g, 503 mmols) in small portions over 20 mins under argon. The mixture was stirred for 30 mins at 0° C. and diluted with benzene (120 mL). The benzene solution prepared above, was added with stirring via an addition funnel over 20 mins. After 8 h, the reaction was quenched by the careful addition of isopropanol (50 mL) at 0° C., followed by water (100 mL). After 15 mins, the reaction mixture was diluted with ether (1100 mL) and water (200 mL), and then neutralized with solid sodium bicarbonate (200 g). The ether layer was washed with water (100 mL), and saturated aqueous NaCl (2×100 mL), and dried over MgSO$_4$. Removal of the solvent under reduced pressure afforded a mixture of the isomeric diketones which were separated by chromatography (5% EtOAc/hexanes).

(Compound D14a):

$^1$H NMR (CDCl$_3$): d 8.55 (1H, d, J=2.0 Hz), 8.13 (1H, dd, J=2.0, 8.3 Hz), 7.53 (1H, d, J=8.3 Hz), 2.77 (2H, t, J=6.6 Hz), 2.62 (3H, s), 2.05 (2H, t, J=6.6 Hz), 1.41 (6H, s).

(Compound D14b):

$^1$H NMR (CDCl$_3$): d 8.10 (1H, d, J=8.1 Hz), 8.02 (1H, d, J=1.6 Hz), 7.82 (1H, dd, J=1.6, 8.1 Hz), 2.77 (2H, t, J=7.1 Hz), 2.64 (3H, s), 2.05 (2H, t, J=7.1 Hz), 1.44 (6H, s).

6-(2-methyl-1,3-dioxolan-2-yl)-3,4-dihydro-4,4-dimethylnaphthalen-1(2H)-one (Compound D15)

A solution of 1.80 g (8.34 mmol) of a 1:5 mixture of 3,4-dihydro-4,4-dimethyl-7-acetyl-naphthalen-1(2H)-one (Compound D14a); and 3,4-dihydro-4,4-dimethyl-6-acetyl-naphthalen-1(2H)-one (Compound D14b) in 50 mL benzene was combined with 517.7 mg (8.34 mmol) of ethylene glycol and 20.0 mg (0.11 mmol) of p-toluenesulfonic acid monohydrate. The resulting solution was heated to reflux for 18 h, cooled to room temperature, and concentrated under reduced pressure. The title compound was isolated by column chromatography (10% EtOAc-hexanes) as a colorless oil.

$^1$H NMR (CDCl$_3$): δ 8.01 (1H, d, J=8.2 Hz), 7.51 (1H, s), 7.43 (1H, dd, J=1.7, 6.4 Hz), 4.07 (2H, m), 3.79 (2H, m), 2.74 (2H, t, J=6.5 Hz), 2.04 (2H, t, J=7.1 Hz), 1.67 (3H, s), 1.46 (6H, s).

(+/−) 6-(2-Methyl-1,3-dioxolan-2-yl)]-1,2,3,4-tetrahydro-4,4-dimethyl-1-hydroxy-1-(carboethoxymethyl)-naphthlene (Compound D16)

Using the same procedure as for the preparation of ethyl 4-[(5,6,7,8-tetrahydro-5,5-dimethyl-8-hydroxy-8-(carboethoxymethyl)naphthalen-2-yl)azo]benzoate, 6-(2-methyl-1,3-dioxolan-2-yl)]-3,4-dihydro-4,4-dimethylnaphthalen-1(2H)-one (Compound D1), 6-(2-methyl-1,3-dioxolan-2-yl)-3,4-dihydro-4,4-dimethylnaphthalen-1(2H)-one (Compound D15, 300 mg, 1.15 mmol) was converted to the title product (321 mg, light yellow oil), using zinc dust (0.5 g, pretreated) and bromo ethyl acetate (0.256 ml, 0.30 mmol) in 10 ml of benzene.

$^1$H NMR (CDCl$_3$): δ 1.29 (t, J=7.08 Hz, 3H), 1.30 (s, 3H), 1.32 (s, 3H), 1.65 (s, 3H), 2.06 (s, 2H), 2.80 (q, J=1.45 Hz, 2H), 3.77 (m, 2H), 4.05 (m, 2H), 4.13 (q, J=7.14 Hz, 2H), 4.22 (q, J=7.14 Hz, 2H), 7.30 (dd, J=1.71, 6.54 Hz, 1H), 7.42 (d, J=1.77 Hz, 1H), 7.53 (d, J=8.18 Hz, 1H).

3,4-Dihydro-4,4-dimethyl-1-(carboethoxymethyl)-6-acetyl-naphthalene (Compound D17)

A solution of (+/−) 6-(2-methyl-1,3-dioxolan-2-yl)-1,2,3,4-tetrahydro-4,4-dimethyl-1-hydroxy-1-(carboethoxymethyl)-naphthlene ((Compound D16, 321 mg, 0.90 mmol) and catalytic amount of TsOH in 20 ml of benzene was refluxed for 12 h. During the reaction the water generated from the reaction was periodically removed by a Dean-Stark trap. The solvent was removed and the residue was purified by column chromatography (silica, ethyl acetate/hexane (1/3)) to give the title compound as an oil (215 mg).

$^1$H NMR (CDCl$_3$): δ 1.20 (t, J=7.14 Hz, 3H), 1.33 (s, 6H), 2.30 (d, J=3.42 Hz, 2H), 2.60 (s, 3H), 3.50 (s, 2H), 4.16 (q, J=7.14 Hz, 2H), 6.06 (t, J=4.64 Hz, 1H), 7.28 (d, J=2.80 Hz, 1H), 7.76 (, J=1.34, 6.10 Hz, 1H), 7.93 (s, 1H).

(E)-4-[3-(3,4-dihydro-4,4-dimethyl-1-(carboethoxymethyl)-naphthalen-6-yl)-prop-1-en-3-one]benzoic acid (Compound D18)

To a solution of 3,4-dihydro-4,4-dimethyl-1-(carboethoxymethyl)-6-acetyl-naphthalene ((Compound D17, 25 mg, 0.10 mmol) and 4-carboxybenzaldehyde (17 mg, 0.13 mmol) in 2 ml of MeOH was added aqueous NaOH (0.75 ml, 12%). The reaction mixture was stirred at room temperature for overnight and quenched by addition of 10% HCl to pH=4.0. The solvent was removed and extracted ethyl acetate, the combined organic layer was washed with water. The organic layer was dried and concentrated to a white solid. This white solid was dissolved in 1 ml of DMF. To this solution was added DMAP (15.2 mg, 0.12 mmol), EDC (22 mg, 0.11 mmol) and 0.5 ml EtOH. The reaction mixture was stirred at room temperature for 5 h and concentrated in vacuo. The residue was passed through a chromatographic column with ethyl acetate/hexane (1/9) to give the title compound as a light tan solid.

$^1$H NMR (CDCl$_3$): δ 1.21 (t, J=7.14 Hz, 3H), 1.36 (s, 6H), 1.42 (t, J=7.14 Hz, 3H), 2.33 (d, J=4.46 Hz, 2H), 4.13 (q, J=7.14 Hz, 2H), 4.41 (q, J=7.14 Hz, 2H), 6.09 (t, J=4.79 Hz, 1H), 7.32 (d, J=8.05 Hz, 1H), 7.60 (d, J=15.6 Hz, 1H), 7.70 (d, J=8.36 Hz, 2H), 7.80 (s, 1H), 7.85 (d, J=8.12 Hz, 1H), 8.00 (d, J=1.77 Hz, 1H), 8.10 (d, J=8.36 Hz, 2H).

3,4-Dihydro-4,4-dimethyl-6-acetyl-1-(1,1-dimethylethyl)naphthalene (Compound D19)

To a solution of 6-(2-methyl-1,3-dioxolan-2-yl)]-3,4-dihydro-4,4-dimethylnaphthlen-1(2H)-one ((Compound D15, 353 mg, 1.36 mmol) in 3 ml of dry ether at −78° C. was added dropwise t-BuLi (1 ml, 1.7 mmol, 1.7M solution in pentane). This clear light yellow solution was left at −78° C. for 30 min. Then, freshly distilled SOCl$_2$ (0.15 ml, 2.0 mmol) was added. The reaction mixture was stirred at −78° C. for additional 30 min and thereafter slowly warmed to room temperature. The reaction was quenched by addition of saturated NH$_4$Cl. The white solids were removed by filtration and the clear solution was concentrated to an oil, and purified by column chromatography with ethyl acetate/hexane (1/10) to give the title compound as a yellow oil.

$^1$H NMR (CDCl$_3$): δ 7.92 (d, J=1.79 Hz, 1H), 7.76 (dd, J=1.80, 8.23 Hz, 1H), 7.73 (d, J=8.23 Hz, 1H), 6.10 (t, J=4.98 Hz, 1H), 2.58 (s, 3H), 2.18 (d, J=5.00 Hz, 2H), 1.34 (s, 9H), 1.25 (s, 6H).

(E)-4-[3-(3,4-Dihydro-4,4-dimethyl-1-(1,1-dimethylethyl)naphth-6-yl)-prop-1-en-3-one]benzoic acid (Compound D20)

To a solution of 3,4-dihydro-4,4-dimethyl-6-acetyl-1-(1,1-dimethylethyl)naphthalene (Compound D19, 60 mg, 0.234 mmol) and 4-carboxybenzaldehyde (35 mg, 0.233 mmol) in 5 ml of EtOH and 1 ml of THF was added 3 ml of 1M aqueous NaOH. The yellow reaction mixture was left overnight when it turned red and then quenched with 6% HCl until it became yellow again. The solvent was removed and the residue was dissolved in ethyl acetate. The organic solution was washed with brine and dried. After evaporation of the solvent, the residue was purified by recrystallization from ethyl acetate to give 28 mg title compound as yellow crystals.

$^1$H NMR (CDCl$_3$): δ 8.15 (d, J=8.31 Hz, 2H), 8.00 (d, J=1.80 Hz, 1H), 7.86 (dd, J=1.83, 8.24 Hz, 1H), 7.83 (d, J=15.82 Hz, 1H), 7.78 (d, J=8.48 Hz, 1H), 7.74 (d, J=8.31 Hz, 2H), 7.65 (d, J=15.87 Hz, 1H), 6.13 (t, J=5.0 Hz, 1H), 2.21 (d, J=4.9 Hz, 2H), 1.38 (s, 9H), 1.30 (s, 6H).

6-Bromo-1(2H)-(propyliden-2-yl)-3,4-dihydro-4,4-dimethylnaphthalene (Compound D21)

To a mixture of TiCl$_3$ (5 g, 32 mmol) of in 80 ml of dry DME under argon atmosphere was added in small portions lithium wire (0.80 g, 92 mmol). The reaction mixture was heated at 85° C. for 1 h and then cooled to room temperature. To the above solution was added a mixture of 6-bromo-3,4-dihydro-4,4-dimethylnaphthalen-1(2H)-one (Compound H, 1.00 g, 4.0 mmol) in 10 ml of dry DME and 10 ml of dry acetone through a cannula. The resulting mixture was heated to reflux and was left for 12 h and then cooled to room temperature. The reaction mixture was diluted with 80 ml of hexane and then filtered through florisil. Purification by column chromatography with pure hexane as the eluent gave the title compound as a clear oil.

$^1$H NMR (CDCl$_3$): δ 1.23 (s, 6H), 1.60 t, J=7.09 Hz, 2H), 1.82 (s, 3H), 1.92 (s, 3H), 2.49 (t, J=6.60 Hz, 2H), 7.10 (d, J=8.30 Hz, 1H), 7.26 (dd, J=1.95, 6.05 Hz, 1H), 7.40 (d, J=2.08 Hz, 1H).

6-Acetyl-1(2H)-(propyliden-2-yl)-3,4-dihydro-4,4-dimethylnaphthalene (Compound D22)

To a solution of 6-bromo-1(2H)-(propyliden-2-yl)-3,4-dihydro-4,4-dimethylnaphthalene (Compound D21, 910 mg, 3.3 mmol) and bis(triphenylphosphine)palladium(II) chloride (100 mg, 0.14 mmol) of in 50 ml of DMF under argon was added (1-ethoxyvinyl)tributyl tin (1.713 ml, 5.07 mmol). The resulting reaction mixture was heated at 85° C.

for 48 h and cooled down to room temperature. The reaction was quenched with 15 ml of 10% HCl and then diluted with ethyl acetate. The organic layer was washed with brine and dried over $MgSO_4$. Purification by column chromatography with pure hexane afforded the title compound as a yellow oil (410 mg).

$^1$H NMR ($CDCl_3$): δ 1.28 (s, 6H), 1.64 (t, J=6.99 Hz, 2H), 1.86 (s, 3H), 1.97 (s, 3H), 2.53 (t, J=6.6 Hz, 2H), 2.61 (s, 3H), 7.31 (d, J=8.06 Hz, 1H), 7.74 (dd, J=1.96, 6.10 Hz, 1H), 7.92 (d, J=1.89 Hz, 1H).

(E)-4[3-{1(2H)-(propyliden-2-yl)-3,4-dihydro-4,4-dimethylnaphthalen-6-yl}-prop-1-en-3-one]benzoic acid (Compound D23)

The title compound can be obtained by following the procedure employed for the preparation of (E)-4-[3-(3,4-dihydro-4,4-dimethyl-1-(carboethoxymethyl)-naphthalen-6-yl)-prop-1-en-3-one]benzoic acid (Compound D18).

(+/−) 1-Hydroxy-6-(1,3-dioxolan-2-yl)]-1,2,3,4-tetrahydro-4,4-dimethylnaphthalene (Compound D24)

To a solution of 6-(1,3-dioxolan-2-yl)]-3,4-dihydro-4,4-yl)azo]benzoate (Compound D12) dimethylnaphthalen-1 (2H)-one (Compound D15, 110 mg, 0.42 mmol) in 6 ml of EtOH at 0° C. was added $NaBH_4$ (16 mg, 0.42 mmol). The reaction mixture was stirred for 4 h and kept in a freezer for overnight. The reaction was quenched with slow addition of cold water and extracted with ethyl acetate. The organic layer was dried and concentrated to an oil. Purification by column chromatography with ethyl acetate/hexane (1/3) gave the title compound as a clear oil.

$^1$H NMR ($CDCl_3$): δ 1.26 (s, 3H), 1.34 (s, 3H), 1.65 (s, 3H), 1.61 (m, 1H), 1.89 (m, 2H), 2.07 (m, 1H), 3.74 (m, 2H), 4.05 (m, 2H), 4.74 (t, J=5.10 Hz, 1H), 7.30 (dd, J=1.65, 6.16, 1H), 7.41 (d, J=7.94 Hz, 1H), 7.45 (d, J=1.83 Hz, 1H).

(+/−) 1-Hydroxy-6-acetyl-1,2,3,4-tetrahydro-4,4-dimethyl-naphthalene (Compound D25)

A solution of 1-hydroxy-6-(1,3-dioxolan-2-yl)]-1,2,3,4-tetrahydro-4,4-dimethylnaphthalene (Compound D24, 54.9 mg, 0.21 mmol) in 3 ml of 10% HCl and 3 ml THF was heated at 100° C. for 1.5 h and cooled to room temperature. The reaction mixture was diluted with ethyl acetate and neutralized with sat. $NaHCO_3$. The organic layer was further washed with brine, dried and concentrated to an oil. Purification by column chromatography (silica) with ethyl acetate/hexane (1/9) gave the title compound as a clear oil (24.8 mg).

$^1$H NMR ($CDCl_3$): δ 1.29 (s, 3H), 1.34 (s, 3H), 1.66 (m, 1H), 1.89 (m, 2H), 2.10 (m, 1H), 2.56 (s, 3H), 4.75 (t, J=4.90, 1H), 7.54 (d, J=8.18 Hz, 1H), 7.75 (dd, J=1.83, 6.29 Hz, 1H), 7.94 (d, J=1.77 Hz, 1H).

(+/−) 1-(Methoxymethyloxy)-6-acetyl-1,2,3,4-tetrahydro-4,4-dimethyl-naphthalene (Compound D26)

A solution of (+/−) 1-hydroxy-6-acetyl-1,2,3,4-tetrahydro-4,4-dimethyl-naphthalene (Compound D25, 24.8 mg, 0.11 mmol), chloromethyl methyl ether (0.12 mmol), triethyl amine (0.02 ml, 0.13 mmol) and catalytic amount of tetrabutylammonium bromide in 2 ml of $CH_2Cl_2$ was stirred at room temperature for 5 h. Purification by column chromatography (silica) with ethyl acetate/hexane (1/10) afforded the title compound as an oil (17.8 mg).

$^1$H NMR ($CDCl_3$): δ 7.95 (d, J=1.7 Hz, 1H), 7.73 (dd, J=1.7, 8.4 Hz, 1H), 7.44 (d, J=8.4 Hz, 1H), 4.88 (d, J=6.41 Hz, 1H), 4.76 (d, J=6.41 Hz, 1H), 4.67 (m, 1H), 3.48 (s, 3H), 2.59 (s, 3H), 2.00 (m, 3H), 1.58 (m, 1H), 1.37 (s, 3H), 1.29 (s, 3H).

(E)-4-[3-(1,2,3,4-Tetrahydro-4,4-dimethyl-1-(methoxymethyloxy)-naphthalen-6-yl)-prop-1-en-3-one]benzoic acid (Compound D27)

The title compound can be prepared by following the procedure employed for the preparation of (E)-4-[3-(3,4-dihydro-4,4-dimethyl-1-(carboethoxymethyl)-naphthalen-6-yl)-prop-1-en-3-one]benzoic acid (Compound D18).

6-Acetyl-1(2H)-(O-methyl oxime)-3,4-dihydro-4,4-dimethylnaphthalene (Compound D28)

To a solution of 6-(1,3-dioxolan-2-yl)]-3,4-dihydro-4,4-dimethylnaphthalen-1(2H)-one (Compound D15, 100 mg, 0.38 mmol), NaOAc (78.8 mg, 0.95 mmol) in 5 ml of EtOH and 2 ml of THF was added methoxyamine hydrochloride (32.1 mg, 0.38 mmol). The resulting mixture was stirred at room temperature for overnight. The solvent was removed and the residue was dissolved in ethyl acetate (5 mL) and washed with saturated $NaHCO_3$, water and brine. The solvent was distilled off and the crude product was purified by column chromatography with ethyl acetate/hexane (1/3) to give the title compound as an oil.

$^1$H NMR ($CDCl_3$): δ 1.42 (s, 6H), 2.03 (t, J=6.07 Hz, 2H), 2.24 (s, 3H), 2.74 (t, J=6.71 Hz, 2H), 4.04 (s, 3H), 7.56 (dd, J=1.52, 6.72 Hz, 1H), 7.70 (d, J=1.75 Hz, 1H), 8.02 (d, J=8.24 Hz, 1H).

(E)-4[3-{1(2H)-(O-methyl oxime)-3,4-dihydro-4,4-dimethylnaphthalen-6-yl}-prop-1-en-3-one]benzoic acid (Compound D29)

The title compound can be prepared by following the procedure employed for the preparation of (E)-4-[3-(3,4-dihydro-4,4-dimethyl-1-(carboethoxymethyl)-naphthalen-6-yl)-prop-1-en-3-one]benzoic acid (Compound D18).

3,4-dihydro-1-(trifluoromethylsulfonyl)oxy-4,4-dimethyl-6-(2-(2-methyl-1,3-dioxolanyl)) naphthalene (Compound D30)

To a cold solution (−78° C.) of 232.7 mg (1.267 mmol) of sodium bis(trimethylsily)amide in 2.0 ml of THF was added a solution of 300.0 mg (1.154 mmol) of 6-(1,3-dioxolan-2-yl)]-3,4-dihydro-4,4-dimethylnaphthalen-1(2H)-one (Compound D15) in 4.0 ml of THF. The reaction mixture was stirred at −78° C. for 30 minutes and then a solution of 498.0 mg (1.269 mmol) of 5-chloro(2-bis-triflouromethylsulfonyl)imide in 3.0 ml of THF was added. After stirring at −78° C. for 1 hour, the solution was warmed to 0° C. and stirred for 12 hours. The reaction was quenched by the addition of saturated aqueous $NH_4Cl$. The mixture was extracted with EtOAc (50 ml) and the combined organic layers were washed with saturated aqueous $NaHCO_3$, water, and brine. The organic phase was dried over $Na_2SO_4$ and then concentrated in vacuo to a yellow oil. Purification by column chromatography (silica, 10% EtOAc-hexanes) yielded the title compound as a clear yellow oil.

$^1$H NMR ($CDCl_3$): δ 7.43 (1H, s), 7.38 (2H, m), 5.95 (1H, t, J=4.8 Hz), 4.07 (2H, m) 3.77 (2H, m) 2.42 (2H, d, J=4.9 Hz), 1.66 (3H, s), 1.32 (6H, s).

3,4-dihydro-1-(2-thienyl)-4,4-dimethyl-6-(2-(2-methyl-1,3-dioxolanyl))naphthalene (Compound D32)

A solution of 2-thienyllithium was prepared by the addition of 106.9 mg (0.67 ml, 1.67 mmol) of n-butyl lithium (2.5M solution in hexanes) to a cold solution (0° C.) of 140.0 mg (1.67 mmol) of thiophene in 1.0 ml of THF. After stirring for 3 h a solution of 364.0 mg (2.67 mmol) of zinc chloride in 2.0 ml of THF was added. The resulting solution was warmed to room temperature, stirred for 30 minutes, and added via cannula to a solution of 262.0 mg (0.668 mmol) of 3,4-dihydro-1-(trifluoromethylsulfonyl)oxy-4,4-dimethyl-6-(2-(2-methyl-1,3-dioxolanyl))naphthalene (Compound D30) and 30 mg (0.03 mmol) of tetrakis(triphenylphosphine)palladium(0) in 2.0 ml of THF. The resulting solution was heated at 50° C. for 12 h, cooled to room temperature and diluted with saturated aqueous $NH_4Cl$. The mixture was extracted with EtOAc and the combined organic layers were washed with water and brine. The organic phase was dried over $Na_2SO_4$ and concentrated in vacuo to a yellow oil. Purification by column chromatography (10% EtOAc-hexanes) yielded the title compound as a yellow solid.

$^1H$ NMR ($CDCl_3$): δ_7.48 (1H, d, J=1.8 Hz), 7.34 (1H, d, J=7.9 Hz), 7.28 (2H, m), 7.08 (2H, m), 6.18 (1H, t, J=4.8 Hz), 4.06 (2H, m), 3.82 (2H, m), 2.34 (2H, d, J=4.8 Hz), 1.70 (3H, s), 1.34 (6H, s).

3,4-dihydro-1-(2-thienyl)-4,4-dimethyl-6-acetylnaphthalene (Compound D33)

A solution of 3,4-dihydro-1-(2-thienyl)-4,4-dimethyl-6-(2-(2-methyl-1,3-dioxolanyl))naphthalene (Compound D32, 103.0 mg, 0.32 mmol) in 4.0 mL THF and 4.0 mL 10% aqueous HCl was refluxed for 1.5 h. Upon cooling to room temperature, the reaction mixture was diluted with EtOAc and washed with water and saturated aqueous NaCl. The organic layer was dried over $MgSO_4$ and the solvents were removed under reduced pressure to give the title compound as a colorless oil after column chromatography (10% EtOAc-hexanes).

$^1H$ NMR ($CDCl_3$): δ 7.98 (1H, d, J=1.8 Hz), 7.75 (1H, dd, J=1.8, 8.1 Hz), 7.46 (1H, d, J=8.1 Hz), 7.29 (1H, d, J=5.0 Hz), 7.09 (2H, m), 6.32 (1H, t, J=4.8 Hz), 2.61 (3H, s), 2.38 (2H, d, J=4.9 Hz), 1.38 (6H, s).

4-[3-oxo-3-(7,8-dihydro-5-(2-thienyl)-8,8-dimethyl-2-naphthalenyl)-1-propenyl]-benzoic acid (Compound D34)

To a solution of 62.6 mg (0.222 mmol) 3,4-dihydro-1-(2-thienyl)-4,4-dimethyl-6-acetylnaphthalene (Compound D33) in 4.0 mL of MeOH were added 33.4 mg (0.222 mmol) of 4-carboxy benzaldehyde, and 240.0 mg (6.00 mmol; 2.0 mL of 3M aqueous NaOH). The resulting solution was stirred at room temperature for 12 h, concentrated under reduced pressure, and the residual oil dissolved in EtOAc. The solution was treated with 10% HCl, and the organic layer washed with $H_2O$, and saturated aqueous NaCl, before being dried over $Na_2SO_4$. Removal of the solvents under reduced pressure gave the title compound as a pale green solid after recrystallization from EtOH.

$^1H$ NMR (acetone-$d_6$): δ_8.16 (1H, s), 8.10 (1H, d, J=8.4 Hz), 8.00 (5H, m), 7.84 (1H, d, J=15.5 Hz), 7.48 (2H, m), 7.14 (2H, m), 6.36 (1H, t, J=4.8 Hz), 2.83 (1H, s), 2.43 (2H, d, J=4.8 Hz), 1.39 (6H, s).

Methyl-5,5-dimethyl-5,6-dihydro-naphthalen-8(7H)-one-2-carboxylate (Compound E2)

A degassed (with carbonmonoxide) solution of 2-bromo-5,5-dimethyl-5,6-dihydro-naphthalen-8(7H)-one (Compound G), palladium(II)-bis(triphenylphosphine)chloride (277 mg, 0.4 mmol), 1,3-bis(diphenylphosphino)-propane (325 mg, 0.8 mmol), DMSO (30 mL), methanol (15 mL) and triethylamine (15 mL) was placed in an oil bath (70° C.), under carbonmonoxide atmosphere) for 16 h. After dilution with water the mixture was extracted with ethyl acetate. The organic layer was washed with water, 10% HCl, saturated sodiumbicarbonate and brine. The organic layer was dried over $MgSO_4$, and the solvent was removed by distillation. The residual crude material was purified by flash chromatography (silica, 1:4 ethyl acetate: hexane) to afford the title compound as a white solid. 1HNMR ($CDCl_3$): δ 1.42 (s, 6H), 2.05 (t, J=6.6 Hz, 2H), 2.77 (dd, J=6.6, 2H), 3.93 (s, 3H), 7.52 (d, J=8.3 Hz, 1H), 8.17 (dd, J=1.8, 8.3 Hz, 1H), 8.67 (d, J=1.8 Hz, 1H).

5,5-Dimethyl-5,6-dihydro-naphthalen-8(7H)-one-2-carboxylic acid (Compound E3)

To a solution of methyl-5,5-dimethyl-5,6-dihydro-naphthalen-8(7H)-one-2-carboxylate (Compound E2, 1.05 g, 4.5 mmol) in 10 mL of ethanol and THF (10 mL) was added sodiumhydroxide 9 mL (1M solution). The solution was stirred for 16 h and thereafter acidified with 10% HCl. The mixture was extracted with ethyl acetate, the combined organic layer was washed with water and brine, and dried over MgSO4. The solvent was distilled off under reduced pressure to afford the title compound as a white solid.

$^1$HNMR (Acetone-$D_6$): δ 1.44 (s, 6H), 2.07 (t, J=6.7 Hz, 2H), 2.73 (t, J=6.7 Hz, 2H), 7.70 (d, J=8.2 Hz, 1H), 8.19 (dd, J=1.9, 8.2 Hz, 1H), 8.57 (d, J=1.9 Hz, 1H).

Methyl 5,5-dimethyl-5,6-dihydro-8-(trifluoromethylsulfonyl)oxy-naphthalene-2-carboxylate (Compound E4)

To a solution of sodium bis(trimethylsilyl)amide (550.1 mg, 3.00 mmol, 3.0 mL of a 1.0M solution in THF) in 5.0 mL of THF at –78° C. was added 620.0 mg (2.67 mmol) of methyl-5,5-dimethyl-5,6-dihydro-naphthalen-8(7H)-one-2-carboxylate (Compound E2) in 8.0 mL of THF. After 30 min a solution of 1.15 g (2.94 mmol) of 2-N,N-bis(trifluoromethylsulfonyl)amino-5-chloropyridine in 6.0 mL of THF was added. Stirring for 45 min at –78° C. was followed by warming to room temperature and stirring for 5 h. The reaction was quenched by the addition of saturated aqueous $NH_4Cl$ and extracted with EtOAc. The combined organic layers were washed with 5% aqueous NaOH and dried over $MgSO_4$. Concentration of the dry solution under reduced pressure to an oil and column chromatography using 10% EtOAc-hexanes afforded the title compound as a yellow oil.

$^1H$ NMR($CDCl_3$): δ 1.33 (s,6H), 2.45 (d, J=4.8 Hz, 2H), 3.93 (s, 3H), 6.03 (t, J=4.8 Hz, 1H), 7.40 (d, J=8.5 Hz, 1H), 8.00 (m, 2H).

Methyl 5,5-dimethyl-5,6-dihydro-8-(2-thienyl)-naphthalene-2-carboxylate (Compound E5)

To a solution of 329.0 mg (3.93 mmol) of thiophene in 2.0 mL THF at 0° C. was added 251.8 mg (3.93 mmol, 1.56 mL of 2.5M solution in hexanes) of n-butyllithium. After stirring for 3 h at 0° C., a solution of 845.0 mg (6.28 mmol) of $ZnCl_2$ in 5.0 mL THF was added and the resulting solution stirred for 30 minutes. This solution was added to a second flask containing 570.0 mg (1.57 mmol) of methyl 5,5-dimethyl-5,6-dihydro-8-(trifluoromethylsulfonyl)oxy-naphthalene-2-carboxylate (Compound E4) and 76.0 mg (0.063 mmol) of tetrakis(triphenyphosphine)palladium(0) in 4.0 mL THF, and the resulting solution was heated to 50° C. for 3 h. Upon cooling to room temperature the reaction was quenched by the addition of saturated aqueous NH₄Cl. Extraction with EtOAc was followed by washing of the combined organic layers with H₂O and saturated aqueous NaCl, and drying over MgSO₄. The dry solution was concentrated under reduced pressure and the title compound was isolated from the residue as a yellow oil by column chromatography (5–10% EtOAc/hexanes).

¹H NMR(CDCl₃): δ 1.34 (s, 6H), 2.35 (d, J=4.9 Hz, 2H), 3.86 (s, 3H), 6.23 (t, J=4.9 Hz, 1H), 7.06 (m, 2H), 7.28 (m, 1H), 7.43 (d, J=8.0 Hz, 1H), 7.92 (dd, J=1.7, 8.0 Hz, 1H), 8.06 (d, J=1.7 Hz, 1H).

5,5-dimethyl-5,6-dihydro-8-(2-thienyl)-naphthalene-2-carboxylic acid (Compound E6)

To a solution of methyl 5,5-dimethyl-5,6-dihydro-8-(2-thienyl)-2-naphthalenecarboxylate (Compound E5, 430.0 mg, 1.44 mmol) in 3.0 mL of EtOH and 3.0 mL THF was added NaOH (240.0 mg, 6.00 mmol; 3.0 mL of a 2N aqueous solution). The resulting solution was warmed to 35° C. for 6 h, cooled to room temperature and quenched with 1M HCl. The mixture was extracted with EtOAc and the combined organic layers washed with H₂O and saturated aqueous NaCl before being dried over MgSO₄. Removal of the solvents under reduced pressure afforded the title compound as a pale yellow solid.

¹H NMR(CDCl₃) 1 1.34 (s, 6H), 2.38 (d, J=4.8 Hz, 2H), 6.25 t, J=4.8 Hz, 1H), 7.12 (m, 3H), 7.45 (dd, J=1.8, 4.7 Hz, 1H), 7.54 (d, J=8.0 Hz, 1H), 7.92 (dd, J=1.8, 8.0 Hz, 1H), 8.06 (d, J=1.8 Hz, 1H).

Ethyl 4-[[(5,5-dimethyl-5,6-dihydro-8-(2-thienyl)-naphthalen-2-yl)carboxamido]-benzoate (Compound E7)

A solution of 5,5-dimethyl-5,6-dihydro-8-(2-thienyl)-naphthalene-2-carboxylic acid (Compound E6, 180.0 mg, 0.638 mmol), ethyl 4-aminobenzoate (137.0 mg, 0.829 mmol), 1-(3-dimethylaminopropyl)-3-ethylcarbodiimide hydrochloride (160.0 mg, 0.829 mmol), and 4-N,N-dimethylaminopyridine (101.0 mg, 0.829 mmol) in 6.0 mL DMF was stirred overnight at room temperature. EtOAc (100 mL) was added and the solution washed with H₂O, 5% HCl, saturated aqueous NaHCO₃, and saturated aqueous NaCl before being dried over MgSO₄. Removal of the sovents under reduced pressure and column chromatography (10–25% EtOAc-hexanes) of the residual oil afforded the title compound as a colorless solid.

¹H NMR(CDCl₃): δ 1.36 (s, 6H), 1.39 (t, J=7.1 Hz, 3H), 2.38 (d, J=4.8 Hz, 2H), 4.36 (q, J=7.1 Hz, 2H), 6.27 (t, J=4.8 Hz, 1H), 7.09 (m, 2H), 7.29 (m, 1H), 7.48 (d, J=8.0 Hz, 1H), 7.68 (d, J=8.8 Hz, 2H), 7.76 (dd, J=1.9, 8.0 Hz, 1H), 7.83 (s, 1H), 7.88 (d, J=1.9 Hz, 1H), 8.03 (d, J=8.8 Hz, 2H).

4-[[(5,5-Dimethyl-5,6-dihydro-8-(2-thienyl)-naphthalen-2-yl)carboxamido]-benzoic acid (Compound E8)

To a solution of ethyl 4-[[(5,5-dimethyl-5,6-dihydro-8-(2-thienyl)-naphthalen-2-yl)carboxamido]-benzoate (Compound E7, 110.0 mg, 0.255 mmol) in 2.0 mL of EtOH and 1.0 mL THF was added NaOH (80.0 mg, 2.00 mmol; 2.0 mL of a 1N aqueous solution). After stirring overnight at room temperature the reaction was quenched by the addition of 1M aqueous HCl. The mixture was extracted with EtOAc and the combined organic layers washed with H₂O and saturated aqueous NaCl before being dried over MgSO₄. Removal of the solvents under pressure afforded the title compound as a pale yellow solid.

¹H NMR(acetone-d₆): δ 1.34 (s, 6H), 2.38 (d, J=4.9 Hz, 2H), 6.27 (t, J=4.9 Hz, 1H), 7.12 (m, 2H), 7.44 (dd, J=1.3, 5.0 Hz, 1H), 7.55 (d, J=8.0 Hz, 1H), 7.88 (m, 3H), 8.02–7.91 (m, 3H), 9.75 (s, 1H).

Ethyl 4-[[(5,5-dimethyl-5,6-dihydro-8-(2-thienyl)-naphthalen-2-yl)carbonyl]oxy]-benzoate (Compound E9)

A solution of 5,5-dimethyl-5,6-dihydro-8-(2-thienyl)-naphthalene-2-carboxylic acid (Compound E6, 50.0 mg, 0.177 mmol), ethyl 4-hydroxybenzoate (38.2 mg, 0.230 mmol), 1-(3-dimethylaminopropyl)-3-ethylcarbodiimide hydrochloride (44.0 mg, 0.230 mmol), and 4-N,N-dimethylaminopyridine (28.0 mg, 0.230 mmol) in 2.0 mL DMF was stirred overnight at room temperature. EtOAc (50 mL) was added and the solution washed with H₂O, 5% HCl, saturated aqueous NaCO₃, and saturated aqueous NaCl before being dried over MgSO₄. Removal of the sovents under reduced pressure and column chromatography (10% EtOAc-hexanes) of the residual oil afforded the title compound as a colorless solid.

¹H NMR(CDCl₃): δ 1.36 (s, 6H), 1.39 (t, J=7.2 Hz, 3H), 2.39 (d, J=4.9 Hz, 2H), 4.38 (q, J=7.2 Hz, 2H), 6.26 (t, J=4.9 Hz, 1H), 7.09 (m, 2H), 7.25 (m, 2H), 7.49 (d, J=8.2 Hz, 1H), 8.08 (m, 3H), 8.22(d, J=1.8 Hz, 1H). 2-trimethylsilylethyl 4-[[(5,5-dimethyl-5,6-dihydro-8-(2-thienyl)-naphthalen-2-yl)carbonyl]oxy]-benzoate (Compound E10)

A solution of 5,5-dimethyl-5,6-dihydro-8-(2-thienyl)-naphthalene-2-carboxylic acid (Compound E6, 79.0 mg, 0.280 mmol), 2-trimethylsilylethyl 4-hydroxybenzoate (73.3 mg, 0.308 mmol), 1-(3-dimethylaminopropyl)-3-ethylcarbodiimide hydrochloride (70.0 mg, 0.364 mmol), and 4-N,N-dimethylaminopyridine (44.5 mg, 0.364 mmol) in 2.0 mL DMF was stirred overnight at room temperature. Et₂O (100 mL) was added and the solution washed with H₂O, 5% HCl, saturated aqueous NaCO₃, and saturated aqueous NaCl before being dried over MgSO₄. Removal of the sovents under reduced pressure and column chromatography (10% EtOAc-hexanes) of the residual off afforded the title compound as a colorless solid.

¹H NMR(CDCl₃): δ 0.10 (s, 9H), 1.15 (t, J=8.2 Hz, 2H), 1.38 (s, 6H), 2.39 (d, J=4.0 Hz, 2H), 4.43 (t, J=8.2 Hz, 2H), 6.28 (t, J=4.0 Hz, 1H), 7.09 (m, 2H), 7.26 (m, 3H), 7.52 (d, J=7.2 Hz, 1H), 8.09 (m, 3H), 8.22 (s, 1H).

4-[[(5,5-Dimethyl-5,6-dihydro-8-(2-thienyl)-naphthalen-2-yl)carbonyl]oxy]-benzoic acid (Compound E11)

To a solution of 2-trimethylsilylethyl 4-[[(5,5-dimethyl-5,6-dihydro-8-(2-thienyl)-naphthalen-2-yl)carbonyl]oxy]-benzoate (Compound E10, 100.0 mg, 0.198 mmol) in 2.0 mL THF at room temperature was added 155.3 mg of tetrabutylammonium fluoride (0.594 mmol 0.6 mL of a 1M solution in THF). After stirring overnight the reaction was diluted with EtOAc and washed with H₂O and saturated aqueous NaCl before being dried over MgSO₄. The solvents were removed under reduced pressure and the residue washed with hot acetonitrile leaving the product as a colorless solid.

¹H NMR(acetone-d₆): δ 1.37 (s, 6H), 2.42 (d, J=4.8 Hz, 2H), 6.30 (t, J=4.8 Hz, 1H), 7.14 (m, 2H), 7.37 (d, J=8.6 Hz, 2H), 7.44 (dd, J=1.1, 5.0 Hz, 1H), 7.65 (d, J=8.1 Hz, 1H), 8.12 (m, 4H).

1(2H)-(Propyliden-2-yl)-3,4-dihydro-4,4-dimethylnaphthalene-7-carboxylic acid (Compound E12)

To a cold (−78° C.) solution of 7-bromo-1(2H)-(propyliden-2-yl)-3,4-dihydro-4,4-dimethylnaphthalene (Compound A37, 640.0 mg, 2.30 mmol) in 20 mL THF was added t-butyllithium (294.7 mg, 4.60 mmol; 2.7 mL of a 1.7M solution in pentane). After 1 h dry $CO_2$ gas was bubbled through the solution for 1 h. The resulting mixture was allowed to warm to room temperature and then quenched with 10% aqueous HCl. The mixture was extracted with EtOAc and the combined organic layers washed with $H_2O$ and saturated aqueous NaCl before being dried over $Na_2SO_4$. Concentration of the dry solution under reduced pressure and washing of the residue with hexanes afforded the title compound as a pale yellow solid.

$^1$H NMR(acetone-$d_6$): δ 1.25 (s, 6H), 1.63 (t, J=6.9 Hz, 2H), 1.85 (s, 3H), 1.95 (s, 3H), 2.53 (t, J=6.9 Hz, 2H), 7.43 (d, J=8.1 Hz, 1H), 7.82 (dd, J=1.8, 8.1 Hz, 1H), 7.94 (d, J=1.8 Hz, 1H).

2-(Trimethylsilyl)ethyl-4-[{(5,5-dimethyl-8(7H)-(propyliden-2-yl)-5,6-dihydronaphthalen-2-yl)}carbonyl}oxy]benzoate (Compound E13)

A solution of 5,5-dimethyl-5,6-dihydro-8(7H)-(1-propyliden-2-yl)-naphthalene-2-carboxylic acid (Compound E12, 70.0 mg, 0.287 mmol), 2-trimethylsilylethyl 4-hydroxybenzoate (71.0 mg, 0.298 mmol), 1-(3-dimethylaminopropyl)-3-ethylcarbodiimide hydrochloride (71.0 mg, 0.370 mmol), and 4-N,N-dimethylaminopyridine (45.0 mg, 0.370 mmol) in 2.0 mL DMF was stirred overnight at room temperature. $Et_2O$ (100 mL) was added and the solution washed with $H_2O$, 5% HCl, saturated aqueous $NaHCO_3$, and saturated aqueous NaCl before being dried over $MgSO_4$. Removal of the solvents under reduced pressure and column chromatography (5% EtOAc-hexanes) of the residual oil afforded the title compound as a colorless oil.

$^1$H NMR(CDCl$_3$): δ 0.09 (s, 9H), 1.14 (t, J=8.4 Hz, 2H), 1.28 (s, 6H), 1.66 (d, J=6.9 Hz, 2H), 1.86 (s, 3H), 2.00 (s, 3H), 2.54 (t, J=6.9 Hz, 2H), 4.30 (t, J=8.4 Hz, 2H), 7.28 (d, J=8.7 Hz, 2H), 7.43 (d, J=8.1 Hz, 1H), 7.97 (dd, J=1.9, 8.1 Hz, 1H), 8.08 (d, J=1.9 Hz, 1H), 8.11 (d, J=8.7 Hz, 2H).

4-[{(5,5-Dimethyl-8(7H)-(propyliden-2-yl)-5,6-dihydronaphthalen-2-yl)}carbonyl}oxy]benzoic acid (Compound E14)

To a solution of 2-trimethylsilylethyl 4-[[(5,5-dimethyl-5,6-dihydro-8(7H)-(propyliden-2-yl)-2-naphthalenyl)carbonyl]oxy]-benzoate (Compound E13, 84.0 mg, 0.181 mmol) in 2.0 mL THF at 0° C. was added 130.7 mg of tetrabutylammonium fluoride (0.50 mmol; 0.5 mL of a 1M solution in THF). After stirring at 0° C. for 1.5 h and at room temperature for 4.5 h, the reaction was diluted with EtOAc and washed with $H_2O$ and saturated aqueous NaCl before being dried over $MgSO_4$. The solvents were removed under reduced pressure and the residue crystalized from $CH_3CN$ to give the product as a colorless solid.

$^1$H NMR(acetone-$d_6$): δ 1.29 (s, 6H), 1.67 (t, J=6.9 Hz, 2H), 1.87 (s, 3H), 1.99 (s, 3H), 2.56 (t, J=6.9 Hz, 2H), 7.43 (d, J=8.6 Hz, 2H), 7.54 (d, J=8.2 Hz, 1H), 7.97 (dd, J=1.9, 8.2 Hz, 1H), 8.06 (d, J=1.9 Hz, 1H), 8.14 (d, J=8.7 Hz, 2H).

Ethyl 4-[{(5,5-dimethyl-8(7H)-(propyliden-2-yl)-5,6-dihydronaphthalen-2-yl)}carbonyl}oxy]benzoate (Compound E15)

A solution of 5,5-dimethyl-5,6-dihydro-8(7H)-(propyliden-2-yl)-2-naphthalenecarboxylic acid (Compound E12, 31.0 mg, 0.127 mmol), ethyl 4-hydroxybenzoate (27.4 mg, 0.165 mmol), 1-(3-dimethylaminopropyl)-3-ethylcarbodiimide hydrochloride (31.6 mg, 0.165 mmol), and 4-N,N-dimethylaminopyridine (20.2 mg, 0.165 mmol) in 2.0 mL DMF was stirred overnight at room temperature. EtOAc (50 mL) was added and the solution washed with $H_2O$, 5% HCl, saturated aqueous $NaCO_3$, and saturated aqueous NaCl before being dried over $MgSO_4$. Removal of the solvents under reduced pressure and column chromatography (5% EtOAc-hexanes) of the residual oil afforded the title compound as a colorless oil.

$^1$H NMR(CDCl$_3$): δ 1.28 (s, 6H), 1.41 (t, J=7.1 Hz, 2H), 1.66 (t, t J=6.9 Hz, 2H), 1.86 (s, 3H), 2.00 (s, 3H), 2.56 (t, J=6.9 Hz, 2H), 4.40 (q, J=7.1 Hz, 2H), 7.29 (d, J=8.7 Hz, 2H), 7.43 (d, J=8.1 Hz, 1H), 7.98 (dd, J=1.8, 8.1 Hz, 1H), 8.09 (d, J=1.8 Hz, 1H), 8.12 (d, J=8.7 Hz, 2H).

Ethyl 4-[(5,5-dimethyl-8(7H)-(propyliden-2-yl)-5,6-dihydronaphthalen-2-yl)}carboxamido]benzoate (Compound E16)

A solution of 1(2H)-(propyliden-2-yl)-3,4-dihydro-4,4-dimethylnaphthalene-7-carboxylic acid (Compound E12, 100.0 mg, 0.410 mmol), ethyl 4-aminobenzoate (81.0 mg, 0.490 mmol), 1-(3-dimethylaminopropyl)-3-ethylcarbodiimide hydrochloride (117.0 mg, 0.615 mmol), and 4-N,N-dimethylaminopyridine (61.0 mg, 0.500 mmol) in 3.0 mL DMF was stirred overnight at room temperature. EtOAc (100 mL) was added and the solution washed with $H_2O$, 10% HCl, saturated aqueous $NaCO_3$, and saturated aqueous NaCl before being dried over $MgSO_4$. Removal of the solvents under reduced pressure and column chromatography (10–15% EtOAc-hexanes) of the residual oil afforded the title compound as a colorless solid.

$^1$H NMR(CDCl$_3$): δ 1.29 (s, 6H), 1.40 (t, J=7.1 Hz, 2H), 1.64 (t, J=7.0 Hz, 2H), 1.86 (s, 3H), 2.00 (s, 3H), 2.52 (t, J=6.6 Hz, 2H), 4.37 (q, J=7.1 Hz, 2H), 7.60 (d, J=8.1 Hz, 1H), 7.63 (dd, J=1.8, 8.1 Hz, 1H), 7.73 (d, J=8.6 Hz, 2H), 7.75 (d, J=1.8 Hz, 1H), 7.92 (s, 1H), 8.06 (d, J=8.6 Hz, 2H).

4-[(5,5-Dimethyl-8(7H)-(propyliden-2-yl)-5,6-dihydronaphthalen-2-yl)}carboxamido]benzoic acid (Compound E17)

To a solution of ethyl 4-[(5,5-dimethyl-8(7H)-(propyliden-2-yl)-5,6-dihydronaphthalen-2-yl)}carboxamido]benzoate (Compound E16, 25.0 mg, 0.064 mmol) in 3.0 mL of EtOH and 3.0 mL THF was added NaOH (80.0 mg, 2.00 mmol; 2.0 mL of a 1N aqueous solution). After stirring overnight at room temperature the reaction was quenched by the addition of 10% aqueous HCl. The mixture was extracted with EtOAc and the combined organic layers were washed with $H_2O$ and saturated aqueous NaCl and thereafter dried over $Na_2SO_4$. Removal of the solvents under pressure and crystallization from $CH_3CN$ afforded the title compound as a colorless solid.

$^1$H NMR(acetone-$d_6$): δ 1.25 (s, 6H), 1.64 (t, J=6.9 Hz, 2H), 1.85 (s, 3H), 1.96 (s, 3H), 2.55 (t, J=6.9 Hz, 2H), 7.45 (d, J=8.1 Hz, 1H), 7.78 (dd, J=1.9, 8.1 Hz, 1H), 7.88 (d, J=1.9 Hz, 1H), 7.95–8.05 (m, 4H), 9.71 (s, 1H).

Methyl-5,5-dimethyl-5,6-dihydro-8-(phenylthio)-naphthalene-2-carboxylate (Compound E18)

To a solution of methyl-5,5-dimethyl-5,6-dihydro-naphthalen-8(7H)-one-2-carboxylate (Compound E2, 835.0 mg, 3.60 mmol) in 25.0 mL of THF at room temperature was added TiCl$_4$ (670.0 mg, 3.55 mmol). Thereafter a solution of thiophenol (430.0 mg, 3.90 mmol) and Et₃N (730.0 mg, 7.20 mmol) in 10 mL THF was added. The resulting brown mixture was stirred for 6 h before H₂O was carefully added to quench the reaction. The product was extracted into Et₂O and the combined organic layers washed with saturated aqueous NaCl and dried over MgSO₄. Removal of the solvents under reduced pressure afforded a solid from which the title compound was isolated as a yellow solid by column chromatography (5% EtOAc-hexanes).

¹H NMR (CDCl₃): δ 1.34 (s, 6H), 2.40 (d, J=4.7 Hz, 2H), 3.85 (s, 3H), 6.51 (t, J=4.7 Hz, 1H), 7.10–7.36 (m, 5H), 7.38 (d, J=8.1 Hz, 1H), 7.88 (dd, J=1.8, 8.0 Hz, 1H), 8.30 (d, J=1.8 Hz, 1H).

5,5-Dimethyl-5,6-dihydro-8-(phenylthio)-naphthalene-2-carboxylic acid (Compound E19)

To a solution of methyl 5,5-dimethyl-5,6-dihydro-8-(phenylthio)-naphthalene-2-carboxylate (Compound E18, 300.0 mg, 0.926 mmol) in 4.0 mL of EtOH and 2.0 mL THF was added NaOH (200.0 mg, 5.00 mmol; 5.0 mL of a 1N aqueous solution). After stirring overnight at room temperature the reaction was quenched by the addition of 10% aqueous HCl. The mixture was extracted with EtOAc and the combined organic layers washed with H₂O and saturated aqueous NaCl before being dried over Na₂SO₄. Removal of the solvents under pressure afforded the title compound as a yellow solid.

¹H NMR(CDCl₃): δ 1.35 (s, 6H), 2.41 (d, J=4.6 Hz, 2H), 6.54 (t, J=4.6 Hz, 1H), 7.10–7.34 (m, 5H), 7.40 (d, J=8.1 Hz, 1H), 7.92 (dd, J=1.8, 8.1 Hz), 8.36 (d, J=1.8 Hz, 1H).

Ethyl 4-[(5,5-dimethyl-8-(phenylthio)-5,6-dihydronaphthalen-2-yl)}carboxamido]benzoate (Compound E20)

A solution of 5,5-dimethyl-5,6-dihydro-8-(phenylthio)-naphthalene-2-carboxylic acid (Compound E19, 183.0 mg, 0.580 mmol), ethyl 4-aminobenzoate (107.0 mg, 0.650 mmol), 1-(3-dimethylaminopropyl)-3-ethylcarbodiimide hydrochloride (144.0 mg, 0.750 mmol), and 4-dimethylaminopyridine (85.0 mg, 0.700 mmol) in 5.0 mL DMF was stirred overnight at room temperature. EtOAc (100 mL) was added and the solution washed with H₂O and saturated aqueous NaCl before being dried over MgSO₄. Removal of the solvents under reduced pressure and column chromatography (20% EtOAc-hexanes) of the residual oil afforded the title compound as a colorless solid.

¹H NMR(CDCl₃): δ 1.37 (s, 6H), 1.40 (t, J=7.1 Hz, 3H), 2.45 (d, J=4.7 Hz, 2H), 4.37 (q, J=7.1 Hz, 2H), 6.65 (t, J=4.7 Hz, 1H), 7.17–7.35 (m, 5H), 7.45 (d, J=8.1 Hz, 1H), 7.52 (s, 1H), 7.60 (d, J=8.7 Hz, 2H), 7.77 (dd, J=1.8, 8.1 Hz, 1H), 7.96 (d, J=2.0 Hz, 1H), 8.03 (d, J=8.7 Hz, 2H).

4-[(5,5-Dimethyl-8-(phenylthio)-5,6-dihydronaphthalen-2-yl)carboxamido]benzoic acid (Compound E21)

To a solution of ethyl 4-[(5,5-dimethyl-8-(phenylthio)-5,6-dihydronaphthalen-2-yl)}carboxamido]benzoate (Compound E20, 90.0 mg, 0.196 mmol) in 3.0 mL of EtOH and 3.0 mL THF was added NaOH (120.0 mg, 3.00 mmol; 3.0 mL of a 1N aqueous solution). After stirring overnight at room temperature the reaction was quenched by the addition of 10% aqueous HCl. The mixture was extracted with EtOAc and the combined organic layers washed with H₂O and saturated aqueous NaCl before being dried over Na₂SO₄. Removal of the solvents under pressure afforded the title compound as a pale yellow solid.

¹H NMR(acetone-d₆): δ 1.36 (s, 6H), 2.46 (d, J=4.7 Hz, 2H), 6.11 (t, J=4.7 Hz, 1H), 7.13–7.36 (m, 5H), 7.51 (d, J=8.0 Hz, 1H), 7.85 (dd, J=1.9, 8.0 Hz, 1H), 7.91–8.03 (m, 4H), 8.24 (d, J=1.9 Hz, 1H), 9.67 (s, 1H).

4-[(5,5-Dimethyl-8-(phenylsulfonyl)-5,6-dihydronaphthalen-2-yl)carboxamido]benzoic acid (Compound E22)

To a solution of 4-[(5,5-dimethyl-8-(phenylsulfonyl)-5,6-dihydronaphthalen-2-yl)carboxamido]benzoic acid (Compound E21, 60.0 mg, 0.140 mmol) in 6.0 mL Et₂O, 3.0 mL CH₂Cl₂, and 2.0 mL THF at 0° C. was added m-chloroperbenzoic acid (57–80%) (74–110 mg, 0.430–0.640 mmol). The resulting solution was warmed to room temperature and stirred overnight. Water was added and the mixture extracted with EtOAc. The combined organic layers were washed with H₂O and saturated aqueous NaCl before being dried over Na₂SO₄. Removal of the solvents under reduced pressure and crystallization of the residue from CH₃CN afforded the title compound as a colorless solid.

¹H NMR (acetone-d₆): δ 1.23 (s, 6H), 2.60 (d, J=4.9 Hz, 2H), 7.51–7.62 (m, 5H), 7.89 (dd, J=1.8, 7.9 Hz, 1H), 7.94 (s, 1H), 7.95–8.06 (m, 6H), 8.61 (d, J=1.9 Hz, 1H).

Ethyl 4-[{(5,5-dimethyl-8-(phenylthio)-5,6-dihydronaphthalen-2-yl)}carbonyl}oxy]benzoate (Compound E23)

A solution of 5,5-dimethyl-5,6-dihydro-8-(phenylthio)-naphthalene-2-carboxylic acid (Compound E19, 150.0 mg, 0.484 mmol), ethyl 4-hydroxybenzoate (88.5 mg, 0.530 mmol), 1-(3-dimethylaminopropyl)-3-ethylcarbodiimide hydrochloride (120.6 mg, 0.630 mmol), and 4-N,N-dimethylaminopyridine (77.0 mg, 0.630 mmol) in 5.0 mL DMF was stirred overnight at room temperature. EtOAc (50 mL) was added and the solution washed with H₂O and saturated aqueous NaCl before being dried over MgSO₄. Removal of the solvents under reduced pressure and column chromatography (10–15% EtOAc-hexanes) of the residual oil afforded the title compound as a colorless solid.

¹H NMR(CDCl₃): δ 1.37(s, 6H), 1.40 (t, J=7.1 Hz, 3H), 2.44 (d, J=4.8 Hz, 2H), 4.39 (q, J=7.1 Hz, 2H), 6.57 (t, J=4.8 Hz, 1H), 7.15–7.36 (m, 7H), 7.45 (d, J=8.1 Hz, 1H), 8.01 (dd, J=1.8, 81.Hz, 1H), 8.10 (d, J=8.7 Hz, 2H), 8.44 (d, J=1.8 Hz, 1H).

Ethyl 4-[{(5,5-dimethyl-8-(phenylsulfonyl)-5,6-dihydronaphthalen-2-yl)}carbonyl}oxy]benzoate (Compound E24)

A solution of ethyl 4-[{(5,5-dimethyl-8-(phenylthio)-5,6-dihydronaphthalen-2-yl)}carbonyl}oxy]benzoate (Compound E23, 50.0 mg, 0.109 mmol) in 5.0 mL Et₂O at 0° C. was added m-chloroperbenzoic acid (50%) (25 mg, 0.145 mmol). The resulting solution was warmed to room temperature and stirred overnight. Et₂O was added and the organic layer washed with H₂O, saturated aqueous NaHCO₃, and saturated aqueous NaCl before being dried over Na₂SO₄. Removal of the solvents under reduced pressure and and column chromatography (20% EtOAc-hexanes) afforded the title compound as a colorless solid.

¹H NMR (CDCl₃): δ 1.27 (s, 6H), 1.42 (t, J=7.1 Hz, 3H), 2.56 (d, J=4.9 Hz, 2H), 4.40 (q, J=7.1 Hz, 2H), 7.27 (d, J=8.7 Hz, 2H), 7.43–7.57 (m, 5H), 8.02 (m, 3H), 8.14 (d, J=8.7 Hz, 2H), 8.68 (d, J=1.7 Hz, 1H).

2-(Trimethylsilyl)ethyl 4-[{(5,5-dimethyl-8-(phenylthio)-5,6-dihydronaphthalen-2-yl)}carbonyl}oxy]benzoate (Compound E25)

A solution of 5,5-dimethyl-5,6-dihydro-8-(phenylthio)-naphthalene-2-carboxylic acid (Compound E19, 170.0 mg, 0.548 mmol), 2-trimethylsilylethyl 4-hydroxybenzoate (130.0 mg, 0.548 mmol), 1-(3-dimethylaminopropyl)-3-ethylcarbodiimide hydrochloride (126.0 mg, 0.657 mmol), and 4-N,N-dimethylaminopyridine (74.0 mg, 0.600 mmol) in 4.0 mL DMF was stirred overnight at room temperature. EtOAc (100 mL) was added and the solution washed with $H_2O$, 10% HCl, and saturated aqueous NaCl before being dried over $MgSO_4$. Removal of the solvents under reduced pressure and column chromatography (5% EtOAc-hexanes) of the residual oil afforded the title compound as a colorless off.

$^1$H NMR($CDCl_3$): δ 0.10 (s, 9H), 1.15 (t, J=8.4 Hz, 2H), 1.38 (s, 6H), 2.44 (d, J=4.7 Hz, 2H), 4.43 (d, J=8.4 Hz, 2H), 6.58 (t, J=4.7 Hz, 1H), 7.16–7.36 (m, 7H), 7.45 (d, J=8.1 Hz, 1H), 8.02 (dd, J=1.8, 8.1 Hz, 1H), 8.10 (d, J=8.7 Hz, 2H), 8.45 (d, J=1.8 Hz, 1H).

4-[{(5,5-Dimethyl-8-(phenylthio)-5,6-dihydronaphthalen-2-yl)}carbonyl}oxy]benzoic acid (Compound E26)

To a solution of 2-(trimethylsilyl)ethyl 4-[[(5,5-dimethyl-5,6-dihydro-8-(phenylthio)-naphthalen-2-yl)carbonyl]oxy]-benzoate (Compound E25, 200.0 mg, 0.377 mmol) in 2.0 mL THF at 0° C. was added tetrabutylammonium fluoride (295.5 mg, 1.13 mmol; 1.13 mL of a 1M solututioin in THF). After 2 h the solution was warmed to room temperature and stirred overnight. EtOAc was added and the organic layer washed with $H_2O$ and saturated aqueous NaCl. Removal of the solvents under reduced pressure and recrystallization of the residue from $CH_3CN$ afforded the title compound as a pale yellow solid.

$^1$H NMR(acetone-$d_6$): δ 1.39 (s, 6H), 2.51 (d, J=4.7 Hz, 2H), 6.67 (t, J=4.7 Hz, 1H), 7.19–7.38 (m, 6H), 7.61 (d, J=8.1 Hz, 1H), 8.02 (dd, J=1.8, 8.1 Hz, 1H), 8.12 (d, J=8.6 Hz, 1H), 8.43 (d, J=8.1 Hz, 1H).

4-[{(5,5-Dimethyl-8-(phenylsulfonyl)-5,6-dihydronaphthalen-2-yl)}carbonyl}oxy]benzoic acid (Compound E27)

To a solution of 4-[[(5,5-dimethyl-5,6-dihydro-8-(phenylthio)-naphthalen-2-yl)carbonyl]oxy]-benzoic acid (Compound E26, 50.0 mg, 0.116 mmol) in 3.0 mL $CH_2Cl_2$, and 1.0 mL THF at 0° C. was added m-chloroperbenzoic acid (57–80%) (34–52 mg, 0.197–0.299 mmol). The resulting solution was warmed to room temperature and stirred overnight. Water was added and the mixture extracted with EtOAc. The combined organic layers were washed with $H_2O$ and saturated aqueous NaCl before being dried over $Na_2SO_4$. Removal of the solvents under reduced pressure and crystallization of the residue from $CH_3CN$ afforded the title compound as a colorless solid.

$^1$H NMR (acetone-$d_6$): δ 1.27 (s, 6H), 2.65 (d, J=4.8 Hz, 2H), 7.14 (d, J=8.7 Hz, 2H), 7.57–7.68 (m, 5H), 8.03 (m, 3H), 8.17 (d, J=8.7 Hz, 2H), 8.77 (d, J=1.8 Hz, 1H). Ethyl 4-[(5,5-Dimethyl-8(7H)-one-5,6-dihydronaphthalen-2-yl) carboxamido]benzoate (Compound E28)

To a solution of 5,5-dimethyl-5,6-dihydro-8(7H)-one-naphthalene-2-carboxylic acid (Compound E3, 400.0 mg, 1.833 mmol), ethyl 4-aminobenzoate (317.8 mg, 1.924 mmol), 1-(3-dimethylaminopropyl)-3-ethylcarbodiimide hydrochloride (386.5 mg, 2.016 mmol), and 4-dimethylaminopyridine (246.3 mg, 2.016 mmol) in 18.0 mL $CH_2Cl_2$ was stirred at room temperature for 2h. EtOAc (25 mL) was added and the solution washed with $H_2O$, 1M HCl, and saturated aqueous NaCl before being dried over $MgSO_4$. Removal of the solvents under reduced pressure and column chromatography (30% EtOAc-hexanes) of the residue afforded the title compound as a colorless solid.

$^1$H NMR($CDCl_3$): δ 1.41 (t, J=7.1 Hz, 3H), 1.45 (s, 6H), 2.08 (t, J=7.1 Hz, 2H), 2.80 (t, J=6.6 Hz, 2H), 4.38 (q, J=7.2 Hz, 2H), 7.62 (d, J=8.3 Hz, 1H), 7.78 (d, J=8.7 Hz, 2H), 8.09 (d, J=8.6 Hz, 2H), 8.14 (bs, 1H), 8.21 (dd, J=2.1, 8.3 Hz, 1H), 8.42 (d, J=2.1 Hz, 1H).

4-[(5,5-Dimethyl-8(7H)-one-5,6-dihydronaphthalen-2-yl)carboxamido]benzoic acid (Compound E29)

A solution of ethyl 4-[(5,5-dimethyl-8(7H)-one-5,6-dihydronaphthalen-2-yl)carboxamido]benzoate (Compound E28, 50.0 mg, 0.137 mmol) and NaOH (54.7 mg, 1.37 mmol; 0.68 mL of a 2N aqueous solution) in 2.0 mL EtOH and 1.0 mL THF was stirred at room temperature overnight. The reaction mixture was acidified with 10% HCl and extracted with EtOAc. The combined organic layers were washed with $H_2O$ and saturated aqueous NaCl before being dried over $Na_2SO_4$. Removal of the solvents under reduced pressure and crystallization of the residual solid from $MeOH/H_2O$ afforded the title compound as yellow crystals.

$^1$H NMR (DMSO-$d_6$): δ 1.40 (s, 6H), 2.01 (t, J=6.7 Hz, 2H), 2.74 (t, J=7.0 Hz, 2H), 7.74 (d, J=8.4 Hz, 1H), 7.93 (m, 4H), 8.16 (dd, J=2.1, 8.3 Hz, 1H), 8.45 (d, J=2.0 Hz, 1H), 10.68 (s, 1H), 12.75 (bs, 1H).

Ethyl 4-[(5,5-dimethyl-8(7H)-anti-(O-methyloxime)-5,6-dihydronaphthalen-2-yl)carboxamido]benzoate (Compound E30)

A mixture of ethyl 4-[(5,5-dimethyl-5,6-dihydro-8(7)-one-naphthalen-2-yl)carboxamido]-benzoate (Compound E28, 100.0 mg, 0.274 mmol), O-methylhydroxylamine hydrochloride (25.1 mg, 0.301 mmol), and $NaOAc)3H_2O$ (81.9 mg, 0.602 mmol) in 3.0 mL of EtOH was heated to 65° C. for 3 h and then stirred at room temperature for 68 h. The reaction was diluted with $H_2O$ and extracted with EtOAc. The combined organic layers were washed with $H_2O$ and saturated aqueous NaCl before being dried over $MgSO_4$. Removal of the solvents under reduced pressure and column chromatography (20–30% EtOAc-hexanes) of the residue afforded the title compound as a colorless solid.

$^1$H NMR ($CDCl_3$): δ 1.32 (s, 6H), 1.40 (t, J=7.2 Hz, 2H), 1.75 (t, J=7.0 Hz, 2H), 2.81 (t, J=7.0 Hz, 2H), 4.04 (s, 3H), 4.37 (q, J=7.1 Hz, 2H), 7.49 (d, J=8.2 Hz, 1H), 7.76 (dd, J=1.9, 8.7 Hz, 2H), 7.88 (dd, J=2.1, 8.3 Hz, 1H), 8.06 (dd, J=1.7, 8.7 Hz, 2H), 8.12 (bs, 1H), 8.40 (d, J=2.0 Hz, 1H).

4-[(5,5-Dimethyl-8(7H)-anti-(O-methyloxime)-5,6-dihydronaphthalen-2-yl)carboxamido]benzoic acid (Compound E31)

A solution of ethyl (E)-4-[[(5,5-dimethyl-5,6-dihydro-8 (7H)-anti-(O-methyloxime)-naphthalen-2-yl)carboxamido]-benzoate (Compound E30, 31.4 mg, 0.080 mmol) and NaOH (31.8 mg, 0.796 mmol; 0.40 mL of a 2N aqueous solution) in 2 mL EtOH was stirred at room temperature overnight. The reaction was acidified with 10% HCl and extracted with EtOAc. The combined organic layers were dried ($Na_2SO_4$) and concentrated under reduced pressure to give an off-white solid. Crystallization from $Et_2O$ afforded the title compound as a colorless solid.

$^1$H NMR (DMSO-$d_6$): δ 1.27 (s, 6H), 1.69 (t, J=6.9 Hz, 2H), 2.74 (t, J=6.9 Hz, 2H), 3.96 (s, 3H), 7.58 (d, J=8.3 Hz, 1H), 7.90 (m, 5H), 8.36 (d, J=2.0 Hz, 1H), 10.57 (s, 1H), 12.73 (bs, 1H).

(+/−) Ethyl 4-[(5,5-dimethyl-8-hydroxy-5,6,7,8-tetrahydronaphthalen-2-yl)carboxamido]benzoate (Compound E32)

A solution of ethyl 4-[(5,5-dimethyl-5,6-dihydro-8(7H)-one-naphthalen-2-yl)carboxamido]-benzoate (Compound E28, 125.0 mg, 0.342 mmol) in 2.0 mL EtOH and 2.0 mL THF was cooled to 0° C. and treated with NaBH₄ (11.5 mg, 0.304 mmol). After 4 h the reaction was quenched by the careful addition of H₂O, followed by 0.5 mL 1M HCl. EtOAc (25 mL) was added and the solution washed with 1M HCl, dilute aqueous NaHCO₃, H₂O and saturated aqueous NaCl before being dried over Na₂SO₄. Removal of the solvents under reduced pressure afforded the title compound as a colorless solid.

¹H NMR (acetone-d₆): δ 1.28 (s, 3H), 1.31 (s, 3H), 1.35 (t, J=7.2 Hz, 3H), 1.65 (m, 1H), 1.88 (m, 3H), 4.32 (q, J=7.1 Hz, 2H), 4.69 (q, J=5.8 Hz, 1H), 7.49 (d, J=8.2 Hz, 1H), 7.83 (dd, J=2.2, 8.3 Hz, 1H), 7.99 (s, 4H), 8.09 (d, J=1.9 Hz, 1H), 9.81 (bs, 1H).

(+/−) 4-[(5,5-Dimethyl-8-hydroxy-5,6,7,8-tetrahydronaphthalen-2-yl)carboxamido]benzoic acid (Compound E33)

A mixture of (+/−) ethyl -4-[(5,5-dimethyl-5,6,7,-tetrahydro-8-hydroxy-naphthalen-2-yl)carboxamido]-benzoate (Compound E32, 50.0 mg, 0.136 mmol) and NaOH (54.4 mg, 1.36 mmol; 0.68 mL of a 2N aqueous solution) in 3 mL EtOH was stirred at room temperature for 19h. The resulting solution was acidified with 10% HCl and extracted with EtOAc. The combined organic layers wre washed with H₂O and saturated aqueous NaCl, and then dried over Na₂SO₄. Removal of the solvents under reduced pressure afforded the title compound as a colorless solid.

¹H NMR (DMSO-d₆): δ 1.25 (s, 3H), 1.28 (s, 3H), 1.61 (m, 1H), 1.80 (m, 2H), 1.95 (m, 1H), 4.87 (m, 1H), 5.30 (bs, 1H), 7.49 (d, J=8.2 Hz, 1H), 7.78 (dd, J=1.9, 8.2 Hz, 1H), 7.49 (s, 4H), 8.01 (s, 1H), 10.47 (s, 1H), 12.72 (bs, 1H).

(+/−) Ethyl 4-[(5,5-dimethyl-8-(O-methoxymethyl)-5,6,7,8-tetrahydronaphthalen-2-yl)carboxamido] benzoate (Compound E34)

To a solution of (+/−) ethyl 4-[(5,5-dimethyl-8-hydroxy-5,6,7,8-tetrahydronaphthalen-2-yl)carboxamido]benzoate (Compound E32, 57.0 mg, 0.155 mmol) in 5.0 mL CH₂Cl₂ at 0° C. was added diisopropylethyl amine (276.2 mg, 2.137 mmol), chloromethyl methyl ether (37.7 mg, 0.469 mmol), and a catalytic amount of tetrabutylammonium iodide. The resulting solution was stirred at 45° C. overnight. Upon cooling to room temperature the solution was diluted with EtOAc and washed with 5% HCl, H₂O, saturated aqueous NaHCO₃, and saturated aqueous NaCl, before being dried over MgSO₄. Removal of the solvents under reduced pressure, followed by column chromatography (15% EtOAc-hexanes) afforded the title compound as a colorless oil.

¹H NMR (CDCl₃): δ 1.27 (s, 3H), 1.35 (s, 3H), 1.39 (t, J=7.1 Hz, 3H), 1.64 (m, 1H), 1.90–2.13 (m, 3H), 3.48 (s, 3H), 4.36 (q, J=7.1 Hz, 2H), 4.67 (t, J=5.0 Hz, 1H), 4.79 (d, J=6.9 Hz, 1H), 4.89 (d, J=6.9 Hz, 1H), 7.43 (d, J=8.2 Hz, 1H), 7.74 (m, 3H), 7.88 (d, J=2.0 Hz, 1H), 8.03 (d, J=8.7 Hz, 2H), 8.18 (s, 1H).

(+/−) 4-[(5,5-Dimethyl-8-(O-methoxymethyl)-5,6,7,8-tetrahydronaphthalen-2-yl)carboxamido]benzoic acid (Compound E35)

A mixture of (+/−) ethyl 4-[(5,5-dimethyl-8-(O-methoxymethyl)-5,6,7,8-tetrahydronaphthalen-2-yl) carboxamido]benzoate (Compound E34, 30.0 mg, 0.073 mmol) and NaOH (40.0 mg, 1.00 mmol; 1.0 mL of a 1N aqueous solution) in 1.0 mL EtOH and 1.0 mL THF was stirred at room temperature overnight. The resulting solution was acidified with 10% HCl and extracted with EtOAc. The combined organic layers wre washed with H₂O and saturated aqueous NaCl, and then dried over Na₂SO₄. Removal of the solvents under reduced pressure afforded the title compound as a colorless oil.

¹H NMR (acetone-d₆): δ 1.27 (s, 3H), 1.34 (s, 3H), 1.65 (m, 1H), 1.95 (m, 2H), 2.08 (m, 1H), 3.42 (s, 3H), 4.66 (t, J=5.0 Hz, 1H), 4.77 (d, J=6.9 Hz, 1h), 4.84 (d, J=6.9 Hz, 1h), 7.53 (d, J=8.2 Hz, 1H), 7.86 (dd, J=2.0, 8.2 Hz, 1H), 8.00 (m, 5H), 9.78 (s, 1H).

2-(Trimethylsilyl)ethyl 4-[[(5,5-dimethyl-8(7H)-one-5,6-dihydronaphthalen-2-yl)carbonyl]oxy]benzoate (Compound E36)

To a solution of 5,5-dimethyl-5,6-dihydro-8(7H)-one-naphthalene-2-carboxylic acid (Compound E3, 154.0 mg, 0.706 mmol), 2-(trimethylsilyl)ethyl 4-hydroxybenzoate (185.0 mg, 0.777 mmol), 1-(3-dimethylaminopropyl)-3-ethylcarbodiimide hydrochloride (176.0 mg, 0.918 mmol), and 4-dimethylaminopyridine (112.2 mg, 0.918 mmol) in 4.0 mL DMF was stirred at room temperature overnight. EtOAc (100 mL) was added and the solution washed with H₂O, 1M HQ, saturated aqueous NaHCO₃, and saturated aqueous NaCl before being dried over MgSO₄. Removal of the solvents under reduced pressure and column chromatography (10% EtOAc-hexanes) of the residue afforded the title compound as a colorless solid.

¹H NMR(CDCl₃): δ 0.09 (s, 9H), 1.15 (t, J=8.3 Hz, 2H), 1.45 (s, 6H), 2.08 (t, J=7.0 Hz, 2H), 2.81 (t, J=7.0 Hz, 2H), 4.43 (t, J=8.3 Hz, 2H), 7.28 (d, J=8.7 Hz, 2H), 7.60 (d, J=8.3 Hz, 1H), 8.12 (d, J=8.7 Hz, 2H), 8.30 (dd, 1H, J=1.9, 8.3 Hz, 1H), 8.85 (d, J=1.9 Hz, 1H).

(+/−)2-Trimethylsilylethyl 4-[[(5,5-dimethyl-8-hydroxy-5,6,7,8-tetrahydronaphthalen-2-yl)carbonyl]oxy]benzoate (Compound E37)

A solution of 2-(trimethylsilyl)ethyl 4-[[(5,5-dimethyl-8 (7H)-one-5,6-dihydronaphthalen-2-yl)carbonyl]oxy] benzoate (Compound E36, 160.0 mg, 0.365 mmol) in 2.0 mL EtOH and 2.0 mL THF was cooled to 0° C. and treated with NaBH₄ (13.8 mg, 0.365 mmol). After 3 h the reaction was quenched by the careful addition of 5% aqueous HCl. EtOAc (100 mL) was added and the solution washed with H₂O, dilute aqueous NaHCO₃, and saturated aqueous NaCl before being dried over MgSO₄. Removal of the solvents under reduced pressure followed by column chromatography (10–15% EtOAc) afforded the title compound.

¹H NMR (CDCl₃): δ 0.09 (s, 9H), 1.14 (t, J=8.4 Hz, 2H), 1.30 (s, 3H), 1.37 (s, 3H), 1.68 (m, 1H), 1.92 (m, 2H), 2.12 (m, 1H), 4.45 (t, J=8.4 Hz, 2H), 4.82 (m, 1H), 7.28 (d, J=8.7 Hz, 2H), 7.48 (d, J=8.3 Hz, 1H), 8.04 (dd, J=2.0, 8.3 Hz, 1H), 8.11 (d, J=8.7 Hz, 2H), 8.30 (d, J=2.0 Hz, 1H).

(+/−) 2-(Trimethylsilyl)ethyl 4-[[(5,5-dimethyl-8-(O-methoxymethyl)-5,6,7,8-tetrahydronaphthalen-2-yl)carbonyl]oxy]benzoate (Compound E38)

To a solution of (+/−) 2-trimethylsilylethyl 4-[[(5,5-dimethyl-8-hydroxy-5,6,7,8-tetrahydronaphthalen-2-yl) carbonyl]oxy]benzoate (Compound E37, 70.0 mg, 0.159 mmol) in 5.0 mL CH₂Cl₂ at 0° C. were added diisopropylethylamine (276.2 mg, 2.137 mmol), and chloromethyl methyl ether (37.7 mg, 0.469 mmol). The resulting solution was stirred at room temperature overnight. The reaction mixture was diluted with EtOAc and washed with 5% HCl, H₂O, saturated aqueous NaHCO₃, and saturated aqueous NaCl, before being dried over MgSO₄. Removal of the solvents under reduced pressure, followed by column chromatography (10% EtOAc-hexanes) afforded the title compound as a colorless oil.

¹H NMR (CDCl₃): δ 0.09 (s, 9H), 1.14 (t, J=8.3 Hz, 2H), 1.30 (s, 3H), 1.39 (s, 3H), 1.63 (m, 2H), 1.97 (m, 2H), 3.50 (s, 3H), 4.43 (t, J=8.3 Hz, 2H), 4.71 (t, J=5.0 Hz, 1H), 4.81 (d, J=7.0 Hz, 1H), 4.91 d, J=7.0 Hz, 1H), 7.28 (d, J=8.7 Hz, 2H), 7.49 (d, J=8.3 1 Hz, 1H), 8.05 (dd, J=1.8, 8.3 Hz, 1H), 8.10 (d, J=8.7 Hz, 2H), 8.19 (d, J=1.8 Hz, 1H).

(+/−) 4-[[(5,5-dimethyl-8-(O-methoxymethyl)-5,6,7,8-tetrahydronaphthalen-2-yl)carbonyl]oxy]benzoic acid (Compound E39)

To a solution of (+/−) 2-trimethylsilylethyl-4-[[(5,5-dimethyl-5,6,7,8-tertahydro-8-(O-methoxymethyl)naphthalen-2-yl)carbonyl]oxy]-benzoate (Compound E38, 72.0 mg, 0.148 mmol) in 2.0 mL THF was added tetrabutylammonium fluoride (130.7 mg, 0.500 mmol; 0.5 mL of a 1M solution in THF). The resulting solution was stirred overnight at room temperature, diluted with EtOAc, and washed with H₂O and saturated aqueous NaCl. The solution was dried (MgSO₄) and then concentrated under reduced pressure. The title compound was isolated as a colorless oil by preparative TLC (5% MeOH—CH₂Cl₂).

1H MNR (acetone-d₆): δ 1.30 (s, 3H), 1.37 (s, 3H), 1.67 (m, 1H), 1.95 (m, 2H), 2.11 (m, 1H), 3.42 (s, 3H), 4.70 (t, J=5.0 Hz, 1H), 4.88 (d, J=7.0 Hz, 2H), 7.42 (d, J=8.7 Hz, 2H), 7.62 (d, J=8.3 Hz, 1H), 7.77 (d, J=7.0 Hz, 2H), 8.03 (dd, J=1.9, 8.3 Hz, 1H), 8.15 (d, J=8.7 Hz, 2H), 8.19 d, J=1.9 Hz, 1H).

(+/−) Ethyl 4-[[(5,5-dimethyl-8-hydroxy-5,6,7,8-tetrahydronaphthalen-2-yl)carbonyl]oxy]benzoic acid (Compound E40)

A solution of ethyl 4-[[(5,5-dimethyl-5,6-dihydro-8(7H)-one-naphthalen-2-yl)carbonyl]oxy]-benzoate (Compound E44, 126.0 mg, 0.344 mmol) in 1.5 mL EtOH and 1.5 mL THF was cooled to 0° C. and treated with NaBH₄ (13.0 mg, 0.344 mmol). After 3 h the reaction was quenched by the careful addition of H₂O. EtOAc (50 mL) was added and the solution washed with H₂O and saturated aqueous NaCl before being dried over MgSO₄. Removal of the solvents under reduced pressure followed by column chromatography (15–20% EtOAc) afforded the title compound as a colorless oil.

¹H NMR (CDCl₃): δ 1.30 (s, 3H), 1.37 (s, 3H), 1.41 (t, J=7.1 Hz, 3H), 1.68 (m, 1H), 1.83–1.99 (m, 2H), 2.15 (m, 1H), 4.39 (q, J=7.1 Hz, 2H), 4.82 (m, 1H), 7.28 (d, J=8.7 Hz, 2H), 7.49 (d, J=8.3 Hz, 1H), 8.05 (dd, J=1.8, 8.3 Hz, 1H), 8.12 (d, J=8.7 Hz, 2H), 8.29 (d, J=1.8 Hz, 1H). (+/−)Ethyl 4-[(+/−)

Ethyl 4-[[(5,5-dimethyl-8-(O-methoxymethyl)-5,6,7,8-tetrahydronaphthalen-2-yl)carbonyl]oxy]benzoate (Compound E41)

To a solution of (+/−) ethyl 4-[[(5,5-dimethyl-5,6,7,8-tetrahydro-8-hydroxy-naphthalen-2-yl)carbonyl]oxy]-benzoate (Compound E40, 131.8 mg, 0.358 mmol) in 5.0 mL CH₂Cl₂ at 0° C. was added diisopropylethylamine (277.5 mg, 2.147 mmol), and chloromethyl methyl ether (86.9 mg, 1.08 mmol). The resulting solution was stirred at room temperature overnight. The reaction mixture was diluted with EtOAc and washed with 10% HCl, H₂O, saturated aqueous NaHCO₃, and saturated aqueous NaCl, before being dried over MgSO₄. Removal of the solvents under reduced pressure, followed by column chromatography (15% EtOAc-hexanes) afforded the title compound as a colorless oil ¹H NMR (CDCl₃): δ 1.29 (s, 3H), 1.38 (s, 3H), 1.41 (t, J=7.1 Hz, 3H), 1.62 (m, 2H), 1.96 (m, 2H), 3.50 (s, 3H), 4.39 (q, J=7.1 Hz, 2H), 4.71 (t, J=5.0 Hz, 1H), 4.80 d, J=7.0 Hz, 1H), 4.92 (d, J=7.0 Hz, 1H), 7.28 (d, J=8.7 Hz, 2H), 7.49 (d, J=8.3 Hz, 1H), 8.05 (dd, J=1.8, 8.3 Hz, 1H), 8.12 (d, J=8.7 Hz, 2H), 8.19 (d, J=1.8 Hz, 1H).

2-(Trimethylsilyl)ethyl-4-[[(5,5-dimethyl-8(7H)-anti-(O-methyloxime)-5,6-dihydronaphthalen-2-yl) carbonyl]oxy]benzoate (Compound E42)

A mixture of 2-(trimethylsilyl)ethyl 4-[[(5,5-dimethyl-5,6-dihydro-8(7H)-one-naphthalen-2-yl) carbonyl]oxy]-benzoate (Compound E36, 80.0 mg, 0.182 mmol), O-methylhydroxylamine hydrochloride (22.8 mg, 0.273 mmol), and NaOAc X 3H₂O (62.0 mg, 0.455 mmol) in 3.0 mL of EtOH was stirred at room temperature for 5 days. The reaction was diluted with H₂O and extracted with EtOAc. The combined organic layers were washed with H₂O and saturated aqueous NaCl before being dried over MgSO₄. Removal of the solvents under reduced pressure and column chromatography (4–8% EtOAc-hexanes) of the residue, followed by preparative TLC (20% EtOAc-hexanes, afforded the title compound.

¹H NMR (CDCl₃): δ 0.09 (s, 9H), 1.14 (t, J=8.6 Hz, 2H), 1.33 (s, 6H), 1.76 (t, J=6.9 Hz, 2H), 2.82 (t, J=6.9 Hz, 2H), 4.04 (s, 3H), 4.43 (q, J=8.4 Hz, 2H), 7.30 (d, J=8.7 Hz, 2H), 7.49 (d, J=8.3 Hz, 1H), 8.08 (dd, J=1.9, 8.3 Hz, 1H), 8.12 (d, J=8.7 Hz, 2H), 8.78 (d, J=1.9 Hz, 1H).

4-[[(5,5-dimethyl-8(7H)-anti-(O-methyloxime)-5,6-dihydronaphthalen-2-yl)carbonyl]oxy]benzoic acid (Compound E43)

To a solution of (trimethylsilyl)ethyl 4-[[(5,5-dimethyl-8(7H)-anti-(O-methyloxime)-5,6-dihydronaphthalen-2-yl) carbonyl]oxy]benzoate (Compound E42, 40.0 mg, 0.086 mmol) in 1.5 mL THF was added tetrabutylammonium fluoride (68.0 mg, 0.260 mmol; 0.26 mL of a 1M solution in THF). The resulting solution was stirred for 6 h at room temperature, diluted with EtOAc, and washed with H₂O and saturated aqueous NaCl. The solution was dried (MgSO₄) and then concentrated under reduced pressure. The title compound was isolated as a colorless oil by preparative TLC (5% MeOH—CH₂Cl₂).

¹H NMR (acetone-d₆): δ 1.34 (s, 6H), 1.78 (t, J=7.0 Hz, 2H), 2.81 (t, J=7.0 Hz, 2H), 3.98 (s, 3H), 7.45 (d, J=8.7 Hz, 2H), 7.67 (d, J=8.3 Hz, 1H), 8.10 (dd, J=1.9, 8.3 Hz, 1H), 8.15 (d, J=8.7 Hz, 2H), 8.74 (d, J=1.9 Hz, 1H).

Ethyl 4-[[(5,5-dimethyl-8(7H)-one-5,6-dihydronaphthalen-2-yl)carbonyl]oxy]benzoate (Compound F44)

To a solution of 5,5-dimethyl-5,6-dihydro-8(7H)-one-2-a naphthalenecarboxylic acid (Compound E3, 270.0 mg, 1.24 mmol), ethyl 4-hydroxybenzoate (226.0 mg, 1.364 mmol), 1-(3-dimethylaminopropyl)-3-ethylcarbodiimide hydrochloride (309.0 mg, 1.61 mmol), and 4-N,N-dimethylaminopyridine (197.0 mg, 1.61 mmol) in 5.0 mL DMF was stirred at room temperature overnight. EtOAc (25 mL) was added and the solution washed with H₂O, 1M HCl, and saturated aqueous NaCl before being dried over MgSO₄.

Removal of the solvents under reduced pressure and a column chromatography (7% EtOAc-hexanes) of the residue afforded the title compound as a pale-orange solid.

$^1$H NMR(CDCl$_3$): δ 1.41 (t, J=7.1 Hz, 3H), 1.45 (s, 6H), 2.08 (t, J=6.7 Hz, 2H), 2.80 (t, J=6.7 Hz, 2H), 4.39 (q, J=7.1 Hz, 2H), 7.30 (d, J=8.7 Hz, 2H), 7.60 (d, J=8.4 Hz, 1H), 8.13 (d,=8.7 Hz, 2H), 8.31 (dd, J=1.8, 8.4 Hz, 1H) 8.04 (d, J=1.8 Hz, 1H).

Ethyl 4-[[(5,5-dimethyl-8(7H)-anti-(O-methyloxime)-5,6-dihydronaphthalen-2-yl)carbonyl]oxy]benzoate (Compound E46)

A mixture of ethyl 4-[[(5,5-dimethyl-8(7H)-one-5,6-dihydronaphthalen-2-yl)carbonyl]oxy]benzoate (Compound E44, 66.0 mg, 0.180 mmol), O-methylhydroxylamine hydrochloride (23.0 mg, 0.270 mmol), and NaOAc)3H$_2$O (62.0 mg, 0.455 mmol) in 3.0 mL of EtOH was stirred at room temperature for 6 days. The reaction was diluted with H$_2$O and extracted with EtOAc. The combined organic layers were washed with H$_2$O and saturated aqueous NaCl before being dried over MgSO$_4$. Removal of the solvents under reduced pressure and column chromatography (4–8% EtOAc-hexanes) of the residue, followed by preparative TLC (5% EtOAc-hexanes) afforded the title compound.

$^1$H NMR (CDCl$_3$): δ 1.33 (s, 6H), 1.41 (t, J=7.1 Hz, 3H), 1.76 (t, J=6.9 Hz, 2H), 2.82 (t, J=6.9 Hz, 2H), 4.03 (s, 3H), 4.39 (q, J=7.1 Hz, 2H), 7.30 (d, J=8.6 Hz, 2H), 7.50 (d, J=8.3 Hz, 1H), 8.11 (dd, J=1.9, 8.3 Hz, 1H), 8.13 (d, J=8.6 Hz, 2H), 8.78 (d, J=1.9 Hz, 1H).

(+/−) Ethyl 2-(1-hydroxy-1,2,3,4-tetrahydro-4,4-dimethyl-7-bromo-naphthalen-1-yl)acetate (Compound E47)

To a suspension of Zn (1.20 g, 18.4 mmol) in 10 mL benzene at 100° C. was slowly added a solution of ethyl 2-bromoacetate (658.0 mg, 3.94 mmol) and 3,4-dihydro-4,4-dimethyl-7-bromo-naphthalen-1(2H)-one (Compound G, 500.0 mg, 1.97 mmol) in 20.0 mL benzene. The resulting mixture was heated for 2 h, cooled to room temperature, and the solution decanted from the residual solids. The solids were washed with EtOAc and the combined organic layers were washed with cold 15% H$_2$SO$_4$, saturated aqueous NaHCO$_3$, and saturated aqueous NaCl before being dried over MgSO$_4$. Removal of the solvents undr reduced pressure and column chromatography (10% EtOAc-hexanes) afforded the title compound as a yellow oil.

$^1$H NMR (CDCl$_3$): δ 1.26 (s, 3H), 1.29 (s, 3H), 1.31 (t, J=7.1 Hz, 3H), 1.62–1.82 (m, 2H), 2.05 (m, 2H), 2.75 (s, 2H), 4.21 (q, J=7.1 Hz, 2H), 7.16 (d, J=8.5 Hz, 1H), 7.33 (dd, J=2.1, 8.5 Hz, 1H), 7.71 (d, J=2.1 Hz, 1H).

(+/−) Ethyl 2-(1-acetoxy-1,2,3,4-tetrahydro-4,4-dimethyl-7-bromo-naphthalen-1-yl)acetate (Compound E48)

To a solution of (+/−) ethyl 2-(1-hydroxy-1,2,3,4-tetrahydro-4,4-dimethyl-7-bromo-naphthalen-1-yl)acetate (Compound E47, 200.0 mg, 0.586 mmol) and 4-N,N-dimethylaminopyridine (86.0 mg, 0.703 mmol) in 4.0 mL CH$_2$Cl$_2$ at 0° C. was added acetic anhydride (239.3 mg, 2.344 mmol). The resulting solution was warmed to room temperature and stirred overnight. The reaction was warmed to 50° C. for 3 h, cooled to room temperature, and diluted with EtOAc (70 mL). The solution was washed with H$_2$O, saturated aqueous NaHCO$_3$, 10% aqueous HCl, and saturated aqueous NaCl, before being dried over MgSO$_4$. Removal of the solvents under reduced pressure followed by column chromatography afforded the title compound as a colorless oil.

$^1$H NMR (CDCl$_3$): δ 1.23 (t, J=7.1 Hz, 3H), 1.30 (s, 3H), 1.31 (s, 3H), 1.76 (t, J=6.9 Hz, 2H), 2.05 (s, 3H), 2.48 (m, 1H), 2.67 (m, 1H), 3.03 (s, 2H), 4.12 (q, J=7.1 Hz, 2H), 7.19 (d, J=8.5 Hz, 1H), 7.33 (dd, J=2.1, 8.5 Hz, 1H), 7.45 (d, J=2.1 Hz, 1H).

(+/−) Ethyl 4-[(5,5-dimethyl-5,6,7,8-tetrahydro-8-acetoxy-8-carbethoxymethyl-naphthalen-2-yl)carboxamido]-benzoate (Compound E49)

A solution of ethyl 2-(1-acetoxy-1,2,3,4-tetrahydro-4,4-dimethyl-7-bromo-naphthalen-1-yl)acetate (Compound E48, 450.0 mg, 1.23 mmol), ethyl 4-aminobenzoate (810.0 mg, 4.90 mmol), 1,3-bis(diphenylphosphino)propane (100.0 mg, 0.245 mmol) in 5.0 mL Et$_3$N, and 10.0 mL DMSO was sparged with CO (g) for 10 minutes. To this solution was added bis(triphenylphosphine)palladium(II) chloride (105.0 mg, 0.150 mmol). The solution was placed under 1 atm of CO (balloon) and heated to 75° C. for 4 days. Upon cooling to room temperature the mixture was diluted with EtOAc and the solution washed with 10% HCl, H$_2$O, and saturated aqueous NaCl before being dried over Na$_2$SO$_4$. Removal of the solvents under reduced pressure and column chromatography (5–25% EtOAc-hexanes) afforded the title compound.

$^1$H NMR (CDCl$_3$): δ 1.20 (t, J=7.1 Hz, 3H), 1.35 (s, 6H), 1.40 (t, J=7.1 Hz, 3H), 1.78 (m, 2H), 2.03 (s, 3H), 2.50 (m, 1H), 2.71 (m, 1H), 3.12 (m, 2H), 4.11 (q, J=7.1 Hz, 2H), 4.37 (q, J=7.1 Hz, 2H), 7.42 (d, J=8.2 Hz, 1H), 7.70 (dd, J=1.9, 8.2 Hz, 1H), 7.73 (d, J=8.7 Hz, 2H), 7.95 (d, J=1.9 Hz, 1H), 8.04 (d, J=8.7 2H), 8.20 (s, 1H).

Ethyl (E)-4-[[(5,5-dimethyl-5,6-dihydro-8(7H)-(carbethoxymethylidenyl)-naphthalen-2-yl)carboxamido]-benzoate (Compound E50a(trans));

Ethyl (Z)-4-[[(5,5-dimethyl-5,6-dihydro-8(7H)-(carbethoxymethylidenyl)-naphthalen-2-yl)carboxamido]-benzoate (Compound E50a(cis)) and

Ethyl (E)-4-[[(5,5-dimethyl-5,6-dihydro-8-(carbethoxymethyl)-naphthalen-2-yl)carboxamido]-benzoate (Compound E50b)

To a solution of (+/−) ethyl 4-[(5,5-dimethyl-5,6,7,8-tetrahydro-8-acetoxy-8-carbethoxymethyl-naphthalen-2-yl)carboxamido]-benzoate (Compound E49, 210.0 mg, 0.438 mmol) in 6.0 mL CH$_2$Cl$_2$ was added 1,8-diazobicyclo[5.4.0]undec-7-ene (200.0 mg, 1.314 mmol). The resulting solution was stirred at room temperature for 21 h, diluted with EtOAc, and the combined solution washed with 10% aqueous HCl and saturated aqueous NaCl before being dried over MgSO$_4$. Removal of the solvents under reduced pressure and column chromatography (15% EtOAc-hexanes) afforded pure (Compound 50b) and a mixture of Compound E50a(trans) and Compound E50a (cis). Compound E50a (trans) and Compound E50a(cis) were isolated using reverse phase HPLC (5% H$_2$O—CH$_3$CN), each as a colorless solid.

Compound E50a(trans):

$^1$H NMR (CDCl$_3$): δ 1.30 (s, 6H), 1.31 (t, J=7.1 Hz, 3H), 1.40 (t, J=7.1 Hz, 3H), 1.73 (t, J=6.1 Hz, 2H), 3.21 (t, J=6.1 Hz, 2H), 4.16 (q, J=7.1 Hz, 2H), 4.36 (q, J=7.1 Hz, 2H), 6.35 (s, 1H), 7.46 (d, J=8.1 Hz, 1H), 7.78 (d, J=8.7 Hz, 2H), 7.82 (dd, J=1.8, 8.1 Hz, 1H), 8.04 (d, J=8.7 Hz, 2H), 8.06 (d, J=1.8 Hz, 1H), 8.41 (s, 1H).

Compound E50a(cis):

¹H NMR (CDCl₃): δ 1.31 (t, J=7.1 Hz, 3H), 1.34 (s, 6H), 1.40 (t, J=7.1 Hz, 3H), 1.88 (t, J=6.5 Hz, 2H), 2.61 (t, J=6.5 Hz, 2H), 4.21 (q, J=7.1 Hz, 2H), 4.37 (q, J=7.1 Hz, 2H), 5.92 (t, J=1.1 Hz, 1H), 7.46 (d, J=8.2 Hz, 1H), 7.77 (d, J=8.7 Hz, 2H), 7.88 (dd, J=1.9, 8.2 Hz, 1H), 8.06 (d, J=8.7 Hz, 2H), 8.39 (s, 1H).

(Compound E50b):

¹H NMR (CDCl₃): δ 1.19 (t, J=7.1 Hz, 3H), 1.28 (s, 6H), 1.39 (t, J=7.1 Hz, 3H), 2.26 (d, J=4.5 Hz, 2H), 3.49 (s, 2H), 4.11 (q, J=7.1 Hz, 2H), 4.38 (q, J=7.1 Hz, 2H), 5.97 (t, J=4.5 Hz, 1H), 7.35 (d, J=8.0 Hz, 1H), 7.70 (dd, J=1.8, 8.0 Hz, 1H), 7.74 (m, 3H), 8.00 (d, J=8.7 Hz, 2H), 8.41 (s, 1H).

(Z)-4-[[(5,5-Dimethyl-5,6-dihydro-8(7H)-(carboxymethylidenyl)-naphthalen-2-yl)carboxamido]-benzoic acid (Compound E52)

A solution of ethyl (Z)-4-[(5,5-dimethyl-5,6-dihydro-8(7H)-(carbethoxymethylidenyl)-naphthalen-2-yl)carboxamido]-benzoate (Compound E50a(cis), 15.0 mg, 0.034 mmol) and NaOH (80.0 mg, 2.00 mmol; 2.0 mL of a 1M aqueous solution) in 2.0 mL EtOH and 1.0 mL THF was stirred overnight at room temperature. The reaction was quenched by the addition of 10% HCl and extracted with EtOAc. The combined organic layers were washed with H₂O and saturated aqueous NaCl, and dried over Na₂SO₄. Removal of the solvents under reduced pressure and crystallization from CH₃CN afforded the title compound as a colorless solid.

¹H NMR (acetone-d₆): δ 1.35 (s, 6H), 1.87 (t, J=6.6 Hz, 2H), 2.61 (m, 2H), 5.91 (t, J=1.3 Hz, 1H), 7.55 (d, J=8.3 Hz, 1H), 7.91–8.04 (m, 5H), 8.29 (d, J=1.9 Hz, 1H), 9.66 (s, 1H).

(E)-4-[[(5,5-Dimethyl-5,6-dihydro-8(7H)-(carboxymethylidenyl)-naphthalen-2-yl)carboxamido]-benzoic acid (Compound E53)

A solution of ethyl (E)-4-[(5,5-dimethyl-5,6-dihydro-8(7H)-(carbethoxymethylidenyl)-naphthalen-2-yl)carboxamido]-benzoate (Compound E50a(trans), 20.0 mg, 0.046 mmol) and NaOH (160.0 mg, 4.00 mmol; 4.0 mL of a 1M aqueous solution) in 3.0 mL EtOH and 1.0 mL THF was stirred overnight at room temperature. The reaction was quenched by the addition of 10% HCl and extracted with EtOAc. The combined organic layers were washed with H₂O and saturated aqueous NaCl, and dried over Na₂SO₄. Removal of the solvents under reduced pressure and crystallization from CH₃CN afforded the title compound as a colorless solid.

¹H NMR (acetone-d₆): δ 1.34 (s, 6H), 1.76 (t, J=6.9 Hz, 2H), 3.24 (m, 2H), 6.46 (t, J=1.8 Hz, 1H), 7.62 (d, J=8.2 Hz, 1H), 7.95–8.05 (m, 5H), 8.29 (d, J=1.9 Hz, 1H), 9.91 (s, 1H).

(+/−) Ethyl 4-[[(5,5-dimethyl-8-hydroxy-8-(carbethoxy)-5,6,7,8-tetrahydronaphthalen-2-yl)carbonyl]oxy]benzoate (Compound E54)

To a suspension of Zn (500.0 mg, 7.65 mmol) in 10 mL benzene at 100° C. was slowly added a solution of ethyl 2-bromoacetate (150.3 mg, 0.900 mmol) and ethyl 4-[[(5,5-dimethyl-8(7H)-one-5,6-dihydronaphthalen-2-yl)carbonyl]oxy]benzoate (Compound E44, 110.0 mg, 0.300 mmol) in 10.0 mL benzene. The resulting mixture was heated for 2 h, cooled to room temperature, and the solution decanted from the residual solids. The solids were washed with EtOAc and the combined organic layers washed with cold 15% H₂SO₄, saturated aqueous NaHCO₃, and saturated aqueous NaCl before being dried over MgSO₄. Removal of the solvents under reduced pressure and column chromatography (15% EtOAc-hexanes) afforded the title compound as a pale-yellow oil.

¹H NMR (CDCl₃): δ 1.30 (t, J=7.1 Hz, 3H), 1.33 (s, 3H), 1.37 (s, 3H), 1.43 (t, J=7.1 Hz, 3H), 1.72–1.90 (m, 2H), 2.11 (m, 2H), 2.84 (m, 2H), 4.23 (q, J=7.1 Hz, 2H), 4.31 (s, 1H), 4.39 (q, J=7.1 Hz, 2H), 7.27 (d, J=8.8 Hz, 2H), 7.46 (d, J=8.3 Hz, 1H), 8.03 (dd, J=1.8, 8.3 Hz, 1H), 8.12 (d, J=8.8 Hz, 2H), 8.43 (d, J=1.8 Hz, 1H).

Ethyl 4-[[(5,5-dimethyl-8-(carbethoxy)-5,6-dihydronaphthalen-2-yl)carbonyl]oxy]benzoate (Compound E55)

To a solution of (+/−) ethyl 4-[[(5,5-dimethyl-8-hydroxy-8-(carbethoxy)-5,6,7,8-tetrahydronaphthalen-2-yl)carbonyl]oxy]benzoate (Compound E54, 35.0 mg, 0.077 mmol) in 10 mL benzene was added a catalytic amount (approximately 2 mg) of p-toluenesulfonic acid monohydrate. The solution was heated to reflux under a Dean-Stark trap for 3 h, and then cooled to room temperature and stirred overnight. The solvent was removed under reduced pressure and the title compound isolated from the residue by column chromatography (10% EtOAc-hexanes).

¹H NMR (CDCl₃): δ 1.21 (t, J=7.1 Hz, 3H), 1.33 (s, 6H), 1.41 (t, J=7.1 Hz, 3H), 2.31 (d, J=4.6 Hz, 2H), 3.54 (s, 2H), 4.14 (q, J=7.1 Hz, 2H), 4.39 (q, J=7.1 Hz, 2H), 6.01 (t, J=4.6 Hz, 1H), 7.28 (d, J=8.7 Hz, 2H), 7.46 (d, J=8.1 Hz, 1H), 8.00 (d, J=1.7 Hz, 1H), 8.04 (dd, J=1.7, 8.1 Hz, 1H), 8.13 (d, J=8.7 Hz, 2H).

Ethyl 4-[5,6,7,8-tetrahydro-8(R or S)-(2'(R or S)-tetrahydropyranoxy)-5,5-dimethyl-2-napthoyloxy] benzoate (Compound E56a) and Ethyl 4-[5,6,7,8-tetrahydro-8(R or S)-(2'(S or R)-tetrahydropyranoxy)-5,5-dimethyl-2-napthoyloxy] benzoate (Compound E56b)

To a solution of ethyl 4-[5,6,7,8-tetrahydro-8(R or S)-hydroxy-5,5-dimethyl-2-napthoyloxy]benzoate (Compound E40, 243 mg, 0.66 mmol) in anhydrous CH₂Cl₂ (10 mL) was added 3,4-dihydro-2H-pyran (184 mg, 2.2 mmol) followed by pyridinium p-toluenesulfonate (26 mg, 0.1 mmol). The reaction mixture was stirred at ambient temperature for 16 h, and diluted with CH₂Cl₂ (20 mL). The mixture was washed successively with water (5 mL), saturated NaHCO₃ (10 mL), water (10 mL) and brine (10 mL). The organic phase was dried over MgSO₄ and then concentrated in vacuo to a pale yellow oil. Purification by flash column chromatography (silica, 20% EtOAc-hexane) followed by HPLC separation (partisil 10, 10% EtOAc-hexane) afforded the title compounds as colorless oil.

Ethyl 4-[5,6,7,8-tetrahydro-8(R or S)-(2'(R or S)-tetrahydropyranoxy)-5,5-dimethyl-2-napthoyloxy] benzoate (Compound E56a)

¹H NMR (CDCl₃): δ 1.28 (s, 3H), 1.35 (s, 3H), 1.37 (t, J=7.1 Hz, 3H), 1.51–2.11(m, 10H), 3.54–3.61 (m, 1H), 3.96–4.03 (m, 1H), 4.35 (q, J=7.1 Hz, 2H), 4.70 (t, J=5.0 Hz, 1H), 4.87 (t, J=2.3 Hz, 1H), 7.28 (d, J=8.3 Hz, 2H), 7.45 (d, J=8.2 Hz, 1H), 8.02 (dd, J=1.9, 8.3 Hz, 1H), 8.10–8.13 (m, 3H).

Ethyl 4-[5,6,7,8-tetrahydro-8(R or S)-(2'(S or R)-tetrahydropyranoxy)-5,5-dimethyl-2-napthoyloxy] benzoate (Compound E56b)

¹H NMR (CDCl₃): δ 1.29 (s, 3H), 1.35 (s, 7.1 Hz, 7 (t, J=7.1 Hz, 3H), 1.58–2.10(m, 10H), 3.57–3.63 (m, 1H), 4.01–4.08 (m, 1H), 4.35 (q, J=7.1 Hz, 2H), 4.82 (t, J=4.8 Hz, 1H), 4.93 (t, J=3.6 Hz, 1H), 7.26 (d, J=8.3 Hz, 2H), 7.44 (d, J=8.2 Hz, 1H), 8.01 (dd, J=1.9, 8.3 Hz, 1H), 8.10 (d, J=8.6 Hz, 2H), 8.37 (d, J=1.8 Hz, 1H).

Ethyl 4-[5,6,7,8-tetrahydro-8(S or R)-(2'(R or S)-tetrahydropyranoxy)-5,5-dimethyl-2-napthoyloxy]benzoate (Compound E58a) and Ethyl 4-[5,6,7,8-tetrahydro-8(S or R)-(2'(S or R)-tetrahydropyranoxy)-5,5-dimethyl-2-napthoyloxy]benzoate (Compound E58b)

Employing the same general procedure as for the preparation of ethyl 4-[5,6,7,8-tetrahydro-8(R or S)-2(2'(R or S)-tetrahydropyranoxy)-5,5-dimethyl-2-napthoyloxy]benzoate and ethyl 4-[5,6,7,8-tetrahydro-8(R or S)-2(2'(S or R)-tetrahydropyranoxy)-5,5-dimethyl-2-napthoyloxy]benzoate, ethyl 4-[5,6,7,8-tetrahydro-8(R or S)-hydroxy-5,5-dimethyl-2-napthoyloxy]benzoate (Compound E40, 222 mg, 0.6 mmol) was converted to a mixture of diastereomers using 3,4-dihydro-2H-pyran (184 mg, 2.2 mmol) and pyridinium p-toluenesulfonate (26 mg, 0.1 mmol). Purification by flash column chromatography (silica, 20% EtOAc-hexane) followed by HPLC separation (partisil 10, 10% EtOAc-hexane) afforded the title compounds as colorless oils.

Ethyl 4-[5,6,7,8-tetrahydro-8(S or R)-(2'(R or S)-tetrahydropyranoxy)-5,5-dimethyl-2-napthoyloxy]benzoate (Compound E58a):

1H NMR (CDCl₃): δ 1.29 (s, 3H), 1.35 (s, 3H), 1.37 (t, J=7.1 Hz, 3H), 1.52–2.15(m, 10H), 3.54–3.61 (m, 1H), 3.96–4.03 (m, 1H), 4.35 (q, J=7.1 Hz, 2H), 4.70 (t, J=5.0 Hz, 1H), 4.87 (t, J=2.3 Hz, 1H), 7.26 (d, J=8.3 Hz, 2H), 7.46 (d, J=8.3 Hz, 1H), 8.02 (dd, J=1.9, 8.3 Hz, 1H), 8.10–8.13 (m, 3H).

Ethyl 4-[5,6,7,8-tetrahydro-8(S or R)-(2'(S or R)-tetrahydropyranoxy)-5,5-dimethyl-2-naphthoyloxy]benzoate (Compound E58b)

1H NMR (CDCl₃): δ 1.32 (s, 3H), 1.35 (s, 3H), 1.37 (t, J=7.1 Hz, 3H), 1.57–2.10(m, 10H), 3.57–3.64 (m, 1H), 4.01–4.08 (m, 1H), 4.35 (q, J=7.1 Hz, 2H), 4.82 (t, J=4.5 Hz, 1H), 4.94 (t, J=3.6 Hz, 1H), 7.26 (d, J=8.3 Hz, 2H), 7.44 (d, J=8.2 Hz, 1H), 8.00 (dd, J=1.9, 8.3 Hz, 1H), 8.10 (d, J=8.6 Hz, 2H), 8.36 (d, J=1.8 Hz, 1H).

Benzyl 4-[5,6,7,8-tetrahydro-8(R or S)-(2'(R or S)tetrahydropyranoxy)-5,5-dimethyl-2-napthoyloxy]benzoate (Compound E60a) and

Benzyl 4-[5,6,7,8-tetrahydro-8(R or S)-(2'(S or R)tetrahydropyranoxy)-5,5-dimethyl-2-napthoyloxy]benzoate (Compound E60b)

Employing the same general procedure as for the preparation of ethyl 4-[5,6,7,8-tetrahydro-8(R or S)-(2'(R or S)-tetrahydropyranoxy)-5,5-dimethyl-2-napthoyloxy]benzoate and ethyl 4-[5,6,7,8-tetrahydro-8(R or S)-(2'(S or R)-tetrahydropyranoxy)-5,5-dimethyl-2-napthoyloxy]benzoate, benzyl 4-[5,6,7,8-tetrahydro-8(R or S)-hydroxy-5,5-dimethyl-2-napthoyloxy]benzoate (Compound E82, 142 mg, 0.3 mmol) was converted to a mixture of diastereomers using 3,4-dihydro-2H-pyran (184 mg, 2.2 mmol) and pyridinium p-toluenesulfonate (26 mg, 0.1 mmol). Purification by flash column chromatography (silica, 20% EtOAc-hexane) followed by HPLC separation (partisil 10 PAC, 10% EtOAc-hexane) afforded the title compounds as colorless oil.

Benzyl 4-[5,6,7,8-tetrahydro-8(R or S)-(2'(R or S)tetrahydropyranoxy)-5,5-dimethyl-2-napthoyloxy]benzoate (Compound 60a)

¹H NMR (CDCl₃): δ 1.30 (s, 3H), 1.37 (s, 3H), 1.54–2.16 (m, 10H), 3.55–3.63 (m, 1H), 3.98–4.05 (m, 1H), 4.72 (t, J=4.9 Hz, 1H), 4.89 (t, J=4.6 Hz, 1H), 5.39 (s, 2H), 7.28 (d, J=8.6 Hz, 2H), 7.31–7.50 (m, 6H), 8.03 (dd, J=1.9, 8.3 Hz, 1H), 8.12–8.18 (m, 3H).

Benzyl 4-[5,6,7,8-tetrahydro-8(R or S)-(2'(S or R)tetrahydropyranoxy)-5,5-dimethyl-2-napthoyloxy]benzoate (Compound E60b)

¹H NMR (CDCl₃): δ 1.30 (s, 3H), 1.35 (s, 3H), 1.54–2.08 (m, 10H), 3.57–3.64 (m, 1H), 4.01–4.08 (m, 1H), 4.82 (t, J=4.4 Hz, 1H), 4.94 (t, J=3.9 Hz, 1H), 5.37 (s, 2H), 7.27 (d, J=6.8 Hz, 2H), 7.34–7.47 (m, 6H), 8.00 (dd, J=2.0, 8.3 Hz, 1H), 8.10 (d, J=9.2 Hz, 2H), 8.36 (d, J=1.9 Hz, 1H).

Benzyl 4-[5,6,7,8-tetrahydro-8(S or R)-(2'(R or S)tetrahydropyranoxy)-5,5-dimethyl-2-napthoyloxy]benzoate (Compound E62a) and

Benzyl 4-[5,6,7,8-tetrahydro-8(S or R)-(2'(S or R)tetrahydropyranoxy)-5,5-dimetethyl-2-napthoyloxy]benzoate (Compound E62b)

Employing the same general procedure as for the preparation of ethyl 4-[5,6,7,8-tetrahydro-8(R or S)-(2'(R or S)-tetrahydropyranoxy)-5,5-dimethyl-2-napthoyloxy]benzoate and ethyl 4-[5,6,7,8-tetrahydro-8(R or S)-(2'(S or R)-tetrahydropyranoxy)-5,5-dimethyl-2-napthoyloxy]benzoate, benzyl 4-[5,6,7,8-tetrahydro-8(R or S)-hydroxy-5,5-dimethyl-2-napthoyloxy]benzoate (Compound E82, 142 mg, 0.3 mmol) was converted to a mixture of diastereomers using 3,4-dihydro-2H-pyran (184 mg, 2.2 mmol) and pyridinium p-toluenesulfonate (26 mg, 0.1 mmol). Purification by flash column chromatography (silica, 20% EtOAc-hexane) followed by HPLC separation (partisil 10 PAC, 10% EtOAc-hexane) afforded the title compounds as colorless oils. Separation of the diastereomers gave a 1:1 ratio of the title compounds both as colorless oils (RT=32 minutes and 39 minutes), respectively.

Benzyl 4-[5,6,7,8-tetrahydro-8(S or R)-(2'(R or S)tetrahydropyranoxy)-5,5-dimethyl-2-napthoyloxy]benzoate (Compound E62a):

¹H NMR (CDCl₃): δ 1.30 (s, 3H), 1.37 (s, 3H), 1.52–2.15 (m, 10H), 3.54–3.61 (m, 1H), 3.96–4.03 (m, 1H), 4.70 (t, J=5.0 Hz, 1H), 4.87 (t, J=4.5 Hz, 1H), 5.37 (s, 2H), 7.26 (d, J=6.7 Hz, 2H), 7.29–7.49 (m, 6H), 8.02 (dd, J=1.9, 8.3 Hz, 1H), 8.10–8.17 (m, 3H).

Benzyl 4-[5,6,7,8-tetrahydro-8(S or R)-(2'(S or R)tetrahydropyranoxy)-5,5-dimethyl-2-napthoyloxy]benzoate (Compound E62b):

¹H NMR (CDCl₃): δ 1.30 (s, 3H), 1.35 (s, 3H), 1.54–2.10 (m, 10H), 3.57–3.64 (m, 1H), 4.01–4.08 (m, 1H), 4.82 (t, J=4.7 Hz, 1H), 4.94 (t, J=3.5 Hz, 1H), 5.37 (s, 2H), 7.27 (d, J=6.8 Hz, 2H), 7.34–7.47 (m, 6H), 8.00 (dd, J=2.0, 8.3 Hz, 1H), 8.10 (d, J=9.2 Hz, 2H), 8.36 (d, J=1.9 Hz, 1H).

4-[5,6,7,8-tetrahydro-8(R or S)-(2'(R or S)tetrahydropyranoxy)-5,5-dimethyl-2-napthoyloxy]benzoic acid (Compound E64)

To a solution of benzyl 4-[5,6,7,8-tetrahydro-8(R or S)-(2'(R or S)tetrahydropyranoxy)-5,5-dimethyl-2- napthoyloxy]benzoate (Compound E60a, 15 mg, 0.03 mmol) in ethyl acetate (5 mL) was added a catalytic amount of 10% Pd/C. The reaction mixture was then placed under a blanket of $H_2$ by using a $H_2$ balloon and stirred at ambient temperature for 12 h. The reaction mixture was then filtered through a plug of $MgSO_4$ and the filtrate was concentrated under reduced pressure to give a white solid. Recrystallization from acetonitrile gave the title compound as a white solid.

$^1$H NMR (CDCl$_3$): δ 1.30 (s, 3H), 1.37 (s, 3H), 1.51–2.17 (m, 10H), 3.57–3.64 (m, 1H), 3.98–4.06 (m, 1H), 4.72 (t, J=4.9 Hz, 1H), 4.90 (t, J=4.6 Hz, 1H), 7.31 (dd, J=2.5,9.3 Hz, 2H), 7.48 (d, J=8.3 Hz, 1H), 8.04 (dd, J=1.9, 8.3 Hz, 1H) 8.13 (d, J=1.7 Hz, 1H), 8.17 (dd, J=2.4, 9.3 Hz, 2H).

4-[5,6,7,8-tetrahydro-8(R or S)-(2'(S or R) tetrahydropyranoxy)-5,5-dimethyl-2-napthoyloxy] benzoic acid (Compound E65)

Employing the same general procedure as for the preparation of 4-[5,6,7,8-tetrahydro-8(R or S)-(2'(R or S)tetrahydropyranoxy)-5,5-dimethyl-2-napthoyloxy] benzoic acid (Compound E64), benzyl 4-[5,6,7,8-tetrahydro-8(R or S)-(2'(S or R)tetrahydropyranoxy)-5,5-dimethyl-2-napthoyloxy]benzoate (Compound E60b, 15 mg, 0.03 mmol) was converted to the title compound (white solid).

$^1$H NMR (CDCl$_3$): δ 1.30 (s, 3H), 1.36 (s, 3H), 1.55–2.11 (m, 10H), 3.59–3.64 (m, 1H), 4.02–4.10 (m, 1H), 4.83 (t, J=5.0 Hz, 1H), 4.95 (t, J=3.7 Hz, 1H), 7.29 (d, J=8.7 Hz, 2H), 7.4 (d, J=8.3 Hz, 1H), 8.01 (dd, J=1.8, 8.2 Hz, 1H), 8.16 (d, J=8.6 Hz, 2H), 8.37 (d, J=2.0 Hz, 1H).

4-[5,6,7,8-tetrahydro-8(R or S)-(2'(R or S) tetrahydropyranoxy)-5,5-dimethyl-2-napthoyloxy] benzoic acid (Compound E66)

Employing the same general procedure as for the preparation of 4-[5,6,7,8-tetrahydro-8(R or S)-(2'(R or S)tetrahydropyranoxy)-5,5-dimethyl-2-napthoyloxy] benzoic acid (Compound E64), benzyl 4-[5,6,7,8-tetrahydro-8(S or R)-(2'(R or S)tetrahydropyranoxy)-5,5-dimethyl-2-napthoyloxy]benzoate (Compound E62a, 15 mg, 0.03 mmol) was converted to the title compound (white solid).

$^1$H NMR (CDCl$_3$): δ 1.29 (s, 3H), 1.36 (s, 3H), 1.53–2.15 (m, 10H), 3.56–3.63 (m, 1H), 3.97–4.04 (m, 1H), 4.71 (t, J=4.9 Hz, 1H), 4.89 (t, J=4.3 Hz, 1H), 7.30 (d, J=8.8 Hz, 2H), 7.47 (d, J=8.4 Hz, 1H), 8.03 (dd, J=1.9, 8.2 Hz, 1H), 8.11 (d, J=2.0 Hz, 1H), 8.17 (d, J=8.6 Hz, 2H).

4-[5,6,7,8-tetrahydro-8(S or R)-(2'(S or R) tetrahydropyranoxy)-5,5-dimethyl-2-napthoyloxy] benzoic acid (Compound E67)

Employing the same general procedure as for the preparation of 4-[5,6,7,8-tetrahydro-8(R or S)-(2'(R or S)tetrahydropyranoxy)-5,5-dimethyl-2-napthoyloxy] benzoic acid (Compound E64) benzyl 4-[5,6,7,8-tetrahydro-8(S or R)-(2'(S or R)tetrahydropyranoxy)-5,5-dimethyl-2-napthoyloxy]benzoate (Compound E62b, 15 mg, 0.03 mmol) was converted to the title compound (white solid).

$^1$H NMR (CDCl$_3$): δ 1.31 (s, 3H), 1.37 (s, 3H), 1.55–2.09 (m, 10H), 3.60–3.65 (m, 1H), 4.04–4.10 (m, 1H), 4.85 (t, J=4.9 Hz, 1H), 4.96 (t, J=3.8 Hz, 1H), 7.31 (d, J=8.6 Hz, 2H), 7.46 (d, J=8.3 Hz, 1H), 8.03 (dd, J=1.9, 8.2 Hz, 1H), 8.18 (d, J=8.6 Hz, 2H), 8.38 (d, J=1.7 Hz, 1H).

Ethyl 4-[5,6,7,8-tetrahydro-8(S or R)-(2'(R or S) tetrahydropyranoxy)5,5-dimethylnaphthalene-2-yl) carboxamido]benzoate (Compound E70a) and Ethyl 4-[5,6,7,8-tetrahydro-8(S or R)-(2'(S or R) tetrahydropyranoxy)5,5-dimethylnaphthalene-2-yl) carboxamido]benzoate (Compound E70b)

Employing the same general procedure as for the preparation of ethyl 4-[5,6,7,8-tetrahydro-8(R or S)-(2'(R or S)-tetrahydropyranoxy)-5,5-dimethyl-7napthoyloxy] benzoate and ethyl 4-[5,6,7,8-tetrahydro-8(R or S)-(2'(S or R)-tetrahydropyranoxy)-5,5-dimethyl-7-napthoyloxy] benzoate, (+/−) ethyl 4-[(5,5-dimethyl-8-hydroxy-5,6,7,8-tetrahydronaphthalen-2-yl)carboxamido]benzoate (Compound E32, 142 mg, 0.3mmol) was converted to a mixture of diastereomers using 3,4-dihydro-2H-pyran (184 mg, 2.2 mmol) and pyridinium p-toluenesulfonate (26 mg, 0.1 mmol). Purification by flash column chromatography (silica, 20% EtOAc-hexane) followed by HPLC separation (partisil 10 PAC, 20% EtOAc-hexane) of the diastereomers gave a 1:1 ratio of the title compounds, both as colorless oil (RT=53 minutes and 60 minutes), respectively.

Ethyl 4-[5,6,7,8-tetrahydro-8(S or R)-(2'(R or S) tetrahydropyranoxy)5,5-dimethylnaphthalene-2-yl) carboxamido]benzoate (Compound E70a):

$^1$H NMR (CDCl$_3$): δ 1.24 (s, 3H), 1.30 (s, 3H), 1.34 (t, J=7.1 Hz, 3H), 1.48–2.10 (m, 10H), 3.52–3.56 (m, 1H), 3.92–3.98 (m, 1H), 4.30 (t, J=7.1 Hz, 2H), 4.61 (t, J=4.8 Hz, 1H), 4.80 (t, J=4.5 Hz, 1H), 7.36 (d, J=8.2 Hz, 1H), 7.68–7.74 (m, 3H), 7.80 (d, J=1.9 Hz, 1H), 7.98 (d, J=8.7 Hz, 2H), 8.28 (s, 1H).

Ethyl 4-[5,6,7,8-tetrahydropyranoxy)5,5-dimethylnaphthalene-2-yl)carboxamido]benzoate (Compound E70b):

$^1$H NMR (CDCl$_3$): δ 1.26 (s, 3H), 1.32 (s, 3H), 1.36 (t, J=7.1 Hz, 3H), 1.58–2.04 (m, 10H), 3.57–3.61 (m, 1H), 4.00–4.05 (m, 1H), 4.31 (t, J=7.1 Hz, 2H), 4.78 (t, J=4.9 Hz, 1H), 4.86 (t, J=4.6 Hz, 1H), 7.37 (d, J=8.2 Hz, 1H), 7.73–7.75 (m, 3H), 8.00–8.03 (m, 3H), 8.34 (s, 1H).

Ethyl 4-[5,6,7,8-tetrahydro-8(R or S)-(2'(R or S) tetrahydropyranoxy)5,5-dimethylnaphthalene-2-yl) carboxamido]benzoate (Compound E72a) and Ethyl 4-[5,6,7,8-tetrahydro-8(R or S)-(2'(S or R) tetrahydropyranoxy)5,5-dimethylnaphthalene-2-yl) carboxamido]benzoate (Compound E72b)

Employing the same general procedure as for the preparation of ethyl 4-[5,6,7,8-tetrahydro-8-(R or S)-(2'(R or S)-tetrahydropyranoxy)-5,5-dimethyl-7-napthoyloxy] benzoate and ethyl 4-[5,6,7,8-tetrahydro-8(R or S)-(2'(S or R)-tetrahydropyranoxy)-5,5-dimethyl-7-napthoyloxy] benzoate, ethyl 4-[5,6,7,8-tetrahydro-8(R or S)-hydroxy-5,5-dimethylnaphthalene-2-yl)carboxamido]benzoate (Compound E32, 142 mg, 0.3mmol) was converted to a mixture of diastereomers using 3,4-dihydro-2H-pyran (184 mg, 2.2 mmol) and pyridinium p-toluenesulfonate (26 mg, 0.1 mmol). Purification by flash column chromatography (silica, 20% EtOAc-hexane) followed by HPLC separation (partisil 10 PAC, 20% EtOAc-hexane) afforded the title compounds as colorless oil.

Ethyl 4-[5,6,7,8-tetrahydro-8(R or S)-(2'(R or S) tetrahydropyranoxy)5,5-dimethylnaphthalene-2-yl) carboxamido]benzoate (Compound E72a):

$^1$H NMR (CDCl$_3$): δ 1.25 (s, 3H), 1.32 (s, 3H), 1.35 (t, J=7.1 Hz, 3H), 1.54–2.10 (m, 10H), 3.53–3.60 (m, 1H), 3.94–4.01 (m, 1H), 4.31 (t, J=7.1 Hz, 2H), 4.64 (t, J=4.9 Hz, 1H), 4.83 (t, J=4.3 Hz, 1H), 7.39 (d, J=8.2 Hz, 1H), 7.68–7.73 (m, 3H), 7.80 (d, J=1.8 Hz, 1H), 8.01 (d, J=8.7 Hz, 2H), 8.12 (s, 1H).

Ethyl 4-[5,6,7,8-tetrahydro-8(R or S)-(2'(S or R) tetrahydropyranoxy)5,5-dimethylnaphthalene-2-yl) carboxamido]benzoate (Compound E72b)

$^1$H NMR (CDCl$_3$): δ 1.29 (s, 3H), 1.34 (s, 3H), 1.37 (t, J=7.1 Hz, 3H), 1.56–2.10 (m, 10H), 3.58–3.65 (m, 1H), 4.01–4.08 (m, 1H), 4.33 (t, J=7.1 Hz, 2H), 4.81 (t, J=4.9 Hz, 1H), 4.88 (t, J=4.6 Hz, 1H), 7.42 (d, J=8.3 Hz, 1H), 7.72–7.78 (m, 3H), 8.02–8.07 (m, 3H), 8.11 (s, 1H).

4-[5,6,7,8-tetrahydro-8(S or R)-(2'(R or S) tetrahydropyranoxy)5,5-dimethyl-naphthalene-2-yl) carboxamido]benzoic acid (Compound E74)

To a solution of ethyl 4-[5,6,7,8-tetrahydro-8(S or R)-(2'(R or S)tetrahydropyranoxy)5,5-dimethylnaphthalene-2-yl)carboxamido]benzoate (Compound E70a, 54 mg, 0.12 mmol) in THF (2 mL) and methanol (1 mL) was added 0.5M lithiumhydroxide (2 mL, 1 mmol). The reaction mixture was stirred at ambient temperature for 12 h. The reaction mixture was diluted with EtOAc (15 mL), and acidified with 10% HCl to pH 4. The organic layer was washed with water (5 mL), brine (10 mL), dried (MgSO$_4$) and the solvent removed under reduced pressure. Recrystallization from EtOAc/ hexane afforded the title compound as a white solid.

$^1$H NMR (acetone-d$_6$): δ 1.27 (s, 3H), 1.33 (s, 3H), 1.49–2.11 (m, 10H), 2.80 (br, 1H), 3.51–3.58 (m, 1H), 3.89–3.96 (m, 1H), 4.67 (t, J=4.4 Hz, 1H), 4.89 (t, J =4.5 Hz, 1H), 7.52 (d, J=8.2 Hz, 1H), 7.80 (d, J=1.9 Hz, 1H), 7.91–8.04 (m, 5H), 9.73 (s, 1H).

4-[5,6,7,8-tetrahydro-8(S or R)-(2'(S or R) tetrahydropyranoxy)5,5-dimethyl-naphthalene-2-yl) carboxamido]benzoic acid (Compound E75)

Employing the same general procedure as for the preparation of 4-[5,6,7,8-tetrahydro-8(S or R)-(2'(R or S)tetrahydropyranoxy)5,5-dimethyl-naphthalene-2-yl) carboxamido]benzoic acid (Compound E74) ethyl 4-[5,6,7, 8-tetrahydro-8(S or R)-(2'(S or R)tetrahydropyranoxy)5,5-dimethyl-naphthalene-2-yl)carboxamido]benzoate (Compound E70b, 36 mg, 0.08 mmol) was converted into the title compound (white solid).

$^1$H NMR (acetone-d$_6$): δ 1.28 (s, 3H), 1.34 (s, 3H), 1.51–2.02 (m, 10H), 2.80 (br, 1H), 3.55–3.60 (m, 1H), 3.96–4.03 (m, 1H), 4.77 (t, J=5.4 Hz, 1H), 4.92 (t, J=3.8 Hz, 1H), 7.50 (d, J=8.3 Hz, 1H), 7.82 (dd, J=2.0, 8.3 Hz, 1H), 7.97–8.02 (m, 4H), 8.09 (d, J=1.9 Hz, 1H), 9.77 (s, 1H).

4-[5,6,7,8-tetrahydro-8(R or S)-(2'(R or S) tetrahydropyranoxy)5,5-dimethyl-naphthalene-2-yl) carboxamido]benzoic acid (Compound E76)

Employing the same general procedure as for the preparation of 4-[5,6,7,8-tetrahydro-8(S or R)-(2'(R or S)tetrahydropyranoxy)-5,5-dimethyl-naphthalene-2-yl) carboxamido]benzoic acid (Compound E74), ethyl 4-[5,6, 7,8-tetrahydro-8(R or S)-(2'(S or R)tetrahydropyranoxy)5, 5-dimethyl-naphthalene-2-yl)carboxamido]benzoate (Compound E72b, 36 mg, 0.08 mmol) was converted into the title compound (white solid).

$^1$H NMR (CDCl$_3$): δ 1.28 (s, 3H), 1.34 (s, 3H), 1.55–2.08 (m, 10H), 3.59–3.65 (m, 1H), 4.04–4.12 (m, 1H), 4.82 (t, J=4.9 Hz, 1H), 4.88 (t, J=2.6 Hz, 1H), 7.43 (d, J=8.3 Hz, 1H), 7.74–7.81 (m, 3H), 8.02 (d, J=1.8 Hz, 1H), 8.06 (d, J=8.7 Hz, 2H), 8.30 (s, 1H).

4-[5,6,7,8-tetrahydro-8(R or S)-(2'(S or R) tetrahydropyranoxy)5,5-dimethyl-naphthalene-2-yl) carboxamido]benzoic acid (Compound E77)

Employing the same general procedure as for the preparation of 4-[5,6,7,8-tetrahydro-8(S or R)-(2'(R or S)tetrahydropyranoxy)5,5-dimethyl-naphthalene-2-yl) carboxamido]benzoic acid (Compound E74), ethyl 4-[5,6, 7,8-tetrahydro-8(R or S)-(2(S or R)tetrahydropyranoxy)5,5-dimethyl-naphthalene-2-yl)carboxamido]benzoate (Compound E72a, 36 mg 0.08 mmol) was converted into the title compound (white solid).

$^1$H NMR (CDCl$_3$): δ 1.27 (s, 3H), 1.34 (s, 3H), 1.55–2.13 (m, 10H), 3.57–3.63 (m, 1H), 3.97–4.03 (m, 1H), 4.70 (t, J=4.7 Hz, 1H), 4.89 (t, J=2.4 Hz, 1H), 7.44 (d, J=8.3 Hz, 1H), 7.72–7.77 (m, 3H), 7.82 (d,=1.9 Hz, 1H), 8.06–8.10 M, 3H).

5,5-dimethyl-5,6-dihydro-8-(1,1-dimethylethyl)-2-naphthalenecarboxylic acid (Compound E78)

A solution of 7-bromo-1-(1,1-dimethylethyl)-3,4-dihydro-4,4-dimethylnaphthalene (Compound C42, 450.0mg, 1.54 mmol) in 20 mL of THF was cooled to –78° C. and 197.3 mg (3.08 mmol; 1.8 mL of a 1.7M solution in pentane) added giving a pale-yellow solution. After 1 h, CO2 (from evaporation of Dry Ice, dried with CaSO$_4$) was bubbled through the solution for 1h. After stirring at –78° C. for an additional hour, the reaction was quenched with 10% aqueous HCl. The solution was extracted with EtOAc and the combined organic layers washed with H$_2$O and saturated aqueous NaCl before being dried over Na$_2$SO$_4$. Removal of the solvents under reduced pressure, and washing of the residue with hexanes afforded the title compound as a colorless solid.

$^1$H NMR (CDCl$_3$) δ 1.25 (6H, s), 1.38 (9H, s), 2.17 (2H, d, J=4.9 Hz), 6.02 (1H, t, J=4.9 Hz), 7.41 (1H, d, J=8.1 Hz), 7.91 (1H, dd, J=1.6, 8.1 Hz), 8.42 (1H, d, J=1.6 Hz).

Ethyl 4-[(5,5-dimethyl-5,6-dihydro-8-(1,1-dimethylethyl)-2-naphthalenyl)carboxamido]-benzoate (Compound E79)

A solution of 5,5-dimethyl-5,6-dihydro-8-(1,1-dimethylethyl)-2-naphthalenecarboxylic acid (Compound E78, 150.0 mg, 0.581 mmol), ethyl 4-aminobenzoate (115.2 mg, 0.697 mmol), 1-(3-dimethylaminopropyl)-3-ethylcarbodiimide hydrochloride (145.0 mg, 0.755 mmol), and 4-N,N-dimethylaminopyridine (89.0 mg, 0.697 mmol) in 8.0 mL DMF was stirred overnight at room temperature. EtOAc (110 mL) was added and the solution washed with H$_2$O, 5% HCl, saturated aqueous NaHCO$_3$, and saturated aqueous NaCl before being dried over MgSO$_4$. Removal of the sovents under reduced pressure and column chromatography (10–25% EtOAc-hexanes) of the residual oil afforded the title compound as a colorless solid.

$^1$H NMR(CDCl$_3$) δ 1.25 (6H, s), 1.39 (9H, s), 1.40 (3H, t, J=7.1 Hz), 2.18 (2H, d, J=4.9 Hz), 4.37 (2H, q, J=7.1 Hz), 6.05 (1H, t, J=4.9 Hz), 7.41 (1H, d, J=8.0 Hz), 7.58 (1H, dd, J=1.8, 8.0 Hz), 7.24 (2H, d, J=8.7 Hz), 7.91 (1H, s,), 8.06 (2H, d, J=8.7 Hz), 8.26 (1H, d, J=1.8 Hz).

4-[(5,5-dimethyl-5,6-dihydro-8-(1,1-dimethylethyl)-2-naphthalenyl)carboxamido]-benzoic acid (Compound E80)

To a solution of ethyl 4-[(5,5-dimethyl-5,6-dihydro-8-(1, 1-dimethylethyl)-2-naphthalenyl)carboxamido]-benzoate (Compound E79, 50.0 mg, 0.123 mmol) in 2.0 mL of EtOH and 3.0 mL THF was added NaOH (240.0 mg, 6.00 mmol; 3.0 mL of a 2N aqueous solution). After stirring overnight at room temperature the reaction was quenched by the addition of 1M aqueous HCl. The mixture was extracted with EtOAc and the combined organic layers washed with H$_2$O and saturated aqueous NaCl before being dried over Na$_2$SO$_4$. Removal of the solvents under reduced pressure afforded the title compound as a colorless solid.

$^1$H NMR(d$_6$-acetone) δ 1.24 (6H, s), 1.38 (9H, s), 2.17 (2H, d, J=4.9 Hz), 6.08 (1H, t, J=4.9 Hz), 7.45 (1H, d, J=8.1 Hz), 7.81 (1H, dd, J=1.8, 8.1 Hz), 7.97–8.05 (4H, m), 8.31 (1H, d, J=1.8 Hz).

Benzyl-4-[[(5,5-dimethyl-5,6,7,8-tetrahydro-8-oxo-naphthalen-2-yl)carbonyl]oxy]-benzoate
(Compound E81)

To a solution of 5,5-dimethyl-5,6,7,8-tetrahydro-8-oxo-naphthalen-2-carboxylic acid (Compound E3, 386 mg, 1.77 mmol) in dimethylformamide (4 mL) was added 1-(3-dimethylaminopropyl)-3-ethylcarboimide hydrochlorde (440 mg, 2.3 mmol) followed by dimethylamino pyridine (DMAP) (280 mg, 2.3 mmol). The mixture was stirred for 10 minutes, and benzyl 4-hydroxy benzoate (426 mg, 1.9 mmol) was added and stirred at ambient temperature for 16 hours. The mixture was diluted with ethyl acetate (100 mL) and washed with water (10 mL), brine (10 mL), dried and solvent distilled off. The title compound was obtained as a pale yellow solid after chromatographic purification.

$^1$H NMR (CDC$_3$): δ 1.42 (s, 6H), 2.05 (t, J=6.7 Hz, 2H), 2.77 (t, J=6.7 Hz, 2H), 5.37 (s, 2H), 7.25–7.50 (m, 7H), 7.58 (d, J=8.3 Hz, 1H), 8.15 (d, J=8.1 Hz, 2H), 8.28 (dd, J=1.9, 8.3 Hz, 1H), 8.82 (d, J=1.9 Hz, 1H).

Benzyl-4-[[5,5-dimethyl-5,6,7,8-tetrahydro-8-hydroxy-naphthalen-2-yl)carbonyl]oxy]-benzoate
(Compound E82)

To a solution of benzyl-4-[[5,5-dimethyl-5,6,7,8-tetrahydro-8-oxo-naphthalen-2-yl)carbonyl]oxyl]-benzoate ((Compound E81, 377 mg, 0.88 mmol) in dimethoxyethane (20 mL) was added sodiumborohydride (33 mg, 0.9 mmol). The mixture was stirred for 12 hours at room temperature. The mixture was diluted with ethylacetate (50 mL), washed with water (10 mL), brine (10 mL), dried and solvent distilled off. The title compound was obtained as a white solid after chromatographic purification.

$^1$H NMR (CDCl$_3$): δ 1.30 (s, 3H), 1.37 (s, 3H), 1.60–1.75 (m, 1H), 1.85–2.00 (m, 2H), 2.05–2.20 (m, 1H), 2.30 (brs, 1H), 4.81 (t, J=5.6, 1H), 5.38 (s, 2H), 7.27 (d, J=8.7 Hz, 2H), 7.35–7.51 (m, 6H), 8.04 (dd, J=1.9, 8.3 Hz, 1H), 8.15 (d, J=8.7 Hz, 2H), 8.31 (d, J=1.9 Hz).

What is claimed is:

1. A compound of the formula

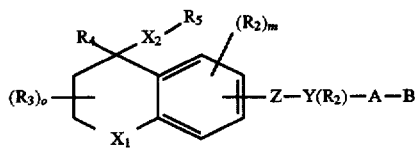

wherein $X_1$ is $[C(R_1)_2]_n$ where $R_1$ is independently H or alkyl of 1 to 6 carbons, and n is an integer between 0 and 2;

$X_2$ is S or O;

Z is —N=N—, —N(O)=N—, —N=N(O)—, —N=CR$_1$—, —CR$_1$=N, —CO—NR$_1$—, —CS—NR$_1$—, —NR$_1$—CO, —NR$_1$—CS, $R_2$ is hydrogen, lower alkyl of 1 to 6 carbons, F, Cl, Br, I, CF$_3$, flouro substituted alkyl of 1 to 6 carbons, OH, SH, alkoxy of 1 to 6 carbons, or alkylthio of 1 to 6 carbons;

$R_3$ is hydrogen, lower alkyl of 1 to 6 carbons or F;

m is an integer having the value of 0–3;

o is an integer having the value of 0–4;

$R_4$ is hydrogen, alkyl of 1 to 10 carbons, alkenyl of 2 to 10 carbons and having 1 to 3 double bonds, alkynyl having 2 to 10 carbons and 1 to 3 triple bonds, carbocyclic aryl selected from the group consisting of phenyl, $C_1$–$C_{10}$-alkylphenyl, naphthyl, $C_1$–$C_{10}$-alkylnaphthyl, phenyl-$C_1$–$C_{10}$alkyl, napthyl-$C_1$–$C_{10}$alkyl; CN, $(CH_2)_pCO_2H$ or $(CH_2)_pCO_2R_8$ where p is an integer between 0 to 10;

$R_5$ is hydrogen, alkyl of 1 to 10 carbons, fluoro-substituted alkyl of 1 to 10 carbons, alkenyl of 2 to 10 carbons and having 1 to 3 double bonds, alkynyl having 2 to 10 carbons and 1 to 3 triple bonds, carbocyclic aryl selected from the group consisting of phenyl, $C_1$–$C_{10}$-alkylphenyl, naphthyl, $C_1$–$C_{10}$-alkylnaphthyl, phenyl-$C_1$–$C_{10}$alkyl, napthyl-$C_1$–$C_{10}$alkyl; Si(C$_{1-6}$alkyl)$_3$, COR$_4$, camphanoyl, C(R$_{15}$)(R$_{16}$)X$_2$R$_{17}$;

Y is a phenyl or naphthyl group optionally substituted with one or two R$_2$ groups;

A is $(CH_2)_q$ where q is 0–5, lower branched chain alkyl having 3–6 carbons, cycloalkyl having 3–6 carbons, alkenyl having 2–6 carbons and 1 or 2 double bonds, alkynyl having 2–6 carbons and 1 or 2 triple bonds;

B is COOH or a pharmaceutically acceptable salt thereof, COOR$_8$, CONR$_9$R$_{10}$, —CH$_2$OH, CH$_2$OR$_{11}$, CH$_2$OCOR$_{11}$, CHO, CH(OR$_{12}$)$_2$, CHOR$_{13}$O, —COR$_7$, CR$_7$(OR$_{12}$)$_2$, CR$_7$OR$_{13}$O, or Si(C$_{1-6}$alkyl)$_3$, where R$_7$ is an alkyl, cycloalkyl or alkenyl group containing 1 to 5 carbons, R$_8$ is an alkyl group of 1 to 10 carbons or (trimethylsilyl)alkyl where the alkyl group has 1 to 10 carbons, or a cycloalkyl group of 5 to 10 carbons, or R$_8$ is phenyl or lower alkylphenyl, R$_9$ and R$_{10}$ independently are hydrogen, an alkyl group of 1 to 10 carbons, or a cycloalkyl group of 5–10 carbons, or phenyl or lower alkylphenyl, R$_{11}$ is lower alkyl, phenyl or lower alkylphenyl, R$_{12}$ is lower alkyl, and R$_{13}$ is divalent alkyl radical of 2–5 carbons;

R$_4$ is hydrogen, alkyl of 1 to 10 carbons, alkenyl of 2 to 10 carbons and having 1 to 3 double bonds, alkynyl having 2 to 10 carbons and 1 to 3 triple bonds, carbocyclic aryl selected from the group consisting of phenyl, $C_1$–$C_{10}$-alkylphenyl, naphthyl, $C_1$–$C_{10}$-alkylnaphthyl, phenyl-$C_1$–$C_{10}$alkyl, napthyl-$C_1$–$C_{10}$alkyl, and R$_{15}$ and R$_{16}$ are hydrogen or lower alkyl of 1 to 6 carbons, R$_{17}$ is lower alkyl of 1 to 6 carbons, or R$_{16}$ and R$_{17}$ jointly form a ring having a total of 4 to 5 carbons and the X$_2$ heteroatom.

2. A compound in accordance with claim 1 wherein Y is phenyl.

3. A compound in accordance with claim 1 wherein Y is naphthyl.

4. A compound in accordance with claim 1 where n is 1.

5. A compound in accordance with claim 1 where Z is selected from the groups consisting of —N=N— and —CONH—.

6. A compound in accordance with claim 1 where A is $(CH_2)_q$.

7. A compound in accordance with claim 1 where B is COOH or a pharmaceutically acceptable salt thereof, COOR$_8$, or CONR$_9$R$_{10}$.

8. A compound of the formula

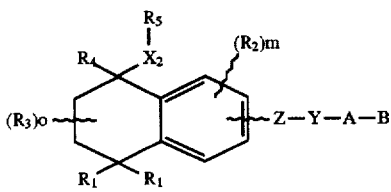

where $R_1$ is independently H or alkyl of 1 to 6 carbons;
X. is S or O;
Z is —N=N—, or
—CO—NH—,
$R_2$ is hydrogen, lower alkyl of 1 to 6 carbons;
$R_3$ is hydrogen, lower alkyl of 1 to 6 carbons or F;
m is an integer having the value of 0–3;
o is an integer having the value of 0–4;
Y is phenyl, or naphthyl;
A is $(CH_2)_q$ where q is 0–5, lower branched chain alkyl having 3–6 carbons, cycloalkyl having 3–6 carbons, alkenyl having 2–6 carbons and 1 or 2 double bonds, alkynyl having 2–6 carbons and 1 or 2 triple bonds;
B is COOH or a pharmaceutically acceptable salt thereof, $COOR_8$, $CONR_9R_{10}$, —$CH_2OH$, $CH_2OR_{11}$, $CH_2OCOR_{11}$, CHO, $CH(OR_{12})_2$, $CHOR_{13}O$, —$COR_7$, $CR_7(OR_{12})_2$, $CR_7OR_{13}O$, or $Si(C_{1-6}alkyl)_3$, where $R_7$ is an alkyl, cycloalkyl or alkenyl group containing 1 to 5 carbons, $R_8$ is an alkyl group of 1 to 10 carbons or (trimethylsilyl)alkyl where the alkyl group has 1 to 10 carbons, or a cycloalkyl group of 5 to 10 carbons, or $R_8$ is phenyl or lower alkylphenyl, $R_9$ and $R_{10}$ independently are hydrogen, an alkyl group of 1 to 10 carbons, or a cycloalkyl group of 5–10 carbons, or phenyl or lower alkylphenyl, $R_{11}$ is lower alkyl, phenyl or lower alkylphenyl, $R_{12}$ is lower alkyl, and $R_{13}$ is divalent alkyl radical of 2–5 carbons;
$R_4$ is hydrogen, alkyl of 1 to 10 carbons, $CH_2COOH$ or $CH_2CO_2R_8$;
$R_5$ is hydrogen, alkyl of 1 to 10 carbons, 2-tetrahydropyranyl, $CH_2OCH_3$ or $COR_{12}$.

9. A compound in accordance with claim 8 where Y is phenyl.

10. A compound in accordance with claim 8 where Y is naphthyl.

11. A compound in accordance with claim 8 where A is $(CH_2)_q$ where q is 0 and where B is COOH or a pharmaceutically acceptable salt thereof, $COOR_8$, or $CONR_9R_{10}$.

12. A compound in accordance with claim 8 where $R_4$ is H $CH_2COOH$ or $CH_2COOR_8$.

13. A compound in accordance with claim 8 where $R_5$ is H, 2-tetrahydropyranyl or $CH_2OCH_3$.

14. A compound of the formula

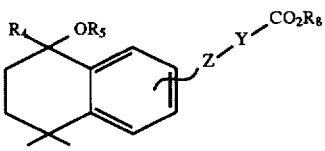

where Z is —N=N— or CONH;
Y is phenyl;
$R_4$ is H, $CH_2COOH$, $CH_2COOR_8$, or lower alkyl of 1–6 carbons,
$R_5$ is H, $CH_2OCH_3$, $COCH_3$ or 2-tetrahydropyranyl, and
$R_8$ is hydrogen or lower alkyl or a pharmaceutically acceptable salt of said compound.

15. A compound in accordance with claim 14 where the Z group is connnected to the 2-position of the tetrahydronaphthalene ring.

16. A compound in accordance with claim 14 where the Z group is connnected to the 3-position of the tetrahydronaphthalene ring.

17. A compound in accordance with claim 14 where $R_8$ is H or ethyl.

18. A compound in accordance with claim 15 where Z is —N=N—.

19. A compound in accordance with claim 18 where $R_4$ is $CH_2COOEt$.

20. A compound in accordance with claim 19 where $R_5$ is H.

21. A compound in accordance with claim 18 where $R_4$ is H.

22. A compound in accordance with claim 21 where $R_5$ is H.

23. A compound in accordance with claim 21 where $R_5$ is $CH_2OCH_3$.

24. A compound in accordance with claim 23 where $R_8$ is ethyl.

25. A compound in accordance with claim 15 where Z is —CONH—.

26. A compound in accordance with claim 25 where $R_4$ is H.

27. A compound in accordance with claim 26 where $R_5$ is H.

28. A compound in accordance with claim 26 where $R_5$ is $CH_2OCH_3$.

29. A compound in accordance with claim 25 where $R_4$ is $CH_2COOEt$.

30. A compound in accordance with claim 28 where $R_5$ is $COCH_3$.

31. A compound in accordance with claim 26 where $R_5$ is 2-(1-tetrahydropyranyl).

* * * * *

UNITED STATES PATENT AND TRADEMARK OFFICE
CERTIFICATE OF CORRECTION

PATENT NO. : 5,741,896
DATED : April 21, 1998
INVENTOR(S) : Vuligonda et al.

It is certified that error appears in the above-identified patent and that said Letters Patent is hereby corrected as shown below:

Column 2, line 7, delete "5,130,335 Chandraratna et al.),".
Column 2, line 13, "(Wuest et al.," should be --(Wuest et al.),--.
Column 2, line 16, "Med" should be --Med.--.
Column 2, line 24, "application" should be --Application--.
Column 2, line 49, delete "headache", as it was previously stated.
Column 2, lines 54-55, after "receptors", add --are--.
Column 3, line 33, "J" should be --J.--.
Column 3, line 34, "Chem" should be --Chem.--.
Column 4, line 15, "napthyl-" should be --naphthyl- --.
Column 4, line 25, "napthyl-" should be --naphthyl- --.
Column 4, line 61, "napthyl-" should be --naphthyl- --.
Column 8, line 61, "bond" should be --bonds--.
Column 8, line 65, "napthyl-" should be --naphthyl- --.
Column 9, line 66, after "COOR$_8$", add --,--.
Column 10, line 34, "papilloma virus" should be --Papilloma Virus--.
Column 10, line 65, "retinoids to" should be --retinoids, to--.
Column 11, line 26, "IC$_{80}$" should be --"IC$_{80}$"--.
Column 11, line 57, "co-tranfection" should be --co-transfection--.

UNITED STATES PATENT AND TRADEMARK OFFICE
CERTIFICATE OF CORRECTION

PATENT NO. : 5,741,896
DATED : April 21, 1998
INVENTOR(S) : Vuligonda et al.

It is certified that error appears in the above-identified patent and that said Letters Patent is hereby corrected as shown below:

Column 12, line 29, after "described", delete "in".

Column 13, line 53, "it" should be --its--.

Column 13, line 66, "milliliter" should be --mililiter--.

Column 15, line 36, "Formula" should be --Formulas--.

Column 16, lines 57-58, "corresponds" should be --correspond--.

Column 17, line 33, "suberan" should be --suberane--.

Column 18, line 24, "of formula" should be --of the formula--.

Column 19, line 18, "of formula" should be --of the formula--.

Column 21, line 47, "sulphur" should be --sulfur--.

Column 23, under "TABLE FOR FORMULA 3A", the columns titled "$R_{19}$'" and "$R_{19}$"" should be --$R'_{19}$-- and --$R''_{19}$--, respectively.

Column 31, line 13, "-1-one" should be -- -1(2H)-one--.

Column 33, line 40, "Chem" should be --Chem.--.

Column 35, line 15, after "which", add --is--.

Column 55, line 41, "naphthlene" should be --naphthalene--.

Column 55, line 58, "therafter" should be --thereafter--.

Column 56, line 43, "Bull" should be --Bull.--.

Column 62, under the first structure in "Reaction Scheme 14", "X=SO2" should be --X=$SO_2$--.

Column 63, line 61, "Formula" should be --Formulas--.

Column 64, line 46, "Formula" should be --Formulas--.

UNITED STATES PATENT AND TRADEMARK OFFICE
CERTIFICATE OF CORRECTION

PATENT NO. : 5,741,896
DATED : April 21, 1998
INVENTOR(S) : Vuligonda et al.

It is certified that error appears in the above-identified patent and that said Letters Patent is hereby corrected as shown below:

Column 64, line 62, "Formula" should be --Formulas--.

Column 65, line 1, after "available", add --in--.

Column 65, line 64, "Formula" should be --Formulas--.

Column 68, line 6, "(Compound G)" should be --(Compound G).--.

Column 68, line 25, "7.69 dd," should be --7.69 (dd,--.

Column 68, line 39, "1H" should be --$^1$H--.

Column 70, line 41, "2[N,N-bis trifloromethylsulfonyl)" should be --2[N,N-bis(trifluoromethylsulfonyl)--.

Column 70, line 59, after "(0.38 g", delete "(" and add --,--.

Column 74, line 27, after "reaction", add --was--.

Column 77, line 6, "seperated" should be --separated--.

Column 78, line 2, "And" should be --and--.

Column 78, line 36, "'HMR" should be --$^1$H NMR--.

Column 79, line 28, after "purified", add --by--.

Column 80, line 10, "naphthlen" should be --naphthalen--.

Column 80, line 32, "naphthlen" should be --naphthalen--.

Column 80, line 38, "naphthlen" should be --naphthalen--.

Column 81, line 3, "7.80 (dd J=1.7," should be --7.80 (dd, J=1.7,--.

Column 81, line 49, "naphthlen" should be --naphthalen--.

Column 82, line 6, "napthlen" should be --naphthalen--.

Column 82, line 14, "naphthlen" should be --naphthalen--.

UNITED STATES PATENT AND TRADEMARK OFFICE
CERTIFICATE OF CORRECTION

PATENT NO. : 5,741,896
DATED : April 21, 1998
INVENTOR(S) : Vuligonda et al.

It is certified that error appears in the above-identified patent and that said Letters Patent is hereby corrected as shown below:

Column 82, line 36, "'H NMR" should begin a new paragraph.
Column 82, line 37, "87" should be --1.87--.
Column 82, line 57, "-dimethy-" should be -- -dimethyl- --.
Column 83, line 21, after "was", delete "and".
Column 86, line 2, after "6.99 (dd, J=12.0, 15.1 Hz", delete ")".
Column 86, line 13, "(m 3H)" should be --(m, 3H)--.
Column 86, line 23, after "quenched", delete "the".
Column 88, line 8, "1.30 (t, J=7.1 Hz, 3)," shouln be --1.30 (t, J=7.1 Hz, 3H),--.
Column 88, line 36, "(MgSO4)" should be --(MgSO$_4$)--.
Column 88, line 42, "(s. 1H)" should be --(s, 1H)--.
Column 89, line 41, "solid" should be --solids--.
Column 92, line 14, after "(m, 3H)", add --.--.
Column 92, line 46, "mimutes" should be --minutes--.
Column 92, line 61, "slurry NaH" should be --slurry of NaH--.
Column 93, line 5, "colunm" should be --column--.
Column 93, lines 10-12, "3-[1(2H)-(Propyliden-2-yl)-3,4-dihydro-4,4-dimethylnaphthalen-7-yl]but-2(E)-en-aldehyde (Compound C35)" should be a separate heading.
Column 93, line 22, "silca" should be --silica--.

UNITED STATES PATENT AND TRADEMARK OFFICE
CERTIFICATE OF CORRECTION

PATENT NO. : 5,741,896
DATED : April 21, 1998
INVENTOR(S) : Vuligonda et al.

It is certified that error appears in the above-identified patent and that said Letters Patent is hereby corrected as shown below:

Column 95, line 54, "-2)E)-" should be -- -2(E)- --.
Column 96, line 40, "(carbethoxymethylideneyl)" should be -- (carbethoxymethylidenyl)--.
Column 96, line 67, "(s 2H)," should be --(s, 2H),--.
Column 97, line 34, "(to pH 4" should be --(to pH 4)--.
Column 98, line 12, "131" should be --1.31--.
Column 98, line 29, "132" should be --1.32--.
Column 98, line 40, "(426.7 mg" should be --(426.7 mg,--.
Column 98, line 62, "HZ" should be --Hz--.
Column 101, line 3, "naphthlene" should be --naphthalene--.
Column 101, line 25, "-naphthlene" should be -- -naphthalene--.
Column 101, line 25, "((Compound" should be --(Compound--.
Column 101, line 31, "(1/3))" should be --(1/3)--.
Column 101, line 36, "7.76 (,J=1.34, 6.10 Hz, 1H)," should be
        --7.76 (J=1.34, 6.10 Hz, 1H),--.
Column 101, line 42, "((Compound" should be --(Compound--.
Column 101, line 67, "-dimethylnaphthlen-" should be
        -- -dimethylnaphthalen- --.
Column 101, line 67, "((Compound" should be --(Compound--.
Column 102, line 26, "and then" should be --and was then--.
Column 102, line 42, after "TiCl$_3$ (5 g, 32 mmol)", delete "of".

UNITED STATES PATENT AND TRADEMARK OFFICE
CERTIFICATE OF CORRECTION

PATENT NO. : 5,741,896  
DATED : April 21, 1998  
INVENTOR(S) : Vuligonda et al.

Page 6 of 10

It is certified that error appears in the above-identified patent and that said Letters Patent is hereby corrected as shown below:

Column 103, lines 36-37, "7.30 (dd, J=1.65, 6.16, 1H)," should be  
--7.30 (dd, J=1.65, 6.16 Hz, 1H),--.

Column 103, lines 53-54, "4.75 (t, J=4.90, 1H)," should be  
--4.75 (t, J=4.90 Hz, 1H),--.

Column 104, line 43, "(trimethylsily)" should be  
--(trimethylsilyl)--.

Column 106, line 12, "2.77 (dd, J=6.6, 2H)," should be  
--2.77 (dd, J=6.6 Hz, 2H),--.

Column 106, line 25, "MgSO4" should be --$MgSO_4$--.

Column 106, line 66, "(triphenyphosphine)" should be  
--(triphenylphosphine)--.

Column 107, line 28, "Î" should be --$\delta$--.

Column 107, line 29, "6.25 t," should be --6.25 (t,--.

Column 107, line 33, "4-[[(5,5-" should be --4-[(5,5- --.

Column 107, line 46, "sovents" should be --solvents--.

Column 107, line 55, "4-[[(5,5-" should be --4-[(5,5- --.

Column 107, line 59, "4-[[(5,5-" should be --4-[(5,5- --.

Column 108, line 5, "(m. 3H)" should be --(m, 3H0--.

Column 108, line 20, "$NaCO_3$" should be --$NaHCO_3$--.

Column 108, line 21, "sovents" should be --solvents--.

Column 108, line 57, "(0.594 mmol 0.6 mL" should be  
(0.594 mmol, 0.6 mL--.

UNITED STATES PATENT AND TRADEMARK OFFICE
CERTIFICATE OF CORRECTION

PATENT NO. : 5,741,896
DATED : April 21, 1998
INVENTOR(S) : Vuligonda et al.

It is certified that error appears in the above-identified patent and that said Letters Patent is hereby corrected as shown below:

```
Column 109, line 23, "-2-yl)}" should be -- -2-yl)--.
Column 109, line 45, "-2-yl)}" should be -- -2-yl)--.
Column 109, line 56, "crystalized" should be --crystallized--.
Column 109, line 64, "-2-yl)}" should be -- -2-yl)--.
Column 110, line 7, "NaCO_3" should be --NaHCO_3--.
Column 110, line 13, "(t, t J=6.9 Hz, 2H)," should be
            --(t, J=6.9 Hz, 2H),--.
Column 110, line 19, "-2-yl)}" should be -- -2-yl)--.
Column 110, line 30, "NaCO_3" should be --NaHCO_3--.
Column 110, line 42, "-2-yl)}" should be -- -2-yl)--.
Column 110, lines 45-46, "-2-yl)}" should be -- -2-yl)--.
Column 111, line 26, after "under", add --reduced--.
Column 111, line 33, "-2-yl)}" should be -- -2-yl)--.
Column 111, line 58, "-2-yl)}" should be -- -2-yl)--.
Column 111, line 66, after "under", add --reduced--.
Column 112, line 25, "-2-yl)}" should be -- -2-yl)--.
Column 112, line 42, "81.Hz" should be --8.1 Hz--.
Column 112, line 45, "-2-yl)}" should be -- -2-yl)--.
Column 112, line 48, "-2-yl)}" should be -- -2-yl)--.
Column 113, line 19, "-2-yl)}" should be -- -2-yl)--.
Column 113, line 38, "-2-yl)}" should be -- -2-yl)--.
Column 114, line 31, "NaOAc)3H_2O" should be --NaOAc3H_2O--.
```

UNITED STATES PATENT AND TRADEMARK OFFICE
CERTIFICATE OF CORRECTION

PATENT NO. : 5,741,896
DATED : April 21, 1998
INVENTOR(S) : Vuligonda et al.

It is certified that error appears in the above-identified patent and that said Letters Patent is hereby corrected as shown below:

Column 115, line 26, "wre" should be --were--.
Column 115, line 63, "of(+/-)" should be --of (+/-)--.
Column 116, line 3, "wre" should be --were--.
Column 116, line 9, the first occurrence of "1h" should be --$^1$H--.
Column 116, line 9, the second occurrence of "1h" should be --$^1$H--.
Column 116, line 33, after "8.30 (dd,", delete "1H"".
Column 117, line 9, "4.91 d," should be --4.91 (d,--.
Column 117, line 18, "tertahydro" should be --tetrahydro--.
Column 117, line 28, "1H MNR" should be --$^1$H NMR--.
Column 117, line 32, "8.19 d," should be --8.18 (d,--.
Column 118, line 8, "4.80 d," should be --4.80 (d,--.
Column 118, line 21, "NaOAc) X 3H$_2$O" should be --NaOAC3H$_2$O--.
Column 118, line 28, "(20% EtOAc-hexanes" should be --(20% EtOAc-hexanes)--.
Column 119, line 17, "NaOAc)3H$_2$O" should be --NaOAc3H$_2$O--.
Column 119, line 45, "undr" should be --under--.
Column 120, line 48, "tertahydro" should be --tetrahydro--.
Column 125, lines 66-67, "prepartion" should be --preparation--.

UNITED STATES PATENT AND TRADEMARK OFFICE
CERTIFICATE OF CORRECTION

PATENT NO. : 5,741,896
DATED : April 21, 1998
INVENTOR(S) : Vuligonda et al.

It is certified that error appears in the above-identified patent and that said Letters Patent is hereby corrected as shown below:

Column 126, line 1, "-7napthoyloxy]" should be
   -- -7-naphthoyloxy]--.
Column 128, lines 8-9, "8.06-8.10 M, 3H)." should be
   --8.06-8.10 (m, 3H).--.
Column 128, line 18, "CO2" should be --$CO_2$--.
Column 128, line 45, "sovents" should be --solvents--.
Column 129, line 13, "hydrochlorde" should be
   --hydrochloride--.
Column 129, line 21, "($CDC_3$)" should be --($CDCl_3$)--.
Column 129, line 26, "Benzyl-4-[[5,5-" should be
   --Benzyl-4-[[(5,5- --.
Column 129, line 30, "benzyl-4-[[5,5-" should be
   --benzyl-4-[[(5,5- --.
Columnn129, line 31, "oxyl]" should be --oxy]--.
Column 129, line 32, "((Compound E81" should be --(Compound E81--.
Column 130, line 9, "napthyl-" should be --naphthyl- --.
Column 130, line 19, "naphtyl-" should be --naphthyl- --.
Column 130, line 48, "napthyl-" should be --naphthyl- --.

UNITED STATES PATENT AND TRADEMARK OFFICE
CERTIFICATE OF CORRECTION

PATENT NO.  : 5,741,896
DATED       : April 21, 1998
INVENTOR(S) : Vuligonda et al.

It is certified that error appears in the above-identified patent and that said Letters Patent is hereby corrected as shown below:

Column 131, line 53, "H" should be --H,--.

Signed and Sealed this

Twenty-first Day of December, 1999

*Attest:*

Q. TODD DICKINSON

*Attesting Officer*   Acting Commissioner of Patents and Trademarks

UNITED STATES PATENT AND TRADEMARK OFFICE
CERTIFICATE OF CORRECTION

PATENT NO. : 5,741,896
DATED : April 21, 1998
INVENTOR(S) : Vuligonda et al.

It is certified that error appears in the above-identified patent and that said Letters Patent is hereby corrected as shown below:

Column 3, line 34, "Meal." should be --Med.--.
Column 5, line 56, after "$R_9$ and $R_{10}$", delete "is".
Column 6, line 1, delete "a".
Column 6, line 17, "-CO-$CR_1$=$CR_1$;" should be -- -CO-$CR_1$=$CR_1$-;--.
Column 7, line 15, "X," should be --$X_1$--.
Column 7, line 21, "-CO-$CR_1$=$CR_1$;" should be -- -CO-$CR_1$=$CR_1$-;--.
Column 8, line 21, "-CO-$CR_1$=$CR_1$;" should be -- -CO-$CR_1$=$CR_1$-;--.
Column 8, line 59, "Si($C_{1-6}$alkyl)3" should be --Si($C_{1-6}$alkyl)$_3$--.
Column 9, line 19, "-CO-$CR_1$=$CR_1$;" should be -- -CO-$CR_1$=$CR_1$-;--.
Column 10, line 50, after "act as", delete "a".
Column 11, line 60, "$K_a$" should be --$K_d$--.
Column 11, line 63, "RXRreceptors" should be --$RXR_\Gamma$ receptors--.
Column 12, line 10, "WO93/" should be --WO93/--.
Column 12, line 26, "RXR transactivation" should be --$RXR_\beta$ transactivation--.
Column 15, line 8, "milliliter" should be --mililiter--.
Column 15, line 62, after "Also", delete "is".
Column 17, line 44, "-Z-Y($R_2$)-A-B B" should be
    -- -Z-Y($R_2$)-A-B--.
Column 18, line 15, after "procedure", delete "a".
Column 18, line 18, after "invention", delete "s".
Column 20, lines 3-4, "$(CH_2)_n$,-COOH" should be --$(CH_2)_n$-COOH--.

UNITED STATES PATENT AND TRADEMARK OFFICE
CERTIFICATE OF CORRECTION

PATENT NO. : 5,741,896
DATED : April 21, 1998
INVENTOR(S) : Vuligonda et al.

It is certified that error appears in the above-identified patent and that said Letters Patent is hereby corrected as shown below:

Column 20, line 21, "$-(CR_1=CR_1)_n-$" should be -- $-(CR_1=CR_1)_{n'}-$ --.

Column 20, in "TABLE For Formula 1A", under the "Y" column, "2,6-" should be --$2,6-C_{10}-H_6^2$--.

Column 20, in "TABLE For Formula 1A", under the "Z" column, delete "$C_{10}-H_6^2$".

Column 21, in "TABLE For Formula 1A", under the column titled "Compound No.", "B-56" should be --E-56--.

Column 24, in "TABLE FOR FORMULA 3A", under the "Z" column, "polyene3" should be --$polyene^3$--.

Column 27, in "TABLE FOR FORMULA 5A", under the "Z" column, the first occurrence of "$polyene_2$" should be --$polyene^2$--.

Column 27, in "TABLE FOR FORMULA 5A", under the "Z" column, the second occurrence of "$polyene_2$" should be --$polyene^2$--.

Column 27, in "TABLE FOR FORMULA 5A", under the "Z" column, the third occurrence of "$polyene_2$" should be --$polyene^2$--.

Column 27, in "TABLE FOR FORMULA 5A", under the "Z" column, the fourth occurrence of "$polyene_2$" should be --$polyene^2$--.

UNITED STATES PATENT AND TRADEMARK OFFICE
CERTIFICATE OF CORRECTION

PATENT NO. : 5,741,896
DATED : April 21, 1998
INVENTOR(S) : Vuligonda et al.

It is certified that error appears in the above-identified patent and that said Letters Patent is hereby corrected as shown below:

Column 27, in "TABLE FOR FORMULA 5A", under the "Z" column, the fifth occurrence of "polyene$_2$" should be --polyene$^2$--.

Column 28, line 20, "C(CH$_3$)" should be --C(CH$_3$)--.

Column 28, in "TABLE FOR FORMULA 6A", under the "Z" column, the first occurrence of "polyene$_2$" should be --polyene$^2$--.

Column 28, in "TABLE FOR FORMULA 6A", under the "Z" column, the second occurrence of "polyene$_2$" should be --polyene$^2$--.

Column 28, in "TABLE FOR FORMULA 6A", under the "Z" column, the third occurrence of "polyene$_2$" should be --polyene$^2$--.

Column 32, by the arrow under "Compound A2", "CH$_3$ONH$_2$.HCl" should be --CH$_3$ONH$_2$•HCl--.

Column 33, above the arrow pointing from "Compound A9" to "Compound A10", "3. Pd(Ph$_3$)$_4$" should be --3. Pd(PPh$_3$)$_4$--.

Column 35, line 60, "organgometal" should be --organometal--.

Column 37, line 20, "phenylsulfonylnaphthalenyl" should be --phenylsulfonyl-naphthalenyl--.

UNITED STATES PATENT AND TRADEMARK OFFICE
CERTIFICATE OF CORRECTION

PATENT NO. : 5,741,896
DATED : April 21, 1998
INVENTOR(S) : Vuligonda et al.

It is certified that error appears in the above-identified patent and that said Letters Patent is hereby corrected as shown below:

Column 37, below the structure following "Compound A2", "EtO.BF$_3$" should be --EtO$\cdot$BF$_3$--.

Column 49, line 11, "tetrahydro naphthalen" should be --tetrahydronaphthalen--.

Column 52, line 27, "Pal(0)" should be --Pd(0)--.

Column 52, on the structure corresponding with "Compound D10", "CO$_2$Et$_2$" should be --CO$_2$Et--.

Column 54, line 46, "(Compound D3)." should be --(Compound D5).--.

Column 55, line 41, "-hydroxyl" should be -- -hydroxyl-1--.

Column 55, line 60, after "compounds", delete "a".

Column 68, line 67, "8.11 (d, S=2.0 Hz, 1 H)." should be --8.11 (d, J=2.0 Hz, 1 H).--.

Column 72, line 56, "naphthalen-2-2-yl)" should be --naphthalen-2-yl)--.

Column 74, lines 14-15, "7.71 (dd, J=1.5, 8.1 Hz), 1 H)" should be --7.71 (dd, J=1.5, 8.1 Hz, 1 H)--.

Column 74, line 53, "(C$_3$OD)" should be --(CD$_3$OD)--.

Column 78, line 48, "(5,6,7,8tetrahydro" should be --(5,6,7,8-tetrahydro--.

Column 80, line 50, "(Compound B5)" should be --(Compound B8)--.

UNITED STATES PATENT AND TRADEMARK OFFICE
CERTIFICATE OF CORRECTION

PATENT NO. : 5,741,896
DATED : April 21, 1998
INVENTOR(S) : Vuligonda et al.

It is certified that error appears in the above-identified patent and that said Letters Patent is hereby corrected as shown below:

Column 81, line 12, "(O-methyloxime)" should be --(O-methyl oxime)--.

Column 81, line 38, after "title", delete "a".

Column 82, line 16, "(DMSO-$D_6$" should be --(DMSO-D6--.

Column 85, lines 5-7, "3-[4,4-dimethyl-1-phenylthio-3,4-dihydronaphthalen-7-yl]but-2-en(E)-aldehyde (Compound C9)" should be a separate heading.

Column 85, line 11, "(DiBA-H)" should be --(DiBAl-H)--.

Column 85, lines 45-48, "Ethyl 7-[4,4-dimethyl-1-phenylsulfoxide-3,4,-dihydronaphthalen-7-yl]-3,7-dimethyl-hept-2(E), 4(E), 6(E)trienoate (Compound C11b)" should be a separate heading.

Column 86, line 14, "a=2.5" should be --J=2.5--.

Column 87, line 55, "4(E)." should be --4(E),--.

Column 88, line 16, "(E)trienoate" should be --6(E)trienoate--.

Column 88, line 58, "($C_3COC_3$)" should be --($CD_3COCD_3$)--.

Column 89, line 15, "(%" should be --(q,--.

Column 89, line 47, "2.56 (t, J=6 Hz, 2H)," should be --2.56 (t, J=6.5 Hz, 2H),--.

Column 90, line 17, "-7-yl3,7-" should be-- -7-yl]3,7- --.

Column 90, line 33, "(%" should be --(q,--.

UNITED STATES PATENT AND TRADEMARK OFFICE
CERTIFICATE OF CORRECTION

PATENT NO. : 5,741,896
DATED : April 21, 1998
INVENTOR(S) : Vuligonda et al.

It is certified that error appears in the above-identified patent and that said Letters Patent is hereby corrected as shown below:

Column 91, line 11, "7.12 (dd, J=11.1 Hz, 1H)." should be
--7.12 (dd, J=11.1, 15.1 Hz, 1H),--.

Column 91, lines 62-65, "(+/-)Ethyl 7-[4,4-dimethyl-1,2,3,4-tetrahydro-1(RS)-(2'(RS)-tetrahydropyranoxy)-3,7-dimethyl-naphth-2-yl]hepta-2(E),4(E),6(E)-trienoate (Compound C29a)" should be a separate heading.

Column 92, line 3, after "7.02 (dd, J=11.1, 15.0 Hz,", add --1H),--.

Column 92, lines 5-8, "(+/-)Ethyl 7-[4,4-dimethyl-1,2,3,4-tetrahydro-1(RS)-(2'(SR)-tetrahydropyranoxy)-3,7-dimethyl-naphth-2-yl]hepta-2(E),4(E),6(E)-trienoate (Compound C29b)" should be a separate heading.

Column 92, lines 62-63, "ethyleyanomethylphosphonate" should be --ethylcyanomethylphosphonate--.

Column 93, line 24, "is" should be --ó--.

Column 93, lines 60-62, "7-Acetyl-1(2H)-(phenylbenzyliden-yl)-3,4-dihydro-4,4-dimethylnaphthalene (Compound C38)" should be a separate heading.

Column 95, line 12, "in s vacuo" should be --in vacuo--.

Column 96, lines 57-59, "Ethyl 4-[(5,5-dimethyl-8(7H)-(carbethoxymethylidenyl)-5,6-dihydronaphthalen-2-yl) azo]benzoate (Compound D2a)" is a separate heading.

UNITED STATES PATENT AND TRADEMARK OFFICE
CERTIFICATE OF CORRECTION

PATENT NO. : 5,741,896
DATED : April 21, 1998
INVENTOR(S) : Vuligonda et al.

It is certified that error appears in the above-identified patent and that said Letters Patent is hereby corrected as shown below:

Column 96, lines 63-65, "Ethyl 4-[(5,5-dimethyl-8-(carbethoxymethyl)-5,6-dihydronaphthalen-2-yl)-azo]benzoate (Compound D2b)" should be a separate heading.

Column 98, line 8, after "solvent", delete "s".

Column 100, line 15, "mmol" should be --mmols--.

Column 103, line 25, delete "yl)azo]benzoate (Compound D12)".

Column 105, line 45, "(0,222 mmol)" should be --(0.222 mmol)--.

Column 106, line 11, "1HNMR" should be --$^1$HNMR--.

Column 106, line 27, "(Acetone $D_6$)" should be --(Acetone-D6)--.

Column 108, lines 28-30, "2-trimethylsilylethyl 4-[[(5,5-dimethyl-5,6-dihydro-8-(2-thienyl)-naphthalen-2-yl)carbonyl]oxy]-benzoate (Compound E10)" should be a separate heading.

Column 108, line 42, "off" should be --oil--.

Column 109, line 44, "5.5" shouldbe --5,5--.

Column 110, line 18, "5.5" should be --5,5--.

Column 111, line 32, "5.5" should be --5,5--.

Column 113, line 11, "off" should be --oil--.

Column 113, lines 55-57, "Ethyl 4-[(5,5-Dimethyl-8(7H)-one-5,6-dihydronaphthalen-2-yl)carboxamido]benzoate (Compound E28)" should be a separate heading.

UNITED STATES PATENT AND TRADEMARK OFFICE
CERTIFICATE OF CORRECTION

PATENT NO. : 5,741,896
DATED : April 21, 1998
INVENTOR(S) : Vuligonda et al.

It is certified that error appears in the above-identified patent and that said Letters Patent is hereby corrected as shown below:

Column 114, line 28, "-8(7)_" should be -- -8(7H)--.
Column 115, line 16, "5.5" should be --5,5--.
Column 115, line 20, "5,6,7,-" should be --5,6,7,8- --.
Column 116, line 25, "HQ" should be --HCl--.
Column 117, line 10, "7.49 (d, J=8.3 1 Hz, 1H)," should be --7.49 (d, J=8.3 Hz, 1H),--.
Column 117, line 53, after "8.12 (d, J=8.7 Hz,", add --2H), 8.29 (d, J=1.8 Hz, 1H).--.
Column 117, lines 55-58, "2H), 8.29 (d, J=1.8 Hz, 1H). (+/-) Ethyl 4-[(+/-) Ethyl 4-[[(5,5-dimethyl-8- (O-methoxymethyl)-5,6,7,8-tetrahydronaphthalen-2-yl)carbonyl]oxy]benzoate" should be --(+/-)Ethyl 4-[[(5,5-dimethyl-8-(O-methoxymethyl)-5,6,7,8-tetrahydronaphthalen-2-yl)carbonyl]oxy]benzoate--.
Column 118, line 57, "(Compound F44)" should be --(Compound E44)--.
Column 118, line 59, after "-one-2-", delete "a".
Column 119, line 1, after "and", delete "a".
Column 122, lines 66-67, "1.35 (s, 7.1 Hz, 7 (t, J=7.1 Hz, 3H)" should be --1.35 (s, 3H), 1.37 (t, J=7.1 Hz, 3H),--.
Column 122, line 67, "(m, tOH)" should be --(m, 10H)--.
Column 123, line 1, "J=4.8 Hz," should be --J=4.5 Hz,--.

UNITED STATES PATENT AND TRADEMARK OFFICE
CERTIFICATE OF CORRECTION

PATENT NO.  : 5,741,896
DATED       : April 21, 1998
INVENTOR(S) : Vuligonda et al.

It is certified that error appears in the above-identified patent and that said Letters Patent is hereby corrected as shown below:

Column 125, line 37, "(Compound E628" should be --(Compound E62a--.

Column 125, lines 55-57, "4.85 (t, J=4.9 Hz," should be --4.85 (t, J=4.8 Hz,--.

Column 126, lines 24-25, "Ethyl 4-[5,6,7,8-tetrahydropyranoxy)-5,5-dimethylnaphthalene-2-yl)carboxamido]benzoate" should be --Ethyl 4-[5,6,7,8-tetrahydro-8(S or R)-(2'(S or R)tetrahydropyranoxy)5,5-dimethylnaphthalene-2-yl)carboxamido]benzoate--.

Column 130, line 20, "COR$_4$" should be --COR$_{14}$--.

Column 130, line 43, "R$_4$" should be --R$_{14}$--.

Column 131, line 12, "X," should be --X$_2$--.

Signed and Sealed this

Tenth Day of April, 2001

Attest:

NICHOLAS P. GODICI

*Attesting Officer*          *Acting Director of the United States Patent and Trademark Office*